(12) United States Patent
Moriarty et al.

(10) Patent No.: US 7,479,495 B2
(45) Date of Patent: Jan. 20, 2009

(54) N-HETEROCYCLIC INHIBITORS OF TNF-α EXPRESSION

(75) Inventors: Kevin Joseph Moriarty, Norristown, PA (US); Yvonne Shimshock, Hillsborough, NJ (US); Gulzar Ahmed, Yardley, PA (US); Junjun Wu, Malden, MA (US); James Wen, Dayton, NJ (US); Wei Li, Acton, MA (US); Shawn David Erickson, Leonia, NJ (US); Jeffrey John Letourneau, East Windsor, NJ (US); Edward McDonald, Banstead (GB); Katerina Leftheris, Skillman, NJ (US); Stephen T. Wrobleski, Whitehouse Station, NJ (US); Zahid Hussain, Monmouth Junction, NJ (US); Ian Henderson, Hopewell, NJ (US); Axel Metzger, East Windsor, NJ (US); John J. Baldwin, Gwynedd Valley, PA (US); Alaric J. Dyckman, Lawrenceville, NJ (US)

(73) Assignees: Pharmacopeia, Inc., Cranbury, NJ (US); Bristol-Myers Squibb Company, Princeton, NJ (US)

( * ) Notice: Subject to any disclaimer, the term of this patent is extended or adjusted under 35 U.S.C. 154(b) by 111 days.

(21) Appl. No.: 11/143,430

(22) Filed: Jun. 2, 2005

(65) Prior Publication Data

US 2005/0239770 A1 Oct. 27, 2005

Related U.S. Application Data

(60) Division of application No. 09/891,750, filed on Jun. 26, 2001, now Pat. No. 6,906,067, which is a continuation-in-part of application No. 09/747,195, filed on Dec. 22, 2000, now abandoned.

(60) Provisional application No. 60/173,227, filed on Dec. 28, 1999.

(51) Int. Cl.
| | |
|---|---|
| C07D 239/32 | (2006.01) |
| C07D 239/48 | (2006.01) |
| C07D 239/50 | (2006.01) |
| C07D 401/04 | (2006.01) |
| C07D 401/12 | (2006.01) |
| C07D 403/04 | (2006.01) |
| C07D 403/12 | (2006.01) |
| A61K 31/505 | (2006.01) |
| A61K 31/506 | (2006.01) |
| A61P 19/02 | (2006.01) |
| A61P 35/00 | (2006.01) |

(52) U.S. Cl. ............... 514/269; 514/272; 514/273; 514/275; 544/317; 544/320; 544/321; 544/323; 544/326

(58) Field of Classification Search .......... 544/309, 544/317, 319, 320, 321, 323, 334, 322, 330, 544/315, 326, 269, 272, 273, 275; 514/272, 514/275
See application file for complete search history.

(56) References Cited

U.S. PATENT DOCUMENTS

| | | | | |
|---|---|---|---|---|
| 3,133,066 | A * | 5/1964 | Hemingway et al. | 544/326 |
| 3,290,305 | A * | 12/1966 | Schmitz et al. | 260/249.5 |
| 3,590,042 | A * | 6/1971 | Cyba | 260/249.6 |
| 3,625,979 | A * | 12/1971 | Heimberger | 260/247.5 R |
| 3,867,383 | A * | 2/1975 | Winter et al. | 260/249.6 |
| 3,940,395 | A * | 2/1976 | Santilli et al. | 544/295 |
| 3,974,162 | A * | 8/1976 | Santilli et al. | 544/321 |
| 4,039,543 | A * | 8/1977 | Kompis et al. | 544/325 |
| 4,617,390 | A * | 10/1986 | Hoppe et al. | 544/197 |
| 4,724,137 | A | 2/1988 | Hoppe et al. | 424/59 |
| 4,904,778 | A * | 2/1990 | Rempfler et al. | 544/323 |
| 5,062,882 | A * | 11/1991 | Newton et al. | 544/211 |
| 5,250,530 | A * | 10/1993 | Giencke et al. | 514/256 |
| 5,346,691 | A * | 9/1994 | Raspani et al. | 544/197 |
| 5,521,184 | A * | 5/1996 | Zimmermann | 514/252.11 |
| 5,707,995 | A * | 1/1998 | Munro et al. | 514/256 |

(Continued)

FOREIGN PATENT DOCUMENTS

EP  834507  4/1998

(Continued)

OTHER PUBLICATIONS

Graninger et al. Curr. Opin. Rheumatol. 13(3): 209-13, 2001.*

(Continued)

*Primary Examiner*—Venkataraman Balasubramanian
(74) *Attorney, Agent, or Firm*—Laurelee A. Duncan; Rosemary M. Miano

(57) ABSTRACT

N-heterocyclic compounds that block cytokine production via inhibition of p38 kinase are disclosed. In one embodiment, compounds of the present invention are represented by Formula I:

$$\begin{array}{c} V-R^6 \\ W \diagdown X \\ Z \diagup Y \diagdown R^{11} \end{array} \quad I$$

Methods of production, pharmaceutical compositions and methods of treating conditions associated with inappropriate p38 kinase activity or TNF-α expression utilizing compounds of the present invention are also disclosed.

32 Claims, No Drawings

U.S. PATENT DOCUMENTS

| | | | | |
|---|---|---|---|---|
| 5,723,412 | A * | 3/1998 | Kanno et al. | 504/243 |
| 5,744,475 | A * | 4/1998 | Yano et al. | 514/274 |
| 5,759,525 | A * | 6/1998 | Raspani et al. | 544/197 |
| 5,801,244 | A * | 9/1998 | Raspani et al. | 544/197 |
| 5,840,893 | A | 11/1998 | Bukrinsky et al. | 544/329 |
| 6,150,360 | A * | 11/2000 | Daeyaert et al. | 544/194 |
| 6,288,228 | B1 * | 9/2001 | Henkin et al. | 544/197 |

FOREIGN PATENT DOCUMENTS

| | | |
|---|---|---|
| EP | 969004 | 1/2000 |
| WO | WO95/30642 | 11/1995 |
| WO | WO98/24782 | 6/1998 |
| WO | WO99/01442 | 1/1999 |
| WO | WO 01/47897 | 7/2001 |

OTHER PUBLICATIONS

Wolft Manfred E. "Burger's Medicinal Chemistry, 5ed, Part 1", John Wiley & Sons, 1995, pp. 975-977.*

Banker, G.S. et al, "Modern Pharmaceutics, 3ed.", Marcel Dekker, New York. 1996, pp. 451 and 596.*

West, Anthony R., Solid State Chemistry and its Applications, Wiley, New York, 1988, pp. 358 & 365.*

Vippagunta et al., Advanced Drug Delivery Reviews 48: 3-26, 2001.*

Graninger et al. Curr. Opin. Rheumatol. 13(3): 209-13, 2001.*

Fujiwara et al., Bioorganic & Medicinal Chemistry Letters, vol. 10, p. 1317-1320 (2000).

Raingeaud et al., Molecular And Cellular Biology, vol. 16, No. 3, p. 1247-1255 (Mar. 1996).

Henry et al., Drugs and the Future, vol. 24 (12), p. 1345-1354 (1999).

Bresnihan et al., Arthritis & Rheumantism, vol. 41, No. 12, p. 2196-2204 (Dec. 1998).

Moreland et al., Annals of Internal Medicine, vol. 130, No. 6, p. 478-486 (Mar. 1999).

Bundgaard, Advanced Drug Delivery Reviews, vol. 3, p. 39-65 (1989).

Sabituro et al., Current Medicinal Chemistry, vol. 6, p. 807-823 (1999).

Rankin et al., British Journal of Rheumatology, vol. 34, p. 334-342 (1995).

Kotlyarov et al., Nature Cell Biology, vol. 1, p. 94-97 (1999).

Bodor et al., Annual Reports In Medicinal Chemistry, vol. 22, p. 303-313 (1987).

Branger, J., et al., "Anti-Inflammatory Effects of a p38 Mitogen-Activated Protein Kinase Inhibitor During Human Endotoxemia", The Journal of Immunology, vol. 168, pp. 4070-4077, (2002).

Davis, J. C., Jr., "Understanding the Role of Tumor Necrosis Factor Inhibition in Ankylosing Spondylitis", Seminars in Arthritis and Rheumatism, vol. 34, pp. 668-677, (2004).

Gottlieb, A. B., et al., TNF Inhibition Rapidly Down-Regulates Multiple Proinflammatory Pathways in Psoriasis Plaques[1], The Journal of Immunology, vol. 175, pp. 2721-2729, (2005).

Hideshima, T. et al, "Targeting p38 MAPK inhibits multiple myeloma cell growth in the bone marrow milieu", Blood, vol. 101(2), pp. 703-706, (2003).

Johansen, C., et al., "Protein Expression of TNF-α in Psoriatic Skin Is Regulated at a Posttranscriptional Level by MAPK-Activated Protein Kinase 2[1]", The Journal of Immunology, vol. 176, pp. 1431-1438, (2006).

Johansen, C., et al., "The mitogen-activated protein kinases p38 and KRK1/2 are increased in lesional psoriatic skin", British Journal of Dermatology, vol. 152, pp. 37-42, (2005).

Kumar, S., et al., "P38 MAP Kinases: Key Signalling Molecules as Therapeutic Targets for Inflammatory Diseases", vol. 2, pp. 717-726, (2003).

Mease, P. J., et al., "Psoriatic arthritis treatment: biological response modifiers", Ann. Rheum. Dis., vol. 64 (Suppl. II), pp. ii78-ii82, (2005).

Navas, TA, et al., Inhibition of p38α MAPK enhances proteasome inhibitor-induced apoptosis of myeloma cells by modulating Hsp27, $Bcl-X_L$, MCI-1 and p53 levels in vitro and inhibits tumor growth in vivo, Leukemia, 1-11 (2006).

Papp. K. A., "The long-term efficacy and safety of new biological therapies for psoriasis", Arch. Dermatol. Res. vol. 298, pp. 7-15, (2006).

Saklatvala, J., "The p38 MAP kinase pathway as a therapeutic target in inflammatory disease", Current Opinion in Pharmacology, vol. 4, pp. 372-377, (2004).

Waetzig G. H., "p38 Mitogen-Activated Protein Kinase is Activated and Linked to TNF-α Signaling in Inflammatory Bowel Disease[1]", The Journal of Immunology, vol. 168, pp. 5342-5351, (2002).

Adams, J.L., "pyrimidinylimidazole Inhibitors of CSBP/P38 Kinase Demonstrating Decreased Inhibition of Hepatic Cytochrome P450 Enzymes", Bioorganic & Medicinal Chemistry Letters, vol. 8, pp. 3111-3116 (1998).

* cited by examiner

N-HETEROCYCLIC INHIBITORS OF TNF-α EXPRESSION

CROSS REFERENCE TO RELATED APPLICATION

This is a Divisional Application of U.S. Ser. No. 09/891,750, filed Jun. 26, 2001, now U.S. Pat. No. 6,906,067, which is a Continuation-in-Part application of U.S. Ser. No. 09/747,195, filed Dec. 22, 2000, now abandoned, which claims priority from provisional application U.S. Ser. No. 60/173,227, filed Dec. 28, 1999.

FIELD OF THE INVENTION

This invention relates to N-heterocyclic compounds that are effective in blocking cytokine production, and in particular the expression of TNF-alpha (TNF-α), via inhibition of p38 kinase. Compounds of the present invention are useful in the treatment of inflammatory diseases such as, for example, rheumatoid arthritis.

BACKGROUND OF THE INVENTION

Overproduction of cytokines such as IL-1 and TNF-α is implicated in a wide variety of inflammatory diseases, including rheumatoid arthritis (RA), psoriasis, multiple sclerosis, inflammatory bowel disease, endotoxin shock, osteoporosis, Alzheimer=s disease and congestive heart failure, among others [Henry et al., *Drugs Fut.*, 24:1345-1354 (1999); Salituro et al., *Curr. Med. Chem.*, 6:807-823 (1999)]. There is convincing evidence in human patients that protein antagonists of cytokines, such as, for example, monoclonal antibody to TNF-α (Enbrel) [Rankin et al., *Br. J. Rheumatol.*, 34:334-342 (1995)], soluble TNF-α receptor-Fc fusion protein (Etanercept) [Moreland et al., *Ann. Intern. Med.*, 130:478-486 (1999)] and or IL-1 receptor antagonist [Bresnihan et al., *Arthritis Rheum.*, 41:2196-2204 (1998)], can provide effective treatment for chronic inflammatory diseases. As none of the current treatments for inflammatory diseases provide complete relief of symptoms, and as most current treatments are associated with various drawbacks such as side effects, improved methods for treating inflammatory diseases are desirable.

TNF-α is a protein whose synthesis occurs in many cell types in response to an external stimulus, such as, for example, a mitogen, an infectious organism, or trauma. Signaling from the cell surface to the nucleus proceeds via several intracellular mediators including kinases that catalyze phosphorylation of proteins downstream in the signaling cascade. Important mediators for the production of TNF-α cytokine are the mitogen-activated protein (MAP) kinases, and in particular, p38 kinase.

p38 Kinases are activated in response to various stress stimuli, including, but not limited to, proinflammatory cytokines, endotoxin, ultraviolet light, and osmotic shock. Activation of p38 requires dual phosphorylation by upstream MAP kinase kinases (MKK3 and MKK6) on threonine and tyrosine within a Thr-Gly-Tyr motif, characteristic of p38 isozymes.

Four iso-forms of p38 have been described. The α and β forms are expressed in inflammatory cells and are thought to be key mediators of TNF-α production. Inhibition of the enzymes p38α and β in cells results in reduced levels of expression of TNF-α, and such inhibitors are effective in animal models of inflammatory disease.

Molecular cloning of human p38α identified two isozymes, which are the splice variant product of a single gene. Three additional gene products have subsequently been identified, p38β, p38γ, and p38δ. p38 kinases phosphorylate and activate the transcription factors, ATF-2, MAX, CHOP, and C/ERPb, suggesting a role of p38 kinases in gene regulation. In addition, p38 kinases phosphorylate other protein kinases, such as MAPK activated protein kinase-2/3 (MAP-KAP-K2/3, or MK2/3), and MAP-kinase-interacting kinase 1/2 (MNK1/2). Recently, activation of MK2 has been shown to be essential for LPS-induced TNF-α expression [Kotlyarov et al., *Nature Cell Biol.*, 1:94-97 (1999)]. Mice lacking MK2 exhibit a 90% reduction in the production of TNF-α and are resistant to shock induced by LPS. The reduction in TNF-α amounts is due not to decreased production of the TNF-α mRNA, but rather to diminished production of the TNF-α protein, suggesting that MK2 regulates biosynthesis of TNF-α at a post-transcriptional level.

Ample evidence indicates that the p38 pathway serves an important role in inflammatory process mediated by IL-1 and TNF-α.

Small molecule inhibitors of p38 are expected to have several advantages over protein inhibitors of TNF-α or IL-1. p38 inhibitors not only block the production of TNF-α and IL-1, but also directly interfere with many of their secondary biological effects. In addition, small molecule inhibitors are unlikely to induce immune reaction in patients, and are believed active following oral administration.

The present invention provides novel compounds that are potent and selective inhibitors of p38α and β, and as such, are also potent inhibitors of TNF-α expression in human cells. Compounds of the present invention are useful in the treatment of p38- and TNF-α expression-mediated inflammatory and other disorders, including, but not limited to, bone resorption, graft vs. host reaction, atherosclerosis, arthritis, osteoarthritis, rheumatoid arthritis, gout, psoriasis, topical inflammatory disease states, adult respiratory distress syndrome, asthma, chronic pulmonary inflammatory disease, cardiac reperfusion injury, renal reperfusion injury, thrombus, glomerulonephritis, Chrohn=s disease, ulcerative colitis, inflammatory bowel disease, multiple sclerosis, endotoxin shock, osteoporosis, Alzheimer=s disease, congestive heart failure and cachexia.

SUMMARY OF THE INVENTION

The compounds of the present invention are effective as inhibitors of inappropriate p38 activity, especially iso forms α and β, and in turn, of cytokine production, and in particular, of cellular TNF-alpha (TNF-α) expression. Accordingly, compounds of the invention are useful for the inhibition, prevention and suppression of various pathologies associated with such activity, such as, for example, inflammation, asthma, arthritis, atherosclerosis, multiple sclerosis, psoriasis, autoimmune diseases, Alzeheimer=s disease and congestive heart failure, among others.

In one embodiment, the principles of the present invention provide a compound, or a salt thereof, represented by Formula I:

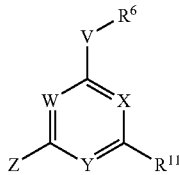

wherein:

V is chosen from —CHR⁵—, —NR⁵—, —O—, and —S—;

W, X, and Y are independently chosen from —CH= and —N=;

Z is chosen from halogen, alkyl, substituted alkyl, aryl, substituted aryl, cycloalkyl, substituted cycloalkyl, heterocyclyl, substituted heterocyclyl, —SR³, —O—R³, and —N(R¹)(R²);

—N(R¹)(R²) taken together can form a heterocyclyl or substituted heterocyclyl or R¹ is chosen from hydrogen, alkyl and susbtituted alkyl; and R² is chosen from hydrogen, alkyl, substituted alkyl, alkoxy, aryl, substituted aryl, cycloalkyl, substituted cycloalkyl, heterocyclyl and substituted heterocyclyl;

R³ is chosen from hydrogen, alkyl, substituted alkyl, aryl, substituted aryl, cycloalkyl, substituted cycloalkyl, heterocyclyl and substituted heterocyclyl;

R⁵ is chosen from hydrogen and alkyl;

R⁶ is

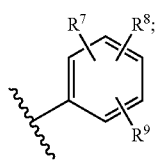

R⁷ is chosen from hydrogen, —N(R³¹)(R³²), halogen, cyano, alkyl, substituted alkyl, alkoxy, and alkylthio;

R⁸ is chosen from hydrogen and halogen;

R⁹ is chosen from nitro, carboxy, —C(O)N(R³¹)(R³²), —SO₂N(R³¹)(R³²), —N(R³³)SO₂R³⁴, —C(O)N(R³³)N(R³¹)(R³²), —N(R³³)C(O)R³⁴, —CH₂N(R³³)C(O)R³⁴, —N(R³¹)(R³²), —CH₂OC(O)R³⁴, alkyl, substituted alkyl, cycloalkyl, substituted cycloalkyl, aryl, substituted aryl, heterocyclyl, substituted heterocyclyl and —C(O)R¹⁰;

R¹⁰ is chosen from heterocyclyl, subsituted heterocyclyl, cycloalkyl, substituted cycloalkyl, aryl, substituted aryl, alkyl, substituted alkyl, and —N(R³¹)(R³²); or R⁸ and R⁹ taken together may form —C(O)N(R³³)CH₂— or —C(O)N(R³³)C(O)—;

R³¹ and R³³ are independently chosen from hydrogen, alkyl, and substituted alkyl;

R³² is chosen from hydrogen, alkyl, substituted alkyl, alkoxy, aryl, substituted aryl, cycloalkyl, aryloxy, substituted cycloalkyl, heterocyclyl and substituted heterocyclyl;

R³⁴ is chosen from alkyl, substituted alkyl, aryl, substituted aryl, cycloalkyl, substituted cycloalkyl, heterocyclyl and substituted heterocyclyl;

when V is —NR⁵, —N(R⁵)(R⁶) taken together may form heterocyclyl or substituted heterocyclyl;

R¹¹ is chosen from halogen, O—R¹³ and —N(R¹²)(R¹³);

R¹² is chosen from hydrogen, alkyl, and substituted alkyl;

R¹³ is —(CH₂)ₘR¹⁴;

m is 0, 1, 2 or 3;

R¹⁴ is chosen from hydrogen, alkyl, substituted alkyl, —C(O)N(R³¹)(R³²), —N(R³³)C(O)R³⁴, aryl, substituted aryl, cycloalkyl, substituted cycloalkyl, heterocyclyl, substituted heterocyclyl and

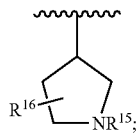

R¹⁵ is chosen from hydrogen, alkyl, substituted alkyl, alkenyl, —C(O)-alkyl, —C(O)-substituted alkyl, —C(O)-aryl, —C(O)-substituted aryl, —C(O)-alkoxy, aryl, substituted aryl, cycloalkyl, substituted cycloalkyl, heterocyclyl and substituted heterocyclyl;

R¹⁶ is chosen from hydrogen, alkyl, substituted alkyl, and

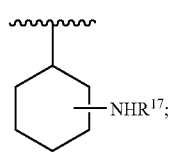

R¹⁷ is chosen from hydrogen, alkyl, substituted alkyl, —C(O)-alkyl, —C(O)-substituted alkyl, —C(O)-aryl, and —C(O)-substituted aryl; or —N(R¹²)(R¹³) taken together may form heterocyclyl or substituted heterocyclyl.

The principles of the present invention also provide methods of inhibiting TNF-α expression in a mammal, wherein the methods comprise administering to the mammal an effective amount of a compound represented by Formula I, or a prodrug or salt thereof. As used herein, inhibiting TNF-α expression is intended to include inhibiting, suppressing and preventing conditions associated with inappropriate TNF-α expression, including, but not limited to, inflammation, asthma, arthritis, atherosclerosis, multiple sclerosis, psoriasis, autoimmune diseases, Alzeheimer=s disease and congestive heart failure.

The principles of the present invention further provide methods of treating p38 kinase and TNF-α mediated disorders in a mammal, the methods comprising administering to a mammal in need of such treatment, an effective amount of a compound represented by Formula I, or a prodrug or salt thereof. As used herein, a p38 kinase mediated disorder means a disorder associated with inappropriate p38 kinase activity; a TNF-α mediated disorder means a disorder associated with inappropriate TNF-α expression. Such disorders include, but are not limited to, inflammation, asthma, arthritis, atherosclerosis, multiple sclerosis, psoriasis, autoimmune diseases, Alzeheimer=s disease and congestive heart failure.

Accordingly, the compounds of the invention, as well as prodrugs or salts thereof, may be used in the manufacture of a pharmaceutical composition or medicament for the prophylactic or therapeutic treatment of disease states in mammals. The compounds of the present invention may be administered as pharmaceutical compositions as a monotherapy, or in combination with, for example, other anti-inflammatory, e.g. a steroid or NSAID (non-steroidal anti-inflammatory drug)

and/or immunosuppressive agents. Such combination therapies can involve the administration of the various pharmaceuticals as a single dosage form or as multiple dosage forms administered simultaneously or sequentially.

Any suitable route of administration may be employed for providing a patient with an effective amount of a compound of the present invention. Suitable routes of administration may include, for example, oral, rectal, nasal, buccal, parenteral (such as, intravenous, intrathecal, subcutaneous, intramuscular, intrasternal, intrahepatic, intralesional, intracranial, intra-articular, and intra-synovial), transdermal (such as, for example, patches), and the like. Due to their ease of administration, oral dosage forms, such as, for example, tablets, troches, dispersions, suspensions, solutions, capsules, soft gelatin capsules, and the like, may be preferred. Administration may also be by controlled or sustained release means and delivery devices. Methods for the preparation of such dosage forms are well known in the art.

Pharmaceutical compositions incorporating compounds of the present invention may include excipients, a pharmaceutically acceptable carrier, in addition to other therapeutic ingredients. Excipients such as starches, sugars, microcrystalline cellulose, diluents, lubricants, binders, coloring agents, flavoring agents, granulating agents, disintegrating agents, and the like may be appropriate depending upon the route of administration. Because of their ease of administration, tablets and capsules represent the most advantageous oral dosage unit forms. If desired, tablets may be coated by standard aqueous or nonaqueous techniques.

The compounds of the present invention may be used in the form of pharmaceutically acceptable salts derived from inorganic or organic bases, and hydrates thereof. Included among such base salts are ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

DETAILED DESCRIPTION OF THE INVENTION

[1] Thus, in a first embodiment, the present invention provides a novel compound of Formula I including isomers, enantiomers, diastereomers, tautomers, pharmaceutically acceptable salts, prodrugs and solvates thereof, comprising:

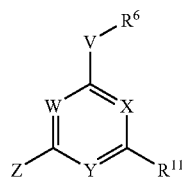

I wherein:

V is chosen from —CHR$^5$—, —NR$^5$—, —O—, and —S—;

W, X, and Y are independently chosen from —CH= and —N=;

Z is chosen from halogen, alkyl, substituted alkyl, aryl, substituted aryl, cycloalkyl, substituted cycloalkyl, heterocyclyl, substituted heterocyclyl, —SR$^3$, —O—R$^3$, and —N(R$^1$)(R$^2$);

—N(R$^1$)(R$^2$) taken together may form a heterocyclyl or substituted heterocyclyl or R$^1$ is chosen from hydrogen, alkyl and subsituted alkyl; and R$^2$ is chosen from hydrogen, alkyl, substituted alkyl, alkoxy, aryl, substituted aryl, cycloalkyl, substituted cycloalkyl, heterocyclyl and substituted heterocyclyl;

R$^3$ is chosen from hydrogen, alkyl, substituted alkyl, aryl, substituted aryl, cycloalkyl, substituted cycloalkyl, heterocyclyl and substituted heterocyclyl;

R$^5$ is chosen from hydrogen and alkyl;

R$^6$ is

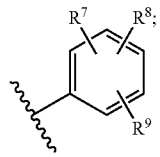

R$^7$ is chosen from hydrogen, —N(R$^{31}$)(R$^{32}$), halogen, cyano, alkyl, substituted alkyl, alkoxy, and alkylthio;

R$^8$ is chosen from hydrogen and halogen;

R$^9$ is chosen from nitro, carboxy, —C(O)N(R$^{31}$)(R$^{32}$), —SO$_2$N(R$^{31}$)(R$^{32}$), —N(R$^{33}$)SO$_2$R$^{34}$—C(O)N(R$^{33}$)N (R$^{31}$)(R$^{32}$), —N(R$^{33}$)C(O)R$^{34}$, —CH$_2$N(R$^{33}$)C(O)R$^{34}$, —N(R$^{31}$)(R$^{32}$), —CH$_2$OC(O)R$^{34}$, alkyl, substituted alkyl, cycloalkyl, substituted cycloalkyl, aryl, substituted aryl, heterocyclyl, substituted heterocyclyl and —C(O)R$^{10}$;

R$^{10}$ is chosen from heterocyclyl, subsituted heterocyclyl, cycloalkyl, substituted cycloalkyl, aryl, substituted aryl, alkyl, substituted alkyl, and —N(R$^{31}$)(R$^{32}$); or R$^8$ and R$^9$ taken together may form —C(O)N(R$^{33}$)CH$_2$— or —C(O)N(R$^{33}$)C(O)—;

R$^{31}$ and R$^{33}$ are independently chosen from hydrogen, alkyl, and substituted alkyl;

R$^{32}$ is chosen from hydrogen, alkyl, substituted alkyl, alkoxy, aryl, substituted aryl, cycloalkyl, substituted cycloalkyl, aryloxy, heterocyclyl and substituted heterocyclyl;

R$^{34}$ is chosen from alkyl, substituted alkyl, aryl, substituted aryl, cycloalkyl, substituted cycloalkyl, heterocyclyl and substituted heterocyclyl;

when V is —NR$^5$, —N(R$^5$)(R$^6$) taken together may form heterocyclyl or substituted heterocyclyl;

R$^{11}$ is chosen from halogen, OR$^{13}$, and —N(R$^{12}$)(R$^{13}$);

R$^{12}$ is chosen from hydrogen, alkyl, and substituted alkyl;

R$^{13}$ is —CH$_2$)$_m$R$^{14}$;

—N(R$^{12}$)(R$^{13}$) taken together may form a heterocyclyl or substituted heterocyclyl;

m is 0, 1, 2 or 3;

R$^{14}$ is chosen from hydrogen, alkyl, substituted alkyl, —C(O)N(R$^{31}$)(R$^{32}$), —N(R$^{33}$)C(O)R$^{34}$, aryl, substituted aryl, cycloalkyl, substituted cycloalkyl, heterocyclyl, substituted heterocyclyl and

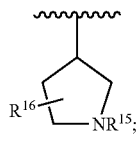

R$^{15}$ is chosen from hydrogen, alkyl, substituted alkyl, alkenyl, —C(O)-alkyl, —C(O)-substituted alkyl, —C(O)-aryl, —C(O)-substituted aryl, —C(O)-alkoxy, aryl, substituted aryl, cycloalkyl, substituted cycloalkyl, heterocyclyl and substituted heterocyclyl;
R$^{16}$ is chosen hydrogen, alkyl, substituted alkyl, and

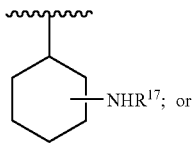

R$^{17}$ is chosen from hydrogen, alkyl, substituted alkyl, —C(O)-alkyl, —C(O)-substituted alkyl, —C(O)-aryl, and —C(O)-substituted aryl.

[2] In a preferred embodiment, the present invention provides the compound of Formula I including isomers, enantiomers, diastereomers, tautomers, pharmaceutically acceptable salts, prodrugs and solvates thereof wherein:
two or more of W, Y and X are =N—;
V is —CHR$^5$—, —NR$^5$, or —O—;
Z is —N(R$^1$)(R$^2$), —S-aryl, or S-substituted aryl;
R$^1$ is hydrogen or alkyl;
R$^2$ is alkyl, substituted alkyl, aryl, substituted aryl, cycloalkyl, substituted cycloalkyl, heterocyclyl or substituted heterocyclyl;
R$^5$ is hydrogen;
R$^7$ is hydrogen, alkyl, substituted alkyl, alkoxy, or halogen;
R$^8$ is hydrogen;
R$^9$ is —C(O)R$^{10}$, heterocyclyl or substituted heterocyclyl;
R$^{10}$ is alkyl, substituted alkyl, cycloalkyl, substituted cycloalkyl, aryl, substituted aryl, heterocyclyl, substituted heterocyclyl or —N(R$^{31}$)(R$^{32}$);
R$^{31}$ is hydrogen, alkyl, or substituted alkyl;
R$^{32}$ is hydrogen, alkyl, substituted alkyl, alkoxy, aryl, substituted aryl, cycloalkyl, substituted cycloalkyl, heterocyclyl or substituted heterocyclyl;
R$^{11}$ is —N(R$^{12}$)(R$^{13}$);
R$^{12}$ is hydrogen, alkyl, or substituted alkyl;
R$^{13}$ is —CH$_2$)$_m$R$^{14}$;
m is 0, 1, 2 or 3;
R$^{14}$ is hydrogen, alkyl substituted alkyl, —C(O)N(R$^{31}$)(R$^{32}$), —N(R$^{33}$)C(O)R$^{34}$, aryl, substituted aryl, cycloalkyl, substituted cycloalkyl, heterocyclyl, substituted heterocyclyl or

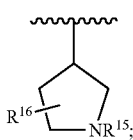

R$^{15}$ is hydrogen, alkyl or substituted alkyl;
R$^{16}$ is hydrogen or alkyl; or
—N(R$^{12}$)(R$^{13}$) taken together may form a heterocyclyl or substituted heterocyclyl;
R$^{33}$ is hydrogen, alkyl, or substituted alkyl; and
R$^{34}$ is alkyl, substituted alkyl, aryl or substituted aryl.

[3] In a more preferred embodiment, the present invention provides a compound of [2] above including isomers, enantiomers, diastereomers, tautomers, pharmaceutically acceptable salts, prodrugs and solvates thereof wherein:
two or more of W, Y and X are =N—;
V is —NH—, or —O—;
Z is —N(R$^1$)(R$^2$), —S-aryl, or S-substituted aryl;
R$^1$ is hydrogen or alkyl or 1 to 4 carbons;
R$^2$ is alkyl or substituted alkyl wherein alkyl is of 1 to 8 carbons;
R$^7$ is hydrogen, alkyl, of 1 to 4 carbons, alkoxy of 1 to 4 carbons, or halogen;
R$^8$ is hydrogen;
R$^9$ is —C(O)R$^{10}$, heterocyclyl or substituted heterocyclyl;
R$^{10}$ is —NH$_2$, —NH-alkyl, —NH-alkoxy, —NH-phenyl, or —NH—CH$_2$-phenyl wherein alkyl and alkoxy are of 1 to 6 carbons;
R$^{11}$ is —N(R$^{12}$)(R$^{13}$) wherein N(R$^{12}$)(R$^{13}$) taken together form a monocyclic heterocyclyl or substituted heterocyclyl of 5 to 7 atoms containing 1, 2, or 3 additional nitrogen atoms or wherein
R$^{12}$ is hydrogen;
R$^{13}$ is alkyl of 1 to 4 carbons or

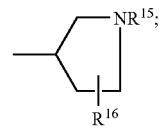

and
R$^{15}$ and R$^{16}$ are independently selected from hydrogen and methyl.

[4] In another preferred embodiment, the present invention provides a compound of [3] above including isomers, enantiomers, diastereomers, tautomers, pharmaceutically acceptable salts, prodrugs and solvates thereof wherein:
W, Y and X are each =N—;
V is —NH—, or —O—;
Z is —N(R$^1$)(R$^2$), —S-aryl, or S-substituted aryl;
R$^1$ is hydrogen or methyl;
R$^2$ is alkyl of 1 to 8 carbons;
R$^7$ is hydrogen, methyl, methoxy, Cl, Br, or F;
R$^8$ is hydrogen;
R$^9$ is —C(O)R$^{10}$, heterocyclyl or substituted heterocyclyl;
R$^{10}$ is —NH$_2$, —NH-alkyl, —NH-alkoxy, —NH-phenyl, or —NH—CH$_2$-phenyl wherein alkyl and alkoxy are of 1 to 6 carbons; and
R$^{11}$ is —N(R$^{12}$)(R$^{13}$) wherein N(R$^{12}$)(R$^{13}$) taken together form a monocyclic heterocyclyl or substituted heterocyclyl of 5 to 7 atoms containing 1, 2, or 3 additional nitrogen atoms.

[5] In another more preferred embodiment, the present invention provides a compound of [3] above including isomers, enantiomers, diastereomers, tautomers, pharmaceutically acceptable salts, prodrugs and solvates thereof wherein:
W, Y and X are each =N—;
V is —NH—, or —O—;
Z is —N(R$^1$)(R$^2$), —S-aryl, or S-substituted aryl;
R$^1$ is hydrogen or methyl;
R$^2$ is alkyl of 1 to 8 carbons;
R$^7$ is hydrogen, methyl, methoxy, Cl, Br, or F;
R$^8$ is hydrogen;
R$^9$ is —C(O)R$^{10}$, heterocyclyl or substituted heterocyclyl;

$R^{10}$ is —$NH_2$, —NH-alkyl, —NH-alkoxy, —NH-phenyl, or —NH—$CH_2$-phenyl wherein alkyl and alkoxy are of 1 o 6 carbons;
$R^{11}$ is

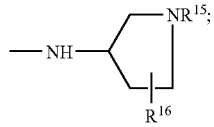

or —NH-alkyl wherein alkyl is of 1 to 4 carbons; and
$R^{15}$ and $R^{16}$ are independently selected from hydrogen and methyl.

[6] In another more preferred embodiment, the present invention provides a compound of [4] above including isomers, enantiomers, diastereomers, tautomers, pharmaceutically acceptable salts, prodrugs and solvates thereof wherein:
$R^{10}$ is —$NH_2$, —NH—$CH_3$, —NH—$C_2H_5$, —NH—$OCH_3$, or —NH—$OC_2H_5$.

[7] In another more preferred embodiment, the present invention provides a compound of [5] above including isomers, enantiomers, diastereomers, tautomers, pharmaceutically acceptable salts, prodrugs and solvates thereof wherein:
$R^{10}$ is —$NH_2$, —NH—$CH_3$, —NH—$C_2H_5$, —NH—$OCH_3$, or —NH—$OC_2H_5$.

[8] In yet another preferred embodiment, the present invention provides a compound of [3] above including isomers, enantiomers, diastereomers, tautomers, pharmaceutically acceptable salts, prodrugs and solvates thereof wherein:
two of W, Y and X are each =N— and the other is —CH=;
V is —NH—, or —O—;
$R^1$ is hydrogen or methyl;
$R^2$ is alkyl of 1 to 8 carbons;
$R^7$ is hydrogen, methyl, methoxy, Cl, Br, or F;
$R^8$ is hydrogen;
$R^9$ is —C(O)$R^{10}$, heterocyclyl or substituted heterocyclyl;
$R^{10}$ is —$NH_2$, —NH-alkyl, —NH-alkoxy, —NH-phenyl, or —NH—$CH_2$-phenyl wherein alkyl and alkoxy are of 1 to 6 carbons;
$R^{11}$ is —$N(R^{12})(R^{13})$ wherein $N(R^{12})(R^{13})$ taken together form a monocyclic heterocyclyl or substituted heterocyclyl of 5 to 7 atoms containing 1, 2, or 3 additional nitrogen atoms.

[9] In yet another more preferred embodiment, the present invention provides a compound of [8] above including isomers, enantiomers, diastereomers, tautomers, pharmaceutically acceptable salts, prodrugs and solvates thereof wherein:
$R^{10}$ is —$NH_2$, —NH—$CH_3$, —NH—$C_2H_5$, —NH—$OCH_3$, or —NH—$OC_2H_5$.

[10] In yet another preferred embodiment, the present invention provides a compound of [3] above including isomers, enantiomers, diastereomers, tautomers, pharmaceutically acceptable salts, prodrugs and solvates thereof wherein:
two of W, Y and X are each =N— and the other is —CH=;
V is —NH—, or —O—;
$R^1$ is hydrogen or methyl;
$R^2$ is alkyl of 1 to 8 carbons;
$R^7$ is hydrogen, methyl, methoxy, Cl, Br, or F;
$R^8$ is hydrogen;
$R^9$ is —C(O)$R^{10}$, heterocyclyl or substituted heterocyclyl;
$R^{10}$ is —$NH_2$, —NH-alkyl, —NH-alkoxy, —NH-phenyl, or —NH—$CH_2$-phenyl wherein alkyl and alkoxy are of 1 to 6 carbons;
$R^{11}$ is

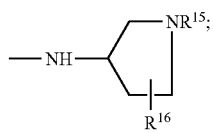

or —NH-alkyl wherein alkyl is of 1 to 4 carbons; and
$R^{15}$ and $R^{16}$ are independently selected from hydrogen and methyl.

[11] In yet another preferred embodiment, the present invention provides a compound of [10] above including isomers, enantiomers, diastereomers, tautomers, pharmaceutically acceptable salts, prodrugs and solvates thereof wherein:
$R^{10}$ is —$NH_2$, —NH—$CH_3$, —NH—$C_2H_5$, —NH—$OCH_3$, or —NH—$OC_2H_5$.

[12] In yet another preferred embodiment, the present invention provides a compound of [4] above including isomers, enantiomers, diastereomers, tautomers, pharmaceutically acceptable salts, prodrugs and solvates thereof wherein:
$R^{11}$ is

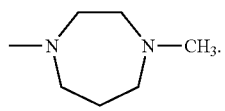

[13] In yet another preferred embodiment, the present invention provides a compound of [8] above including isomers, enantiomers, diastereomers, tautomers, pharmaceutically acceptable salts, prodrugs and solvates thereof wherein:
$R^{11}$ is

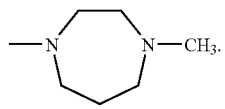

[14] In a second preferred embodiment, the present invention provides a pharmaceutical composition comprising as an active ingredient, the compound of Formula I, or a prodrug or salt thereof and a pharmaceutically acceptable carrier.

[15] In a more preferred embodiment, the present invention provides a pharmaceutical composition according, further comprising one or more additional active ingredients.

[16] In a more preferred embodiment, the present invention provides a pharmaceutical composition wherein said additional active ingredient is an anti-inflammatory compound or an immunosuppressive agent.

[17] In a preferred embodiment, the present invention provides a pharmaceutical composition wherein said additional active ingredient is chosen from a steroid and an NSAID.

[18] In a third preferred embodiment, the present invention provides a method of inhibiting TNF-α expression in a mammal, the method comprising administering to the mammal an effective amount of a composition according to [14] above.

[19] In a more preferred embodiment, the present invention provides a method of treating TNF-α mediated disorder, the method comprising administering to a mammal in need of such treatment, an effective amount of a composition according to [14] above.

[20] In a more preferred embodiment, the present invention provides a method of treating TNF-α mediated disorder, wherein the TNF-α mediated disorder is an inflammatory disorder.

[21] In a even more preferred embodiment, the present invention provides a method of treating TNF-α mediated disorder, wherein the TNF-α mediated disorder is chosen from bone resorption, graft vs. host reaction, atherosclerosis, arthritis, osteoarthritis, rheumatoid arthritis, gout, psoriasis, topical inflammatory disease states, adult respiratory distress syndrome, asthma, chronic pulmonary inflammatory disease, cardiac reperfusion injury, renal reperfusion injury, thrombus, glomerulonephritis, Chron's disease, ulcerative colitis, inflammatory bowel disease, multiple sclerosis, endotoxin shock, osteoporosis, Alzheimer's disease, congestive heart failure and cachexia.

[22] In a more preferred embodiment, the present invention provides a method of treating TNF-α mediated disorder wherein the pharmaceutical composition of the invention is administered with one or more additional anti-inflammatory or immunosuppressive agents as a single dose form or as separate dosage forms.

[23] In an even more preferred embodiment, the present invention provides a method of treating a condition associated with TNF-α expression in a mammal, the method comprising administering to a mammal in need of such treatment, an effective amount of a composition according to [14] above.

[24] In an even more preferred embodiment, the present invention provides a method of treating a condition associated with TNF-α expression in a mammal wherein the condition associated with TNF-α expression is an inflammatory disorder.

[25] In a even more preferred embodiment, the present invention provides a method of treating a condition associated with TNF-α expression in a mammal wherein the condition associated with TNF-α expression is chosen from bone resorption, graft vs. host reaction, atherosclerosis, arthritis, osteoarthritis, rheumatoid arthritis, gout, psoriasis, topical inflammatory disease states, adult respiratory distress syndrome, asthma, chronic pulmonary inflammatory disease, cardiac reperfusion injury, renal reperfusion injury, thrombus, glomerulonephritis, Chron's disease, ulcerative colitis, inflammatory bowel disease, multiple sclerosis, endotoxin shock, osteoporosis, Alzheimer's disease, congestive heart failure and cachexia.

[26] In a more preferred embodiment, the present invention provides a method of treating a condition associated with TNF-α expression in a mammal wherein the pharmaceutical composition of the invention is administered with one or more additional anti-inflammatory or immunosuppressive agents as a single dose form or as separate dosage forms.

[27] In yet another more preferred embodiment, the present invention provides a method of treating a condition associated with p38 kinase activity in a mammal, the method comprising administering to a mammal in need of such treatment, an effective amount of a composition according to [14] above.

[28] In yet another more preferred embodiment, the present invention provides a method of treating a condition associated with p38 kinase activity in a mammal, wherein the condition associated with p38 kinase activity is an inflammatory disorder.

[29] In yet another more preferred embodiment, the present invention provides a method of treating a condition associated with p38 kinase activity in a mammal, wherein the condition associated with p38 kinase activity is chosen from bone resorption, graft vs. host reaction, atherosclerosis, arthritis, osteoarthritis, rheumatoid arthritis, gout, psoriasis, topical inflammatory disease states, adult respiratory distress syndrome, asthma, chronic pulmonary inflammatory disease, cardiac reperfusion injury, renal reperfusion injury, thrombus, glomerulonephritis, Chron's disease, ulcerative colitis, inflammatory bowel disease, multiple sclerosis, endotoxin shock, osteoporosis, Alzheimer's disease, congestive heart failure and cachexia

[30] In yet another more preferred embodiment, the present invention provides a method of treating a condition p38 kinase activity in a mammal wherein the pharmaceutical composition of the invention is administered with one or more additional anti-inflammatory or immunosuppressive agents as a single dose form or as separate dosage forms.

[31] In a further preferred embodiment, the present invention provides a compound of Formula I including isomers, enantiomers, diastereomers, tautomers, pharmaceutically acceptable salts, prodrugs and solvates thereof wherein:

two or more of W, X and Y are —N=.

[32] In a further more preferred embodiment, the present invention provides a compound of [31] above including isomers, enantiomers, diastereomers, tautomers, pharmaceutically acceptable salts, prodrugs and solvates thereof wherein:

V is —NH— or —O—;

$R^1$ is hydrogen or methyl;

$R^2$ is alkyl of 1 to 8 carbons;

$R^6$ is

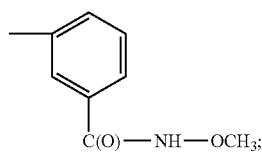

$R^{11}$ is —N($R^{12}$)($R^{13}$) wherein N($R^{12}$)($R^{13}$) taken together form a monocyclic heteroocyclyl or substituted heterocyclyl of 5 to 7 atoms containing 1, 2 or 3 additional nitrogen atoms, —NH-alkyl wherein alkyl is of 1 to 4 carbons, or

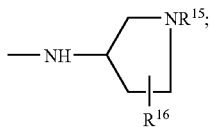

and $R^{15}$ and $R^{16}$ are independently hydrogen or methyl.

[33] In a further more preferred embodiment, the present invention provides a compound of [31] above including isomers, enantiomers, diastereomers, tautomers, pharmaceutically acceptable salts, prodrugs and solvates thereof wherein:

V is —NH— or —O—;
$R^1$ is hydrogen or methyl;
$R^2$ is alkyl of 1 to 8 carbons;
$R^6$ is

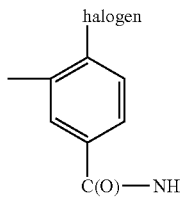

$R^{11}$ is —N($R^{12}$)($R^{13}$) wherein N($R^{12}$)($R^{13}$) taken together form a monocyclic heteroocyclyl or substituted heterocyclyl of 5 to 7 atoms containing 1, 2 or 3 additional nitrogen atoms, —NH-alkyl wherein alkyl is of 1 to 4 carbons, or

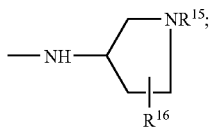

and $R^{15}$ and $R^{16}$ are independently hydrogen or methyl.

[34] In a further preferred embodiment, the present invention provides a compound of [31] above including isomers, enantiomers, diastereomers, tautomers, pharmaceutically acceptable salts, prodrugs and solvates thereof wherein:

V is —NH— or —O—;
$R^1$ is hydrogen or methyl;
$R^2$ is alkyl of 1 to 8 carbons;
$R^6$ is

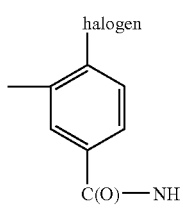

$R^{11}$ is —N($R^{12}$)($R^{13}$) wherein N($R^{12}$)($R^{13}$) taken together form a monocyclic heteroocyclyl or substituted heterocyclyl of 5 to 7 atoms containing 1, 2 or 3 additional nitrogen atoms, —NH-alkyl wherein alkyl is of 1 to 4 carbons, or

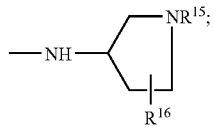

and $R^{15}$ and $R^{16}$ are independently hydrogen or methyl.

[35] In a further more preferred embodiment, the present invention provides a compound of [31] above including isomers, enantiomers, diastereomers, tautomers, pharmaceutically acceptable salts, prodrugs and solvates thereof wherein:

V is —NH— or —O—;
$R^1$ is hydrogen or methyl;
$R^2$ is alkyl of 1 to 8 carbons;
$R^6$ is

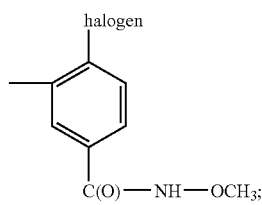

$R^{11}$ is —N($R^{12}$)($R^{13}$) wherein N($R^{12}$)($R^{13}$) taken together form a monocyclic heteroocyclyl or substituted heterocyclyl of 5 to 7 atoms containing 1, 2 or 3 additional nitrogen atoms, —NH-alkyl wherein alkyl is of 1 to 4 carbons, or

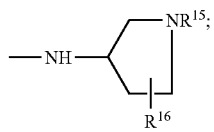

and $R^{15}$ and $R^{16}$ are independently hydrogen or methyl.

[36] In a further more preferred embodiment, the present invention provides a compound of [31] above including isomers, enantiomers, diastereomers, tautomers, pharmaceutically acceptable salts, prodrugs and solvates thereof herein:

V is —NH— or —O—;
$R^1$ is hydrogen or methyl;
$R^2$ is alkyl of 1 to 8 carbons;

$R^6$ is

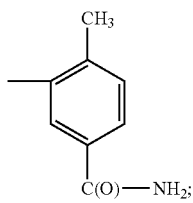

$R^{11}$ is —N($R^{12}$)($R^{13}$) wherein N($R^{12}$)($R^{13}$) taken together form a monocyclic heteroocyclyl or substituted heterocyclyl of 5 to 7 atoms containing 1, 2 or 3 additional nitrogen atoms, —NH-alkyl wherein alkyl is of 1 to 4 carbons, or

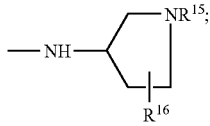

and $R^{15}$ and $R^{16}$ are independently hydrogen or methyl.

[37] In a further more preferred embodiment, the present invention provides a compound of [31] above including isomers, enantiomers, diastereomers, tautomers, pharmaceutically acceptable salts, prodrugs and solvates thereof wherein:
V is —NH— or —O—;
$R^1$ is hydrogen or methyl;
$R^2$ is alkyl of 1 to 8 carbons;
$R^6$ is

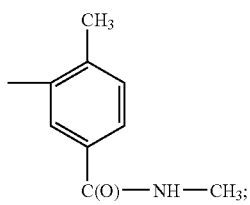

$R^{11}$ is —N($R^{12}$)($R^{13}$) wherein N($R^{12}$)($R^{13}$) taken together form a monocyclic heteroocyclyl or substituted heterocyclyl of 5 to 7 atoms containing 1, 2 or 3 additional nitrogen atoms, —NH-alkyl wherein alkyl is of 1 to 4 carbons, or

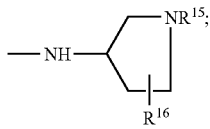

and $R^{15}$ and $R^{16}$ are independently hydrogen or methyl.

[38] In a further more preferred embodiment, the present invention provides a compound of [31] above including isomers, enantiomers, diastereomers, tautomers, pharmaceutically acceptable salts, prodrugs and solvates thereof wherein:
V is —NH— or —O—;
$R^1$ is hydrogen or methyl;
$R^2$ is alkyl of 1 to 8 carbons;
$R^6$ is

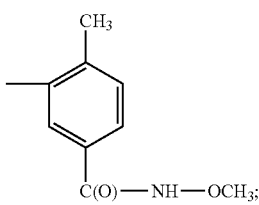

$R^{11}$ is —N($R^{12}$)($R^{13}$) wherein N($R^{12}$)($R^{13}$) taken together form a monocyclic heteroocyclyl or substituted heterocyclyl of 5 to 7 atoms containing 1, 2 or 3 additional nitrogen atoms, —NH-alkyl wherein alkyl is of 1 to 4 carbons, or

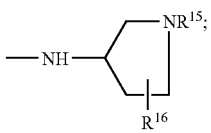

and $R^{15}$ and $R^{16}$ are independently hydrogen or methyl.

[39] In a further more preferred embodiment, the present invention provides a compound of [31] above including isomers, enantiomers, diastereomers, tautomers, pharmaceutically acceptable salts, prodrugs and solvates thereof wherein:
V is —NH— or —O—;
$R^1$ is hydrogen or methyl;
$R^2$ is alkyl of 1 to 8 carbons;
$R^6$ is

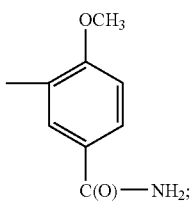

$R^{11}$ is —N($R^{12}$)($R^{13}$) wherein N($R^{12}$)($R^{13}$) taken together form a monocyclic heteroocyclyl or substituted heterocyclyl of 5 to 7 atoms containing 1, 2 or 3 additional nitrogen atoms, —NH-alkyl wherein alkyl is of 1 to 4 carbons, or

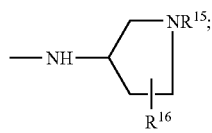

and

R$^{15}$ and R$^{16}$ are independently hydrogen or methyl.

[40] In a further more preferred embodiment, the present invention provides a compound of [31] above including isomers, enantiomers, diastereomers, tautomers, pharmaceutically acceptable salts, prodrugs and solvates thereof wherein:
V is —NH— or —O—;
R$^1$ is hydrogen or methyl;
R$^2$ is alkyl of 1 to 8 carbons;
R$^6$ is

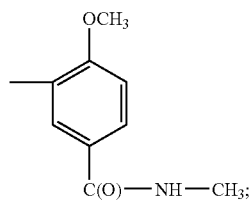

R$^{11}$ is —N(R$^{12}$)(R$^{13}$) wherein N(R$^{12}$)(R$^{13}$) taken together form a monocyclic heteroocyclyl or substituted heterocyclyl of 5 to 7 atoms containing 1, 2 or 3 additional nitrogen atoms, —NH-alkyl wherein alkyl is of 1 to 4 carbons, or

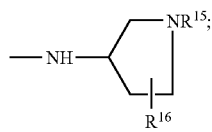

and

R$^{15}$ and R$^{16}$ are independently hydrogen or methyl.

[41] In a further more preferred embodiment, the present invention provides a compound of [31] above including isomers, enantiomers, diastereomers, tautomers, pharmaceutically acceptable salts, prodrugs and solvates thereof wherein:
V is —NH— or —O—;
R$^1$ is hydrogen or methyl;
R$^2$ is alkyl of 1 to 8 carbons;
R$^6$ is

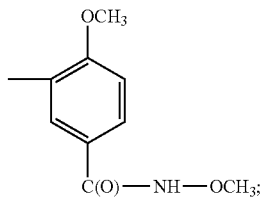

R$^{11}$ is —N(R$^{12}$)(R$^{13}$) wherein N(R$^{12}$)(R$^{13}$) taken together form a monocyclic heteroocyclyl or substituted heterocyclyl of 5 to 7 atoms containing 1, 2 or 3 additional nitrogen atoms, —NH-alkyl wherein alkyl is of 1 to 4 carbons, or

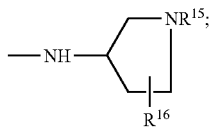

and

R$^{15}$ and R$^{16}$ are independently hydrogen or methyl.

[42] In a further more preferred embodiment, the present invention provides a compound of [31] above including isomers, enantiomers, diastereomers, tautomers, pharmaceutically acceptable salts, prodrugs and solvates thereof wherein:
V is —NH— or —O—;
Z is —N(R$^1$)(R$^2$);
R$^1$ is hydrogen or methyl;
R$^2$ is alkyl of 1 to 8 carbons;
R$^6$ is

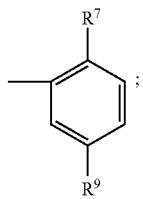

R$^7$ is hydrogen, methyl, methoxy, halogen or cyano;
R$^9$ is chosen from unsubstituted or substituted triazole, oxadiazole, imidazole, thiazole or benzimidazole;
R$^{11}$ is —N(R$^{12}$)(R$^{13}$) wherein N(R$^{12}$)(R$^{13}$) taken together form a monocyclic heteroocyclyl or substituted heterocyclyl of 5 to 7 atoms containing 1, 2 or 3 additional nitrogen atoms, —NH-alkyl wherein alkyl is of 1 to 4 carbons, or

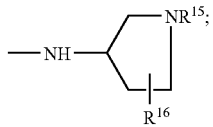

and

R[15] and R[16] are independently hydrogen or methyl.

[43] In a further more preferred embodiment, the present invention provides a compound of [42] above including isomers, enantiomers, diastereomers, tautomers, pharmaceutically acceptable salts, prodrugs and solvates thereof wherein:
R[9] is substituted or unsubstituted 1,2,4-triazole.

[44] In a further more preferred embodiment, the present invention provides a compound of [42] above including isomers, enantiomers, diastereomers, tautomers, pharmaceutically acceptable salts, prodrugs and solvates thereof wherein:
R[9] is substituted or unsubstituted 1,2,4-triazole connected via a C3 or C5 position.

[45] In a further more preferred embodiment, the present invention provides a compound of [42] above including isomers, enantiomers, diastereomers, tautomers, pharmaceutically acceptable salts, prodrugs and solvates thereof wherein:
R[9] is substituted or unsubstituted 1,2,4-triazole connected via an N4, N1 or N2 position.

[46] In a further more preferred embodiment, the present invention provides a compound of [42] above including isomers, enantiomers, diastereomers, tautomers, pharmaceutically acceptable salts, prodrugs and solvates thereof wherein:
R[9] is substituted or unsubstituted thiazole connected via a C2 position.

[47] In a further more preferred embodiment, the present invention provides a compound of [42] above including isomers, enantiomers, diastereomers, tautomers, pharmaceutically acceptable salts, prodrugs and solvates thereof wherein:
R[9] is substituted or unsubstituted thiazole connected via a C4 position.

[48] In a further more preferred embodiment, the present invention provides a compound of [42] above including isomers, enantiomers, diastereomers, tautomers, pharmaceutically acceptable salts, prodrugs and solvates thereof wherein:
R[9] is substituted or unsubstituted thiazole connected via a C5 position.

[49] In a further more preferred embodiment, the present invention provides a compound of [42] above including isomers, enantiomers, diastereomers, tautomers, pharmaceutically acceptable salts, prodrugs and solvates thereof wherein:
R[9] is substituted or unsubstituted 1,3,4-oxdiazole connected via a 2 or 5 position.

[50] In a further more preferred embodiment, the present invention provides a compound of [42] above including isomers, enantiomers, diastereomers, tautomers, pharmaceutically acceptable salts, prodrugs and solvates thereof wherein:
R[9] is substituted or unsubstituted imidazole connected via a C2, C5, N1 or N3 position.

[51] In a fourth embodiment, the present invention provides a compound including isomers, enantiomers, diastereomers, pharmaceutically acceptable salts, prodrugs and solvates selected from:

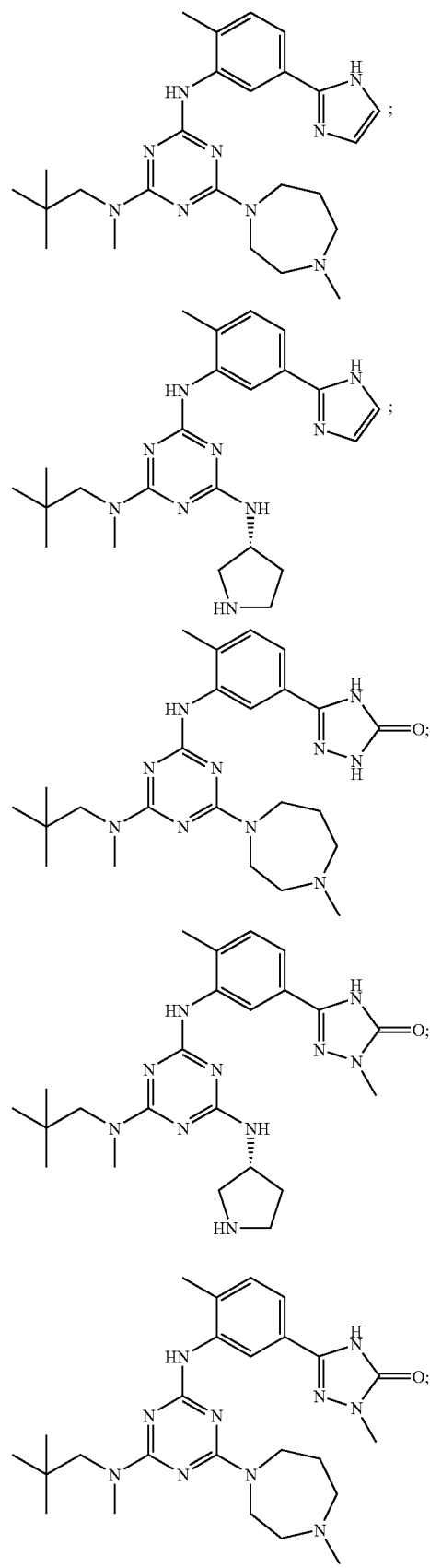

-continued

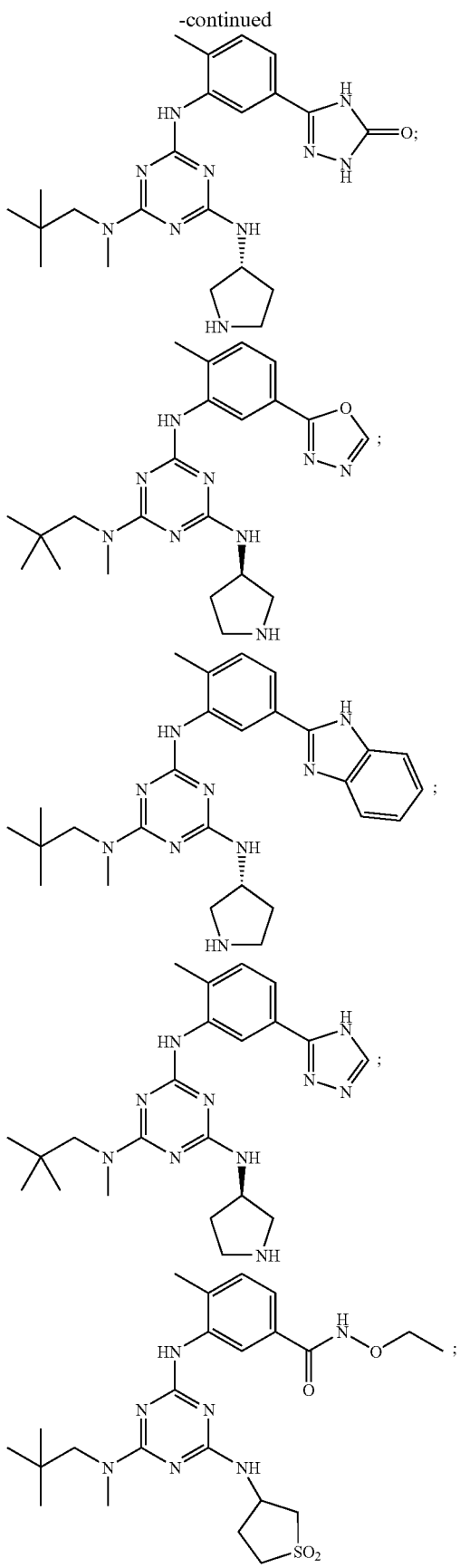

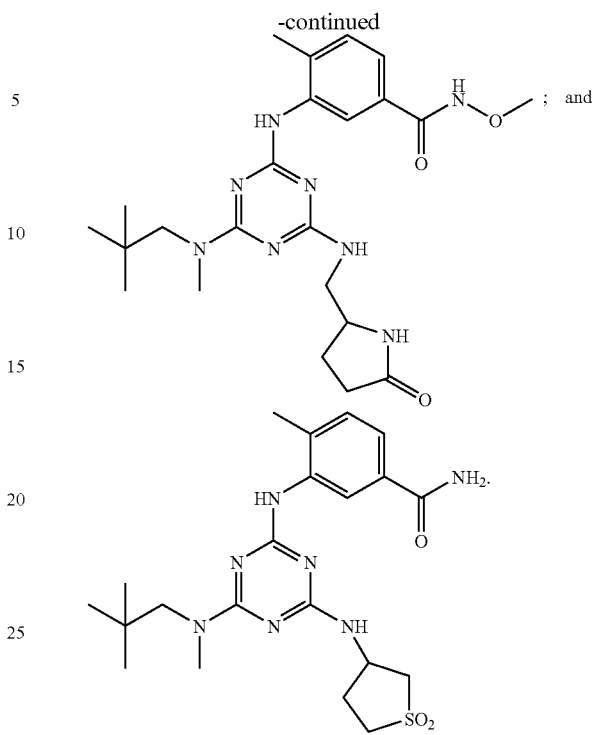

Abbreviations & Definitions

The following terms and abbreviations retain the indicated meaning throughout this disclosure.
ATP=adenosine triphosphate
cDNA=complementary DNA
DCE=dichloroethylene
DCM=dichloromethane=methylene chloride=$CH_2Cl_2$
DIC=diisopropylcarbodiimide
DIEA=N,N-diisopropylethylamine
DMF=N,N-dimethylformamide
DMSO=dimethyl sulfoxide
DTT=dithiothreitol
EDTA=ethylenediaminetetraacetic acid
EIA=enzyme immunoassay
ELISA=enzyme-linked immunosorbent assay
Fmoc=9-fluorenylmethoxycarbonyl
GST=glutathione S-transferase
HOBt=1-hydroxybenzotriazole
LPS=lipopolysaccharide
MBP=myelin basic protein
MES=2-(N-morpholino)ethanesulfonic acid
mRNA=messenger RNA
PCR=polymerase chain reaction
$Pr_2NEt$=dipropylethylamine
i-$Pr_2NEt$=diisopropylethylamine
RPMI=Roswell Park Memorial Institute
TBS=t-butyldimethylsilyl
TFA=trifluoroacetic acid
THF=tetrahydrofuran AAlkyl≅ is intended to include linear or branched hydrocarbon structures and combinations thereof of 1 to 20 carbons. ALower alkyl≅ means alkyl groups of from 1 to about 10, preferably from 1 to about 8, and more preferably, from 1 to about 6 carbon atoms. Examples of such radicals include methyl, ethyl, n-propyl, isopropyl, n-butyl, isobutyl, s-butyl, t-butyl, pentyl, iso-amyl, hexyl, octyl and the like.

"Aryl" means an aromatic hydrocarbon radical of 6 to about 16 carbon atoms, preferably of 6 to about 12 carbon atoms, and more preferably of 6 to about 10 carbon atoms. Examples of aryl groups are phenyl, which is preferred, 1-naphthyl and 2-naphthyl.

"Cycloalkyl" refers to saturated hydrocarbon ring structures of from 3 to 12 carbon atoms, and preferably from 3 to 6 carbon atoms. Examples include cyclopropyl, cyclobutyl, cyclopentyl, cyclohexyl, norbornyl, adamantyl, and the like. "Lower cycloalkyl" refers to cycloalkyl of 3 to 6 carbons.

"Heterocyclyl" refers to saturated, partially saturated or unsaturated monocyclic structures of from 3 to 8 atoms, preferably 5 or 6 atoms, and bicyclic structures of 9 or 10 atoms containing one or more carbon atoms and from 1 to 4 heteroatoms chosen from O, N, and S. The point of attachment of the heterocyclyl structure is at an available carbon or nitrogen atom. Examples include: imidazole, pyridine, indole, thiophene, benzopyranone, thiazole, furan, benzimidazole, quinoline, isoquinoline, quinoxaline, pyrimidine, pyrazine, tetrazole, pyrazole, pyrrolyl, pyridinyl, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, imidazolinyl, imidazolidinyl, pyrazolinyl, pyrazolidinyl, isoxazolyl, isothiazolyl, 1,2,3-oxadiazolyl, 1,2,3-triazolyl, 1,2,4-triazolyl, 1,3,4-thiadiazolyl, 2H-pyranyl, 4H-pyranyl, piperidinyl, 1,4-dithianyl, thiomorpholinyl, pyrazinyl, piperazinyl, 1,3,5-triazinyl, 1,2,5-trithianyl, benzo(b)thiophenyl, benzimidazolyl, quinolinyl, and the like.

The following numbering system is used to indicate points of attachment on heterocycles in the compounds of the invention.

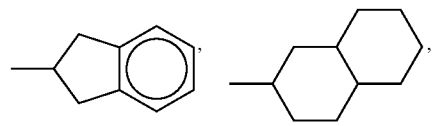

"Alkoxy" means a straight, branched or cyclic hydrocarbon configuration and combinations thereof, including from 1 to 20 carbon atoms, preferably from 1 to 8 carbon atoms, more preferably from 1 to about 4 carbon atoms, and an oxygen atom at the point of attachment. Suitable alkoxy groups include methoxy, ethoxy, n-propoxy, isopropoxy, n-butoxy, iso-butoxy, s-butoxy, t-butoxy, cyclopropyloxy, cyclohexyloxy, and the like. "Lower alkoxy" refers to alkoxy groups having from 1 to 4 carbon atoms. Similarly, "alkylthio" refers to such groups having a sufur atom at the point of attachment.

"Alkenyl" refers to an unsaturated acyclic hydrocarbon radical in so much as it contains at least one double bond. "Lower alkenyl" refers to such radicals containing from about 2 to about 10 carbon atoms, preferably from about 2 to about 8 carbon atoms and more preferably 2 to about 6 carbon atoms. Examples of suitable alkenyl radicals include propenyl, buten-1-yl, isobutenyl, penten-1-yl, 2-methylbuten-1-yl, 3-methylbuten-1-yl, hexen-1-yl, hepten-1-yl, and octen-1-yl, and the like.

"Alkynyl" refers to an unsaturated acyclic hydrocarbon radical containing at least one triple bond. Examples include ethynyl, propynyl, and the like.

"Substituted alkyl" means an alkyl wherein one or more hydrogens, preferably one, two, or three hydrogens, attached to an aliphotic carbon are replaced with a substituent such as —N($R^{31}$)($R^{32}$), alkoxy, alkylthio, halogen, cyano, carboxyl, hydroxyl, —$SO_2$-alkyl, —$CO_2$-alkyl, —C(O)-alkyl, nitro, cycloalkyl, substituted cycloalkyl, aryl, substituted aryl, heterocyclyl, substituted heterocyclyl, —C(O)—N($R^{31}$)($R^{32}$), or —NH—C(O)-alkyl. Examples of such substituent groups include methoxy, ethoxy, propoxy, amino, methylamino, dimethylamino, phenyl naphthyl, chlorine, fluorine, and the like.

"Substituted cycloalkyl" means a cycloalkyl wherein one or more hydrogens, preferably one, two or three hydrogens, attached to a ring carbon are replaced with a substituent such as alkyl, substituted alkyl, —N($R^{31}$)($R^{32}$), alkoxy, alkylthio, aryl, substituted aryl, halogen, cyano, carboxyl, hydroxyl, nitro, —$SO_2$-alkyl, —$CO_2$-alkyl, —C(O)-alkyl, —C(O)—N($R^{31}$)$R^{32}$), or —NH—C(O)-alkyl. Examples of such groups include methyl, isopropyl, methoxy, ethoxy, porpoxy, amino, methylamino, dimethylamino, phenyl, chlorine, fluorine and the like. Also included within this definition are cycloalkyl rings having a fused aryl, preferably phenyl, or cycloalkyl such as

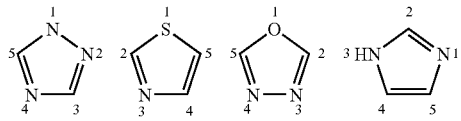

and the like.

"Substituted aryl" means an aryl wherein one or more hydrogens, preferably one, two or three hydrogens, attached to an aromatic carbon are replaced with a substituent such as alkyl, substituted alkyl, N($R^{31}$)($R^{32}$), alkoxy, alkylthio, aryl, substituted aryl, halogen, cyano, nitro, carboxyl, hydroxyl, —$SO_2$-alkyl, —$CO_2$-alkyl, —C(O)-alkyl, —C(O)—N($R^{31}$)($R^{32}$), or —NH—C(O)-alkyl. Examples of such substituents include methyl, isopropyl, methoxy, ethoxy, propoxy, amino, methylamino, dimethylamino, phenyl, chlorine, fluorine, —$CO_2CH_3$, —C(O)—$NH_2$, and the like.

"Substituted heterocyclyl" means a heterocyclyl substituted at one or more available carbon or nitrogen atoms, preferably at one or two carbon and/or nitrogen atoms, with a substituent such as alkyl, substituted alkyl, —N($R^{31}$)($R^{32}$), alkoxy, alkylthio, aryl, substituted aryl, halogen, cyano, nitro, oxo, carboxyl, hydroxyl, —$SO_2$-alkyl, —$CO_2$-alkyl, —C(O)-alkyl, —C(O)—N($R^{31}$)($R^{32}$), or —NH—C(O)-alkyl. Examples of such groups include methyl isopropyl, methoxy, ethoxy, propoxy, amino, methylamino, dimethylamino, phenyl, chlorine, fluorine and the like.

"Halogen" is intended to include for example, F, Cl, Br and I.

The term "prodrug" refers to a chemical compound that is converted to an active agent by metabolic processes in vivo. [See, e.g., N. Boder and J. J. Kaminski, *Ann. Rep. Med. Chem.* 22:303 (1987) and H. Bundgarrd, *Adv. Drug Delivery Rev.,* 3:39 (1989)]. With regard to the present invention, a prodrug of a compound of Formula I is intended to mean any compound that is converted to a compound of Formula I by metabolic processes in vivo. The use of prodrugs of compounds of Formula I in any of the methods described herein is contemplated and is intended to be within the scope of the invention.

Terminology related to "protected," "protecting" and/or "deprotecting" functionalities is used throughout this application. Such terminology is well understood by persons of skill in the art and is used in the context of processes which involve sequential treatment with a series of reagents. In this context, a protecting group refers to a group which is used to mask a functionality during a process step in which it would otherwise react, but in which reaction is undesirable. The protecting group prevents reaction at that step, but may be subsequently removed to expose the original functionality. The removal or Adeprotection≅ occurs after the completion of the reaction or reactions in which the functionality would interfere. Thus, when a sequence of reagents is specified, as it is in the processes of the invention, the person of ordinary skill can readily envision those groups that would be suitable as Aprotecting groups≅ for the functionalities involved.

In the case of the present invention, the typical functionalities that must be protected are amines. Suitable groups for that purpose are discussed in standard textbooks in the field of chemistry, such as *Protective Groups in Organic Synthesis* by T. W. Greene [John Wiley & Sons, New York, 1991], which is incorporated herein by reference. Particular attention is drawn to the chapter entitled AProtection for the Amino Group≅ (pages 309-405). Preferred protecting groups include BOC and Fmoc. Exemplary methods for protecting and deprotecting with these groups are found in Greene and Wuts on pages 318 and 327.

The materials upon which the syntheses described herein are performed are referred to as solid supports, beads, and resins. These terms are intended to include: (a) beads, pellets, disks, fibers, gels, or particles such as cellulose beads, pore-glass beads, silica gels, polystyrene beads optionally cross-linked with divinylbenzene and optionally grafted with poly-ethylene glycol, poly-acrylamide beads, latex beads, dimethylacrylamide beads optionally cross-linked with N,N=-bis-acryloyl ethylene diamine, glass particles coated with hydrophobic polymer, etc., i.e., material having a rigid or semi-rigid surface; and (b) soluble supports such as polyethylene glycol or low molecular weight, non-cross-linked polystyrene. The solid supports may, and usually do, have functional groups such as amino, hydroxy, carboxyl, or halo groups; where amino groups are the most common.

TentaGelθ NH$_2$ (Rapp Polymere, Tubingen, Germany) is a preferred amine functionalized polyethylene glycol-grafted polystyrene resin. TentaGel$^θ$-S-PHB resin has a para-hydroxy benzyl linker which can be cleaved by the use of 90% trifluoroacetic acid in DCM. Techniques for functionalizing the surface of solid phases are well known in the art. Attachment of lysine to the amino groups on a bead (to increase the number of available sites) and subsequent attachment of linkers as well as further steps in a typical combinatorial synthesis are described, for example, in PCT application WO95/30642, the disclosure of which is incorporated herein by reference. In the synthesis described in WO95/30642, the linker is a photolytically cleavable linker, but the general principles of the use of a linker are well illustrated.

Optical Isomers—Diastereomers—Geometric Isomers

Some of the compounds described herein contain one or more asymmetric centers and may thus give rise to enantiomers, diastereomers, and other stereoisometric forms which may be defined in terms of absolute stereochemistry as (R)- or (S)-, or as (D)- or (L)- for amino acids. The present invention is meant to include all such possible diastereomers as well as their racemic and optically pure forms. Optically active (R)- and (S)-, or (D)- and (L)-isomers may be prepared using chiral synthons or chiral reagents, or optically resolved using conventional techniques. When the compounds described herein contain olefinic double bonds or other centers of geometric asymmetry, and unless specified otherwise, it is intended to include both (E)- and (Z)-geometric isomers. Likewise, all tautomeric forms are intended to be included.

Compounds of the invention which incorporate chiral diamines may be resolved into pairs of enantiomers by known techniques. Where pure enantiomers of starting materials are not commercially available, they may be obtained by classic resolution, which may employ, for example, fractional crystallization of diastereomeric salts. Compounds of the invention may have more than one chiral center, for example wherein reductive amination of a homochiral intermediate leads to a mixture of diastereomers. Racemic intermediates and compounds of the invention may also be resolved by chromatographic separation, such as for example, HPLC using a column loaded with a homochiral support, to yield pure isomeric compounds.

The configuration of any carbon-carbon double bond appearing herein is selected for convenience only and is not intended to designate a particular configuration; thus a carbon-carbon double bond depicted arbitrarily herein as trans may be cis, trans, or a mixture of the two in any proportion.

In view of the above definitions, other chemical terms used throughout this application can be easily understood by those of skill in the art. Terms may be used alone or in any combination thereof. The preferred and more preferred chain lengths of the radicals apply to all such combinations.

Utility

The compounds of the present invention have demonstrated utility as selective inhibitors of inappropriate p38 kinase activity, and in particular, isoforms p38α and p38β. As such, compounds of the present invention have utility in the treatment of conditions associated with inappropriate p38 kinase activity. Such conditions include diseases in which cytokine levels are modulated as a consequence of intracellular signaling via p38, and in particular, diseases that are associated with an overproduction of such cytokines as Il-1, Il-4, IL-8, and in particular, TNF-α.

As inhibitors of p-38 kinase activity, compounds of the present invention are useful in the treatment and prevention of p-38 mediated conditions including, but not limited to, inflammatory diseases, autoimmune diseases, destructive bone disorders, proliferative disorders, angiogenic disorders, infectious diseases, neurodegenerative diseases, viral diseases, allergies, myocardial ischemia, reperfusion/ischemia in stroke, heart attacks, organ hypoxia, vascular hyperplasia, cardiac hypertrophy, thrombin-induced platelet aggregation, and conditions associated with prostaglandin endoperoxidase synthase-2.

Inflammatory diseases which may be treated or prevented include, but are not limited to, acute pancreatitis, chronic pancreatitis, asthma, allergies and adult respiratory distress syndrome.

Autoimmune diseases which may be treated or prevented include, but are not limited to, glomerulonephritis, rheumatoid arthritis, systemic lupus erythematosis, scleroderma, chronic thyroiditis, Grave=s disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn=s disease, psoriasis, or graft vs. host disease.

Destructive bone disorders which may be treated or prevented include, but are not limited to, osteoporosis, osteoarthritis and multiple myeloma-related bone disorder.

Proliferative diseases which may be treated or prevented include, but are not limited to, acute myelogenous leukemia, chronic myelogenous leukemia, metastatic melanoma, Kaposi=s sarcoma, and multiple myeloma.

Infectious diseases which may be treated or prevented include, but are not limited to, sepsis, septic shock, and Shigellosis.

Neurodegenerative diseases which may be treated or prevented by the compounds of this invention include, but are not limited to, Alzheimer=s disease, Parkinson=s disease, cerebral ischemias or neurodegenerative disease caused by traumatic injury.

Angiogenic disorders which may be treated or prevented include solid tumors, ocular neovasculization, infantile haemangiomas.

Viral diseases which may be treated or prevented include, but are not limited to, acute hepatitis infection (including hepatitis A, hepatitis B and hepatitis C), HIV infection and CMV retinitis.

In addition, p38 inhibitors of this invention also exhibit inhibition of the expression of inducible pro-inflammatory proteins such as prostaglandin endoperoxide synthase-2 (PGHS-2), also referred to as cyclooxygenase-2 (COX-2). Accordingly, additional p38 mediated conditions include edema, analgesia, fever and pain, such as neuromuscular pain, headache, pain caused by cancer, dental pain and arthritis pain.

As a result of their p38 inhibitory activity, compounds of the present invention have utility in the treatment and prevention of diseases associated with cytokine production. For example, compounds of the present invention are useful in the treatment and prevention of:

Il-1 mediated diseases such as, for example, rheumatoid arthritis, osteoarthritis, stroke, endotoxemia and/or toxic shock syndrome, inflammatory reaction induced by endotoxin, inflammatory bowel disease, tuberculosis, atherosclerosis, muscle degeneration, cachexia, psoriatic arthritis, Reiter=s syndrome, gout, traumatic arthritis, rubella arthritis, acute synovitis, diabetes, pancreatic β-cell disease and Alzheimer=s disease;

IL-8 mediated diseases or conditions such as, for example, those characterized by massive neutrophil infiltration, such as psoriasis, inflammatory bowel disease, asthma, cardiac and renal reperfusion injury, adult respiratory distress syndrome, thrombosis and glomerulonephritis; and TNF-mediated diseases or conditions such as rheumatoid arthritis, rheumatoid spondylitis, osteoarthritis, gouty arthritis and other arthritic conditions, sepsis, septic shock syndrome, adult respiratory distress syndrome, cerebral malaria, chronic pulmonary inflammatory disease, silicosis, pulmonary sarcoisosis, bone resorption disease, reperfusion injury, graft vs. host reaction, allograft rejections, fever and myalgias due to infection, cachexia secondary to infection, AIDS, ARC or malignancy, meloid formation, scar tissue formation, Crohn=s disease, ulcerative colitis, pyresis, viral infections, such as HIV, CMV, influenza and herpes; and veterinary viral infections, such as lentivirus infections, including, but not limited to equine infectious anemia virus; or retro virus infections, including feline immunodeficiency virus, bovine immunodeficiency virus, or canine immunodeficiency virus.

The compounds of formula I including a pharmaceutically acceptable salt or hydrate thereof may be administered by any suitable route as described previously to treat the above mentioned diseases and conditions. The method of administration will, of course, vary depending upon the type of disease being treated. The amount of active compound administered will also vary according to the method of administration and the disease being treated. An effective amount will be within the dosage range of about 0.1 to about 100 mg/kg, preferably about 0.2 to about 50 mg/kg, in a single or multiple doses administered at appropriate intervals throughout the day.

The $IC_{50}$ values (concentration required to inhibit 50% of specific binding) of compounds of the present invention for inhibition of p38 activity are below 30 ΦM. Preferred compounds (exemplified by those of Table 1) have an $IC_{50}$ below 1 ΦM, more preferred compounds have an $IC_{50}$ below 300 nM and most preferred compounds have an $IC_{50}$ below 100 nM.

Compounds shown in Tables 1-4 have been synthesized according to the methods described herein and have been tested in accordance with the protocols described below. These compounds are provided by way of illustration only, and the invention is not intended to be limited thereto.

Biological Assays

Generation of p38 Kinases cDNAs of human p38α, β and γ isozymes were cloned by PCR. These cDNAs were subcloned in the pGEX expression vector (Pharmacia). GST-p38 fusion protein was expressed in *E. Coli* and purified from bacterial pellets by affinity chromatography using glutathione agarose. p38 fusion protein was activated by incubating with constitutively active MKK6. Active p38 was separated from MKK6 by affinity chromatography. Constitutively active MKK6 was generated according to Raingeaud et al. [*Mol. Cell. Biol.*, 1247-1255 (1996)].

TNF-α Production by LPS-Stimulated PBMCS

Heparinized human whole blood was obtained from healthy volunteers. Peripheral blood mononuclear cells (PBMCs) were purified from human whole blood by Ficoll-Hypaque density gradient centrifugation and resuspended at a concentration of $5 \times 10^6$/ml in assay medium (RPMI medium containing 10% fetal bovine serum). 50 μl of cell suspension was incubated with 50 μl of test compound (4×concentration in assay medium containing 0.2% DMSO) in 96 well-tissue culture plates for 5 minutes at room temperature. 100 μl of LPS (200 ng/ml stock) was then added to the cell suspension and the plate was incubated for 6 hours at 37° C. Following incubation, the culture medium was collected and stored at −20° C. TNFα concentration in the medium was quantified using a standard ELISA kit (Pharmingen-San Diego, Calif.). Concentrations of TNFα and IC50 values for test compounds (concentration of compound that inhibited LPS-stimulated TNFα production by 50%) were calculated by linear regression analysis.

LPS-Induced TNF Production in THP-1 Cells

Human monocytic THP-1 cells were maintained in RPMI 1640 medium supplemented with 10% fetal bovine serum. Cells (40,000 cells in 80 Φl) were added to wells of 96-well flat-bottomed plates. Tested compounds (10 Φl) or vehicle (3% DMSO) were added to wells. Subsequently, LPS (Sigma, #L7261; 10 Φl/well) was added to the cells for a final concentration of 1 Φg/mL. Plates were incubated overnight at 37E C and 5% $CO_2$. Supernatant (50 Φl/well) was harvested for an ELISA assay. TNF was captured by an anti-human TNF antibody (R&D, #MAB610) which was pre-absorbed in high binding EIA plates (Costar, #3590). Captured TNF was recognized by a biotinlated anti-human TNF polyclonal antibody (R&D, #BAF210). Streptavidin conjugated with peroxidase was added to each well, and the activity of peroxidase was quantitated by a peroxide substrate kit (Pierce, #34062 and #34006).

p38 Assay

The assays were performed in V-bottomed 96-well plates. The final assay volume was 60 Φl prepared from three 20 Φl additions of enzyme, substrates (MBP and ATP) and test compounds in assay buffer (50 mM Tris pH 7.5, 10 mM MgCl$_2$, 50 mM NaCl and 1 mM DTT). Bacterially expressed, activated p38 was pre-incubated with test compounds for 10 min. prior to initiation of reaction with substrates. The reaction was incubated at 25E C for 45 min. and terminated by adding 5 Φl of 0.5 M EDTA to each sample. The reaction mixture was aspirated onto a pre-wet filtermat using a Skatron Micro96 Cell Harvester (Skatron, Inc.), then wash with PBS. The filtermat was then dried in a microwave oven for 1 min., treated with MeltilLex A scintillation wax (Wallac), and counted on a Microbeta scintillation counter Model 1450 (Wallac). Inhibition data were analyzed by nonlinear least-squares regression using Prizm (GraphPad Software). The final concentration of reagents in the assays are ATP, 1 ΦM; [γ-$^{33}$P]ATP, 3 nM; MBP (Sigma, # M1891), 2 Φg/well; p38, 10 nM; and DMSO, 0.3%.

Methods of Synthesis

General methods of synthesis for compounds of the present invention are illustrated by the following examples. Compounds of the invention may be prepared by standard techniques known in the art, involving both solution and solid phase chemistry. Starting materials are commercially available or may by readily prepared by one of skill in the art with known methods, or by methods disclosed herein. Specific embodiments described are presented by way of illustration only, and the invention is not limited thereto. Modifications and variations in any give material or process step will be readily apparent to one of skill in the art and all are to be included within the scope of the invention.

As illustrated in Scheme 1, compounds of Formula I wherein V is !NR$^5$!; each of W, X and Y are N; and each of Z and R$^{11}$ are attached to the core triazine by !N!, may be prepared from trichlorotriazine by sequential reactions with three different amines (1, 2, 3; 4 represents an N-substitution in amine 3). Preferably, one of the amines will be an aniline and another will be a diamine suitably protected on its distal N. The person of skill will recognize that the amines themselves, as well as the sequence of the three substitutions, may be varied, and are not limited by the particular example shown in Scheme 1.

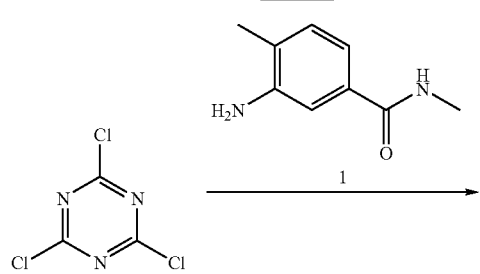

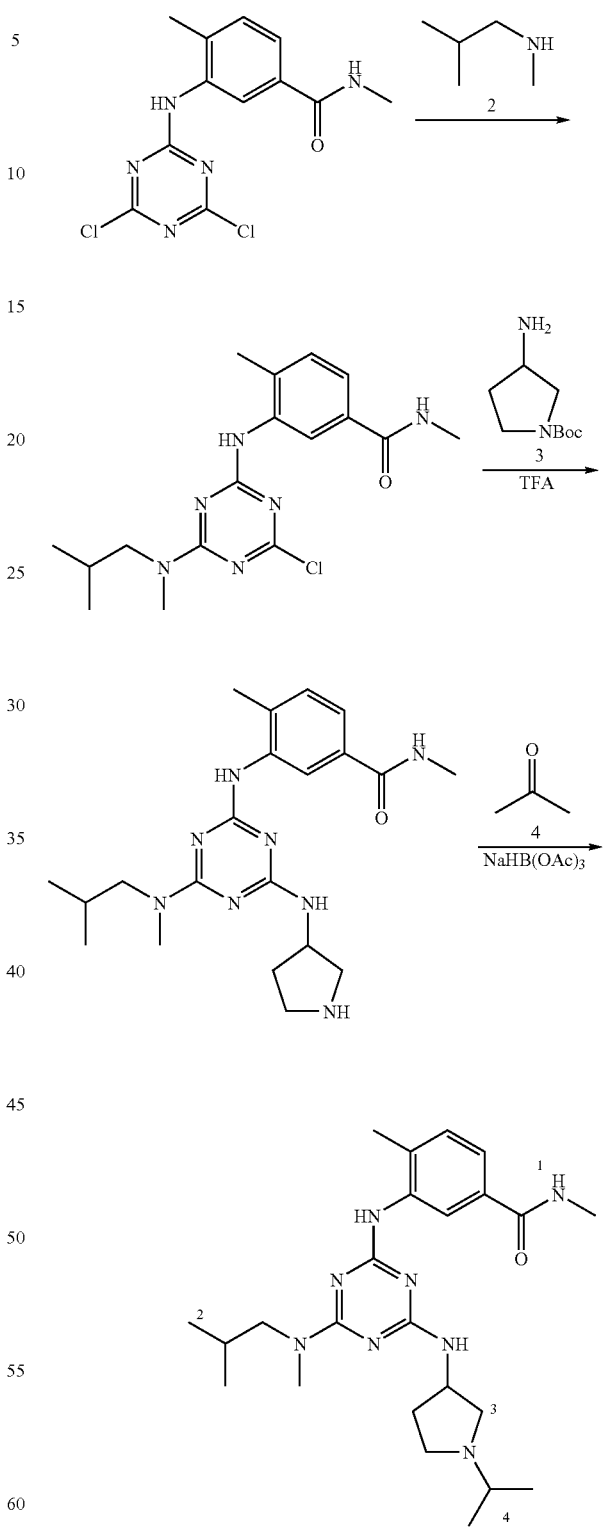

With respect to Formula I of the invention, Amine 1 corresponds to —N(R$^5$)(R$^6$); Amine 2 corresponds to -Z; and Amine 3 corresponds to —R$^{11}$ and such designations are used interchangeably in the description below.

Preparation of Amines 1 [—N(R$^5$)(R$^6$)]N,N-Dimethyl(3-amino-4-methyl)benzamide

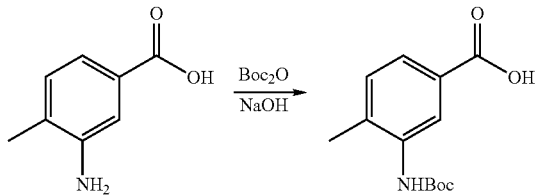

3-Amino-4-methylbenzoic acid (9.06 g, 60 mmol) and NaOH (4.8 g, 120 mmol) were dissolved in 100 mL 50% acetone/water at 0EC. To the solution was added 13.2 g Boc$_2$O (60 mmol) in acetone dropwise. The reaction was proceeded at 0EC for 30 min, then room temp for 3-4 h. The solution was evaporated under vacuum, and the resulting aqueous solution was acidified by 2 N HCl to pH 2, and extracted subsequently with ethyl acetate. The organic layer was washed with water, 1 N HCl solution, saturated NaCl, dried over sodium sulfate. Filtration and evaporation under vacuum provided the desired intermediate (11.6 g, 77%).

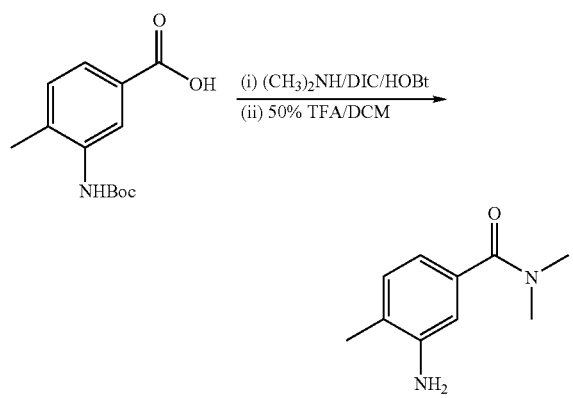

The intermediate (5 g, 20 mmol) so obtained was dissolved in 40 mL THF. To the solution was added 2 N dimethylamine in THF (10 mL), DIC (3.13 mL, 20 mmol), and HOBt (2.7 g, 20 mmol). The solution was stirred at room temp for 16 h and then filtered. The filtrates were evaporated under vacuum. The oily residue was purified by a flash column to afford 4.5 g of product (81%). Further treatment of the product with 20 mL of 50% TFA/DCM at room temp yielded the final desired product.

N-Methyl(3-amino-4-methyl)benzamide

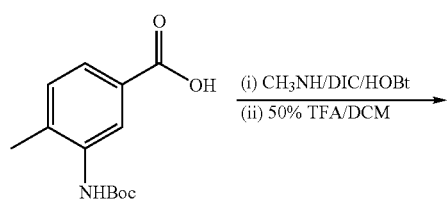

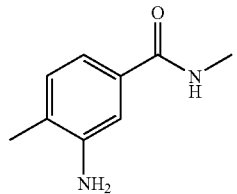

Prepared according to the same protocol as above.

3-Amino-2methylbenzamide

The preparation was accomplished through a combination of solution phase and solid phase chemistry shown below.

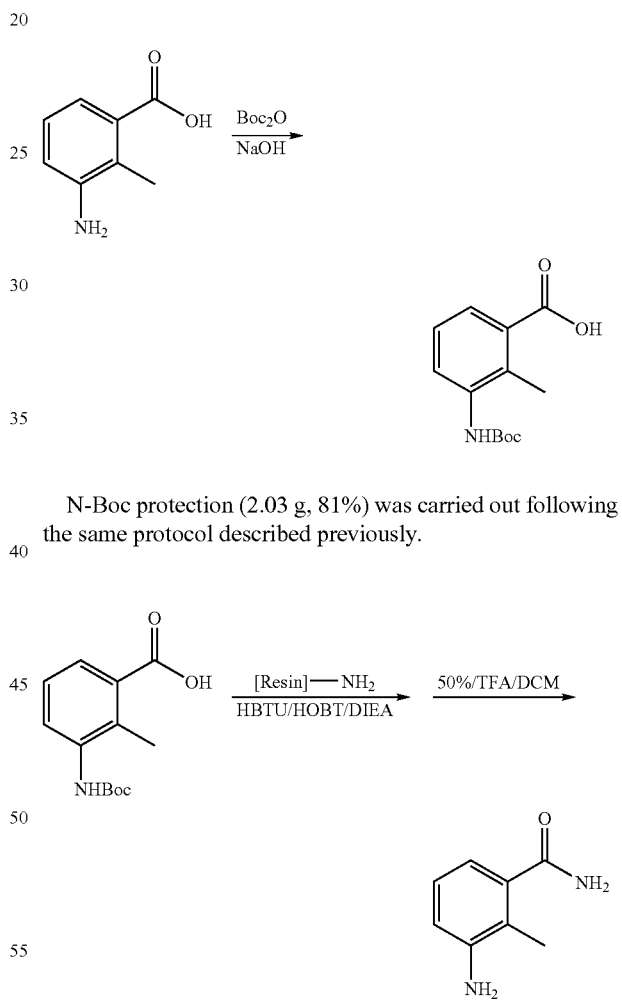

N-Boc protection (2.03 g, 81%) was carried out following the same protocol described previously.

Rink amide resin (2 g, 0.4 mmol/g) in a reaction vessel was treated with 20 mL of 20% piperidine/DMF at room temp for 20 min. The resin was washed by DMF (4×). To this resin/DMF (5 mL) slurry was added Boc-3-amino-2-methylbenzoic acid (0.6 g, 2.4 mmol), HBTU (0.91 g, 2.4 mmol), HOBt (32 g, 2.4 mmol) and DEA (0.43 mL, 2.4 mmol). The vessel was shaken at room temp for 2 h. The resin was washed by DMF, CH$_3$OH, and CH$_2$Cl$_2$ successively. Subsequent treatment of the resin with 20 mL of 50% TFA/DCM yielded the desired product (66 mg, 55%).

3-Amino-4,5-dimethylbenzoic acid and 2-amino-3,4-dimethylbenzoic acid

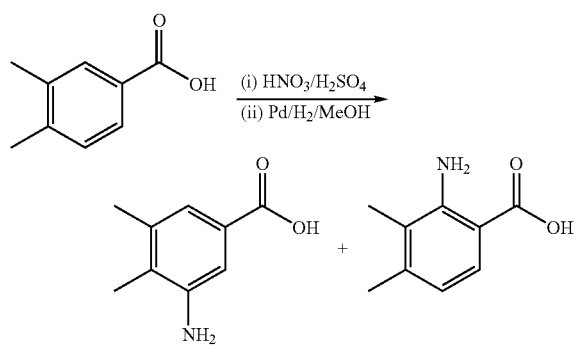

To a solution of concentrated sulfuric acid (20 mL) was added 1.7 mL of nitric acid dropwise. The resultant solution was stirred at 0EC for 5 min and the 3,4-dimethylbenzoic acid (6 mg, 40 mmol) was added in several small portions. The reaction was proceeded at 0EC for 20 min, then room temp for 60 min. Cold water was added to the reaction mixture. The resulting precipitate was filtered, collected and purified by flash column.

The product was dissolved in 25 mL of $CH_3OH$, and subjected to hydrogenation (10% Pd/C, H2, 50 psi) at room temp for 3-4 h. Filtration and evaporation provided the desired products as a 1:1 mixture of Regio isomers (4 g, 61%).

Preparation of Amines 1A

Synthesis of 3-(4-Methyl-3-nitro-phenyl)-4H-[1,2,4]triazole

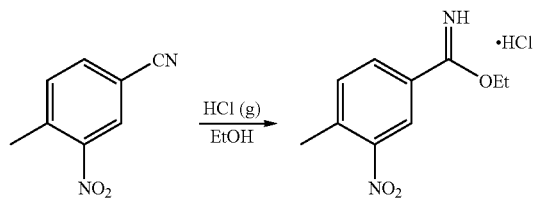

Hydrogen chloride was bubbled through a solution of 3-nitro-p-tolunitrile (0.49 g, 3 mmol) in 40 mL of ethanol at room temp for 10 min. The solution was continued stirring at room temp for 60 min and the solvent was then evaporated under vacuum to dryness to give a white solid.

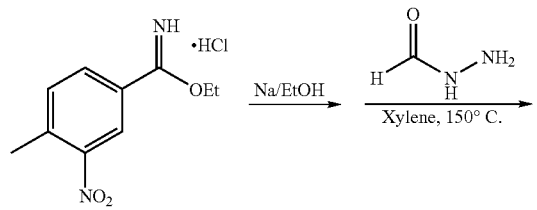

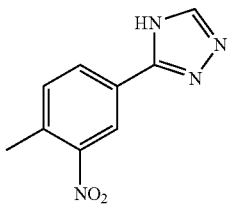

The intermediate so obtained was dissolved in 20 mL of ethanol, neutralized with sodium ethoxide solution and the resulting precipitate was removed by filtration. To the filtrate was added at room temp formic hydrazide (0.2 g, 3 mmol) and the solution was continued stirring at room temp for 2 h. After removal of volatiles in vacuo, the residue was dissolved in 30 mL of m-xylene and refluxed at 150° C. for 16 h. Removal of volatiles in vacuo and purification using flash chromatography afforded 0.26 g of the final product. (Yield: 43%). MS (m/z) calcd for $C_9H_8N_4O_2$ (MH+) 205.2, found, 205.1.

2-(4-Methyl-3-nitro-phenyl)-[1,3,4]oxadiazole

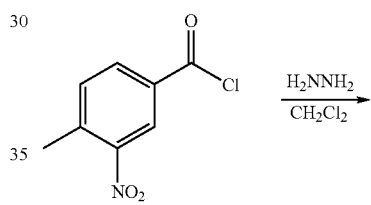

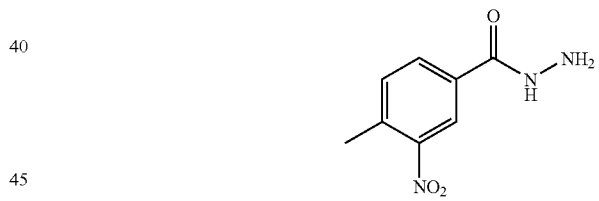

To a solution of hydrazine hydrate (1.47 mL, 50 mmol) in $CH_2Cl_2$ was added dropwise at 0° C. a solution of 3-nitro-4-methyl-benzoychloride (0.63 mL, 5 mmol) in $CH_2Cl_2$. The solution was continued stirring at 0° C. for 10 min, then at room temp for 30 min. Removal of volatiles in vacuo and purification using flash chromatography afforded 0.46 g of the product (yield: 47%). MS (m/z) calcd for $C_8H_9N_3O_3$ (MH+), 196.1, found, 196.1.

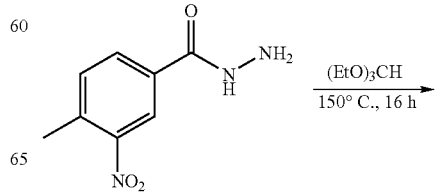

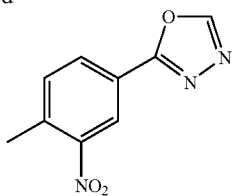

The product (0.3 g, 1.54 mmol) so obtained was dissolved in 15 mL of triethyl orthoformate and the solution was then refluxed at 150° C. for 16 h. The solution was allowed to cool down to room temp, then diluted with water and extracted with ethyl acetate (2×). The combined organic extracts were washed with water, brine, dried over MgSO$_4$. Removal of volatiles in vacuo and purification using flash chromatography afforded 0.23 g of the product (yield: 75%). MS (m/z) calcd for C$_9$H$_7$N$_3$O$_3$ (MH+), 206.1, found, 206.1.

2-Methyl-5-(5-methyl-[1,2,4]oxadiazol-3-yl)-phenylamine

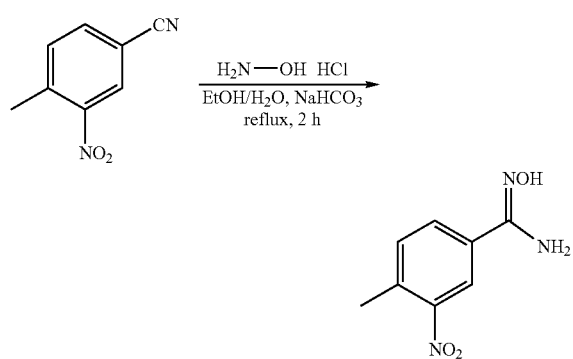

The solution of 3-nitro-p-tolunitrile (0.81 g, 5 mmol), sodium bicarbonate (0.89 g, 10 mmol) and hydroxylamine hydrochloride (0.70 g, 10 mmol) in 20 mL of ethanol/water (2/1, v/v) was refluxed for 2 h. Removal of volatiles in vacuo and purification using flash chromatography afforded 0.75 g of the product (yield: 77%). MS (m/z) calcd for C$_8$H$_9$N$_3$O$_3$ (MH+), 196.1, found, 196.1.

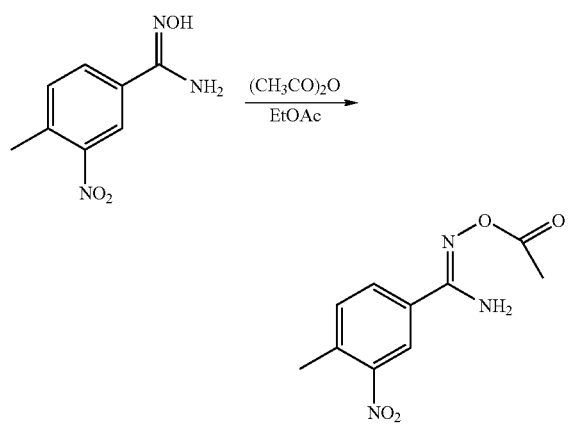

To a solution of the product (0.50 g, 2.56 mmol) so obtained in 15 mL of ethyl acetate was added acetic anhydride (0.24 mL, 2.56 mmol) and the resulting solution was stirred at room temp for 2 h. Removal of volatiles in vacuo and purification using flash chromatography afforded 0.48 g of the product (yield: 78%). MS (m/z) calcd for C$_{10}$H$_{11}$N$_3$O$_4$ (MH+), 238.1, found, 237.9.

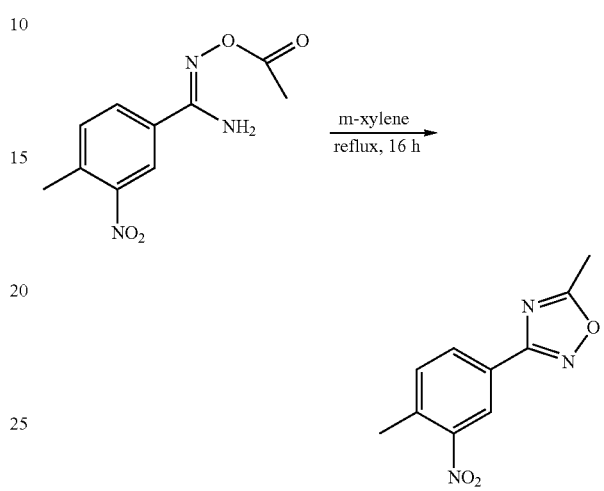

The product (0.40 g, 1.69 mmol) so obtained was dissolved in 15 mL of m-xylene and the solution was refluxed for 16 h. The solvent was then evaporated under vacuum and the crude product was purified by flash chromatography. $^1$H NMR (CDCl$_3$, 300 MHz): δ 1.59 (s, 3H), 2.74 (d, 3H), 7.53 (d, 1H), 8.19 (d, 1H), and 8.72 (s, 1H).

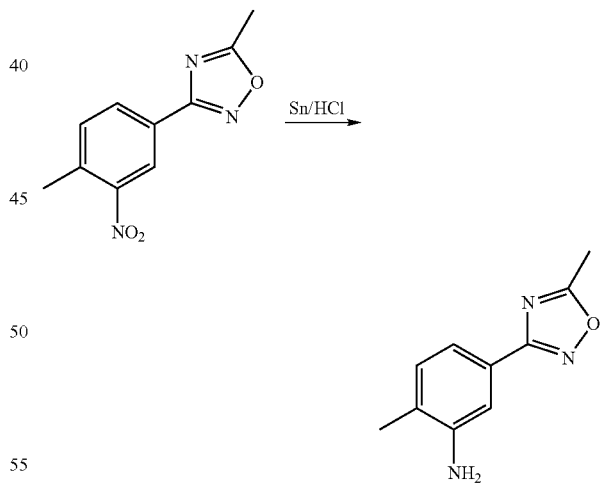

To a mixture of the product (1.69 mmol) so obtained and tin (0.30 g, 2.5 mmol) at 0° C. was added dropwise 10 mL of a 12 N solution of hydrogen chloride in water and the resulting solution was stirred at room temp for 2 h. Then a 2 N NaOH solution in water was added to the reaction mixture until the solution became basic. The resulting solution was extracted with ethyl acetate and the combined organic layer was washed with water, brine, dried over MgSO$_4$. Removal of volatiles in vacuo and purification using flash chromatography afforded 0.14 g of the product (yield: 44% for two steps). MS (m/z) calcd for $C_{10}H_{11}N_3O$ (MH+), 190.1, found, 190.0.

2-Methyl-5-thiazole-2-yl-phenylamine

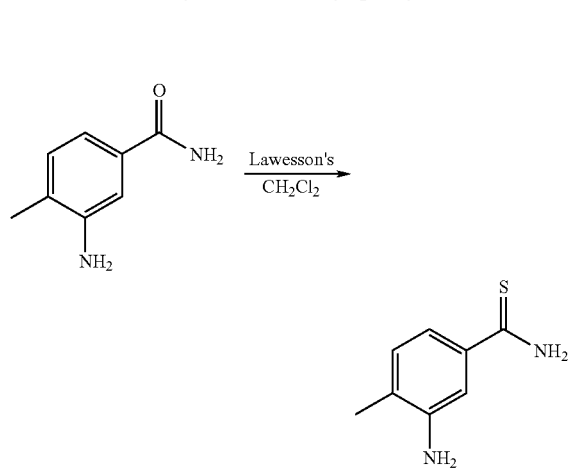

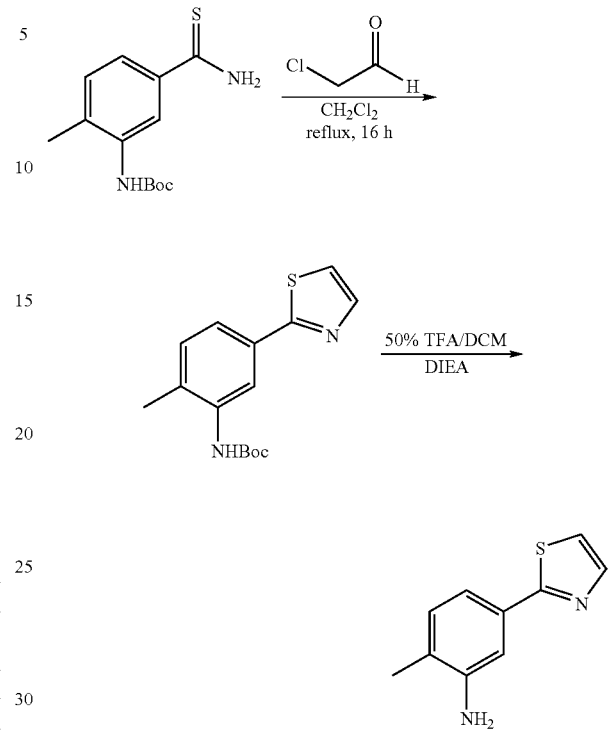

To a solution of 3-amino-4-methylbenzamide (1.5 g, 10 mmol) in 30 mL of $CH_2Cl_2$ was added at room temp in portions Lawesson's reagent (2.2 g, 5 mmol). The solution was stirred at room temp for 48 h and then the solvent was removed under vacuum. The residue was partitioned between water and ethyl acetate and the organic layer was then washed with water, brine, dried over $Na_2SO_4$. Removal of volatiles in vacuo and purification using flash chromatography afforded 0.18 g of the product (yield: 11%). MS (m/z) calcd for $C_8H_{10}N_2S$ (MH+), 167.2, found, 167.1.

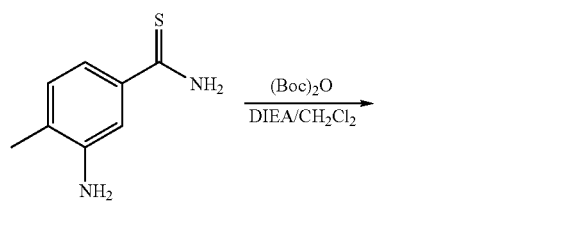

To a solution of the product (0.15 g, 0.93 mmol) so obtained and diisopropylethylamine (0.26 ml, 1.4 mmol) in 15 mL of $CH_2Cl_2$ was added dropwise a solution of di-tert-butyl dicarbonate (0.30 g, 1.4 mmol) in $CH_2Cl_2$ and the resulting solution was stirred at room temp for 16 h. Then volatiles were removed in vacuo and purification using flash chromatography afforded 0.19 g of the product (yield: 75%). MS (m/z) calcd for $C_{13}H_{18}N_2O_2S$ (MH+), 266.4, found, 266.7.

To a solution of the product (0.09 g, 0.34 mmol) so obtained in 5 mL of $CH_2Cl_2$ at 0° C. was added chloroacetaldehyde (0.032 mL, 0.51 mmol). The solution was warmed up to room temp in 20 min then refluxed for 16 h. Removal of volatiles in vacuo and purification using flash chromatography afforded 0.06 g of the product. The purified product was then treated with 50% TFA/$CH_2Cl_2$ at room temp for 30 min. The solvent was then evaporated, dissolved in $CH_2Cl_2$, and evaporated again. The resulting oily residue was dissolved in $CH_2Cl_2$ and neutralized with di-isopropylethylamine to afford the desired product. MS (m/z) calcd for $C_{10}H_{10}N_2S$ (MH+), 191.1, found, 191.2.

Preparation of Amines 2

[-Z]3-Methyl-3-n-propylpyrrolidine

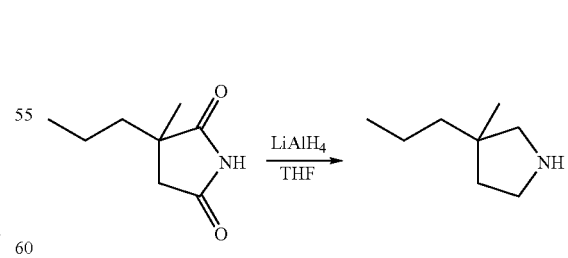

α-Methyl-α-propyl-succinimide (310 mg, 2 mmol) was dissolved in THF and to the solution was added 84 mg $LiAlH_4$ (2.2 mmol) in three small portions. The reaction was proceeded at 0EC for 5 min, then room temp for 2 h. Cold water was added to quench the reduction. The solution was filtered through celite. The filtrates were combined and evaporated under vacuum. The product (160 mg, Yield 63%) was ready for use.

4,4-Dimethylpiperidine

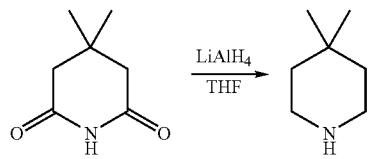

Prepared according to the same protocol as above.

Preparation of Amines 3 [-R[11]]

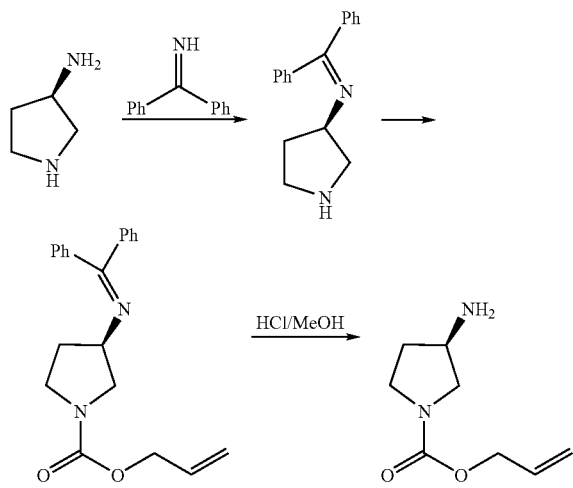

In a 500 mL flask, (3R)-(+)-3-aminopyrrolidine (10.0 g, 116 mmol) was dissolved in DCM (160 mL). The solution was added with benzophenone imine (1.0 equivalent) and stirred at room temp for 16 h. The solvent was removed under vacuum. The crude product was purified with flash chromatography to give the desired imine (24.3 g).

2.4 g of the imine obtained above was dissolved in DCM (30 mL). The solution was added with 2,6-lutidine (2.5 equivalents) and allyl chloroformate (1.2 equivalents) then cooled with ice. The reaction was stirred at room temp for 3 h, and concentrated under vacuum. The resulting mixture was added with ethyl acetate (100 mL) and aqueous ammonium chloride solution (20 mL). Separated from the organic layer, the aqueous layer was extracted with ethyl acetate twice. The combined organic layer was washed with saturated aq. ammonium chloride solution twice, brine twice, and dried with sodium sulfate, and then concentrated.

The above product was dissolved with methanol (30 mL). The solution was added with 0.4 N HCl (30 mL) after cooled with ice. Stirred at room temp for 2 h, the reaction mixture was poured into water and washed with DCM (2×30 mL). Sodium carbonate solution was added to adjust the aqueous phase pH to 10, and the product was extracted with ethyl acetate (3×30 mL). The combined organic layer was washed with saturated aq. ammonium chloride solution twice, brine twice, and dried over sodium sulfate, and then concentrated to give the desired product (1.02 g, yield 63%). MS (m/z) calcd for $C_8H_{14}N_2O_2$ (MH+), 171: found, 171.

1-(2-(Pyridylmethyl)-3-aminopyrrolidine

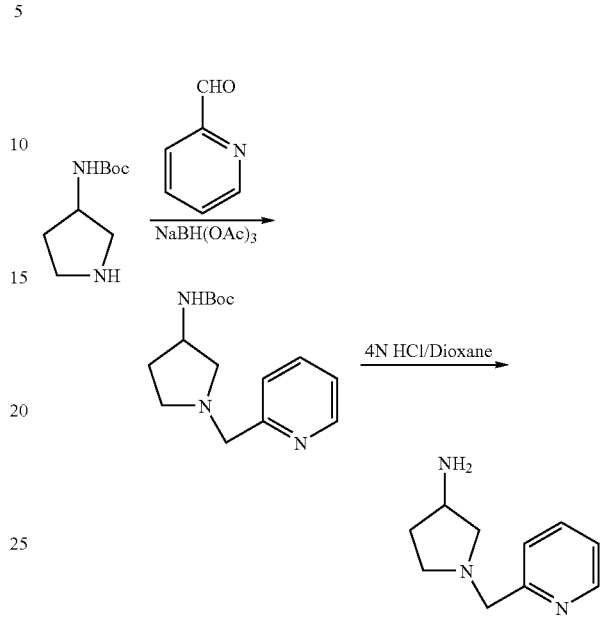

To the solution of 3-(t-butoxycarbonylamino)-pyrrolidine (racemic, 745 mg, 4 mmol) in dichloroethane was added 2-pyridinecarboxaldehyde (0.38 mL, 4.0 mmol) and sodium triacetoxyborohydride (848 mg, 4 mmol). The solution was stirred at room temp for 2 h. The solution was evaporated under vacuum. The oily residue was purified by flash column to afford 790 mg of pure product (71%). The product was further treated with 4 N HCl/dioxane to yield the final product as HCl salt.

1-(3-Methoxyethyl)-3-aminopyrrolidine

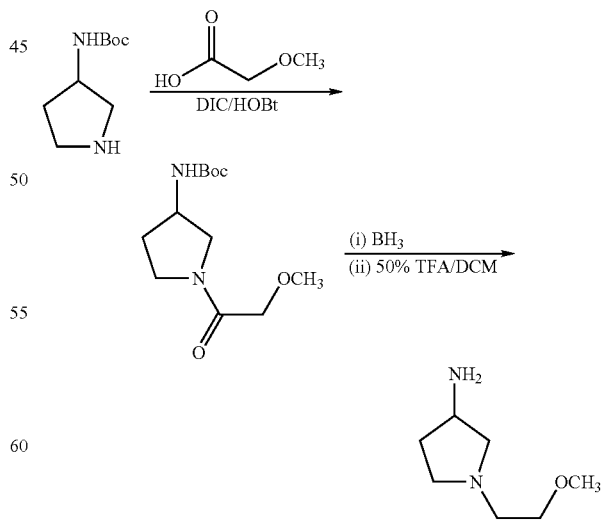

3-(t-Butoxycarbonylamino)-pyrrolidine (racemic, 932 mg, 5 mmol) and 2-methoxyacetic acid (0.39 mL, 5 mL.) were dissolved in DCM. To the solution was added 0.78 mL of DIC (5 mmol) and 675 mg HOBt (5 mmol). The reaction was proceeded at room temp for 16 h. The solution was filtered. The filtrates were combined and evaporated under vacuum. The oily residue was purified by flash column to afford 843 mg of pure product (65%).

To a solution of the above intermediate (258 mg, 1 mmol) in THF was added 3 mL of 1.0 M BH₃ in THF dropwise. The solution was stirred at 60EC for 3 h and then cooled. Methanol was added. The solution was evaporated under vacuum. The resulting residue was extracted with ethyl acetate and saturated with sodium bicarbonate solution. The organic layer was washed with water, sat. sodium chloride solution and dried over sodium sulfate. The oily residue obtained by filtration and evaporation was further treated with 50% TFA/DCM at room temp for 30 min to afford 50 mg of final product (35%) as TFA salt.

1-(3-Methoxypropyl)-3-aminopyrrolidine

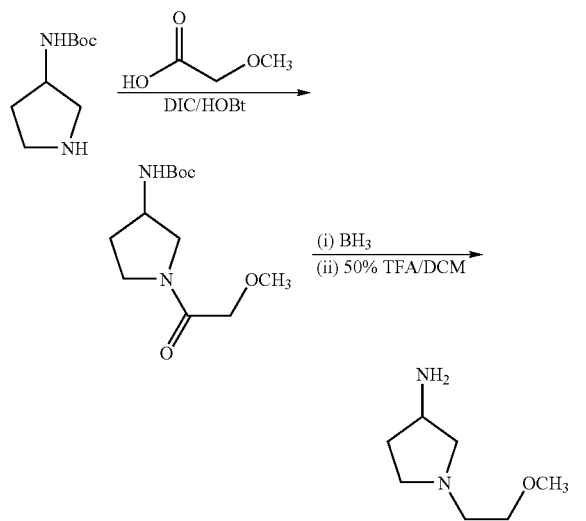

Prepared according to the same protocol as above.

N-t-Butyl Pyrrolidine

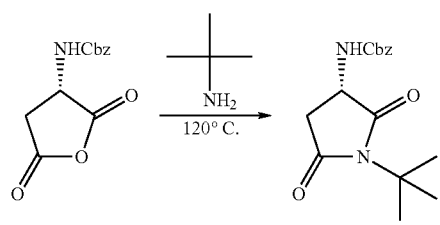

N-Carbonylbenzyloxy-L-aspartic anhydride (2.49 g 10 mmol) and t-butyl amine (0.80 g, 10.9 mmol) were mixed in 5 mL of DMF. The mixture was stirred at room temp overnight, then it was heated in an oil bath at 120EC for 24 h. The reaction mixture was partitioned between water and ethyl acetate. The organic layer was washed once with brine and dried over magnesium sulfate. Filtration, concentration, and purification by flash chromatography (solvent 6:4 hexane: ethyl acetate) provided 0.84 g (yield 28%) of product.

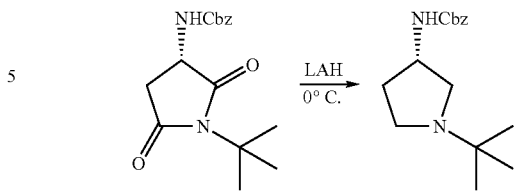

The product from the above step (0.54 g, 1.78 mmol) was dissolved in 5 mL anhydrous THF and cooled with an ice bath. Lithium aluminum hydride (1.0 M in THF, 4.5 mL) was added slowly. The mixture was stirred at 0EC for 3.5 h, then quenched with water until hydrogen evolution ceased. The inorganic residue was filtered and washed with ethyl acetate. The combined filtrates were dried and evaporated to get 0.44 g (89%) of product.

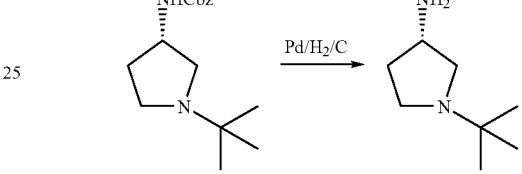

The product from the previous step (180 mg, 1.27 mol) was dissolved in 2 mL acetic acid and shaken with 10% Pd/Cl (18 mg) under 60 psi hydrogen pressure for 2 h. the catalyst was filtered off and the filtrate was concentrated to give 120 mg of t-butyl-3-aminopyrrolidine acetic acid salt (91%).

1-Phenyl-3-aminopyrrolidines

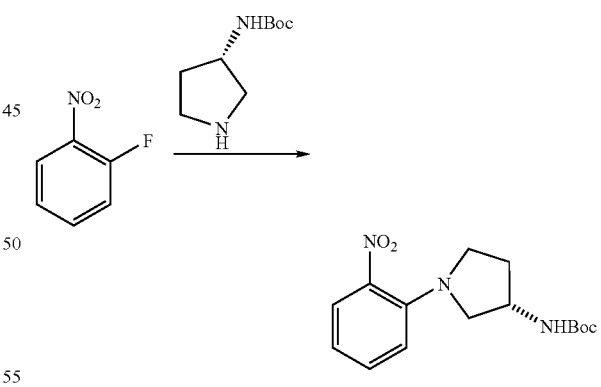

To a solution of 559 mg (3S)-3-(t-butoxycarbonylamino) pyrrolidine (3 mmol) in 5 mL DMSO was added 0.32 mL of 2-fluoro-1-nitrobenzene (3 mmol) and 0.52 mL DIEA (3 mmol). The solution was stirred at 100EC for 16 h. The solution was cooled to room temp, diluted with water and extracted with ethyl acetate. The organic layer was washed with water, 1 N HCl solution, and saturated sodium chloride solution successively and dried over sodium sulfate. Filtration, evaporation and purification by flash chromatography provided 660 mg desired product (72%).

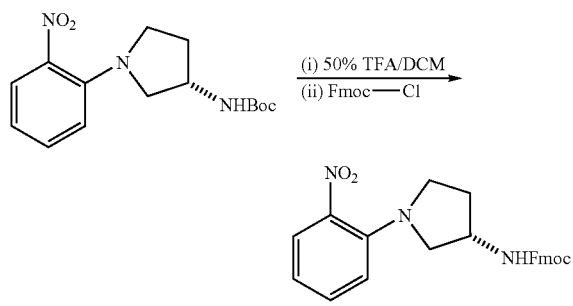

The product (600 mg, 2 mmol) from the above was treated with 10 mL 50% TFA/DCM at room temp for 30 min. The solution was evaporated under vacuum. The oily residue was dissolved in acetone at 0EC. To the solution was added 777 mg of Fmoc-Cl (3 mmol) and 828 mg of potassium carbonate (6 mmol). The reaction was proceeded at 0EC for 30 min, then room temp for 16 h. The solution was evaporated under vacuum. The residue was extracted with ethyl acetate and water. The organic layer was washed with water, saturated sodium chloride solution successively and dried over sodium sulfate. The solvent was removed and the product was purified by flash column. (680 mg, 79%)

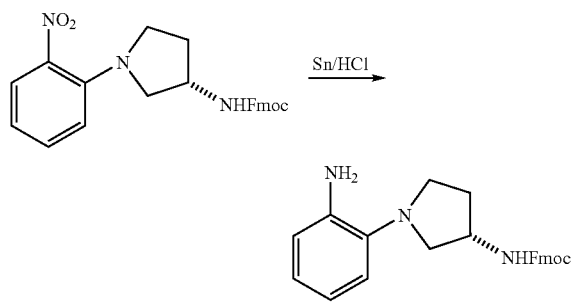

The product (600 mg, 1.4 mmol) thus obtained was mixed with 249 mg of tin (2.1 mmol) in a 50 mL RB flask. To the mixture was added 10 mL of con. hydrogen chloride dropwise (ice water bath was needed if the reaction was too vigorous). The reaction was proceeded at room temp for 2 h. Then 2 N NaOH aq. solution was added to the reaction mixture until the solution became basic. The resulting solution was extracted with ethyl acetate. The organic layer was washed with water, saturated sodium chloride solution, dried over sodium sulfate, and evaporated under vacuum. The crude product was purified by flash column to provide 130 mg of desired product along with 400 mg of recovered starting material.

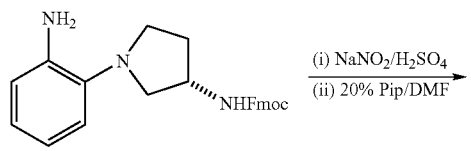

-continued

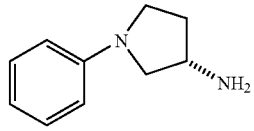

The product (54 mg, 0.14 mmol) thus obtained was dissolved in 3 mL of absolute ethanol at 0EC. To the solution was added 0.22 mL of concentrated sulfuric acid, followed by 37 mg of sodium nitrite in 1 mL of water. The solution was stirred at 0EC for 5 min, then room temp for 60 min. Copper powder (87 mg, pre-washed with ether) was then added to the reaction solution. The solution was stirred at 60EC for 2-3 h. After being cooled down, the solution was extracted with ethyl acetate The organic layer was washed with water, saturated sodium chloride solution, dried over sodium sulfate, filtered and evaporated under vacuum. The crude product was purified by flash column to afford 32 mg of product.

The product was further treated with 1 mL of 20% piperidine/DMF at room temp for 1 h. The final product was purified by flash column (9 mg, 40%).

General Procedures for the Preparation of N-Substituted Pyrrolidines

The reductive aminations of the —NH group of Amines 3 were carried out at room temp in dichloroethane using 2-10 equivalents of aldehydes or ketones and sodium triacetoxyborohydride, $NaHB(OAc)_3$. Separations after workup by chromatography were necessary for purification of the final product. The N-acylations and the N-alkylations via epoxide openings were carried out by procedures commonly used in the literature.

Compounds wherein V is !CHR[5]! may be prepared according to the following examples.

3-{4-(5-Cyano-2-methyl-benzyl)-6-[(2,2-dimethyl-propyl)-methyl-amino]-[1,3,5]triazin-2-ylamino}-pyrrolidine-1-carboxylic acid tert-butyl ester

A

-continued

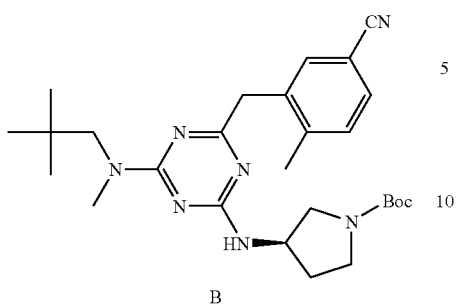

B

A suspension of A (0.036 g, 0.09 mmol), tetrakis(triphenylphosphine)-palladium(0) (0.025 g, 0.02 mmol), and 3-cyanobenzylzinc bromide (0.5 M in THF, 2 mL, 1 mmol) was stirred for 16 h at 80EC in a sealed tube. After filtration and concentration of the solution, the product was purified by Prep-HPLC (36 mg, 81%, $C_{27}H_{39}N_7O_2$, MS M/Z 494 (M+H)+.

3-[4-[(2,2-Dimethyl-propyl)-methyl-amino]-6-(pyrrolidin-3-ylamino)-[1,3,5]triazin-2-ylmethyl]-4-methyl-benzamide

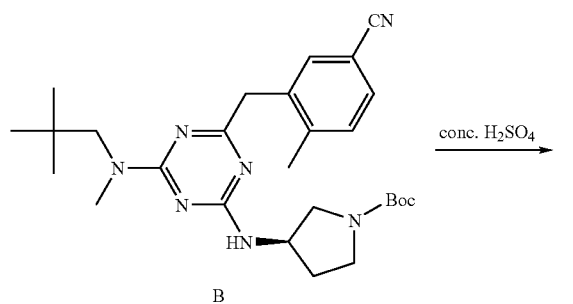

B

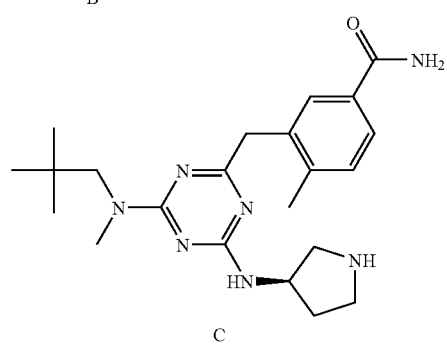

C

A suspension of B (0.03 g, 0.06 mmol) in conc. sulfuric acid (4 mL) was stirred for 90 min at 60EC. After cooling to room temp, the reaction solution was diluted with water (20 mL), and basified with 6N aq. sodium hydroxide. The product was then extracted with ethyl acetate (2×20 mL). The combined organic layers was dried (anhyd. sodium sulfate), filtered and concentrated. The product was then purified by Prep-HPLC (5.2 mg, 21%, $C_{22}H_{33}N_7O$, MS m/z 412 (M+H)+.

Compounds wherein V is —S— may be prepared according to the following examples.

Preparation of Thiophenols

Step 1: Compound A

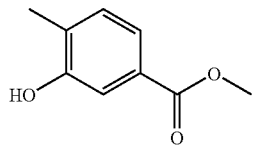

To 3-hydroxy-4-methylbenzoic acid (2.0 g, 13 mmol) in anhydrous methanol (20 mL) at 0EC under argon was added thionyl chloride (1.4 mL, 20 mmol) dropwise over a period of 10 min. The mixture was stirred for 1 h at 0EC then room temp for overnight. The solvent was removed in vacuo and the residue was partitioned between ethyl acetate and water. The organic layer was washed with saturated aqueous sodium bicarbonate (50 mL×2), brine (50 mL) then dried over sodium sulfate and concentrated in vacuo. The crude compound (2.0 g, 91% yield) was used directly in the next reaction with no further purification. HPLC Ret. Time: 2.56 min. $^1$H NMR (400 MHz, CDCl$_3$): δ 2.30 (s, 3H), 3.90 (s, 3H), 5.26 (s, 1H), 7.18 (d, 1H), 7.49 (s, 1H), 7.52 (d, 1H).

Step 2: Compound B

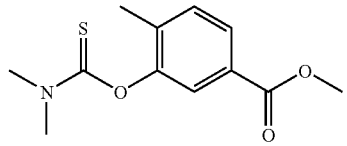

To compound A (2.0 g, 12 mmol) in DMF (60 mL) at room temperature under argon was added sodium hydride (0.67 g, 17 mmol) in one portion. The reaction was stirred at room temp for 0.5 h then dimethylthiocarbonyl chloride (2.1 g, 17 mmol) was added in one portion. The reaction was stirred at room temp for overnight. After quenching with water, the reaction mixture was extracted with ethyl acetate (100 mL×4). The organic layer was washed with water (40 mL×2), brine (50 mL) then dried over magnesium sulfate and concentrated in vacuo. The crude compound was purified by column chromatography to give 2.8 g (92%) of a near white solid. HPLC Ret. Time: 2.90 min. LCMS MH$^+$ (m/z) 253. $^1$H NMR (400 MHz, CDCl$_3$): δ 2.26 (s, 3H), 3.38 (s, 3H), 3.47 (s, 3H), 3.89 (s, 3H), 7.30 (d, 1H), 7.70 (s, 1H), 7.90 (d, 1H).

Step 3: Compound C

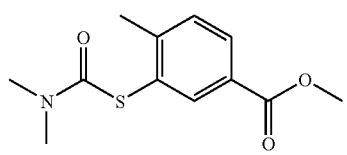

Compound B (4.3 g, 17 mmol) was heated under argon at 240°C for 4 h. After cooling to room temp, 4.1 g (94%) of brown viscous oil was obtained as the desired product. HPLC Ret. Time: 3.11 min. $^1$H NMR (400 MHz, CDCl$_3$): δ 2.46 (s, 3H), 3.02 (br. s, 3H), 3.14 (br. s, 3H), 3.88 (s, 3H), 7.37 (d, 1H), 7.97 (dd, 1H), 8.15 (d, 1H).

Step 4: Compound D

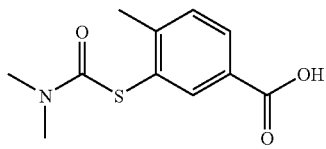

To Compound C (4.1 g, 16 mmol) in 3:1 methanol/water (60 mL) at 0°C was added lithium hydroxide monohydrate (0.68 g, 17 mmol) in one portion. After warming to room temp, the mixture was stirred for overnight. After the solvent was removed in vacuo, the mixture was diluted with water (50 mL) and extracted with diethyl ether (50 mL×2). The aqueous layer was brought to a pH of 1 with aqueous HCl and the resulting solid was collected by filtration to give 3.2 g (83%) of a pale yellow solid. HPLC Ret. Time: 2.79 min. LCMS MH$^+$ (m/z) 240. $^1$H NMR (500 MHz, CDCl$_3$): δ 2.48 (s, 3H), 3.03 (br. s, 3H), 3.15 (br. s, 3H), 7.40 (d, 1H), 8.01 (d, 1H), 8.20 (s, 1H).

Step 5: Compound E

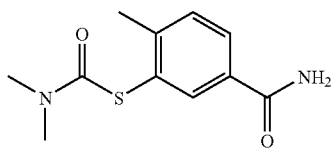

To compound D (1.3 g, 5.7 mmol) in CH$_2$Cl$_2$ (20 mL) cooled at −20°C was added N-methyl morpholine (0.63 mL, 5.7 mmol) and isobutyl chloroformate (0.74 mL, 5.7 mmol) successively. The resulting mixture was stirred at −20°C for 0.5 h. At this time, a 2 M solution of ammonia in methanol (4.3 mL, 8.6 mmol) was added dropwise and followed by stirring at −20°C for 1 h and at room temp for 2 h. Ethyl acetate (300 mL) was added and the organic layer was washed with water (50 mL×2), 10% aqueous sodium carbonate (50 mL), and brine (50 mL), then the solution was dried over magnesium sulfate and concentrated in vacuo. The crude compound was triturated with 20% ethyl acetate in hexane and ether to give 0.77 g (56%) of a near white solid as the pure product. HPLC Ret. Time: 2.20 min. LCMS MH$^+$ (m/z) 239.

$^1$H NMR (400 MHz, CDCl$_3$): δ 2.46 (s, 3H), 3.03 (br. s, 3H), 3.14 (br. s, 3H), 5.5 (br. s, 1H), 6.1 (br. s, 1H), 7.38 (d, 1H), 7.77 (dd, 1H), 7.89 (d, 1H).

Step 6: Compound F

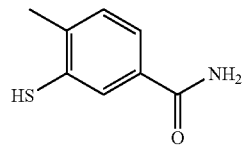

To Compound E (0.77 g, 3.2 mmol) in methanol (10 mL) at room temp was added 5 N aqueous sodium hydroxide solution (3.2 mL, 16 mmol) followed by refluxing for 1 h. After the solvent was removed in vacuo the mixture was diluted with water (30 mL) and extracted with diethyl ether (50 mL×2). The aqueous layer was brought to a pH of 1 with aqueous HCl and the resulting solid was collected by filtration to give 0.40 g (74%) of a pale yellow solid. HPLC Ret. Time: 2.09 min. LCMS MH$^+$ (m/z) 167. $^1$H NMR (400 MHz, CDCl$_3$): δ 2.38 (s, 3H), 3.42 (s, 1H), 5.70 (br. s, 1H), 6.00 (br. s, 1H), 7.22 (d, 1H), 7.45 (dd, 1H), 7.77 (d,1H).

Step 7: Compound G

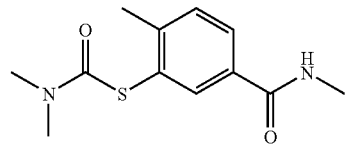

To compound D (1.0 g, 4.2 mmol) in DMF (15 mL) was added 1-hydroxybenzo triazole (0.67 g, 5.0 mmol), 1-[3-(dimethylamino)propyl]-3-ethylcarbodiimide hydrochloride (0.96 g, 5.0 mmol), i-Pr$_2$NEt (2.2 mL, 12 mmol) and methylamine hydrochloride (0.34 g, 5.0 mmol) sequentially at room temp and the resulting mixture was stirred for overnight. Water was added followed by extraction with ethyl acetate. The organic extracts were successively washed with water, 1N aqueous HCl (50 mL×2), water, saturated aqueous NaHCO$_3$, and brine, then the solution was dried over magnesium sulfate. The solvent was removed in vacuo to give 0.89 g (84%) of a pale yellow solid. HPLC Ret. Time: 2.37 min. LCMS MH$^+$ (m/z) 252. $^1$H NMR (400 MHz, CDCl$_3$): δ 2.44 (s, 3H), 2.98 (d, 3H), 3.02 (br. s, 3H), 3.13 (br. s, 3H), 6.12 (br. s, 1H), 7.36 (d, 1H), 7.73 (dd, 1H), 7.82 (d, 1H).

Compound H

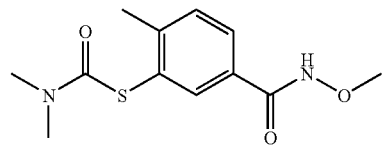

Compound H was prepared from compound D utilizing the same procedure as for compound E by substituting methoxyamine hydrochloride in place of methylamine HCl.

Compound I

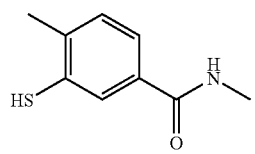

Compound I was prepared from compound G utilizing the same procedure as for compound F.

Compound J

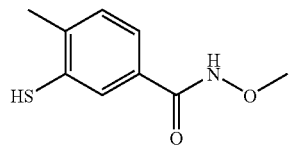

Compound J was prepared from compound H utilizing the same procedure as for compound F.

Compound K

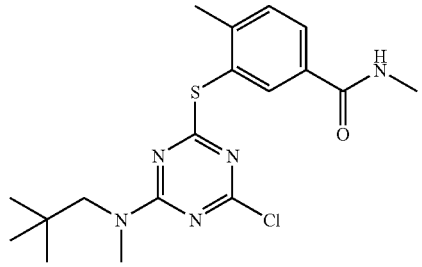

To cyanuric chloride (0.20 g, 1.1 mmol) in DCM (2 mL) cooled in an ice bath was added a solution of N-methyl-neopentylamine hydrochloride (0.15 g, 1.1 mmol) and DIEA (0.60 mL, 3.5 mmol) in 1 mL of DCM dropwise. The resulting mixture was stirred at 0EC for 15 min and at room temp for 15 min, then cooled to 0EC. Compound I in DCM (2 mL) was then added dropwise followed by stirring at 0EC for 15 min and at room temp for 2 h. The resulting mixture was directly purified by column chromatography to give 0.36 g (86%) of a white foam as the pure product. HPLC Ret. Time: 3.60 min. LCMS MH$^+$ (m/z) 394.

Compound L

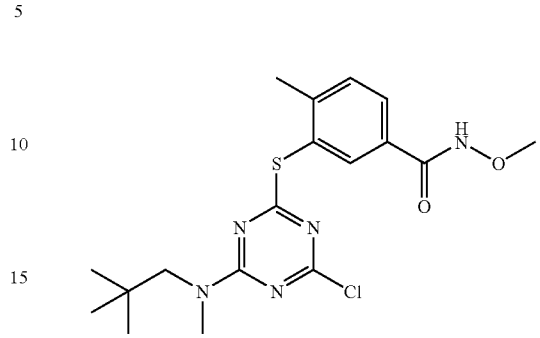

Compound L was prepared from compound K utilizing the same procedure as for compound K.

Compound M

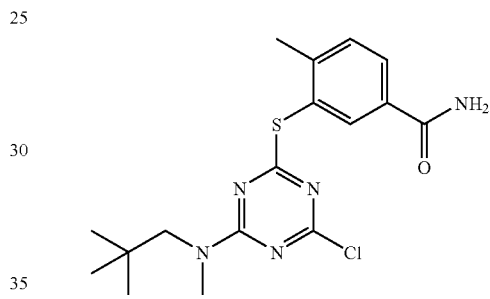

Compound M was prepared from compound F utilizing the same procedure as for compound K.

Compound N

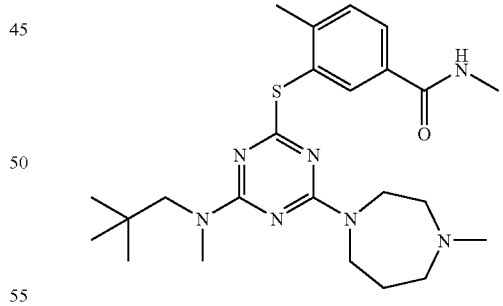

To compound K (25 mg, 0.07 mmol) in acetonitrile (0.2 mL) was added 1-methylhomopiperazine (11 mg, 0.1 mmol) and the resulting mixture was heated at 80EC for 2 h. The pure product was isolated as an off-white solid following preparative HPLC. HPLC Ret. Time: 3.01 min. LCMS MH$^+$ (m/z) 458.

Compounds O to S

Compounds O to S were prepared utilizing a similar procedure as for compound N except that compound L, compound M and 2-(aminomethyl)pyridine were substituted as starting materials when appropriate. See Table 2.

Compounds T to V

Compounds T to V were prepared utilizing a similar procedure as for compound N except that compound L, compound M and 3-(R)-N-tertbutoxycarbonyl pyrrolidine were substituted as starting materials when appropriate. In addition, the intermediates obtained from this procedure were subsequently exposed to 4 N HCl in dioxane at room temp for 1 h to cleave the BOC protecting group followed by concentration in vacuo to afford the corresponding HCl salts of the pure products. See Table 2

Preparation of Fluoro Anilines

Compound W

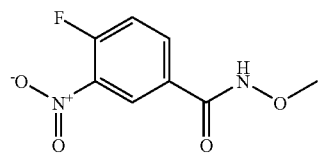

To 4-fluoro-3-nitrobenzoic acid (5.0 g, 27 mmol) in anhydrous dichloromethane (200 mL) at room temp was slowly added oxalyl chloride (12 mL, 0.14 mol) followed by 1 drop of DMF. The reaction was stirred at room temp for 2 h then the solvent was removed in vacuo to afford the intermediate acid chloride as a yellow solid.

To a portion of the crude acid chloride (2.0 g, 9.9 mmol) in anhydrous dichloromethane (35 mL) was added triethylamine (4.1 mL, 30 mmol) followed by methoxylamine hydrochloride (1.2 g, 15 mmol) and the resulting mixture was stirred at room temp for overnight. The reaction mixture was diluted with EtOAc and washed with water (50 mL×2), saturated aqueous NaHCO$_3$ (50 mL×2), brine (50 mL), then dried over magnesium sulfate, filtered, and concentrated in vacuo. The resulting residue was triturated with diethyl ether to give 1.3 g (60%) of a light yellow solid as the pure product. HPLC Ret. Time: 1.57 min. $^1$H NMR (400 MHz, CDCl$_3$): δ 3.86(s, 3H), 7.35 (dd, 1H), 8.24 (ddd,1H), 8.65(dd, 1H), 11.75(s, 1H).

Compound X

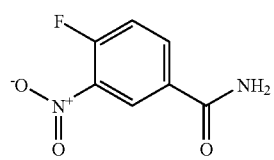

Compound X was prepared utilizing a similar procedure as for compound W except that methoxylamine hydrochloride was substituted for the ammonia in methanol solution as a starting material.

Compound Y

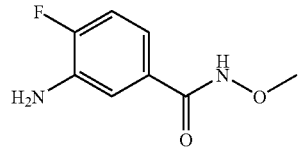

To compound W (0.25 g) in absolute ethanol (20 mL) was added palladium on carbon (50 mg, 10% wt.) and hydrogenated under hydrogen (30 psi) for 3 h. The solution was filtered through a bed of celite and the solvent was removed on vacuo to give 0.21 g light brown thick oil as the product. HPLC Ret. Time: 0.67 min. $^1$H NMR (400 MHz, CDCl$_3$): δ3.86 (br. s, 5H), 6.98 (dd, 1H), 7.00 (dd, 1H), 7.23 (dd, 1H), 8.63 (s, 1H).

Compound Z

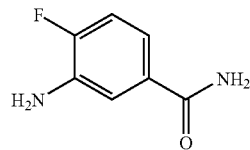

Compound Z was prepared from compound X utilizing the same procedure as for compound Y.

Compounds A$_1$ and B$_1$

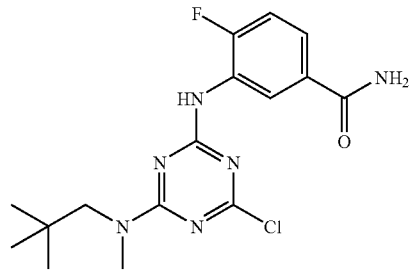

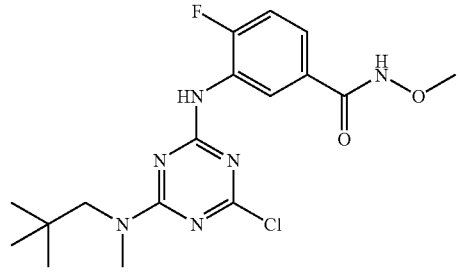

Compounds A$_1$ and B$_1$ were prepared from compounds Y and Z utilizing a similar procedure as for compound K by substituting compound I with compounds Y and Z.

Compounds C₁ and D₁

Compounds C₁ and D₁ were prepared from compounds A₁ and B₁ utilizing a similar procedure as used for compound N. See Table 3.

Compounds E₁ and F₁

Compounds were prepared from compounds A₁ and B₁ utilizing a similar procedure as for compound N except that 3-(R)-amino-N-tertbutoxycarbonyl pyrrolidine was used in place of N-methyl homopiperizine. In addition, the intermediates obtained from this procedure were subsequently exposed to 4 N HCl in dioxane at room temp for 1 h to cleave the BOC protecting group followed by concentration in vacuo to afford the corresponding HCl salts of the pure products. See Table 3.

Compounds wherein V is —O— may be prepared according to the following examples.

Preparation of Phenols

Compound G₁

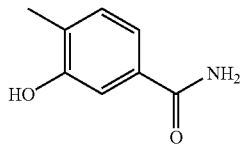

To a suspension of 3-hydroxy-4-methylbenzoic acid (2.5 g, 16 mmol) in 65 mL of DCM at room temp were successively added 5.7 mL of oxalyl chloride and 0.05 mL of DMF and the resulting mixture was stirred at room temp for 17 h then concentrated in vacuo to afford the crude acid chloride intermediate as a viscous, pale yellow oil (~3 g).

Without further purification, the crude oil was dissolved in 30 mL of THF and one-half of this solution (15 mL) was slowly added to 16 mL of a 2 M solution of ammonia in methanol at 0EC. After warming to ambient temperature and stirring for 15 h, the reaction mixture was concentrated in vacuo and the resulting residue was dissolved in 3 N aqueous KOH (50 mL) and washed with DCM (2×75 mL). The aqueous portion was carefully acidified using 6 N aqueous HCl to pH-4, and the product was extracted with DCM (3×50 mL). The combined organic extracts were washed with brine (40 mL), dried over anhydrous sodium sulfate, filtered, and concentrated in vacuo to afford 0.90 g (72%) of pure product as a light tan solid. ¹H NMR (400 MHz, d⁶-DMSO): δ 9.44 (br s, 1H), 7.74 (br s, 1H), 7.27 (s, 1H), 7.21 (d, J=7.6 Hz, 1H), 7.13 (br s, 1H), 7.09 (d, J=8.2 Hz, 1H), 2.14 (s, 3H).

Compound H₁

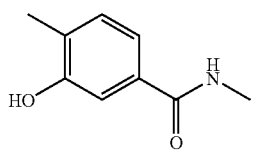

Compound H₁ was prepared using the same procedure as for compound G₁ except 4 mL of a 8M solution of methylamine in methanol was used in substitute for the 16 mL of a 2 M solution of ammonia in methanol. Compound H₁ was isolated as a light tan solid. ¹H NMR (400 MHz, d⁶-DMSO): δ 9.46 (br s, 1H), 8.20 (br s, 1H), 7.25 (s, 1H), 7.16 (d, J=7.6 Hz, 1H), 7.10 (d, J=8.1 Hz, 1H), 2.74 (d, J=4.6 Hz, 3H), 2.14 (s, 3H).

Compound I₁

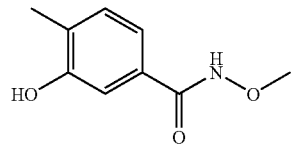

A mixture of 3-hydroxy-4-methylbenzoic acid (2.0 g, 13 mmol), 1-(3-dimethylaminopropyl)-3-ethylcarbodiimide hydrochloride (3.3 g, 17 mmol), HOBt (2.1 g, 16 mmol), DIEA (7.2 mL, 53 mmol) and methoxyamine hydrochloride (1.3 g, 16 mmol) in 30 mL of DMF was stirred at room temp for 3 days. The resulting mixture was poured into 350 mL of water and was extracted with ethyl acetate (4×100 mL). The combined extracts were washed with saturated aqueous sodium bicarbonate (3×75 mL), water (3×75 mL), and brine (2×100 mL), then dried over anhydrous sodium sulfate. The solution was filtered and concentrated in vacuo and the resulting yellow solid was dissolved in 30 mL of 1 N aqueous sodium hydroxide and washed with DCM (2×20 mL). The aqueous portion was then acidified using 3 N aqueous HCl to pH 4 and the aqueous solution was extracted with ethyl acetate (3×30 mL). The combined organic extracts were dried over anhydrous sodium sulfate, filtered, and concentrated in vacuo to afford 0.47 g (20%) of the pure product as an off-white solid. ¹H NMR (400 MHz, d⁶-DMSO): δ 11.54 (s, 1H), 9.59 (s, 1H), 7.18 (s, 1H), 7.12 (d, J=7.7 Hz, 1H), 7.05 (d, J=7.7 Hz, 1H), 3.67 (s, 3H), 2.14 (s, 3H).

Compound J₁

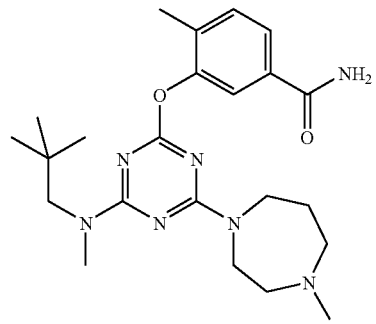

To a 0EC solution of cyanuric chloride (0.20 g, 1.11 mmol) in DCM was slowly added dropwise a solution of compound A (0.17 g, 1.1 mmol) and DIEA (0.23 mL, 1.3 mmol) in 1 mL of DMF. After stirring at 0EC for 15 min, a solution of N-methylneopentylamine hydrochloride (0.16 g, 1.1 mmol) and DIEA (0.62 mL, 3.5 mmol) in 1 mL of DCM was slowly added dropwise at 0EC. The resulting mixture was stirred at 0EC for 1 h, then 4 mL of 1 N aqueous HCl was slowly added followed by dilution of the reaction mixture with 30 mL of methylene chloride. The layers were separated, and the organic layer was washed with additional 1 N aqueous HCl (2×15 mL), water (15 mL), and brine (15 mL), then the solution was dried over anhydrous sodium sulfate, filtered, and concentrated in vacuo to afford 0.4 g of a pale yellow oil as the crude monochloride intermediate.

The crude oil was dissolved in 0.9 mL of DMF, and to one-third (~0.3 mL) of the resulting solution was added N-methylhomopiperizine (56 mg, 0.50 mmol) and DIEA (30 ΦL, 1.7 mmol). The mixture was heated to 85EC for 3 h followed by cooling to room temp. Pure compound D was obtained by preparative HPLC of the reaction mixture to afford 83 mg (92%) of the corresponding TFA salt of the pure product as a white solid. HPLC Ret. Time: 2.66 min. LCMS MH$^+$ (m/z) 442.

Compounds $K_1$ to $O_1$

Compounds $K_1$ to $O_1$ were prepared using the same procedure as for compound $J_1$ except that compound H, compound I and 2-(aminomethyl)pyridine were used as starting materials when appropriate. Pure final compounds were obtained by preparative HPLC of the reaction mixture to afford the pure products as their trifluoroacetic acid salts. See Table 4.

Compounds $P_1$ to $R_1$

Compounds P to R were prepared using the same procedure as for compound J except that compound H or compound I, and 3-(R)-amino-N-(tertbutoxycarbonyl) pyrrolidine were used as starting materials when appropriate. In addition, the intermediates obtained from this procedure were subsequently exposed to 4 N HCl in dioxane at room temp for 1 h to cleave the BOC protecting group followed by concentration in vacuo to afford the corresponding HCl salts of the pure products. See Table 4.

HPLC retention times were determined using a YMC S5 ODS 4.6 mm×50 mm Ballistic chromatography column with a 4 min total gradient elution time and a flow rate of 4 mL/min. The elution gradient uses 100% of solvent A and gradually increases to 100% of solvent B over the 4 min elution time (solvent A=10% methanol/90% water/0.2% phosphoric acid and solvent B=90% methanol/10% water 0.2% phosphoric acid). Eluted products were detected using a UV detector at a wavelength of 220 nm.

Custom Synthon Synthesis 4-Benzyloxy-2-hydroxymethyl-pyrrolidine-1-carboxylic acid t-butyl ester

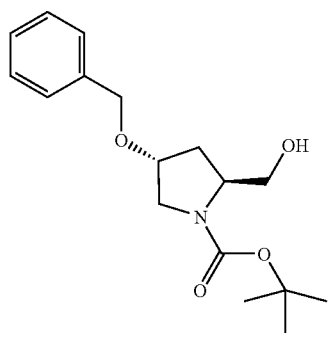

The 4-benzyloxy-pyrrolidine-1,2-dicarboxylic acid 1-t-butyl ester (1.00 g, 3.11 mmol) was taken up in anhydrous THF under argon and cooled to 0EC. BH$_3$, THF (1.0 M, 6.22 mmol, 6.22 mL) was added to the solution dropwise over 10 min. The reaction mixture was then allowed to stir at 0EC for 30 min then warmed to room temp and stirred for an additional 30 min. The reaction was slowly poured into a 1N HCl solution and the aqueous layer was extracted three times with ethyl acetate. The combined organic layers were washed with water and brine then dried over MgSO$_4$. The solution was filtered and the solvent removed under reduced pressure. The product was isolated by flash chromatography. (1:1 hexane-ethyl acetate) Yield 814 mg. $^1$H NMR (CDCl$_3$, 300 MHz) δ 1.48 (s, 9H), 1.63-1.76 (m, 1H), 2.10-2.26 (m, 1H), 3.33 (m, 1H), 3.50-3.60 (m, 1H), 3.63-3.75 (m, 2H), 4.05-4.19 (m, 2H), 4.49 (s, 2H), 7.23-7.39 (m, 5H).

4-Benzyloxy-2-methoxymethyl-pyrrolidine-1-carboxylic acid t-butyl ester

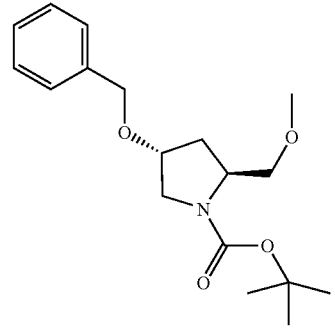

The alcohol (250 mg, 0.81 mmol) and methyl iodide (344.91 mg, 2.43 mmol, 0.15 mL) were dissolved in anhydrous THF under argon. Solid NaH (29.28 mg, 1.22 mmol) was slowly added to the solution under argon. The reaction was then stirred for 12 h at room temp. The reaction was slowly poured into a 1N HCl solution and the aqueous layer was extracted three times with ethyl acetate. The combined organic layers were washed with water and brine then dried over MgSO$_4$. The solution was filtered and the solvent removed under reduced pressure. The product was isolated by flash chromatography. (4:1 hexane-ethyl acetate) Yield 217 mg. $^1$H NMR (CDCl$_3$, 300 MHz): δ 1.27 (s, 9H), 2.06-2.16 (m, 2H), 3.32 (s, 3H), 3.40-3.52 (n, 3H), 4.09-4.21 (m, 1H), 2.49 (s, 2H), 7.23-7.36 (m, 5H).

4-Hydroxy-2-methoxymethyl-pyrrolidine-1-carboxylic acid t-butyl ester

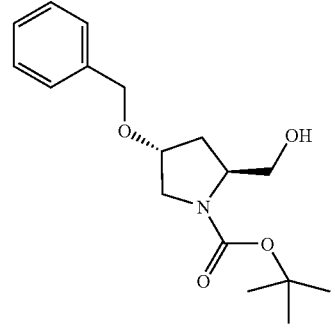

The benzyloxy-2-methoxymethyl-pyrrolidine-1-carboxylic acid t-butyl ester (217.00 mg, 0.68 mmol) was taken up in ethyl acetate in a Paar vessel. The solution was flushed with argon and Pd/C (100 mg) was added to the vessel. The argon atmosphere was replaced by hydrogen at 50 psi. The vessel was shaken for 12 h. The hydrogen atmosphere was replaced by argon and the solution was filtered through a celite pad. The pad was washed twice with ethyl acetate. The solvent was removed under reduced pressure. The product was used without further purification. Yield 148.35 mg. $^1$H NMR (CDCl$_3$, 300 MHz): δ 1.42 (s, 9H), 1.80-2.10 (m, 2H), 3.05 (bs, 1H), 3.30 (s, 3H), 3.34-3.50 (m, 3H), 4.00 (bs, 1H), 4.33-4.40 (m, 1H).

4-Methanesulfonyloxy-2-methoxymethyl-pyrrolidine-1-carboxylic acid t-butyl ester

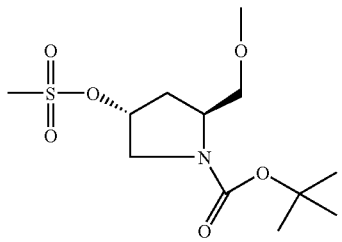

The 4-hydroxy-2-methoxymethyl-pyrrolidine-1-carboxylic acid t-butyl ester (148.35 mg, 0.64 mmol) was dissolved in anhydrous DCM and triethylamine (194.28 mg, 1.92 mmol, 0.27 mL) was added under argon. The reaction mixture was cooled to 0EC and methanesulfonyl chloride (80.64 mg, 0.70 mmol, 0.06 mL) was added via syringe. The reaction was stirred at 0EC for 30 min and then allowed to warm to room temp and stir for 12 h. The reaction was slowly poured into a 1N HCl solution and the aqueous layer was extracted three times with ethyl acetate. The combined organic layers were washed with water and brine then dried over MgSO$_4$. The solution was filtered and the solvent removed under reduced pressure. The product was isolated by flash chromatography. (2:1 hexane-ethyl acetate) Yield 172.26 mg. $^1$H NMR (CDCl$_3$, 300 MHz): δ 1.49 (s, 9H), 2.32 (bs, 2H), 3.04 (s, 3H), 3.35 (s, 3H), 3,44 (d, J=6 Hz, 1H), 3.49-3.88 (m, 3H); 4.11 (bs, 1H), 5.25 (m, 1H).

4-Azido-2-methoxymethyl-pyrrolidine-1-carboxylic acid t-butyl ester

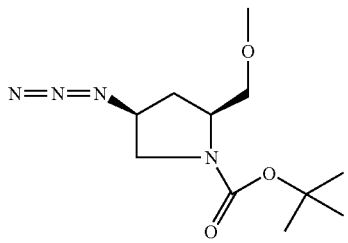

The 4-methanesulfonyloxy-2-methoxymethyl-pyrrolidine-1-carboxylic acid t-butyl ester (172.26 mg, 0.56 mmol) was taken up in dry DMF under argon and sodium azide (182.00 mg, 2.80 mmol) was added. The reaction was then heated to 60EC for 48 h. The reaction was poured into water and the aqueous layer was extracted three times with ethyl acetate. The combined organic layers were washed with sat NaHCO$_3$ and brine then dried over MgSO$_4$. The solution was filtered and the solvent removed under reduced pressure. The product was isolated by flash chromatography. (3:1 hexane-ethyl acetate) Yield 122.00 mg. C$_{11}$H$_{22}$N$_2$O$_3$ MS m/e=257.3 (M+H).

4-Amino-2-methoxymethyl-pyrrolidine-1-carboxylic acid t-butyl ester

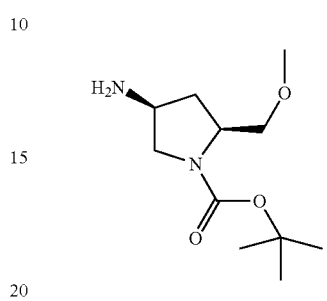

The 4-azido-2-methoxymethyl-pyrrolidine-1-carboxylic acid t-butyl ester (122.00 mg, 0.48 mmol) was taken up in ethyl acetate in a Paar vessel. The solution was flushed with argon and Pd/C (100.00 mg) was added to the vessel. The argon atmosphere was replaced by hydrogen at 50 psi. The vessel was shaken for 12 h. The hydrogen atmosphere was replaced by argon and the solution was filtered through a celite pad. The pad was washed twice with ethyl acetate. The solvent was removed under reduced pressure. The product was used without further purification. Yield 99.76 mg. C$_{11}$H$_{22}$N$_2$O$_3$ MS me/230.2 (M$^+$).

4-Benzyloxy-2-(t-butyl-dimethyl-silanyloxymethyl)-pyrrolidine-1-carboxylic acid t-butyl ester

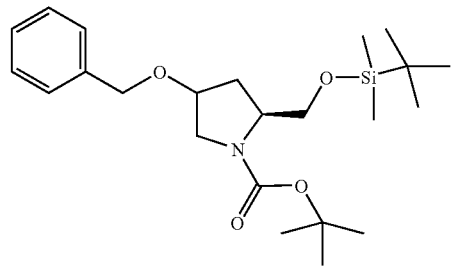

The 4-benzyloxy-2-hydroxymethyl-pyrrolidine-1-carboxylic acid t-butyl ester (250 mg, 0.81 mmol) was taken up in dry DMF under argon and imidazole (110.29 mg, 1.62 mmol) was added. T-butyldimethylsilylchloride (134.29 mg, 0.89 mmol) was added and the solution was stirred at room temp for 12 h. The reaction was slowly poured into a 1N HCl solution and the aqueous layer was extracted three times with ethyl acetate. The combined organic layers were washed with water and brine then dried over MgSO$_4$. The solution was filtered and the solvent removed under reduced pressure. The product was isolated by flash chromatography. (5:1 hexane-ethyl acetate) Yield 267.49 mg. $^1$H NMR (CDCl$_3$, 300 MHz): δ 0.02 (m, 6 h), 0.83 (s, 9H), 1.25 (s, 9H), 1.98-2.13 (m, 1H), 2.13-2.24 (m, 1H), 3.36-3.70 (m, 3H), 3.86-3.95 (m, 1H), 4.00 (bs, 1H), 4.15-4.28 (m, 1H), 4.50 (bs, 2H), 7.23-7.37 (m, 5H).

2-(t-Butyl-dimethyl-silanyloxymethyl)-4-hydroxy-pyrrolidine-1-carboxylic acid t-butyl ester

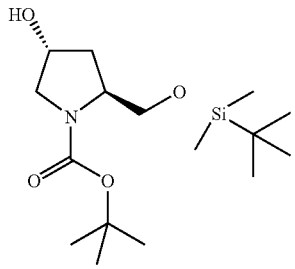

The 4-benzyloxy-2-(t-butyl-dimethyl-silanyloxymethyl)-pyrrolidine-1-carboxylic acid t-butyl ester (267.49 mg, 0.63 mmol) was taken up in ethyl acetate in a Paar vessel. The solution was flushed with argon and Pd/C (100 mg) was added to the vessel. The argon atmosphere was replaced by hydrogen at 50 psi. The vessel was shaken for 12 h. The hydrogen atmosphere was replaced by argon and the solution was filtered through a celite pad. The pad was washed twice with ethyl acetate. The solvent was removed under reduced pressure. The product was used without further purification. Yield 192.15 mg. $C_{16}H_{33}NO_4Si$ ms m/e=3.32.2 (M+H).

2-(t-Butyl-dimethyl-silanyloxymethyl)-4-methane sulfonyloxy-pyrrolidine-1-carboxylic acid t-butyl ester

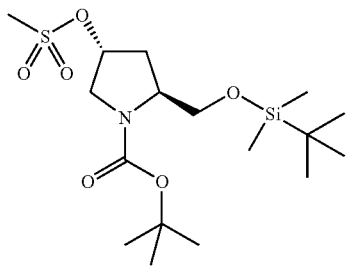

The 4-hydroxy-2-(t-butyl-dimethyl-silanyloxymethyl)-pyrrolidine-1-carboxylic acid t-butyl ester (192.15 mg, 0.58 mmol) was dissolved in anhydrous DCM and triethylamine (176.07 mg, 1.74 mmol, 0.24 mL) was added under argon. The reaction mixture was cooled to 0EC and methanesulfonyl chloride (73.08 mg, 0.64 mmol, 0.05 mL) was added via syringe. The reaction was stirred at 0EC for 30 min and then allowed to warm to room temp and stir for 12 h. The reaction was slowly poured into a 1N HCl solution and the aqueous layer was extracted three times with ethyl acetate. The combined organic layers were washed with water and brine then dried over $MgSO_4$. The solution was filtered and the solvent removed under reduced pressure. The product was isolated by flash chromatography. (4:1 hexane-ethyl acetate) Yield 220.94 mg. $^1$H NMR ($CDCl_3$, 300 MHz): δ 0.05 (m, 6H), 0.89 (s, 9H), 1.46 (s, 9H), 2.20-2.43 (m, 2H), 3.04 (s, 3H), 3.48-3.92 (m, 4H), 3.93-4.10 (m, 1H), 5.31 (bs, 1H).

4-Azido-2-(t-butyl-dimethyl-silanyloxymethyl)-pyrrolidine-1-carboxylic acid t-butyl ester

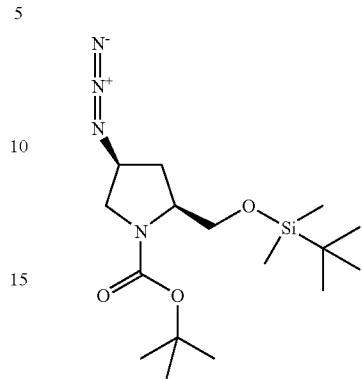

The 4-methanesulfonyloxy-2-(t-butyl-dimethyl-silanyloxymethyl)-pyrrolidine-1-carboxylic acid t-butyl ester (220.94 mg, 0.54 mmol) was taken up in dry DMF under argon and sodium azide (175.31 mg, 2.70 mmol) was added. The reaction was then heated to 60EC for 48 h. The reaction was poured into water and the aqueous layer was extracted three times with ethyl acetate. The combined organic layers were washed with sat $NaHCO_3$ and brine then dried over $MgSO_4$. The solution was filtered and the solvent removed under reduced pressure. The product was isolated by flash chromatography. (5:1 hexane-ethyl acetate) Yield 184.83 mg. $C_{16}H_{32}N_4O_3Si$-MS m/e=357.3 (M+H).

4-Amino-2-(t-butyl-dimethyl-silanyloxymethyl)-pyrrolidine-1-carboxylic acid t-butyl ester

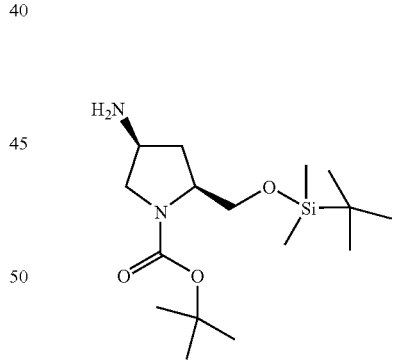

The 4-azido-2-(t-butyl-dimethyl-silanyloxymethyl)-pyrrolidine-1-carboxylic acid t-butyl ester (184.83 mg, 0.52 mmol) was taken up in ethyl acetate in a Paar vessel. The solution was flushed with argon and Pd/C (150 mg) was added to the vessel. The argon atmosphere was replaced by hydrogen at 50 psi. The vessel was shaken for 12 h. The hydrogen atmosphere was replaced by argon and the solution was filtered through a celite pad. The pad was washed twice with ethyl acetate. The solvent was removed under reduced pressure. The product was used without further purification. Yield 154.69 mg. $C_{16}H_{34}N_2O_3Si$ MS m/e=331.2 (M+H).

4-Benzyloxy-2-methanesulfonyloxymethyl-pyrrolidine-1-carboxylic acid t-butyl ester

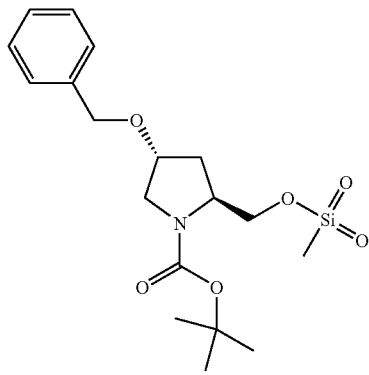

The 4-benzyloxy-2-hydroxymethyl-pyrrolidine-1-carboxylic acid t-butyl ester (219.09 mg, 0.71 mmol) was taken up in anhydrous DCM and triethylamine (215.53 mg, 2.13 mmol, 0.30 mL) was added under argon. The reaction mixture was cooled to 0EC and methanesulfonyl chloride (89.81 mg, 0.78 mmol, 0.06 mL) was added via syringe. The reaction was stirred at 0EC for 30 min and then allowed to warm to room temp and stir for 12 h. The reaction was slowly poured into a 1N HCl solution and the aqueous layer was extracted three times with ethyl acetate. The combined organic layers were washed with water and brine then dried over MgSO$_4$. The solution was filtered and the solvent removed under reduced pressure. The product was isolated by flash chromatography. (3:1 hexane-ethyl acetate) Yield 234.14 mg. $^1$H NMR (CDCl$_3$, 300 MHz): δ 1.47 (bs, 9H), 2.05-2.32 (m, 2H), 2.98 (s, 3H), 3.31-3.63 (m, 2H), 4.04-4.78-(m, 6H), 7.27-7.40 (m, 5H).

4-Hydroxy-2-methoxymethyl-pyrrolidine-1-carboxylic acid t-butyl ester

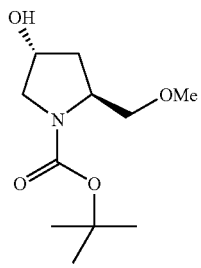

The 4-benzyloxy-2-methanesulfonyloxymethyl-pyrrolidine-1-carboxylic acid t-butyl ester (234.14 mg, 0.65 mmol) was taken up in anhydrous THF under argon and cooled to 0EC. Super-Hydride (1.0M, 0.98 mmol, 0.98 mL) was added via a syringe over 10 min. The solution was stirred for 1 h at 0EC, the TLC indicated that no starting material remained. The reaction mixture was slowly poured into a 1N HCl solution and the aqueous layer was extracted three times with ethyl acetate. The combined organic layers were washed with water and brine then dried over MgSO$_4$. The solution was filtered and the solvent removed under reduced pressure. The product was isolated by flash chromatography. (4:1 hexane-ethyl acetate) Yield 168.57 mg. $^1$H NMR (CDCl$_3$, 300 MHz): δ 1.22 (d, J=9.0 Hz, 3H), 1.44 (s, 9H), 1.65-1.77 (m, 1H), 2.13-2.24 (m, 1H), 3.45 (dd, J=7, 12 Hz, 1H), 3.61 (d, J=7 Hz, 1H), 3.94-4.04 (m, 1H), 4.50 (s, 2H), 7.27-7.39 (m, 5H).

4-Hydroxy-2-methyl-pyrrolidine-1-carboxylic acid t-butyl ester

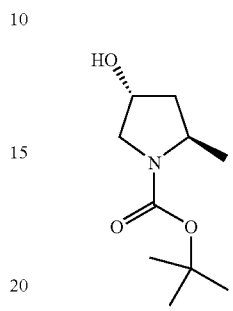

The 4-benzyloxy-2-methyl-pyrrolidine-1-carboxylic acid t-butyl ester (168.57 mg, 0.58 mmol) was taken up in ethyl acetate in a Paar vessel. The solution was flushed with argon and Pd/C (100.00 mg) was added to the vessel. The argon atmosphere was replaced by hydrogen at 50 psi. The vessel was shaken for 12 h. The hydrogen atmosphere was replaced by argon and the solution was filtered through a celite pad. The pad was washed twice with ethyl acetate. The solvent was removed under reduced pressure. The product was used without further purification. Yield 110.89 mg. C$_{10}$H$_{19}$NO$_3$ MS m/e=202.1(M+H).

4-Methanesulfonyloxy-2-methyl-pyrrolidine-1-carboxylic acid t-butyl ester

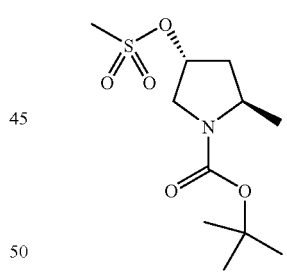

The 4-hydroxy-2-methyl-pyrrolidine-1-carboxylic acid t-butyl ester (110.89 mg, 0.55 mmol) was dissolved in anhydrous DCM and triethylamine (166.96 mg, 1.65 mmol, 0.23 mL) was added under argon. The reaction mixture was cooled to 0EC and methanesulfonyl chloride (69.30 mg, 0.61 mmol, 0.05 mL) was added via syringe. The reaction was stirred at 0EC for 30 min and then allowed to warm to room temp and stir for 12 h. The reaction was slowly poured into a 1N HCl solution and the aqueous layer was extracted three times with ethyl acetate. The combined organic layers were washed with water and brine then dried over MgSO$_4$. The solution was filtered and the solvent removed under reduced pressure. The product was isolated by flash chromatography. (3:1 hexane-ethyl acetate) Yield 135.21 mg. $^1$H NMR (CDCl$_3$, 300 MHz):

δ 1.27 (D, J=9 Hz, 3H), 1.48 (s, 9H), 1.81-1.92 (m, 1H), 2.43 (bs, 1H), 3.04 (s, 3H), 3.56 (dd, J=7.17 Hz, 1H), 3.84 (bs, 1H), 4.01 (bs, 1H), 5.17 (bs, 1H).

4-Azido-2-methyl-pyrrolidine-1-carboxylic acid t-butyl ester

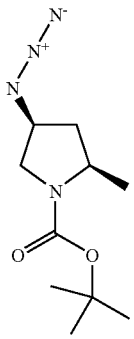

The 4-methanesulfonyloxy-2-methyl-pyrrolidine-1-carboxylic acid t-butyl ester (135.21 mg, 0.48 mmol) was taken up in dry DMF under argon and sodium azide (156.00 mg, 2.40 mmol) was added. The reaction was then heated to 60EC for 48 h. The reaction was poured into water and the aqueous layer was extracted three times with ethyl acetate. The combined organic layers were washed with sat NaHCO₃ and brine then dried over MgSO₄. The solution was filtered and the solvent removed under reduced pressure. The product was isolated by flash chromatography. (5:1 hexane-ethyl acetate) Yield 93.41 mg.

¹H NMR (CDCl₃, 300 MHz): δ 1.32 (d, J=9 Hz, 3H), 1.47 (s, 3H), 1.72 (dt, J=2, 12 Hz, 1H), 2.28-2.37 (m, 1H), 3.34 (dd, J=7, 12 Hz, 1H), 3.63-3.72 (m, 1H), 3.93 (bs, 1H), 4.05-4.14 (m, 1H).

4-Amino-2-methyl-pyrrolidine-1-carboxylic acid t-butyl ester

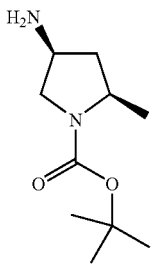

The 4-azido-2-methyl-pyrrolidine-1-carboxylic acid t-butyl ester (93.41 mg, 0.41 mmol) was taken up in ethyl-acetate in a Paar vessel. The solution was flushed with argon and Pd/C (100.00 mg) was added to the vessel. The argon atmosphere was replaced by hydrogen at 50 psi. The vessel was shaken for 12 h. The hydrogen atmosphere was replaced by argon and the solution was filtered through a celite pad. The pad was washed twice with ethyl acetate. The solvent was removed under reduced pressure. The product was used without further purification. Yield 79.65 mg.C₁₀H₂₀N₂O₂ MS m/e=200.2 (M+).

2-Methyl-4-(4-nitro-benzoyloxy)-pyrrolidine-1-carboxylic acid t-butyl ester

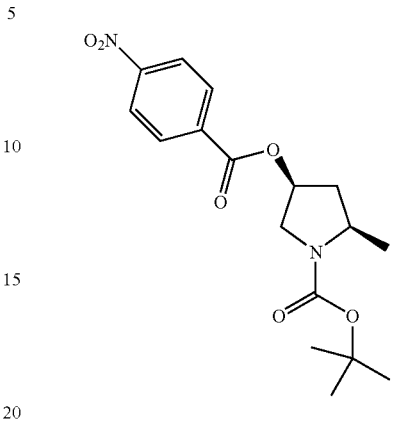

The 4-hydroxy-2-methyl-pyrrolidine-1-carboxylic acid t-butyl ester (300.00 mg, 1.49 mmol) and triphenyl phosphine (512.54, 1.95 mmol) were dissolved in anhydrous THF and added to a mixture of para-nitrobenzoic acid (249.00 mg, 1.49 mmol) and DEAD (268.00 mg, 1.54 mmol, 0.24 mL) in anhydrous THF at 0EC under argon. The mixture was stirred for 1 h at 0EC. After 1 h the TLC indicated no starting material remained and the reaction mixture was poured into a 1N HCl solution and the aqueous layer was extracted three times with ethyl acetate. The combined organic layers were washed with water and brine then dried over MgSO₄. The solution was filtered and the solvent removed under reduced pressure. The product was isolated by flash chromatography. (2:1 hexane-ethyl acetate) Yield 391.54 mg. ¹H NMR (CDCl₃, 300 MHz): δ 1.39 (d, J=9 Hz, 3H), 1.49 (s, 9H), 1.99 (d, J=15 Hz, 1H), 2.24-2.33 (m, 1H), 3.62-3.71 (m, 1H), 3.82 (dd, J=7, 12 Hz, 1H), 4.13 (bs, 1H), 5.52-5.56 (m, 1H), 8.20-8.35 (m, A₂B₂, 4H).

4-Hydroxy-2-methyl-pyrrolidine-1-carboxylic acid t-butyl ester

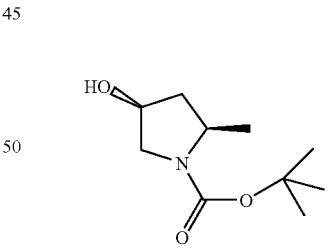

The 4-hydroxy-2-methyl-pyrrolidine-1-carboxylic acid t-butyl ester (391.54 mg, 1.12 mmol) was dissolved in a 4:1 mixture of THF-water and LiOH (5.59 mmol) was added. The mixture was stirred for 12 h at room temp. The reaction mixture was poured into a 1N HCl solution and the aqueous layer was extracted three times with ethyl acetate. The combined organic layers were washed with water and brine then dried over MgSO₄. The solution was filtered and the solvent removed under reduced pressure. The product was isolated by flash chromatography. (2:1 hexane-ethyl acetate) Yield 220.90 mg.

$^1$H NMR (CDCl$_3$, 300 MHz): δ 1.35 (d, J=9 Hz, 3H), 1.46 (s, 9H), 1.67 (dt, J=2, 15 Hz, 1H), 3.38 (bs, 1H), 3.60 (dd, J=7, 17 Hz, 1H), 3.84-3.97 (m, 1H), 4.34-4.42 (m, 1H).

4-Amino-2-methyl-pyrrolidine-1-carboxylic acid t-butyl ester

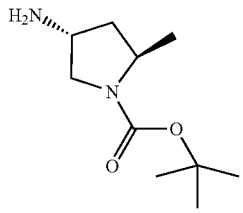

The R-isomer was prepared by the proceeding experimental procedures. Yield 163.99 mg

4-Hydroxy-pyrrolidine-1,2-dicarboxylic acid 1-t-butyl ester 2-methyl ester

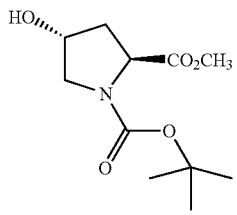

4-Benzyloxy-pyrrolidine-1,2-dicarboxylic acid 1-t-butyl ester 2-methyl ester (500 mg, 1.49 mmol) was taken up in ethyl acetate in a Paar vessel. The solution was flushed with argon and Pd/C (200 mg) was added to the vessel. The argon atmosphere was replaced by hydrogen at 50 psi. The vessel was shaken for 12 h. The hydrogen atmosphere was replaced by argon and the solution was filtered through a celite pad. The pad was washed twice with ethyl acetate. The solvent was removed under reduced pressure. The product was used without further purification. Yield 350.98 mg. C$_{11}$H$_{19}$NO$_5$ MS m/e=246.2 (M+H).

4-Methanesulfonyloxy-pyrrolidine-1,2-dicarboxylic acid 1-t-butyl ester 2-methyl ester

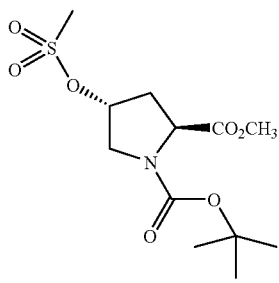

4-Hydroxy-pyrrolidine-1,2-dicarboxylic acid 1-t-butyl ester 2-methyl ester (350.98 mg, 1.43 mmol) was dissolved in anhydrous DCM and triethylamine (434.11 mg, 4.29 mmol, 0.6 mL) was added under argon. The reaction mixture was cooled to 0EC and methanesulfonyl chloride (180.19 mg, 1.57 mmol, 0.12 mL) was added via syringe. The reaction was stirred at 0EC for 30 min and then allowed to warm to room temp and stir for 12 h. The reaction was slowly poured into a 1N HCl solution and the aqueous layer was extracted three times with ethyl acetate. The combined organic layers were washed with water and brine then dried over MgSO$_4$. The solution was filtered and the solvent removed under reduced pressure. The product was isolated by flash chromatography. (2:1 hexane-ethyl acetate) Yield 406.92 mg. C$_{12}$H$_{21}$NO$_7$S MS m/e=323.1 (M+H).

4-Azido-pyrrolidine-1,2-dicarboxylic acid 1-t-butyl ester 2-methyl ester

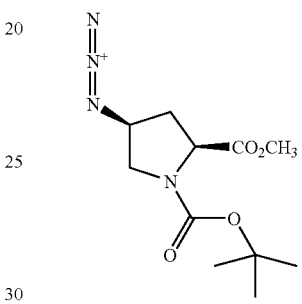

4-Methanesulfonyloxy-pyrrolidine-1,2-dicarboxylic acid 1-t-butyl ester 2-methyl ester (406.92 mg, 1.26 mmol) was taken up in dry DMF under argon and sodium azide (409.50 mg, 6.30 mmol) was added. The reaction was then heated to 60EC for 48 h. The reaction was poured into water and the aqueous layer was extracted three times with ethyl acetate. The combined organic layers were washed with sat NaHCO$_3$ and brine then dried over MgSO$_4$. The solution was filtered and the solvent removed under reduced pressure. The product was isolated by flash chromatography. (3:1 hexane-ethyl acetate) Yield 303.10 mg. C$_{11}$H$_{18}$N$_4$O$_4$ MS m/e 271.2 (M+H).

4-Amino-pyrrolidine-1,2-dicarboxylic acid 1-t-butyl ester 2-methyl ester

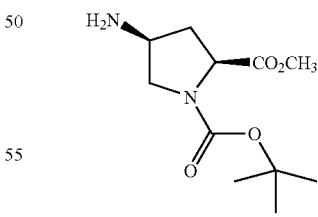

4-Azido-pyrrolidine-1,2-dicarboxylic acid 1-t-butyl ester 2-methyl ester (303.10 mg, 1.12 mmol) was taken up in ethyl acetate in a Paar vessel. The solution was flushed with argon and Pd/C (400.00 mg) was added to the vessel. The argon atmosphere was replaced by hydrogen at 50 psi. The vessel was shaken for 12 h. The hydrogen atmosphere was replaced by argon and the solution was filtered through a celite pad. The pad was washed twice with ethyl acetate. The solvent was removed under reduced pressure. The product was used without further purification. Yield 262.66 mg. $C_{11}H_{20}N_2O_4$ MS m/e=244.2 (M+).

(3R)-3-Aminopyrrolidine-1-carboxylic acid t-butyl ester

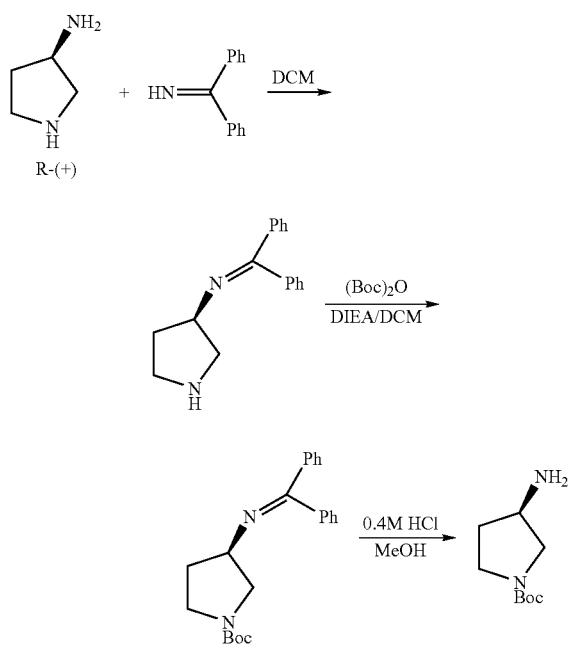

To a solution of (3R)-(+)-3-aminopyrrolidine (5.0 G, 58.0 mmol) in DCM (100 mL), benzophenone imine (10.52 g, 58.0 mmol) was added at room temp. The mixture was stirred for 18 h. Imine was obtained by removal of the solvent under reduced pressure.

DCM (120 mL) and DIEA (20.0 mL, 115.1 mmol) were added to the imine, and di-t-butyl dicarbonate (14.0 g, 63.8 mmol) was then added to the solution in portions. The reaction was stirred for 4 h at room temp. The mixture was poured into brine and extracted with DCM (3×40 mL). The combined organic phase was dried over $Na_2SO_4$ and then concentrated. The residue was purified by silica gel chromatography (first with 10% ethyl acetate-hexane, and then 20% ethyl acetate-hexane as eluent). The Boc-amine was obtained as white solid. (12.89 g, 63%). MS (m/z) calcd for $C_{22}H_{26}N_2O_2$ (MH+), 351; found, 351.

To the methanol solution (100 mL) of Boc-amine at) 0EC, 0.4 M HCl (110.0 mL, 44.2 mmol) was added, and the resulting solution was stirred for 2 h at 0EC. The mixture was poured into water and washed with DCM (3×40 mL). 6N NaOH was added to adjust the aqueous phase to pH 10, and the product was extracted with ethyl acetate (3×40 mL). The organic layer was dried over $Na_2SO_4$, and subsequent concentration yielded the product, (3R)-3-amino-pyrrolidine-1-carbonylic acid t-butyl ester as white solid (6.0 g, 88%). MS (m/z) calcd for $C_9H_{18}N_2O_2$ (MH=), 187; found, 187.

(2,2-Dimethyl-propyl)-ethyl-amine

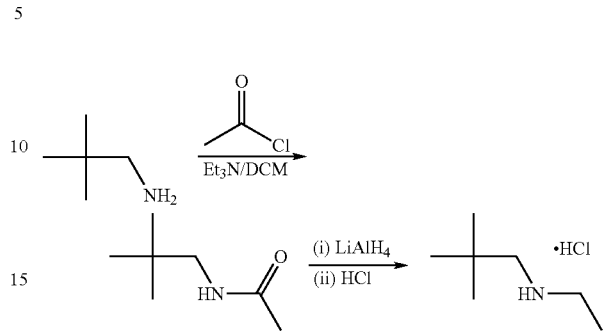

A solution of neopentylamine (2.0 g, 23.0 mmol), acetyl chloride (1.96 mL, 27.6 mmol), triethylamine (3.84 mL, 27.5 mmol), and DCM (100 mL) were stirred at room temp for 2 h. The mixture was poured into water and extracted with DCM (3×40 mL). The organic phase was dried over $Na_2SO_4$, and the solvent was removed to afford N-neopentylacetamide as white solid (2.90 g, 98%). NMR confirmed the structure of N-neopentylacetamide.

To a THF (100 mL) solution of N-neopentylacetamide (2.90 g, 22.5 mmol), 1M LiAlH$_4$ (28 mL, 28.0 mmol) in THF was added dropwise at room temp, and the reaction was stirred for 18 h at 70EC. After cooling, 1N NaOH (28.0 mL) was added dropwise to the solution. The mixture was stirred for 15 min, and the white suspension solution was filtered through celite. 1M HCl in dioxane (10 mL) was added to the solution, and the mixture was stirred for 15 min. The solvent was removed to afford (2,-dimethyl-propyl)-ethyl-amine as HCl salt (3.10 g, 89%). MS (m/z) calcd for $C_7H_{17}N$ (MH+), 116; found, 231 (dimer).

Methyl-(1-methyl-cyclopentylmethyl)-amine

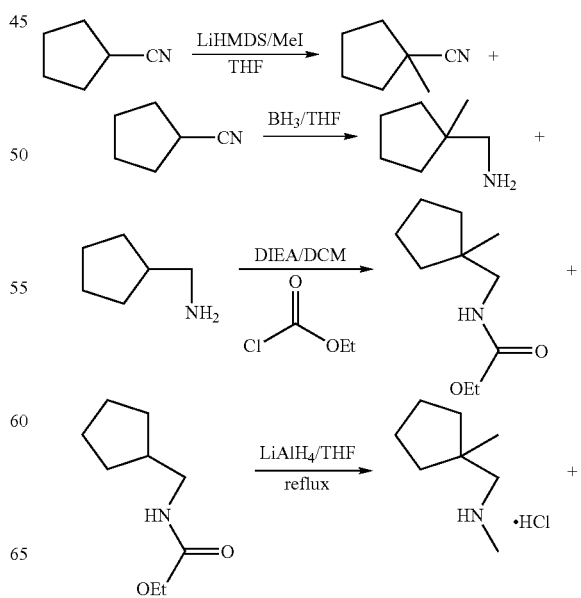

-continued

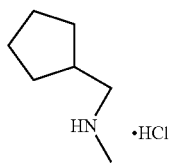

To a THF solution (5 mL) of cyclopentanecarbonitrile (4.39 mL, 42.0 mmol), 2M NaHMDS (25.0 mL, 50.0 mmol) in THF was added dropwise under argon at 0EC. The reaction was stirred for 15 min and methyl iodide (3.14 mL, 50.4 mmol) was then added dropwise to the solution at 0EC. The reaction was stirred for 2 h at 0EC, and 1M BH$_3$ (126 mL, 126 mmol) in THF was added to the mixture at room temp. The mixture was stirred for 3 h, and 6N HCl was added dropwise to the mixture at 0EC until pH reached 2. The mixture was stirred for 15 min. The mixture was poured into water and washed with DCM (3×40 mL). NaOH was added to the aqueous phase to adjust the pH to 11. (1-methyl-dicyclopentylmethyl)-amine was extracted with ethyl acetate (3×40 mL). The organic phase was dried over Na$_2$SO$_4$. The solvent was removed to afford (1-methyl-cyclopentylmethyl)-amine as yellow oil (2.0 g, 44%). MS (m/z) calced for C$_7$H$_{15}$N (MH$^+$), 114; found, 227 (dimer), 340 (trimer).

A solution of (1-methyl-cyclopentylmethyl)-amine (1.5 g, 13.3 mmol), ethyl chloroformate (1.52 mL, 16 mmol), and N,N-DIEA (2.79 mL, 16.0 mmol) in DCM (50 mL) was stirred at room temp for 18 h. The mixture was poured into water and extracted with DCM (3×40 mL). The organic phase was dried over Na$_2$SO$_4$, and the solvent was removed to afford (1-methyl-cyclopentylmethyl)-carbamic acid ethyl este4 as colorless oil (1.62 g, 66%). MS (m/z) calced for C$_{10}$H$_{19}$NO$_2$ (MH$^+$), 186; found 186.

To a THF solution (15 mL) of (1-methyl-cyclopentylmethyl)-carbamic acid ethyl ester (0.84 g, 4.54 mmol), 1M LiAlH$_4$ (5.45 mL, 5.45 mmol) in THF was added dropwise at room temp. The reaction was stirred for 18 h at 70EC. After cooling, 1N, NaOH (5.45 mL) was added dropwise to the solution. The mixture was stirred for 15 min. The white suspension was filtered through celite. 1M HCl (3 mL) in dioxane was added to the solution. The mixture was stirred for 15 min. The solvent was removed to afford methyl-(1-methyl-cyclopentylmethyl)-amine as HCl salt (380 mg, 51%). MS (m/z) calced for C$_8$H$_{17}$N (MH$^+$), 128; found, 128; found 128, 255 (dimer).

3-Amino-N-ethyl-4-methyl-benzamide

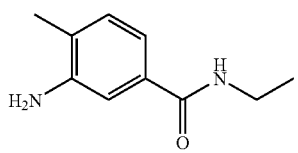

4-methyl-3-nitro-benzoyl chloride (1.0 g, 5.0 mmol) was dissolved in DCM, and the solution was cooled to 0EC. Ethyl amine (2.0M in THF, 5.0 mL, 10 mmol) was added dropwise to the acid chloride, and the reaction stirred at 0EC for 5 min. The ice bath was removed and reaction continued to stir for 3. The solution was washed with brine, dried (Na$_2$SO$_4$), and concentrated in vacuo. The resulting aniline (0.75 g) was used without further purification.

Coupling of Cyanuric Chloride with Aminobenzamide 1. 3-Chloro-5-(4,6-dichloro-[1,3,5]triazin-2-ylamino)-4-methyl-benzamide

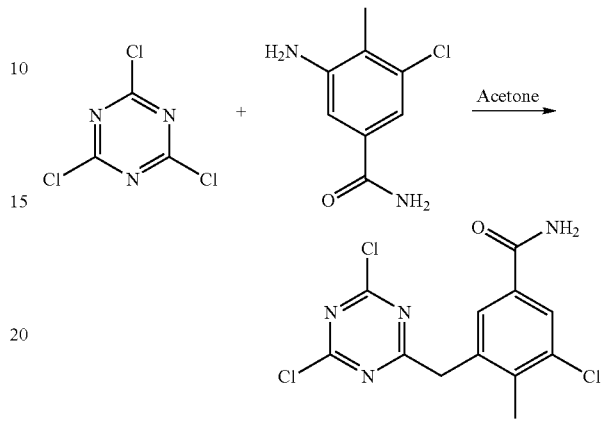

Cyanuric chloride (65.0 mg, 0.35 mmol) was added to an acetone solution (5 mL) of 3-amino-5-chloro-4-methyl-benzamide (65.0 mg, 0.35 mmol) at 0EC. The mixture was stirred for 1 h at 0EC. Ice was added to the mixture and subsequent filtration yielded of 3-chloro-5-(4,6-dichloro-[1,3,5]triazin-2-ylamino)-4-methyl-benzamide (101.0 mg, 87%) as white solid. MS (m/z) calced for C$_{11}$H$_8$N$_5$O (MH$^+$), 331: found, 331.

2. 3-(4,6-Dichloro-[1,3,5]triazin-2-ylamino)-4-methyl N-phenethyl-benzamide

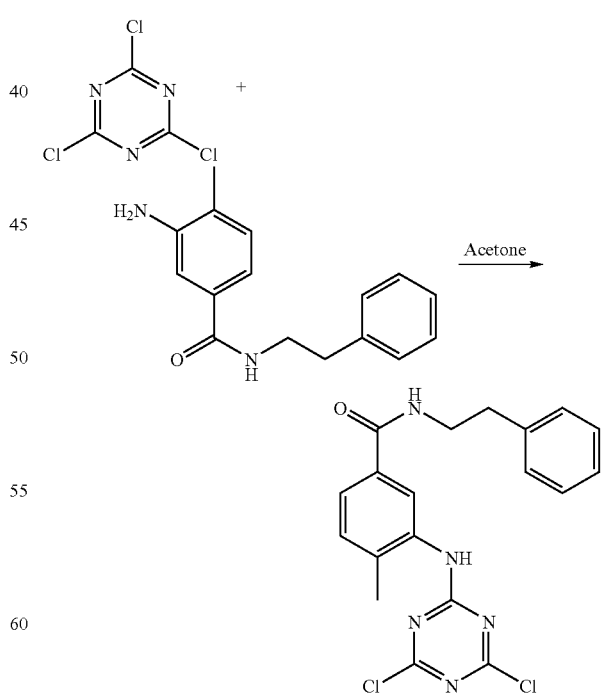

Cyanuric chloride (0.74 g, 4.02 mL) was added to an acetone solution (15 mL) of 3-amino-4-methyl-N-phenethyl-benzamide (1.02 g, 4.02 mmol) at 0EC. The mixture was stirred for 1 h at 0EC. Ice was added to the mixture and stirred for 15 min. The solvent was removed to afford 3-(4,6-dichloro-[1,3,5]triazin-2-ylamino)-4-methyl N-phenethyl-benzamide (1.52 g, 94%) as white solid MS (m/z) calced for $C_{19}H_{17}Cl_2N_5O$ (MH+), 402; found, 402.

N,N-Diethyl-4-methyl-benzamide

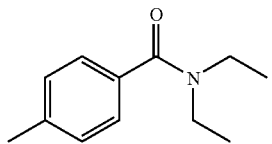

Dimethyl amine (13.00 g, 177.87 mmol, 18.40 mL) and pyridine (38.37 g, 485.10 mmol, 39.23 mL) were dissolved in 500 mL of anhydrous DCM under argon and cooled to 0EC. p-Tolyl chloride (25.00 g, 161.70 mmol), dissolved in 75 mL of anhydrous DCM, was added to the solution slowly. On completion of addition the solution was slowly warmed to room temp and stirred for 12 h. The reaction mixture was poured into 1N HCl and the aqueous layer was extracted three times with ethyl acetate. The combined organic layers were washed with saturated sodium bicarbonate, water, brine and dried over anhydrous magnesium sulfate. The solution was filtered and the solvent removed under reduced pressure. The product was isolated by flash chromatography. (4:1 hexane/ethyl acetate) Yield 25.36 g.

N,N-Diethyl-2-formyl-4-methyl-benzamide

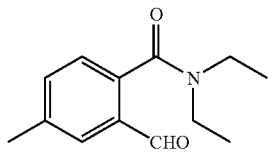

Tetramethylethyleneamine (6.20 g, 5336 mmol, 8.05 mL) was dissolved in anhydrous THF (100 mL) under argon and cooled to minus 78EC. s-Butyl lithium (1.30M, 53.36 mmol, 41.04 mL) was added to the solution slowly via syringe. The solution was stirred for 10 min at minus 78EC, then N,N-diethyl-4-methyl-benzamide (9.28 g, 48.51 mmol), dissolved in 50 mL of anhydrous THF was added to the reaction mixture over 15 min. The reaction was stirred for 1 h at minus 78EC, the DMF (7.09 g, 97.02 mol, 7.51 mL) was added to the solution rapidly. The reaction mixture was allowed to slowly warm to room temp and stir for 12 h. The reaction mixture was poured into 1N HCl and the aqueous layer was extracted three times with ethyl acetate. The combined organic layers were washed with saturated sodium bicarbonate, water, brine and dried over anhydrous magnesium sulfate. The solution was filtered and the solvent removed under reduced pressure. The product was isolated by flash chromatography. (3:1 hexane/ethyl acetate) Yield 7.98 g. $^1$H NMR (CDCl$_3$, 300 MHz):

δ 1.08 (t, 3H), 1.32 (t, 3H), 2.46 (s, 3H), 3.13 (q, 2H), 3.42 (a, 2H), 7.28 (d, J=8, 1H), 7.45 (d, J=7, 1H), 7.77 (s, 1H), 10.01 (s, 1H).

3-Hydroxy-5-methyl 3H-isobenzofuran-1-one

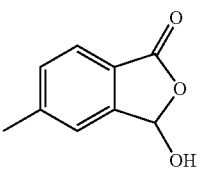

N,N-diethyl-2-formyl-4-methyl-benzamide (7.98 g, 36.39 mmol) was taken up in 100 mL of 6N HCl and heated to reflux for 48 h. The reaction was then cooled to room temp and diluted with 50 mL of water. The aqueous layer was extracted three times with ethyl acetate. The combined organic layers were washed with saturated sodium bicarbonate, water, brine and dried over anhydrous magnesium sulfate. The solution was filtered and the solvent removed under reduced pressure. The product was isolated by flash chromatography. (3:1 hexane/ethyl acetate) Yield 4.66 g. $^1$H NMR (CDCl$_3$, 300 MHz): δ 2.47 (s, 3H), 6.05 (bs, 1H), 7.12 (s, 1H), 7.33 (d, J=9, 1H), 7.95 (d, J=9, 1H).

8-Methyl-3-phenyl-23-dihydro-9bH-oxazolo[2,3-a]isoindol-5-one

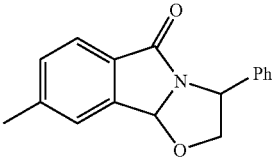

3-hydroxy-5-methyl-3H-isobenzofuran-1-one (4.66 g, 28.39 mmol) and H-phenylglycinol (3.89 g, 28.39 mmol) was taken up in dry toluene and heated to reflux under argon for 12 h. The water generated was collected in a Dean-Stark trap. The reaction mixture was cooled to room temp and poured into 1N HCl and the aqueous layer was extracted three times with ethyl acetate. The combined organic layers were washed with saturated sodium bicarbonate, water, brine and dried over anhydrous magnesium sulfate. The solution was filtered and the solvent removed under reduced pressure. The product was isolated by flash chromatography. (4:1 hexane/ethyl acetate) Yield 5.20 g.

$^1$H NMR (CDCl$_3$, 300 MHz): δ 2.49 (s, 3H), 4.16 (dd, J=7, 9 Hz, 1H), 4.83 (dd, J=8, 9 Hz, 1H), 5.21 (t, J=7, 1H), 6.01 (s, 1H), 7.31-7.45 (m, 1H), 7.73 (d, J=8 Hz, 1H).

2-(2-Hydroxy-1-phenyl-ethyl)-5-methyl-2,3-dihydro-isoindol-1-one

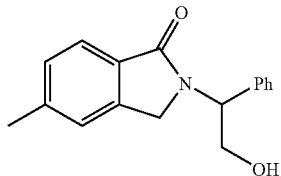

8-methyl-3-phenyl-2,3-dihydro-9bH-oxazolo[2,3-a]isoindol-5-one (5.20 g, 19.60 mmol) was taken up in anhydrous DCM (100 mL) under argon and cooled to minus 78EC. Triethylsilane (9.12 g, 78.40 mmol, 12.52 mL) was added via syringe followed by titanium tetrachloride in DCM (1.0M, 58.80 mmol, 58.80 mL). The solution was stirred at minus 78EC for 5 h then allowed to warm to room temp and stir for 12 h. The reaction was slowly poured into ice and the aqueous layer was extracted three times with ethyl acetate. The combined organic layers were washed with saturated sodium bicarbonate, water, brine and dried over anhydrous magnesium sulfate. The solution was filtered and the solvent removed under reduced pressure. The product was isolated by flash chromatography. (1:1 hexane/ethyl acetate) Yield 4.72 g. $^1$H NMR (CDCl$_3$, 300 MHz): δ 2.40 (s, 3H), 4.12-4.42 (m, 5H), 5.31 (dd, J=4, 8 Hz, 1H), 7.10-7.39 (m, 7H), 7.67 (d, J=8, 1H).

Methanesulfonic acid 2-(5-methyl-1-oxo-1,3-dihydro-isoindol-2-yl)-2-phenyl-ethyl ester

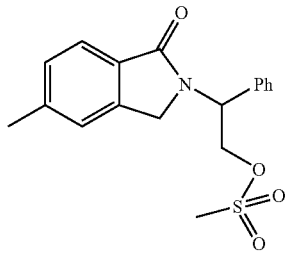

2-(2-Hydroxy-1-phenyl-ethyl)-5-methyl-2,3-dihydro-isoindol-1-one (4.72 g, 17.66 mmol) and triethylamine (5.36 g, 53.97 mmol, 7.38 mL) were taken up in anhydrous DCM (50 mL), under argon and cooled to 0EC. Methanesulfonyl chloride (2.22 g, 19.43 mmol, 1.5 mL) was added to the reaction over 10 min. The reaction was stirred for 1 h at 0EC then allowed to slowly warm to room temp and stirred for 4 h. The reaction was slowly poured into saturated sodium bicarbonate and the aqueous layer was extracted three times with ethyl acetate. The combined organic layers were washed with 1N HCl, water, brine and dried over anhydrous magnesium sulfate. The solution was filtered and the solvent removed under reduced pressure. The product was used in the next step without further purification. Yield 5.61 g. $^1$H NMR (CDCl$_3$, 300 MHz): δ 2.44 (s, 3H), 3.01 (s, 3H), 4.15 (d, J=16 Hz, 1H), 4.43 (d, J=17 Hz, 1H), 4.77 (dd, J=5, 11 Hz, 1H), 5.03 (dd, J=9, 11 Hz, 1H), 5.76 (dd, J=5, 9 Hz, 1H), 7.20-7.38 (, 7H), 7.76 (d, J=8, 1H).

5-Methyl-2-(phenyl-allyl)-2,3-dihydro-isoindol-1-one

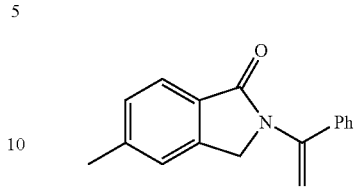

Under argon sodium metal (0.58 g, 24.37 mmol) was slowly added to anhydrous ethanol. After all the sodium was reacted methanesulfonic acid 2-(5-methyl-1-oxo-1,3-dihydro-isoindol-2-yl)-2-phenyl-ethyl ester (5.61 g, 16.25 mmol) dissolved in ethanol was added to the reaction mixture and the solution was stirred for 6 h at room temp. The reaction was poured into water and the aqueous layer was extracted three times with ethyl acetate. The combined organic layers were washed with brine and dried over anhydrous magnesium sulfate. The solution was filtered and the solvent removed under reduced pressure. The product was used in the next step without further purification. Yield 3.64 g.
$^1$H NMR (CDCl$_3$, 300 MHz): δ 2.45 (s, 3H), 4.49 (s, 2H), 5.50 (s, 1H), 5.54 (s, 1H), 7.22-7.36 (m, 7H), 7.80 (d, J=8 Hz, 1H).

5-Methyl-2,3-dihydro-isoindol-1-one

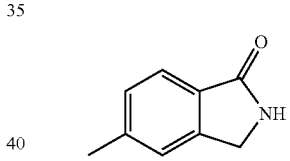

5-Methyl-2-(phenyl-allyl)-2,3-dihydro-isoindol-1-one (3.64 g, 14.61 mmol) was taken up in a 50/50 mixture of ethanol-3M HCl (100 mL) and heated to 80EC for 12 h. The reaction mixture was cooled and the ethanol was removed under reduced pressure. The aqueous layer was extracted three times with ethyl acetate and the combined organic layers were washed with water, brine and dried over anhydrous magnesium sulfate. The solution was filtered and the solvent removed under reduced pressure. The product was isolated by flash chromatography. (1:1 hexane/ethyl acetate) Yield 1.40 g. $^1$H NMR (CDCl$_3$, 300 MHz): δ 2.51 (s, 3H), 4.48 9s, 2H), 7.27-7.36 (m, 2H), 7.75 (d, J=8 Hz, 1H).

5-Methyl-4-nitro-2,3-dihydro-isoindol-1-one

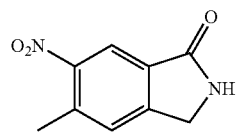

5-Methyl-6-nitro-2,3-dihydro-isoindol-1-one

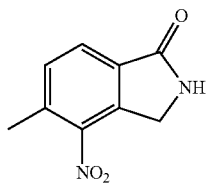

5-Methyl-2,3-dihydro-isoindol-1-one (1.00 g, 6.79 mmol) was taken up in sulfuric acid and cooled to 0EC. One equivalent of nitric acid was added to the solution and the mixture was allowed to slowly warm to room temp and stir for 12 h. The reaction mixture was poured into ice water and the aqueous layer was extracted four times with ethyl acetate and the combined organic layers were washed with water, brine and dried over anhydrous magnesium sulfate. The solution was filtered and the solvent removed under reduced pressure. Two products were isolated by flash chromatography. (10% methanol-ethyl acetate) Yield 813.40 mg of the 4-nitro and 100 mg of the 6-nitro. $^1$H NMR (300 MHz, $d_6$-DMSO): 4-nitro δ 7.76 (s, 1H), 8.19 (s, 1H), 8.98 (bs, 1H); 6-nitro δ 7.69 (d, J=9 Hz, 1H), 7.84 (d, J=9 Hz, 1H), 8.91 (bs, 1H).

6-Amino-5-methyl-2.3-dihydro-isoindol-1-one

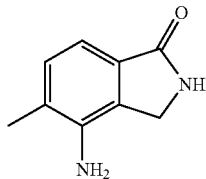

5-Methyl-6-nitro-2,3-dihydro-isoindol-1-one (100.00 mg, 0.52 mmol) was taken up in ethyl acetate in a Paar vessel and flushed with argon. Palladium on carbon (25 mg) was added and the argon atmosphere was replaced with hydrogen at 50 psi. The vessel was shaken for 12 h. The hydrogen was then replaced with argon and the catalyst was removed by filtration through celite. The solvent was removed under reduced pressure to yield 65.8 mg of the desired amine. $C_9H_{10}N_2O$ MS m/e=163.2 (M+H).

4-Amino-5-methyl-2,3-dihydro-isoindol-1-one

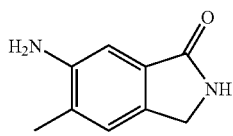

5-Methyl-4-nitro-2,3-dihydro-isoindol-1-one (800.00 mg, 4.16 mmol) was taken up in ethyl acetate in a Paar vessel and flushed with argon. Palladium on carbon (100 mg) was added and the argon atmosphere was replaced with hydrogen at 50 psi. The vessel was shaken for 12 h. The hydrogen was then replaced with argon and the catalyst was removed by filtration through celite. The solvent was removed under reduced pressure to yield 539.8 mg of the desired amine. $C_9H_{10}N_2O$ MS m/e=163.2 (M+H).

2,2,2-Trifluoro-N-(2-methyl-5-nitro-phenyl)-acetamide

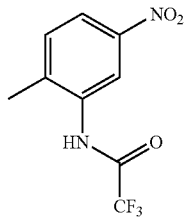

2-Methyl-5-nitro-phenylamine (3.00 g, 1972 mmol) was taken up in dry DCM, under argon, and triethylamine (3.99 g, 39.44 mmol, 5.50 mL) and DMAP (0.24 g, 1.97 mmol) were added. The reaction was cooled to 0EC and trifluoroacetic anhydride (6.21 g, 29.58 mmol, 4.18 mL) was added slowly via syringe. The reaction was allowed to slowly warm to room temp and stirred for 12 h. The reaction mixture poured into 1N HCl and the aqueous layer was extracted three times with ethyl acetate. The combined organic layers were washed with saturated sodium bicarbonate, water, brine and dried over anhydrous magnesium sulfate. The solution was filtered and the solvent removed under reduced pressure. The product was isolated by flash chromatography. (3:1 hexane/ethyl acetate) Yield 3.91 g. $^1$H NMR (CDCl$_3$, 300 MHz): δ 2.43 (s, 3H), 7.45 (d, J=9 Hz, 1H), 8.10 (d, J=9 Hz, 1H), 8.69 (s, 1H).

N-(5-Amino-2-methyl-phenyl)-2,2,2-trifluoro-acetamide

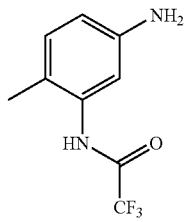

2,2,2-Trifluoro-N-(2-methyl-5-nitro-phenyl)-acetamide-(3.91 g, 15.78 mmol) was taken up in ethyl acetate in a Paar vessel and flushed with argon. Palladium on carbon (400 mg) was added and the argon atmosphere was replaced with hydrogen at 50 psi. The vessel was shaken for 12 h. The hydrogen was then replaced with argon and the catalyst was removed by filtration through celite. The solvent was removed under reduced pressure to yield 3.27 g of the desired amine. $C_9H_9F_3N_2O$ MS m/e=219.1 (M+H).

N-(5-Acetylamino-2-methyl-phenyl)-2,2,2-trifluoro-acetamide

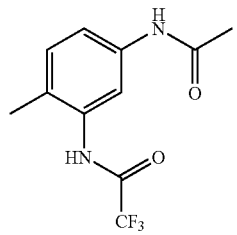

N-(5-Amino-2-methyl-phenyl)-2,2,2-trifluoro-acetamide (3.27 gm 14.99 mmol) was taken up on anhydrous DCM (75 mL) and cooled to 0EC. Pyridine (3.56 g, 44.97 mmol, 3.64 mL) was added followed by a slow addition of acetyl chloride (1.18 g, 14.99 mol, 1.07 mL). The reaction was allowed to warm to room temp and stir for 30 min. The reaction mixture poured into 1N HCl and the aqueous layer was extracted three times with ethyl acetate. The combined organic layers were washed with saturated sodium bicarbonate, water, brine and dried over anhydrous magnesium sulfate. The solution was filtered and the solvent removed under reduced pressure. The product was isolated by flash chromatography. (3:1 hexane/ethyl acetate) Yield 2.93 g. $^1$H NMR (CDCl$_3$, 300 MHz) δ 2.13 (s, 3H), 2.23 (s, 3H), 7.25 (d, J=9 Hz, 1H), 7.23 (d, J=9 Hz, 1H), 7.61 (s, 1H).

N-(3-Amino-4-methyl-phenyl)-acetamide

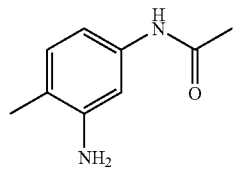

N-(5-Acetylamino-2-methyl-phenyl)-2,2,2-trifluoro-acetamide (2.93 g, 11.24 mmol) was taken up in methanol (50 mL) and sodium carbonate (5.96 g, 56.20 mmol) was added. The reaction was stirred at room temp for 12 h. The reaction mixture was into water and the aqueous layer was extracted three times with ethyl acetate. The combined organic layers were washed with brine and dried over anhydrous magnesium sulfate. The solution was filtered and the solvent removed under reduced pressure. The product was utilized without further purification. Yield 1.60 g. $^1$H NMR (CDCl$_3$, 300 MHz): 82.16 (s, 3H). 2.31 (s, 3H), 7.18 (d, J=9 Hz, 1H), 7.32 (d, J=9 Hz, 1H), 7.64 (s, 1H).

Methanesulfonic acid 4-methyl-3-nitro-benzyl ester

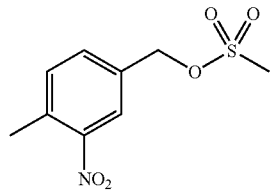

(4-Methyl-3-nitro-phenyl)-methanol (3.00 g, 17.95 mmol) was taken up in anhydrous DCM, under argon, and triethyl amine (5.45 g, 53.85 mmol, 7.51 mL) was added. The solution was cooled to 0EC and methanesulfonyl chloride (2.26 g, 19.74 mmol, 1.53 mL) was added slowly via syringe. The solution was allowed to warm to room temp and stir for 12 h. The reaction mixture poured into 1N HCl and the aqueous layer was extracted three times with ethyl acetate. The combined organic layers were washed with water, brine and dried over anhydrous magnesium sulfate. The solution was filtered and the solvent removed under reduced pressure. The product was isolated by flash chromatography. (5:1 hexane/ethyl acetate) Yield 2.00 g. $^1$H NMR (CDCl$_3$, 300 MHz): δ 2.62 (s, 3H), 4.61 (s, 2H), 7.36 (d, J=8 Hz, 1H), 7.36 (d, J=8 Hz, 1H), 8.02 (s, 1H).

2-(Methyl-3-nitro-benzyl)-isoindole-1,3-dione

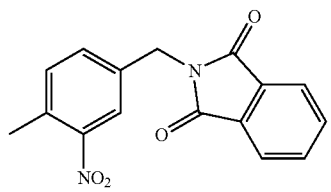

Methanesulfonic acid 4-methyl-3-nitro-benzyl ester (0.45 g, 1.83 mmol) was added to anhydrous DMF (20 mL), under argon, and potassium phthalimide (0.34 g, 1.83 mmol) was added. The reaction mixture was heated to 60EC for 12 h. The reaction mixture was cooled and poured into 1N HCl and the aqueous layer was extracted three times with ethyl acetate. The combined organic layers were washed with water, brine and dried over anhydrous magnesium sulfate. The solution was filtered and the solvent removed under reduced pressure. The product was isolated by flash chromatography. (4:1 hexane/ethyl acetate) Yield 0.45 g. $^1$H NMR (CDCl$_3$, 300 MHz): δ 2.58 (s, 3H), 4.88 (s, 2H), 7.30 (d, J=7 Hz, 1H), 7.57 (d, J=7 Hz, 1H), 7.24-7.77 (m, 2H), 7.84-7.89 (m, 2H), 8.02 (s, 1H).

2-(3-Amino-4-methyl-benzyl)-isoindole-1,3-dione

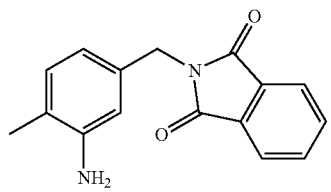

2-(Methyl-3-nitro-benzyl)-isoindole-1,3-dione (0.45 g, 1.52 mmol) was taken up in ethyl acetate in a Paar vessel and flushed with argon. Palladium on carbon (100 mg) was added and the argon atmosphere was replaced with hydrogen at 50 psi. The vessel was shaken for 12 h. The hydrogen was then replaced with argon and the catalyst was removed by filtration through celite. The solvent was removed under reduced pressure to yield 0.40 g of the desired amine. $C_{16}H_{14}N_2O_2$ MS m/e=267.3 (M+H).

General Procedure for Synthesis of N-alkyl-3-(4,6-dichloro-[1,3,5]triazin-2-ylamino)-4-methyl-benzamides

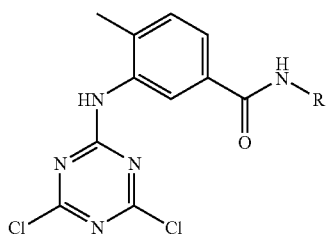

4-Methyl-3-nitro-benzoyl chloride (1 molar equivalent) was dissolved in CH$_2$Cl$_2$, and the solution was cooled to 0EC. The appropriate amine (2 M equiv) was added drop wise to the acid chloride, and the reaction stirred at 0EC for 5 min. The ice bath was removed and reaction continued to stir for 3 h. The solution was washed with brine, dried (Na$_2$SO$_4$), and concentrated in vacuo. The resulting amide was purified by silica gel chromatography.

The amide was then dissolved in EtOAc, and a catalytic amount of Pd/C was added. The solution was pressurized to 50 psi H$_2$ for 15 h. The solution was filtered through celite and concentrated in vacuo. The aniline was used without further purification.

A solution of aniline (1 molar equivalent) in acetone was added drop wise to a 0EC solution of cyanuric chloride (1 molar equivalent) in acetone. The cold bath was removed, and the reaction stirred at room temp for 3 h. Acetone was removed in vacuo. The resulting solid was washed with hexane then dried under high vacuum.

Carbamates

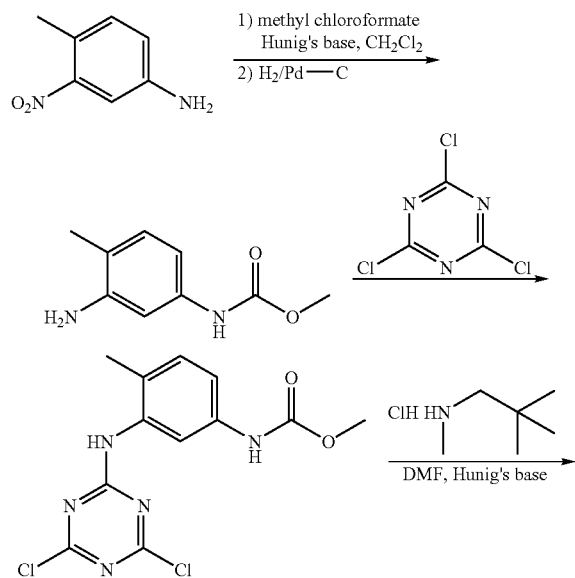

-continued

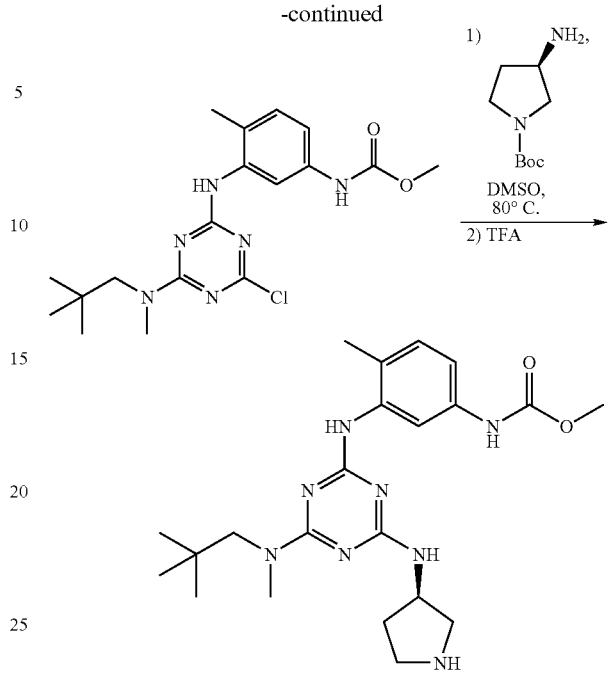

To the solution of 4-methyl-3-nitroaniline (0.75 g, 5.0 mmol) in DCM (10 mL) cooled in an ice-bath was added methyl chloroformate (1.01 equiv.) and Hunig=s base (1.1 equiv.). The solution was stirred at 0EC for 0.5 h. The reaction mixture was diluted with ethyl acetate (20 mL) and washed with aqueous ammonium chloride solution twice, and brine twice. The organic layer was dried with anhydrous sodium sulfate and concentrated under vacuum. The crude product was then-dissolved in ethyl acetate (20 mL) and the solution was added with 10% palladium on carbon powder. The reaction mixture was put onto the hydrogenation apparatus. Hydrogenolysis was proceeded at room temp for 0.5 h. The reaction mixture was filtered and the filtrate was concentrated under vacuum. Purification of the crude product with flash chromatography gave 0.75 g of 3-amino-4-methylphenylamino methyl carbamate (yield 85%).

In a 50 mL round-bottomed flask was added 3-amino-4-methylphenylamino methyl carbamate (0.75 g) and acetone (10 mL). The solution was cooled with an ice-bath and added with trichlorotriazine (1.0 equiv.). The mixture was stirred at 0EC for 5 min before the addition of sat. aq. sodium bicarbonate solution (20 mL). Continued stirring at 0EC for 15 min, the mixture was filtered and washed with cold ethanol. The solid was dried and dissolved into anhydrous DMF (10 mL). Cooled in an ice-bath, the solution was added with N-methylneopentylamine hydrochloride (1.0 equiv.) and Hunig=s base (1.2 equiv.). The solution was stirred at 0EC for 0.5 h before the addition of ethyl acetate and aq. solution of ammonium chloride. The organic layer was separated and washed with aq. ammonium solution and brine twice, dried with anhydrous sodium sulfate and concentrated under vacuum. The crude product was purified with flash chromatography.

The above-obtained product (80 mg) was dissolved into DMSO (1 mL). The solution was added 1-Boc-(3R)-aminopyrrolidine (1.5 equiv.) and Hunig=s base (2 equiv.). The mixture was heated to 80EC for overnight. The reaction mixture was cooled to room temp and diluted with ethyl acetate and aq. ammonium chloride solution. The organic layer was separated and washed with aq. ammonium solution and brine twice, dried with anhydrous sodium sulfate and concentrated under vacuum. The crude was then dissolved into an 50% solution of trifluoroacetic acid in DCM and stirred at room temp for 2 h. The solvent was removed under vacuum. The product was purified with HPLC and 50.1 mg of final compound was obtained.

Solid Phase Preparations of Compounds of Formula I

Compounds of Formula I may also be prepared on solid phase. Typically, an amino-functionalized resin, such as PEG-grafted polystyrene beads (e.g., ArgoGelθ), may be modified by reaction with bis-Fmoc lysine to increase the available reaction sites for ligand attachment. After deprotection, an aldehyde linker may be attached via the free amine sites. Reductive amination with a primary amine yields a resin-bound secondary amine. The following descriptions are illustrative of methods of preparing compounds of Formula I on solid phase.

Method 1

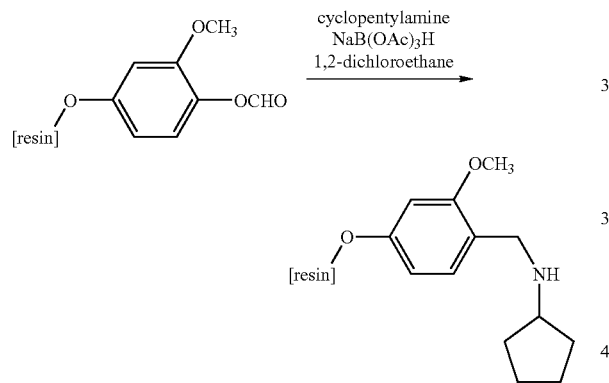

ArgoGel resin (3.0 g) with acid cleavable linker in a shaking vessel was washed with 1,2-dichloroethane twice. After draining, 120 mL of 1,2-dichloroethane was added, followed with the addition of cyclopentylamine (20 equivalents). The pH of the reaction mixture was adjusted to 5 with the addition of acetic acid. The reaction mixture was shaken at room temp for 15 min, and added with sodium triacetoxyborohydride (20 equivalents). After completion of the addition, the reaction mixture was shaken at room temp for 16 h. The resin was then filtered and washed with methanol and DCM (5 cycles).

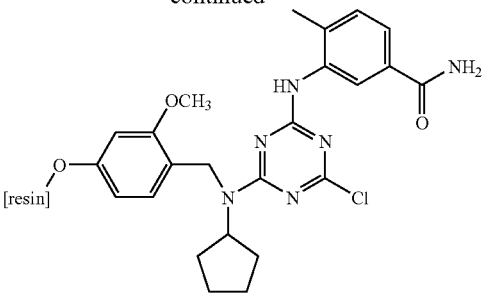

The ArgoGel resin obtained above was washed with DMF twice. After draining, 50 mL of anhydrous DMF and Hunig=s base (10 equivalents) were added, followed with the addition of 2-(5-aminocarbonyl-2-methyl)phenylamino-4,6-dichlorotriazine (3.0 equivalents). The reaction was allowed to proceed at room temp for 4 h. The resin was then filtered and washed with methanol and DCM (5 cycles), and dried over vacuum.

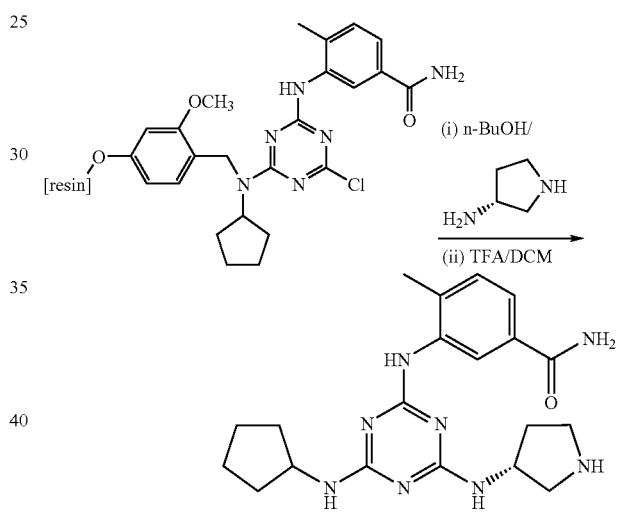

ArgoGel resin (50 mg) obtained above was put into a small reaction vial. To the vial was added with anhydrous n-BUOH (1.0 mL) and 1-N-Boc-(3R)-aminopyrrolidine (0.5 mmol). The reaction mixture was heated to 70EC for 16 h. The resin was then filtered and washed with methanol and DCM (5 cycles) and treated with a 50% solution of trifluoroacetic acid in DCM. The product was collected through filtration and purified by HPLC.

Method 2

This method allows for N-derivatization the solid supports.

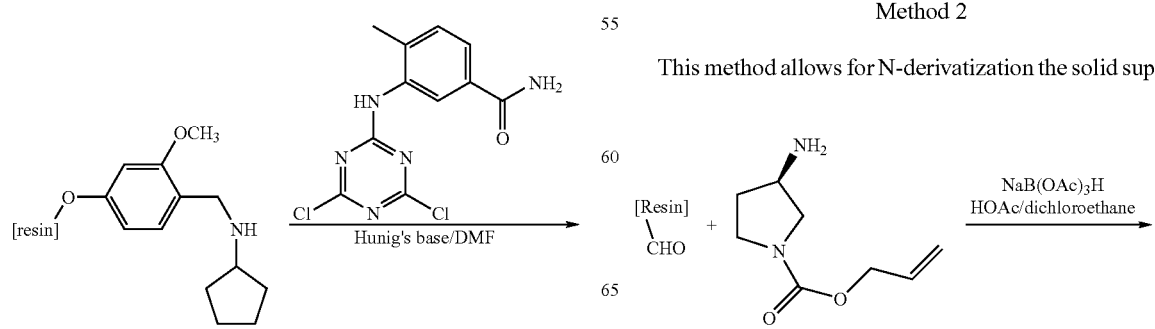

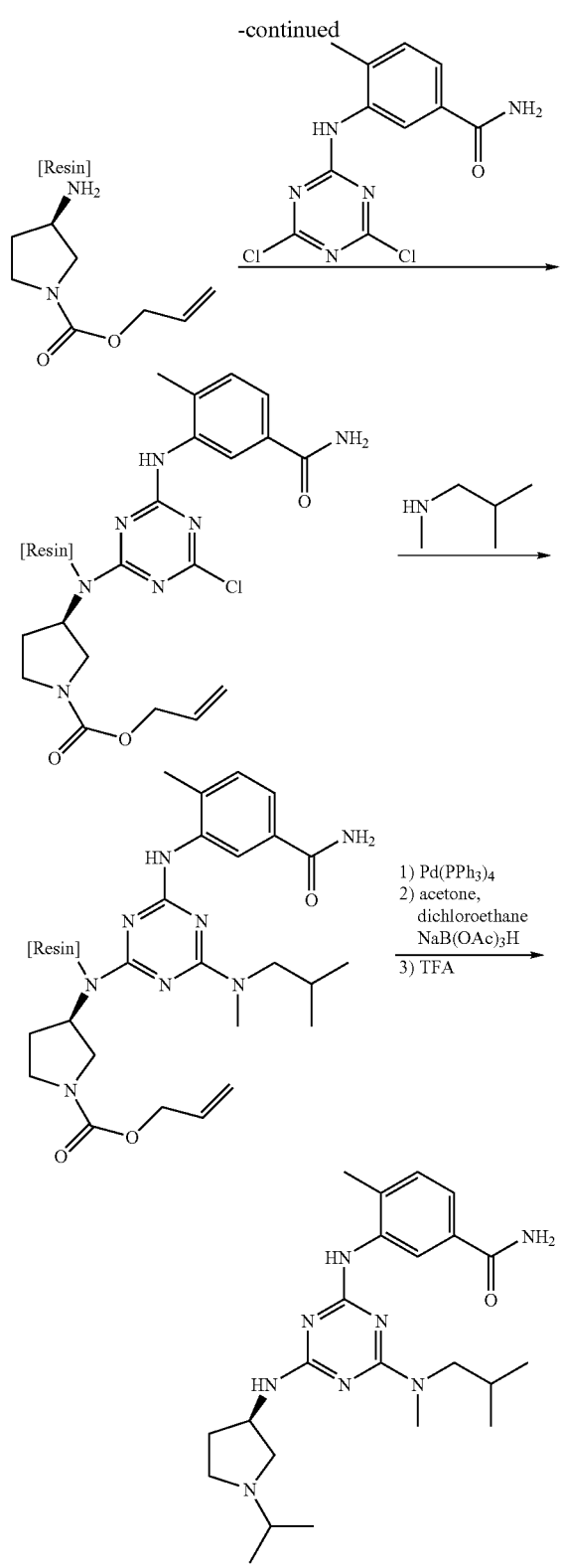

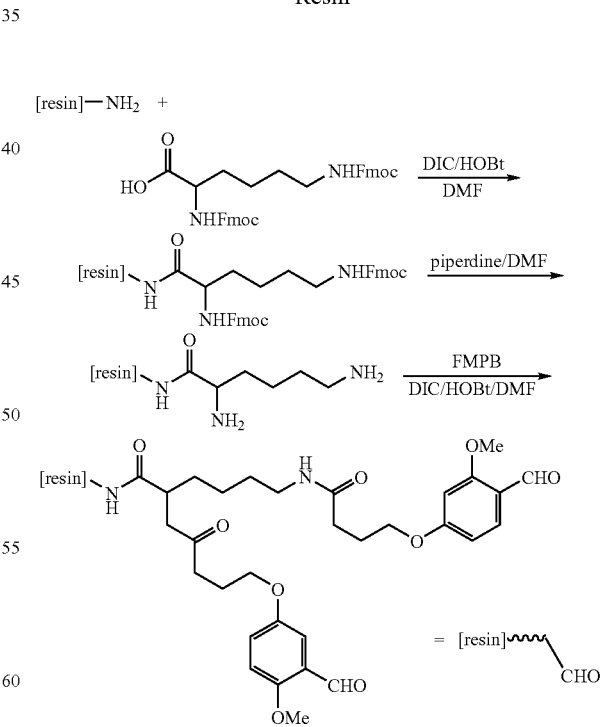

adjusted to 5 by the addition of acetic acid. The reaction mixture was shaken at room temp for 15 min, before the addition of sodium triacetoxyborohydride (10 equiv.). The reaction mixture was shaken at room temp for overnight. The resin was filtered and washed with methanol, DCM, and THF. Then it was dried over vacuum.

0.9 g of the above-obtained resin was washed with DMF twice and suspended into DMF (8 mL). To the resin suspension, Hunig's base (5.0 equiv.) was added, and then the dichlorotriazine derivative (3.0 equiv.). The reaction mixture was shaken at room temp for 4 h. The resin was filtered and washed with DMF, methanol, DCM, and then suspended in DMSO (6 mL). The suspension was added with 1-isobutyl-1-methylamine (10 equiv.). The reaction mixture was heated to 80EC overnight. The resin was filtered and washed with methanol, DCM, and THF. Then it was dried over vacuum.

50 mg of the above-obtained resin was suspended into THF (3 mL). Tetrakis(triphenylphosphine)palladium(0) (0.15 g) and 5,5-dimethyl-1,3-cyclohexane-dione (10 equiv.) were added. The reaction mixture was shaken at room temp for overnight. The resin was washed with 0.5% solution of sodium diethyldithiocarbamate in DMF, and then 0.5% DMF solution of Hunig=s base before it was washed with methanol, DCM.

The resin was washed with 1,2-dichloroethane twice and suspended in 1,2-dichloroethane (3 mL). Acetone (0.1 mL) and sodium triacetoxyborohydride (10 equiv.) were added. The reaction mixture was shaken at room temp for overnight. The resin was filtered and washed with methanol, DCM, and cleaved with TFA/DCM (1:1). The cleavage gave the crude final product in an 80% overall yield.

Method 3—Attachment of Acid Cleavable Linker to Resin

The TentaGelθ resin (3.5 g) attached with the acid cleavable linker was washed with 1,2-dichloroethane twice (5 min shaking each time). After drained, the resin was added with 1,2-dichloroethane (30 mL). (3R)-amino-1-pyrrolidine allyl carbamate (1.00 g) was added and the pH of the solution was Bis-Fmoc lysine was coupled to amino-functionalized TentaGelθ by amide bond formation, Coupling was achieved by reacting a suspension of the resin (40 g, 11.2 mmol) in 100 mL of DMF with bis-Fmoc lysine (20 g, 33.8 mmol), HOBt (5.2 g, 33.9 mmol) and DIC (10.6 mL, 67.6 mmol). The suspension was shaken overnight, then drained and washed in succession with MeOH, DMF and DCM, then dried in vacuo.

A suspension of resin in 1:3 piperidine:DMF (50 mL) was shaken about 2 h, then washed with MeOH, DMF and DCM. This diamine resin (40 g, 20 mmol) was suspended in 160 mL of DMF, and treated with MPB (9.6 g, 40.3 mmol) and HOBt (6.2 g, 40.5 mmol). DIC (12 mL, 76.6 mmol) was added after 30 min. The suspension was shaken overnight, then drained and the resin was washed with MeOH, DMF and DCM. The MPB resin was dried in vacuo.

Attachment of (3R)-3-Amino-pyrrolidine-1-carboxylic acid t-butyl ester to resin

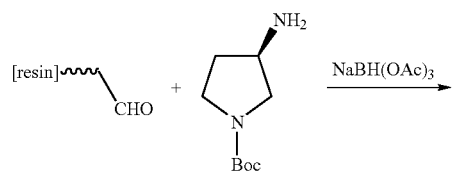

Pyrrolidine amine (0.5 mg, 2.68 mmol) was added to a suspension of resin (5 g, 2.5 mmol) in 45 mL of DCE and the mixture was shaken 30 min. Sodium triacetoxyborohydride (0.8 g, 3.7 mmol) was then added and the resulting mixture was shaken for 18 h and the suspension was drained. The resin was washed with MeOH, DMF and DCM, and dried overnight under vacuum.

Coupling of resin-linked amino-pyrrolidine with 3-(4,6-dichloro-[1,3,5]triazin-2-ylamino)-4-methyl-benzamide

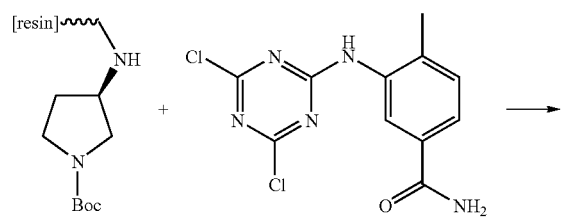

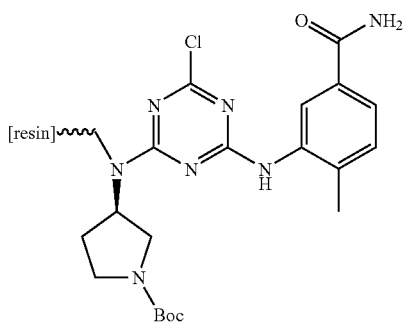

A suspension of the resin (2.7 g, 1.35 mmol), DIEA (0.5 mL) and 3-(4,6-dichloro-[1,3,5]triazin-2-ylamino)-4-methyl-benzamide (0.5 g, 1.67 mol) in 10 mL of dry THF was stirred for 16 h at 70EC. The suspension was drained, the resin was washed with MeOH, DMF and DCM and dried under vacuum.

3-[4-(i-Butyl-methyl-amino)-6-(3R)-(pyrrolidin-3-ylamino)-[1,3,5]triazin-2-ylamino]-4-methyl-benzamide

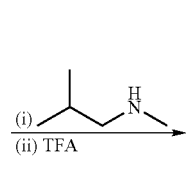

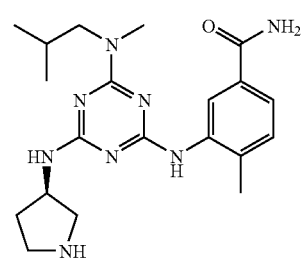

A suspension of the resin (0.1 g, 0.05 mmol) and N-methylisobutylamine (0.1 mL, 0.8 mmol) in 1 mL of dry THF was stirred for 3 h at 80EC. The suspension was drained, the resin was washed with MeOH, DMF, and DCM. In order to cleave the product from the resin, the resin was treated with 1 mL of TFA for 1 h with stirring. After filtration and concentration of the solution, the product was purified by Prep-HPLC as TFA salt (4.2 mg, 21%, $C_{20}H_{30}N_8O$, ms m/z 399 $(M+H)^+$).

3-[4-(6,6-Dimethyl-bicyclo[3,1,1]hept-2-yl-methoxy)-6-(pyrrolidin-3-ylamino)-[1,3,5]triazin-2-ylamino]-4-methyl-benzamide

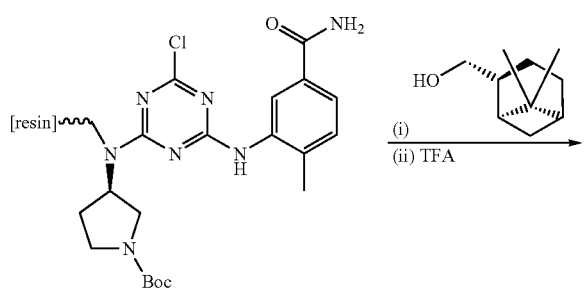

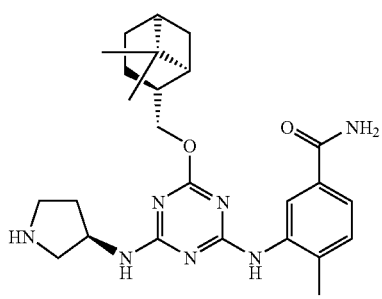

To a suspension of the resin (0.1 g, 0.05 mmol), DEA (0.1 mL) and (1S,2S,5S)-(−)-myrtanol (0.08 mL, 0.5 mmol) in 1 mL of dry THF was added NaH (60% in oil, 0.04 g, 1 mmol), and the resulting suspension was stirred for 16 h at 75EC. The suspension was drained, the resin was washed with MeOH, DMF, and DCM. In order to cleave the product from the resin, the resin was treated with 1 mL of TFA for 1 h with stirring. After filtration and concentration of the solution, the product was purified by Prep-HPLC as a TFA salt (1.2 mg, 5.2%, $C_{25}H_{35}N_7O_2$, MS m/z 466 (M+H)$^+$.

3-[4-(3-Chloro-phenyl)-6-(pyrrolidin-3-ylamino)-[1,3,5]triazin-2-ylamino]-4-methyl benzamide

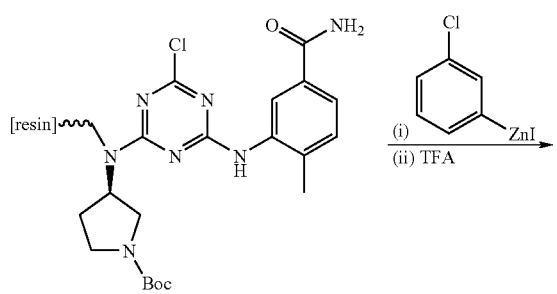

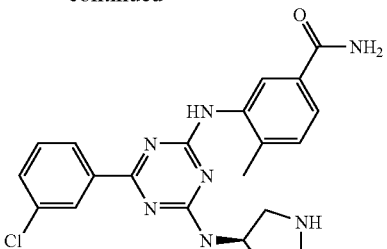

A suspension of the resin (0.1 g, 0.05 mmol), tetrakis(triphenylphosphine)-palladium(0) (0.015 g, 0.012 mmol), and 3-chloro-phenylzinc iodide (0.5M in THF, 1.5 mL, 0.75 mmol) was stirred for 16 h at 80EC. The suspension was drained, the resin was washed with water, THF, MEOH, DMF, and DCM. In order to cleave the product from the resin, the resin was treated with 1 mL of TFA for 2 h under stirring. After filtration and concentration of the solution, the product was purified by Prep-HPLC as a TFA salt (1.9 mg, 9%, $C_{21}H_{22}ClN_7O$, MS m/z 424 (M+H)$^+$.

3-[4-Isobutylsulfonyl-6-(pyrrolidin-3-ylamino)-[1,3,5]triazin-2-ylamino]-4-methyl-benzamide

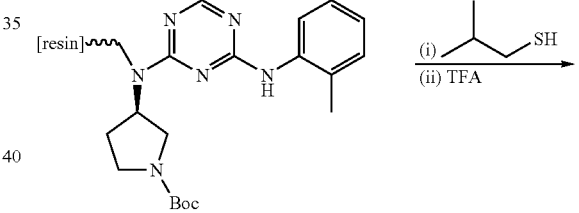

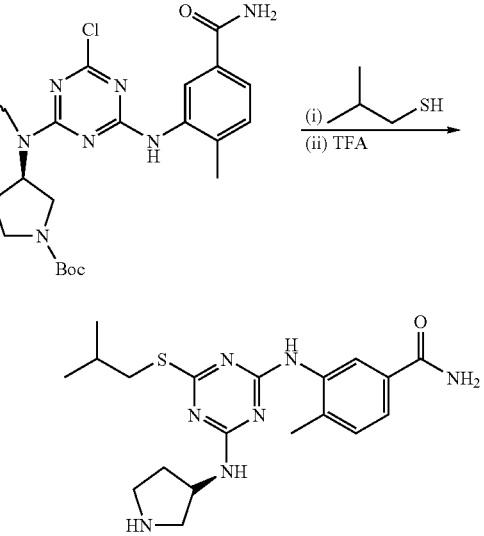

To a stirring suspension of NaH (60% in oil, 0.06 g, 1.5 mmol) in 2 mL of dry THF was added i-butylthiol (0.07 mL, 0.6 mmol) dropwise at room temp. After the evolution of the hydrogen gas ceased, this mixture was added to the resin (0.1 g, 0.05 mmol), and the resulting suspension was stirred for 30 min at room temp and 16 h at 80° C. The suspension was drained, the resin was washed with MeOH, DMF, and DCM. In order to cleave the product from the resin, the resin was treated with 1 mL of TFA for 1 h under stirring. After filtration and concentration of the solution, the product was purified by Prep-HPLC as a TFA salt (3.5 mg, 5.2%, $C_{19}H_{27}N_7OS$. MS m/z 402 (M+H)$^+$.

General Procedures for Synthesis of 3-(4,6-Bis-alkylamino-pyrimidin-2-ylamino)-4-methyl-benzamides

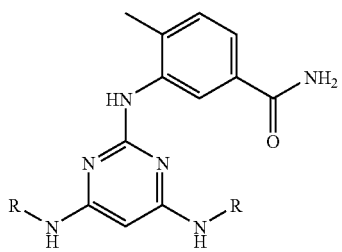

3-{4-Cyclopentylamino-6-[(2,2-dimethyl-propyl)-methyl-amino]-pyrimidin-2-ylamino}-4-methyl-benzamide

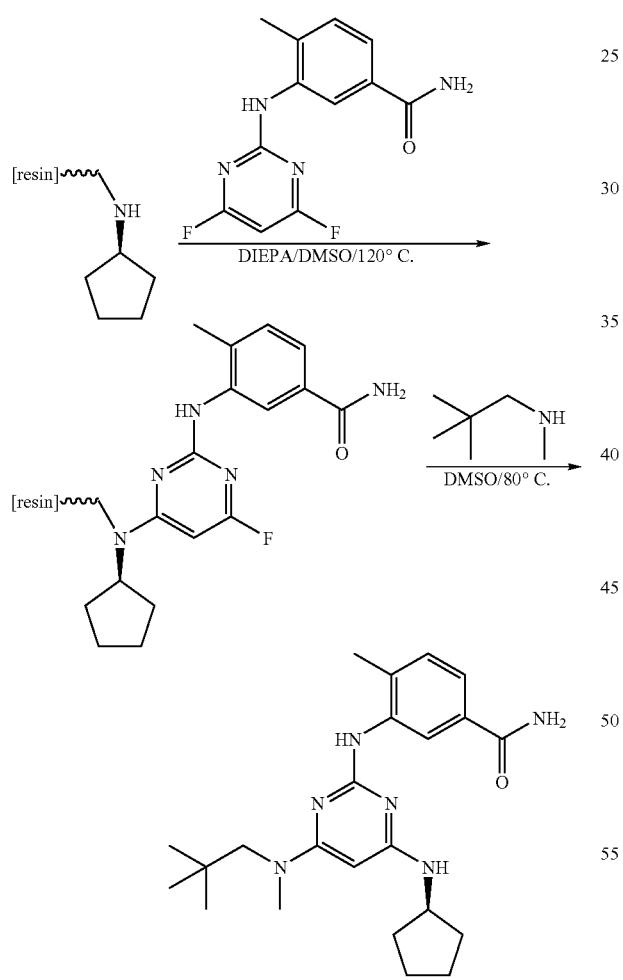

3-Amino-4-methyl-benzamide (1 molar equivalent) was added to a room temp solution of trifluoropyrimidine (1 molar equivalent) and DIEPA (1.5 molar equivalents), in THF. The reaction stirred for 24 h, then was concentrated in vacuo. The resulting mixture of 2- and 4-pyrimidine products were separated by silica gel chromatography.

The substituted pyrimidine (34 mg, 0.12 mmol), resin bound-amine (140 mg, 0.07 mmol) and DIPEA (50 ΦL, 0.28 mmol) in DMSO (1 mL) was heated to 120EC for 24 h. The resin was washed with DMF (3x) and DCM (3x).

The resulting resin was reacted with amine (120 mg 1.1 mmol) in DMSO (0.5 mL) at 80EC for 18 h. The resin was washed with DMF (3x), MeOH (3x), DCM (3x), then treated with TFA to release the product. The crude product was purified by preparative HPLC. MS (m/z) calcd for $C_{23}H_{35}N_6O$ (MH$^+$), 411; found, 411.

N-(3-{4-Cyclopentylamino-6-[(2,2-dimethyl-propyl)-methyl-amino]-pyrimidin-2-ylamino}-4-methyl-benzyl)-acetamide

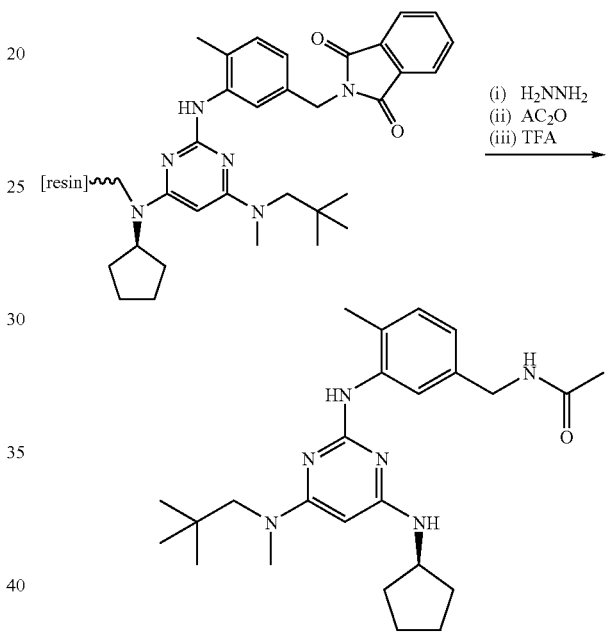

The resin-bound phthalimide was prepared using standard methods. A suspension of resin (200 mg) in 2M hydrazine/ethanol (20 mL) was stirred for 4 h at room temp. The resin was washed with MeOH (3x), DMF (3x), DCM (3x), then dried under high vacuum.

Acetic anhydride (40 ΦL, 0.42 mmol), was added to a vial containing resin (80 mg, 0.04 mmol), DMAP (cat.) in 10% pyridine/DCM. The reaction stirred for 16 h at room temp. The resin was washed with DCM (3x), MeOH (3x), DCM (3x). Upon stirring of the resin in 1 mL of TFA for 3 h, the product was released. The solution was concentrated in vacuo and the residue was purified by Prep-HPLC. MS (m/z) calcd for $C_{25}H_{39}N_6O$ (MH$^+$), 440; found, 440.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

TABLE 1
| # | MW | |
|---|---|---|
| 1 | 347.81 | 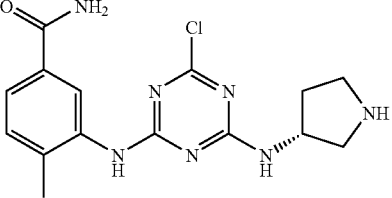 |
| 2 | 398.515 | 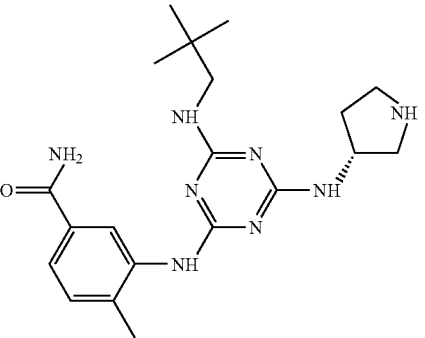 |
| 3 | 444.543 | 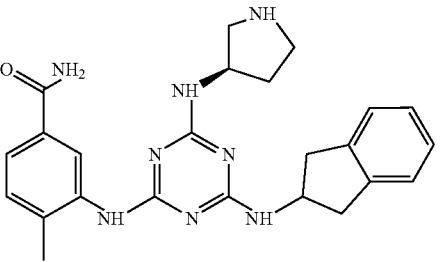 |
| 4 | 446.559 | 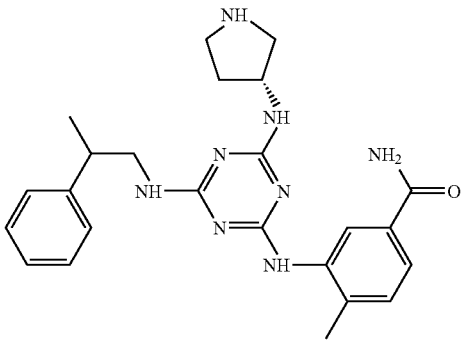 |
| 5 | 464.618 | 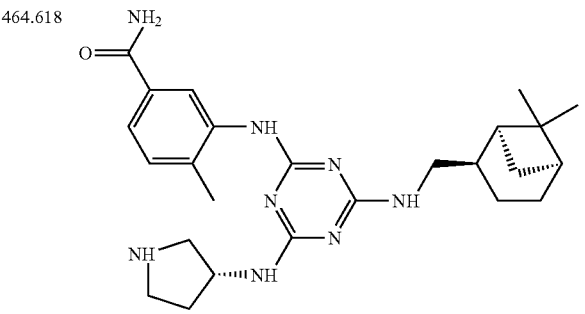 |

TABLE 1-continued

| # | MW | |
|---|---|---|
| 6 | 439.524 | |
| 7 | 476.629 | |
| 8 | 458.57 | |
| 9 | 493.015 | |

TABLE 1-continued
| # | MW | |
|---|---|---|
| 10 | 444.543 | 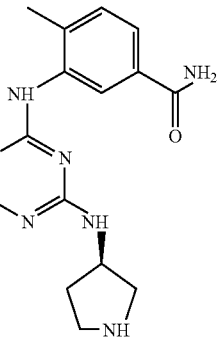 |
| 11 | 395.511 | 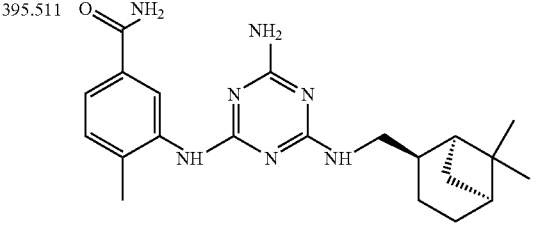 |
| 12 | 481.004 | 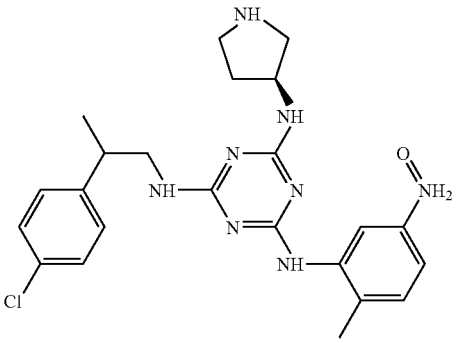 |
| 13 | 448.531 | 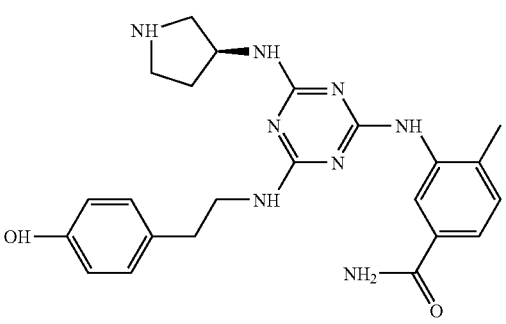 |
| 14 | 476.541 | 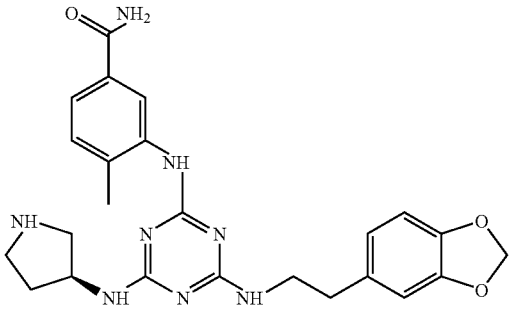 |

TABLE 1-continued

| # | MW | |
|---|---|---|
| 15 | 436.564 | |
| 16 | 444.543 | |
| 17 | 458.57 | |
| 18 | 466.977 | |
| 19 | 446.559 | |

TABLE 1-continued
| # | MW | |
|---|---|---|
| 20 | 464.618 | 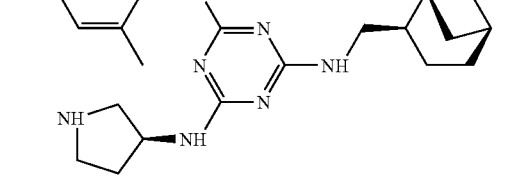 |
| 21 | 476.629 | 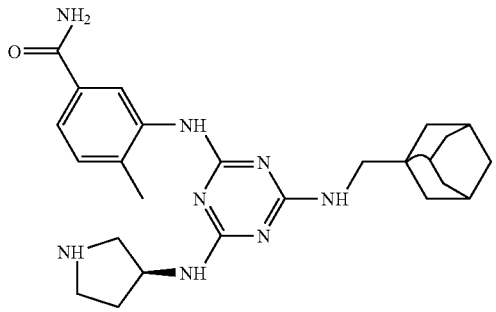 |
| 22 | 434.504 | 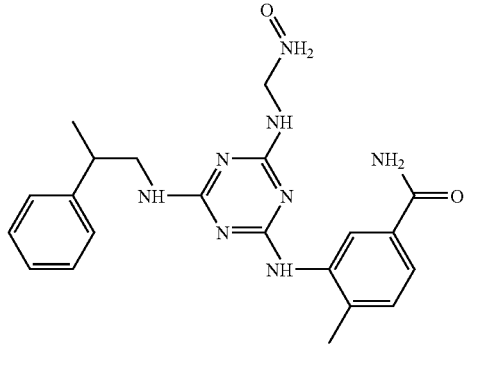 |
| 23 | 378.436 | 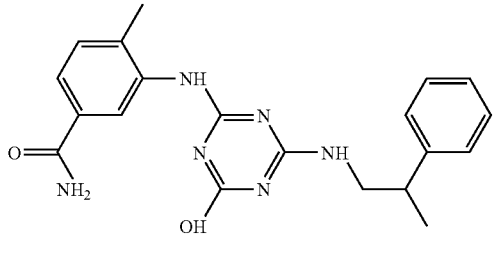 |
| 24 | 342.407 | 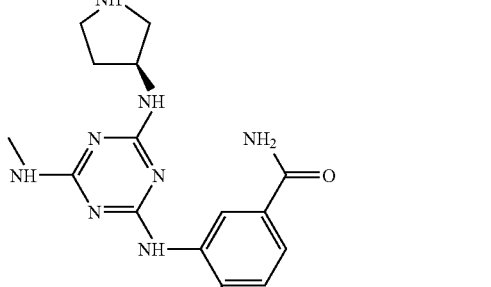 |

TABLE 1-continued
| # | MW |
|---|---|
| 25 | 435.536 |
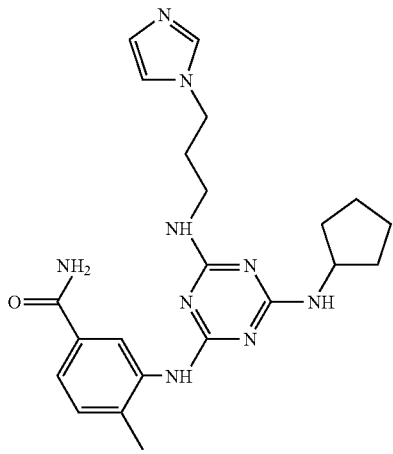
| 26 | 328.376 |
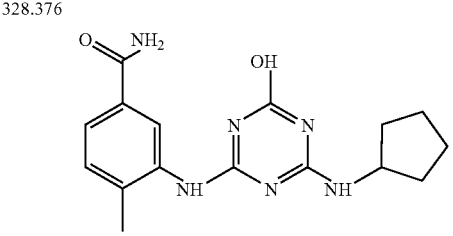
| 27 | 396.499 |
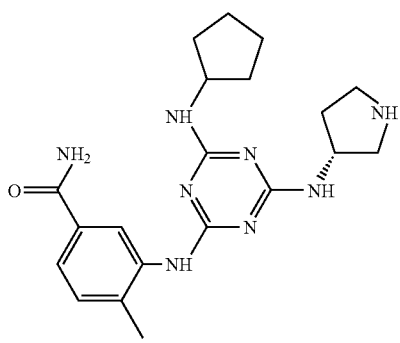
| 28 | 419.489 |
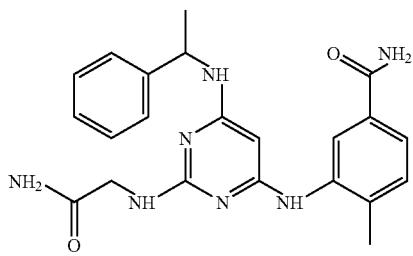

TABLE 1-continued
| # | MW | |
|---|---|---|
| 29 | 461.57 | 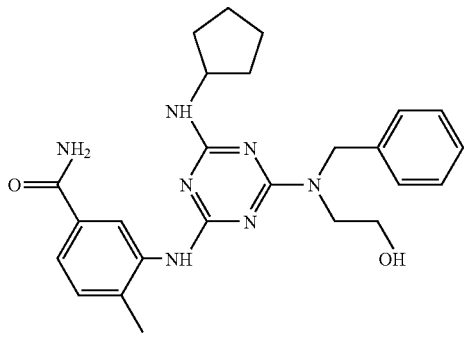 |
| 30 | 492.628 | 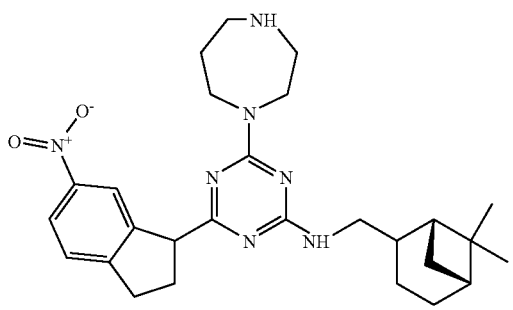 |
| 31 | 492.628 | 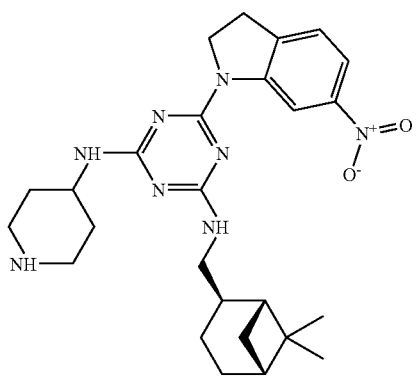 |
| 32 | 465.602 | 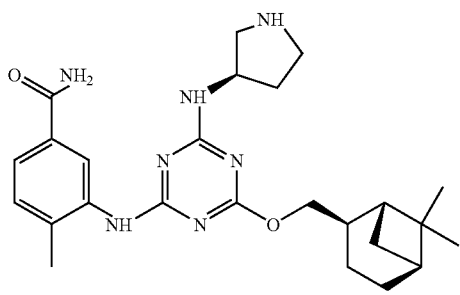 |

TABLE 1-continued
| # | MW |
|---|-----|
| 33 | 478.645 |
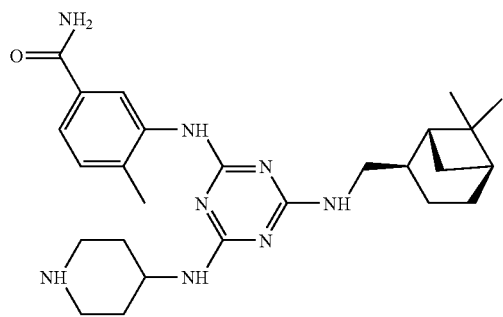
| 34 | 398.515 |
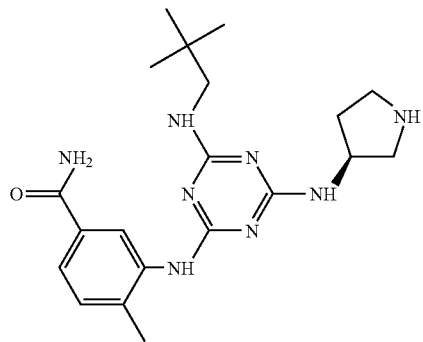
| 35 | 464.618 |
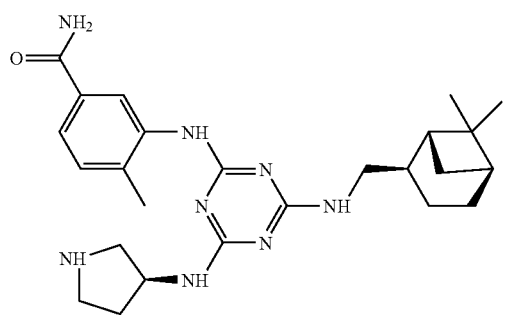
| 36 | 399.499 |
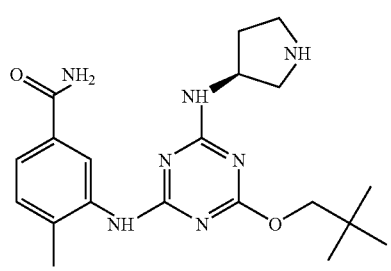

TABLE 1-continued
| # | MW |
|---|-----|
| 37 | 485.036 |
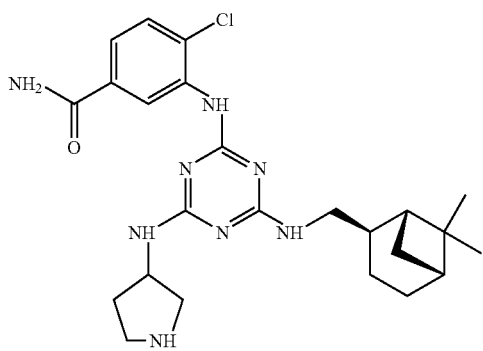
| 38 | 398.515 |
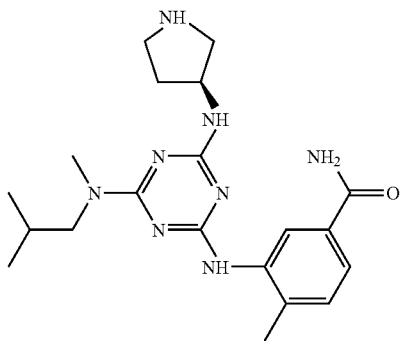
| 39 | 412.542 |
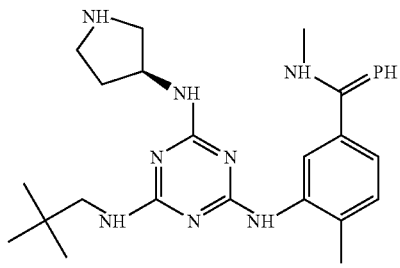
| 40 | 412.542 |
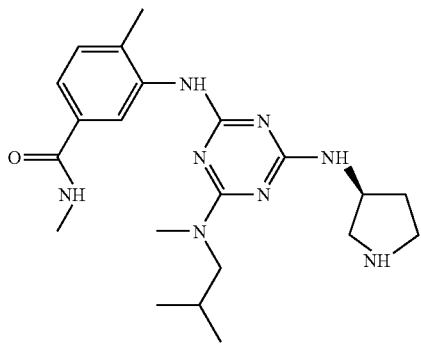

TABLE 1-continued
| # | MW | |
|---|---|---|
| 41 | 478.645 | 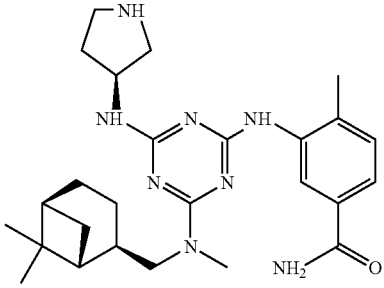 |
| 42 | 487.612 | 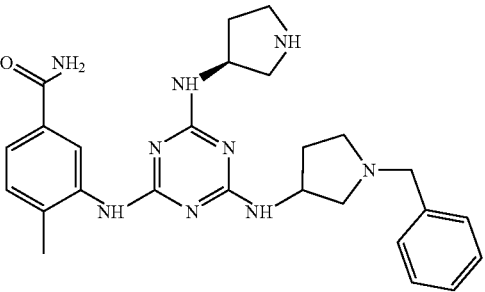 |
| 43 | 476.629 | 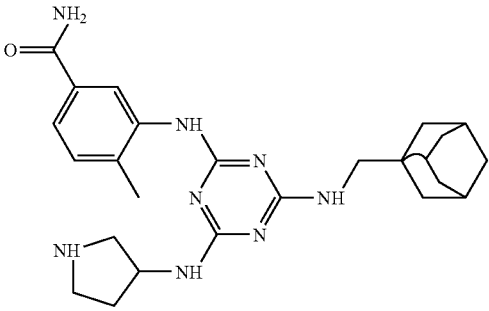 |
| 44 | 464.618 | 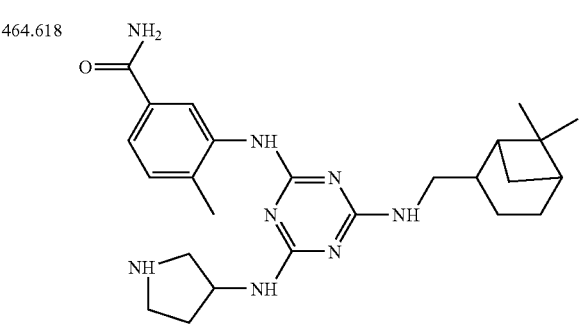 |
| 45 | 486.624 | 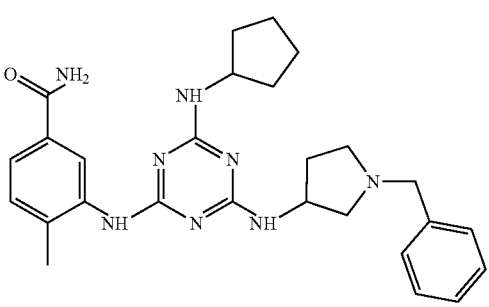 |

TABLE 1-continued
| # | MW |
|---|---|
| 46 | 424.553 |
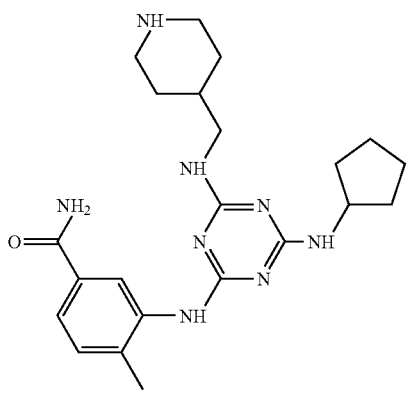
| 47 | 384.484 |
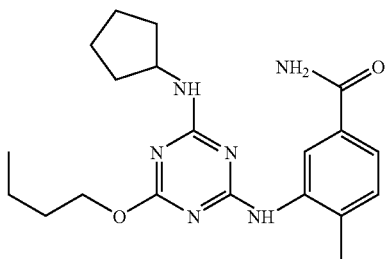
| 48 | 403.49 |
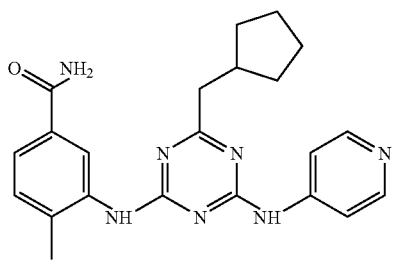
| 49 | 410.526 |
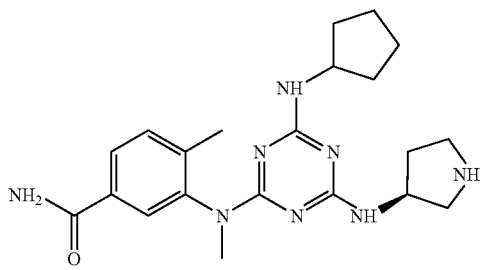

TABLE 1-continued
| # | MW | |
|---|---|---|
| 50 | 438.584 | 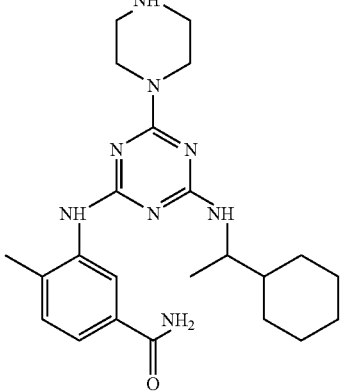 |
| 51 | 466.634 | 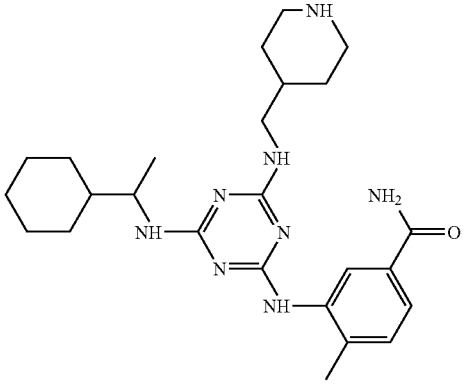 |
| 52 | 438.58 | 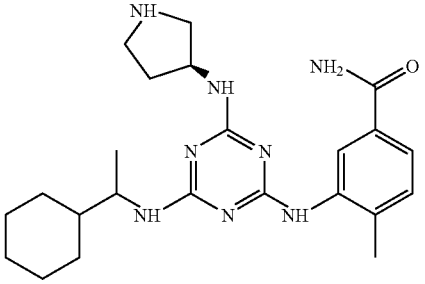 |
| 53 | 450.522 | 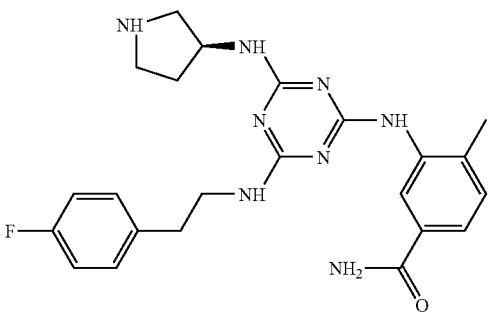 |

TABLE 1-continued
| # | MW | |
|---|---|---|
| 54 | 426.569 | 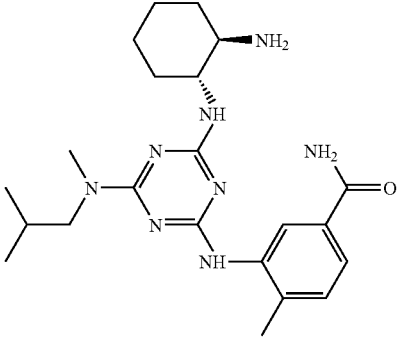 |
| 55 | 488.64 | 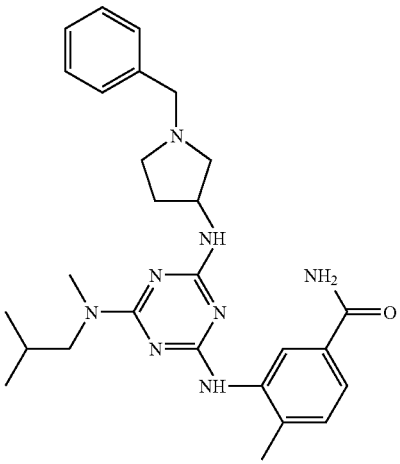 |
| 56 | 398.515 | 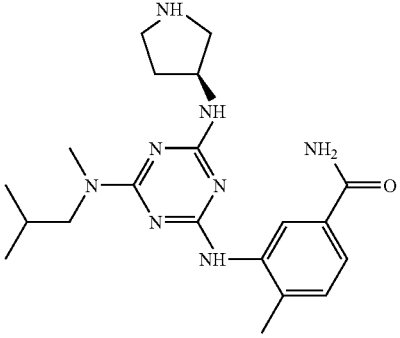 |
| 57 | 384.488 | 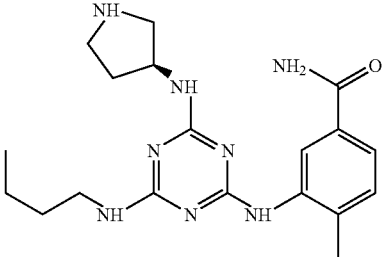 |

TABLE 1-continued
| # | MW | |
|---|---|---|
| 58 | 412.542 | 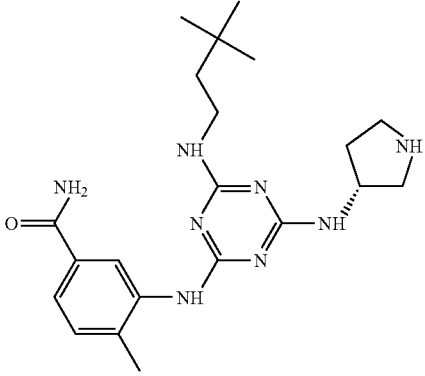 |
| 59 | 468.565 | 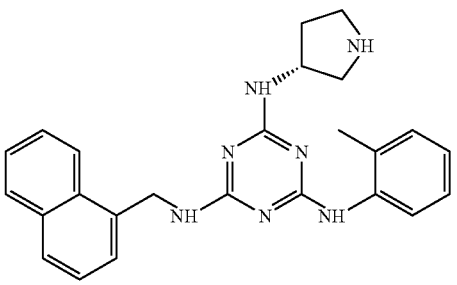 |
| 60 | 424.553 | 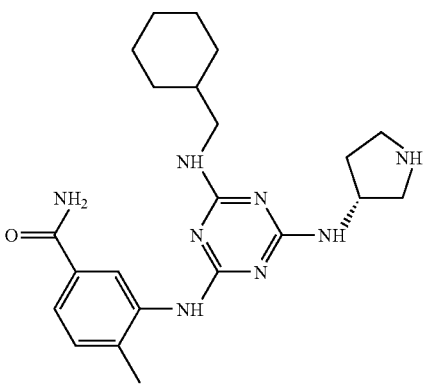 |
| 61 | 398.515 | 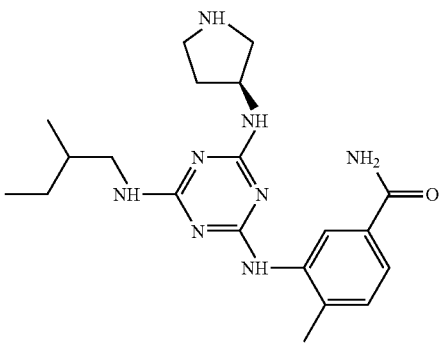 |

TABLE 1-continued
| # | MW | |
|---|---|---|
| 62 | 487.612 | 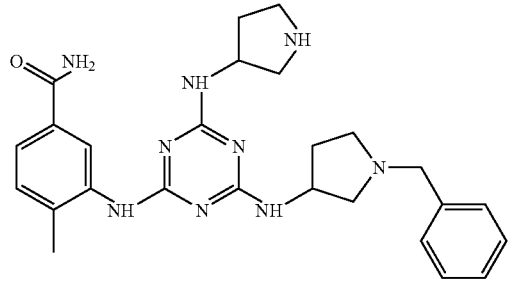 |
| 63 | 398.515 | 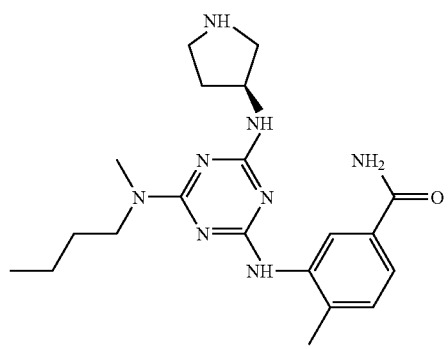 |
| 64 | 398.515 | 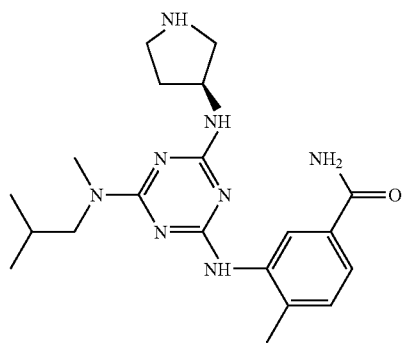 |
| 65 | 464.618 | 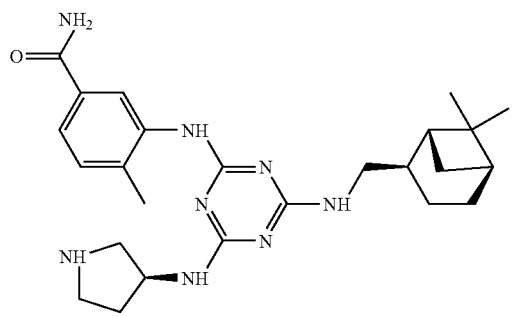 |

TABLE 1-continued

| # | MW |
|---|---|
| 66 | 398.515 |
| 67 | 465.646 |
| 68 | 384.488 |
| 69 | 384.488 |
| 70 | 410.526 |

TABLE 1-continued
| # | MW | |
|---|---|---|
| 71 | 622.859 | 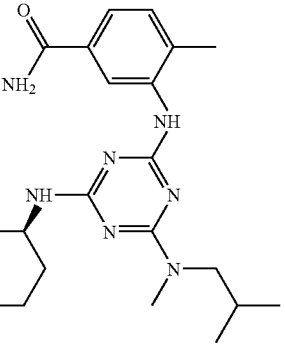 |
| 72 | 510.687 | 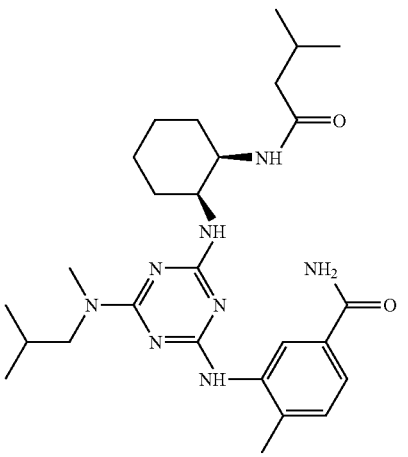 |
| 73 | 426 | 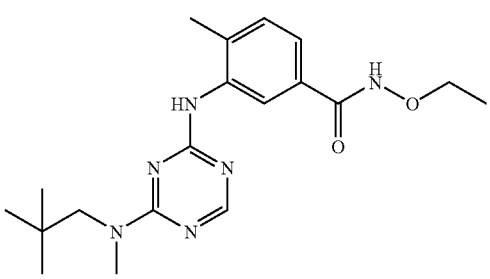 |
| 74 | 484.605 | 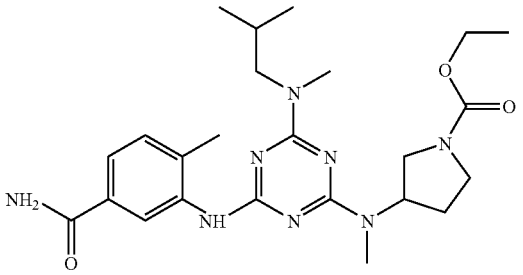 |

TABLE 1-continued
| # | MW |
|---|---|
| 75 | 412.542 |
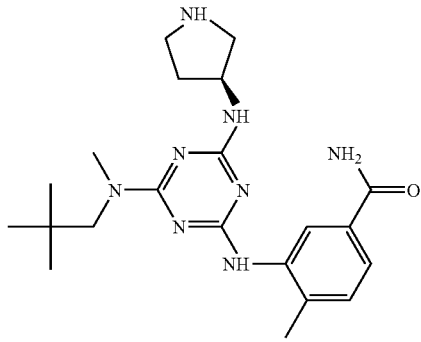
| | |
|---|---|
| 76 | 438.58 |
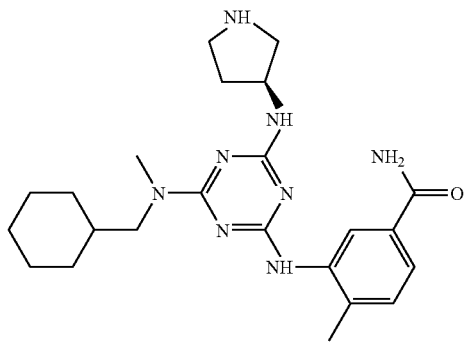
| | |
|---|---|
| 77 | 460.586 |
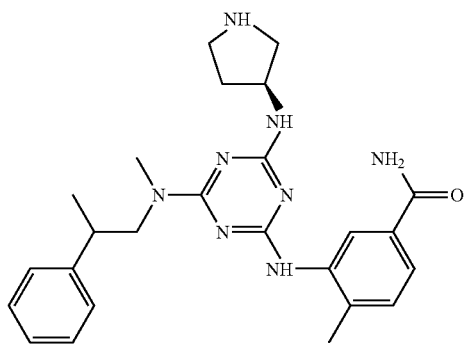
| | |
|---|---|
| 78 | 397.527 |
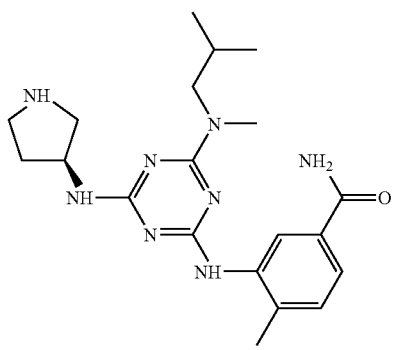

TABLE 1-continued

| # | MW |
|---|---|
| 79 | 427.553 |
| 80 | 518.666 |
| 81 | 489.628 |
| 82 | 532.649 |

TABLE 1-continued
| # | MW |
|---|---|
| 83 | 489.628 |
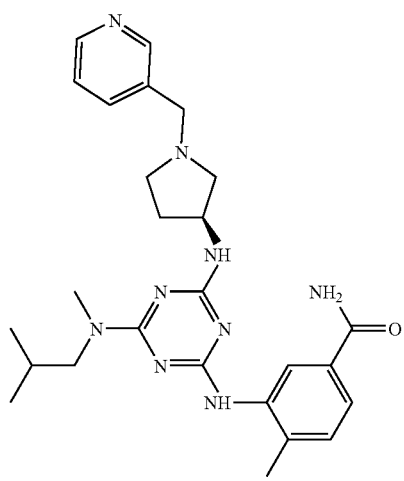
| 84 | 488.64 |
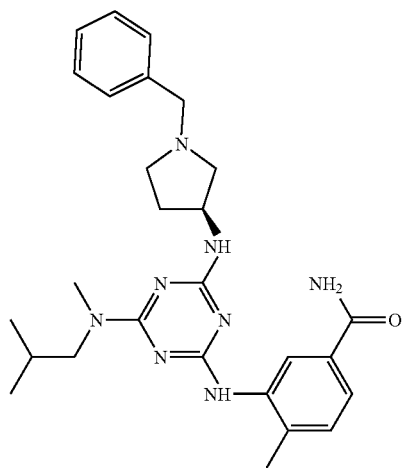
| 85 | 412.54 |
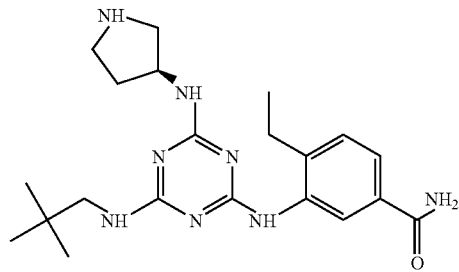

TABLE 1-continued
| # | MW |
|---|---|
| 86 | 513.65 |
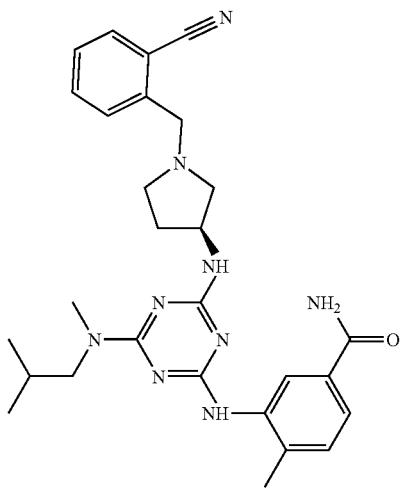
| 87 | 523.085 |
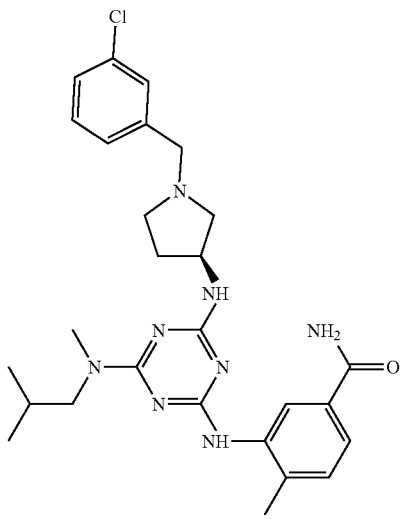
| 88 | 412.542 |
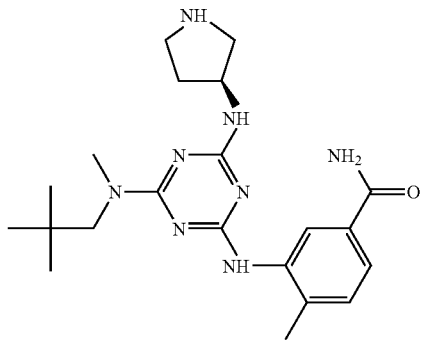

TABLE 1-continued

| # | MW |
|---|---|
| 89 | 488.64 |
| 90 | 426.569 |
| 91 | 440.596 |
| 92 | 495.031 |

TABLE 1-continued

| # | MW | |
|---|---|---|
| 93 | 426.569 | |
| 94 | 383.46 | |
| 95 | 518.666 | |
| 96 | 484.605 | |

TABLE 1-continued
| # | MW |
|---|---|
| 97 | 489.628 |
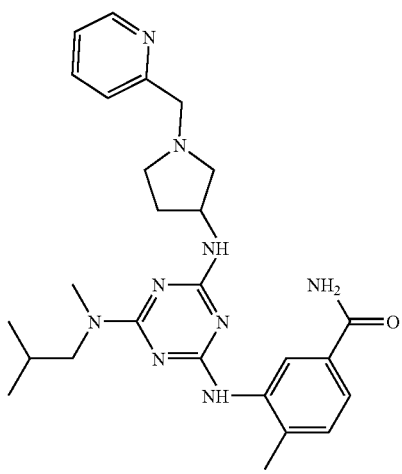
| 98 | 502.667 |
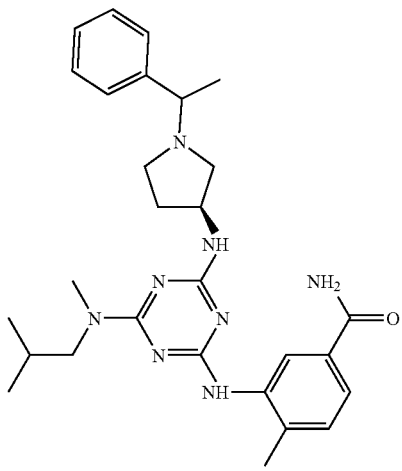
| 99 | 410.526 |
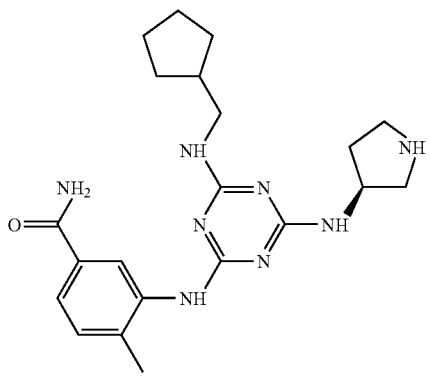

TABLE 1-continued
| # | MW |
|---|---|
| 100 | 424.553 |
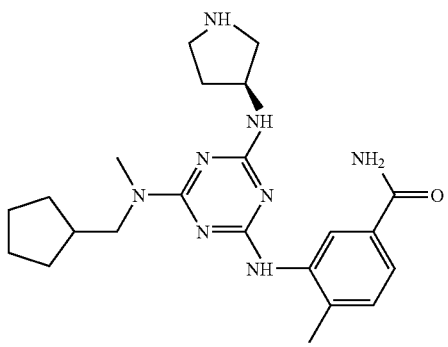
| 101 | 502.667 |
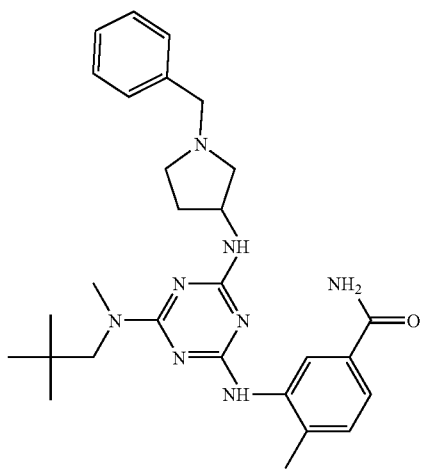
| 102 | 502.667 |
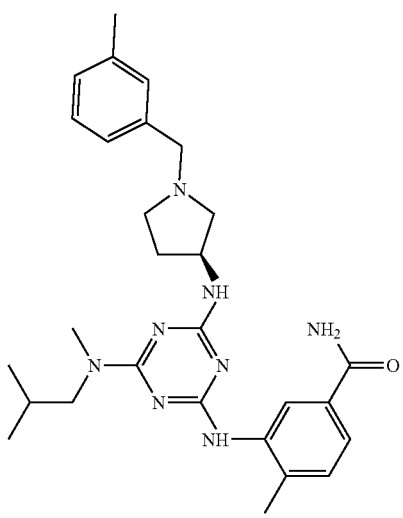

TABLE 1-continued
| # | MW |
|---|-----|
| 103 | 456.595 |
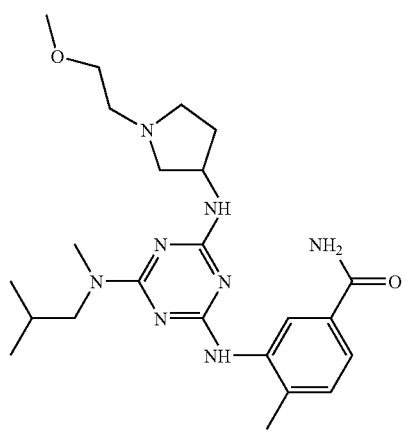
| 104 | 502.667 |
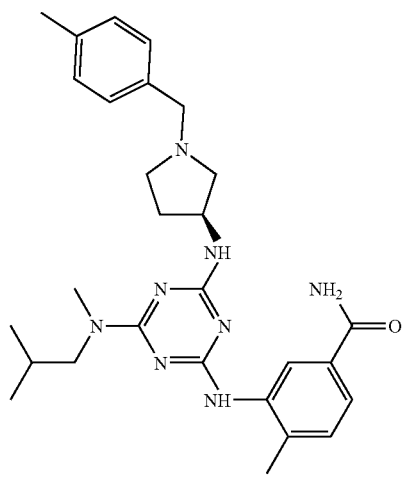
| 105 | 502.667 |
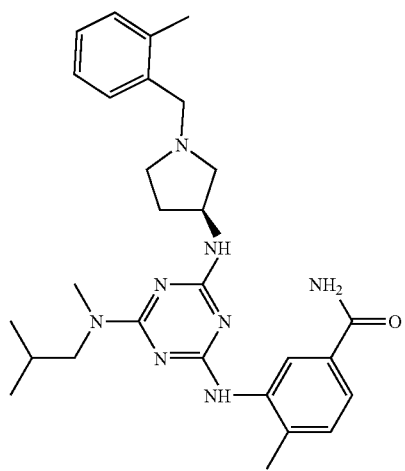

TABLE 1-continued
| # | MW | |
|---|---|---|
| 106 | 383.5 | 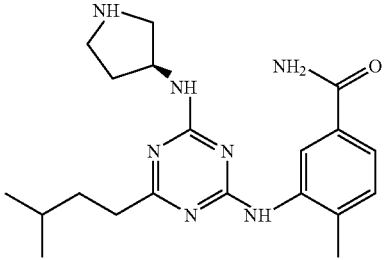 |
| 107 | 502.667 | 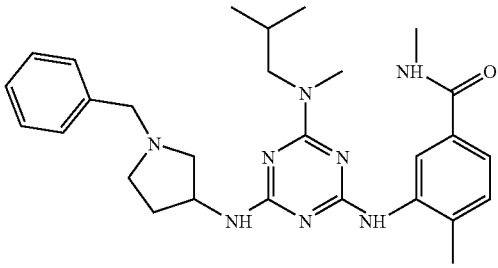 |
| 108 | 426.569 | 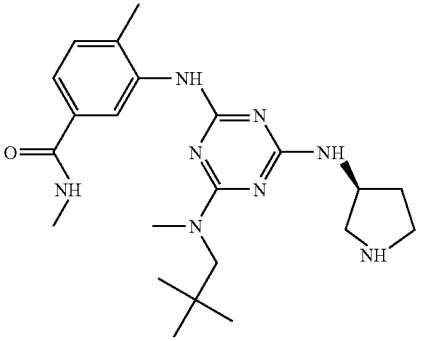 |
| 109 | 517.682 | 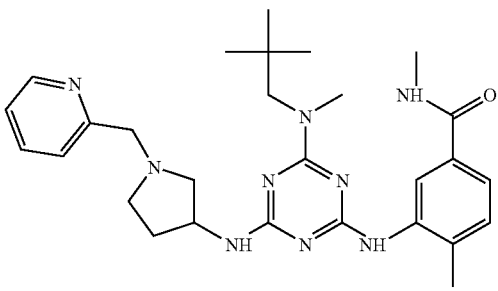 |
| 110 | 432.96 | 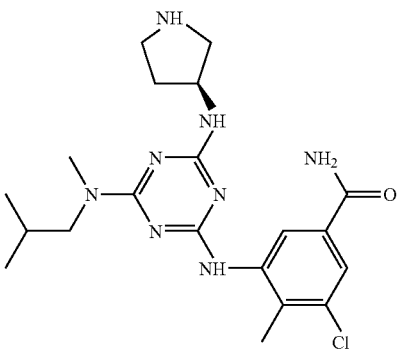 |

TABLE 1-continued
| # | MW |
|---|-----|
| 111 | 446.987 |
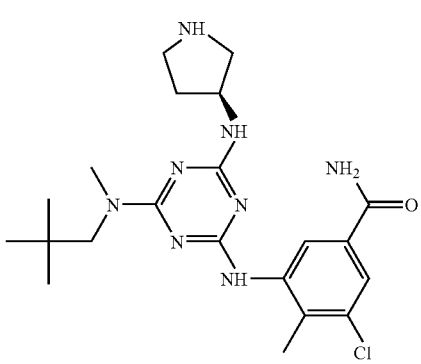
| 112 | 415.929 |
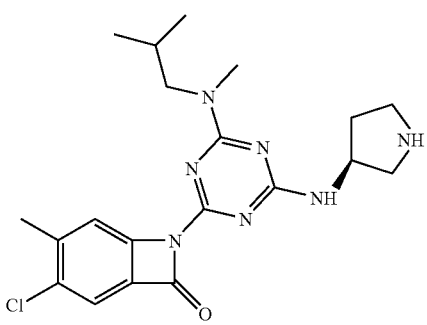
| 113 | 429.956 |
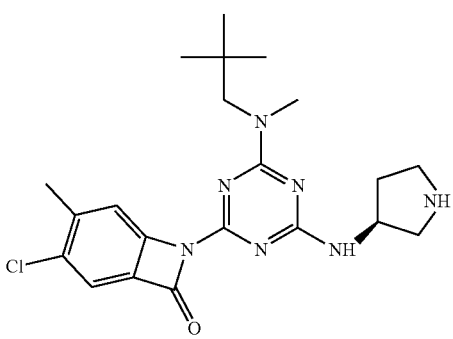
| 114 | 412.542 |
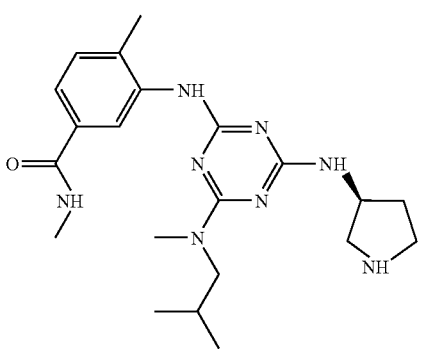

TABLE 1-continued
| # | MW |
|---|---|
| 115 | 532.649 |
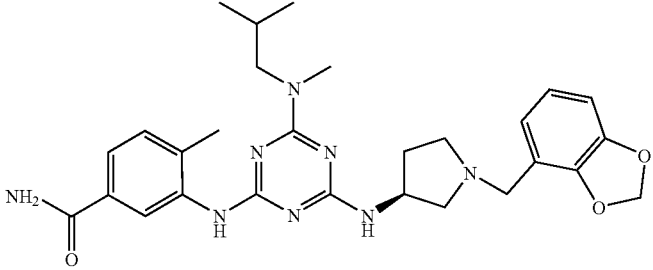
| 116 | 506.63 |
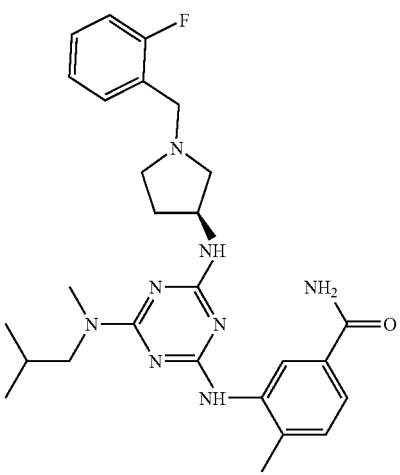
| 117 | 502.667 |
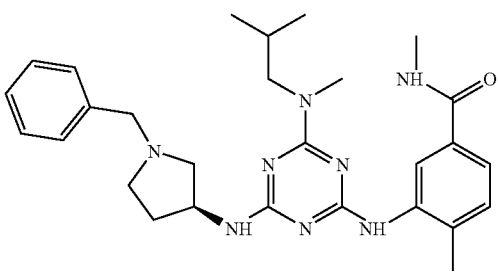
| 118 | 532.693 |
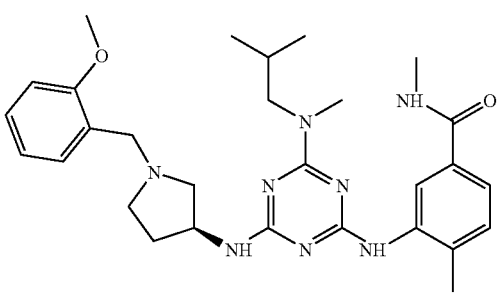

TABLE 1-continued
| # | MW | |
|---|---|---|
| 119 | 489.628 | 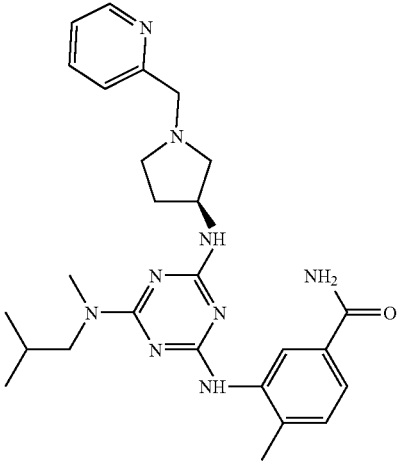 |
| 120 | 502.623 | 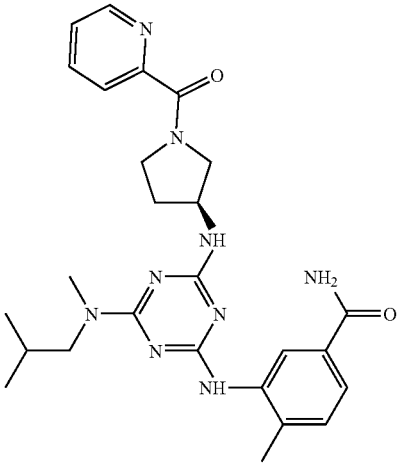 |
| 121 | 489.628 | 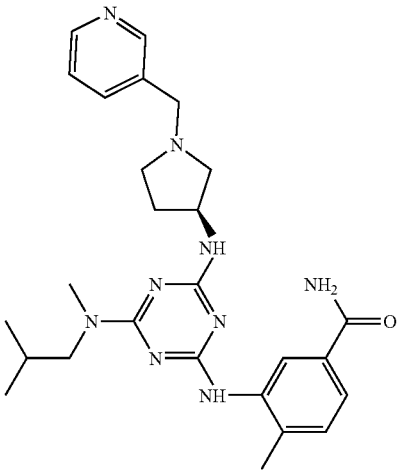 |

TABLE 1-continued
| # | MW |
|---|---|
| 122 | 489.628 |
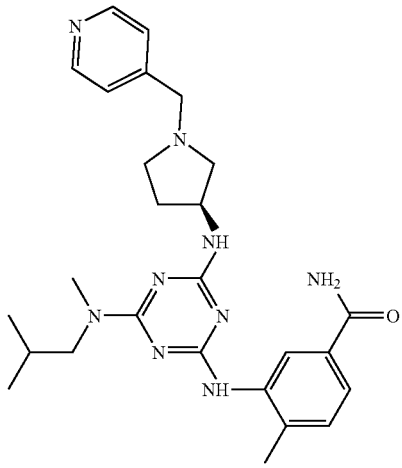
| 123 | 506.638 |
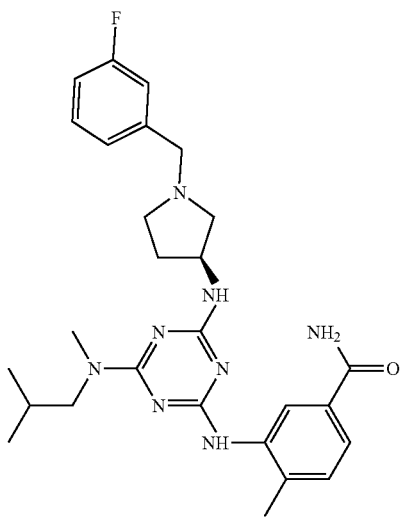
| 124 | 412.542 |
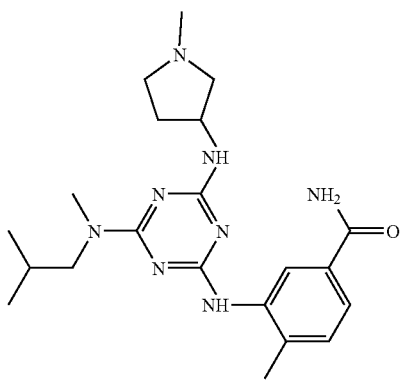

TABLE 1-continued

| # | MW |
|---|-----|
| 125 | 513.65 |
| 126 | 506.63 |
| 127 | 523.085 |

TABLE 1-continued
| # | MW | |
|---|---|---|
| 128 | 557.53 | 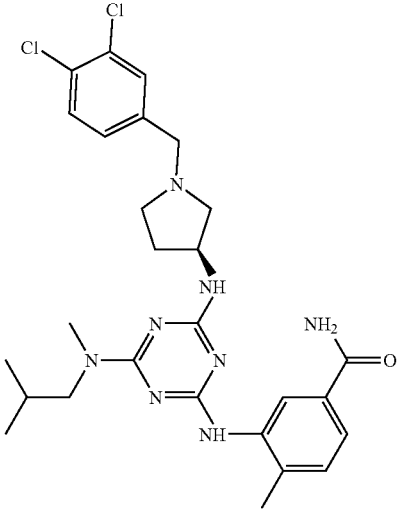 |
| 129 | 513.65 | 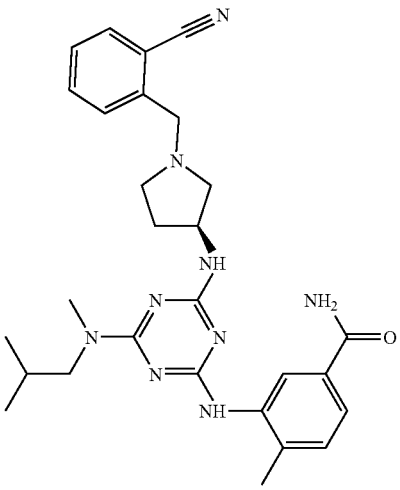 |
| 130 | 516.694 | 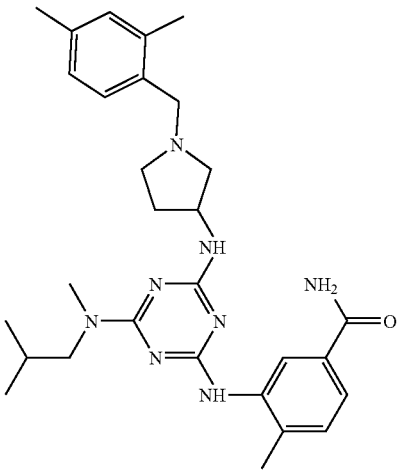 |

TABLE 1-continued

| # | MW |
|---|---|
| 131 | 412.542 |
| 132 | 426.569 |
| 133 | 397.527 |
| 134 | 502.667 |

TABLE 1-continued
| # | MW |
|---|---|
| 135 | 440.596 |
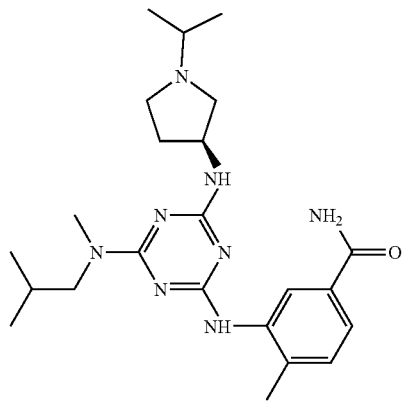
| 136 | 412.542 |
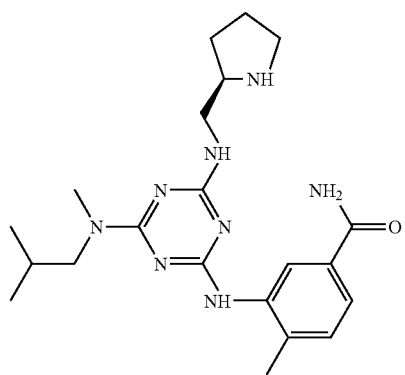
| 137 | 329.364 |
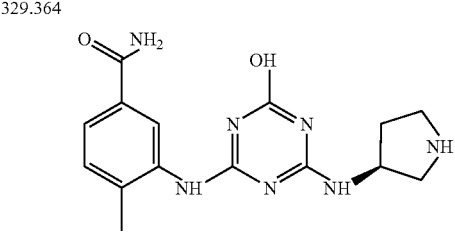
| 138 | 424.553 |
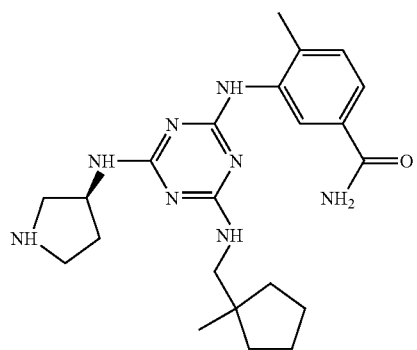

TABLE 1-continued
| # | MW | |
|---|---|---|
| 139 | 438.58 | 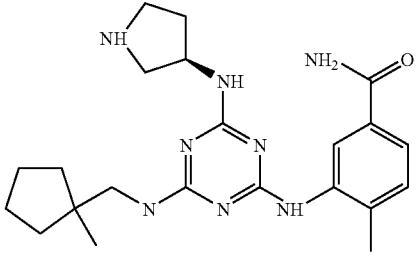 |
| 140 | 432.96 | 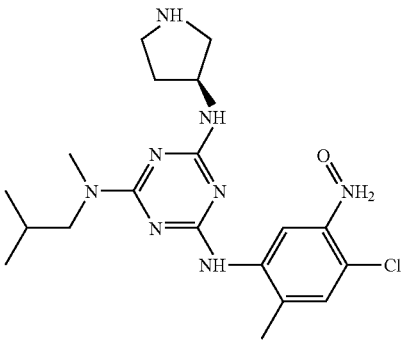 |
| 141 | 446.987 | 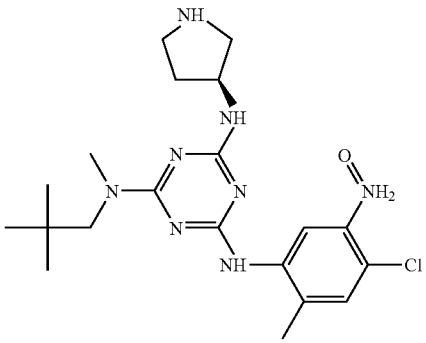 |
| 142 | 516.694 | 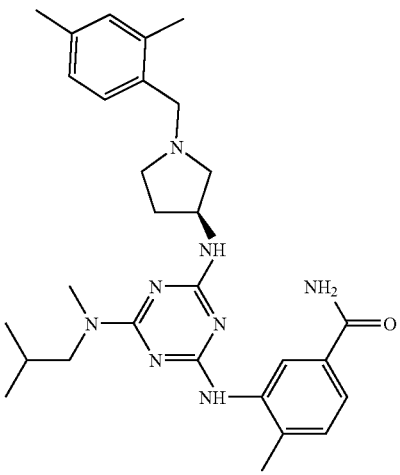 |

TABLE 1-continued
| # | MW | |
|---|---|---|
| 143 | 516.694 | 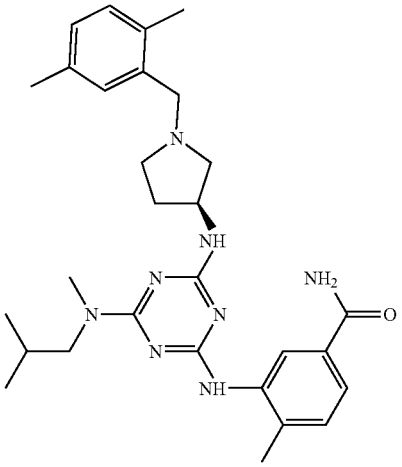 |
| 144 | 516.694 | 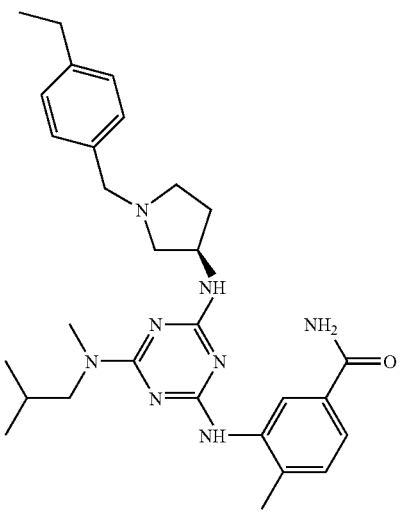 |
| 145 | 530.721 | 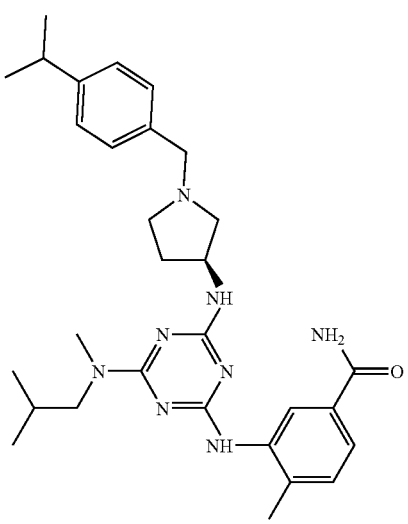 |

TABLE 1-continued
| # | MW |
|---|---|
| 146 | 544.748 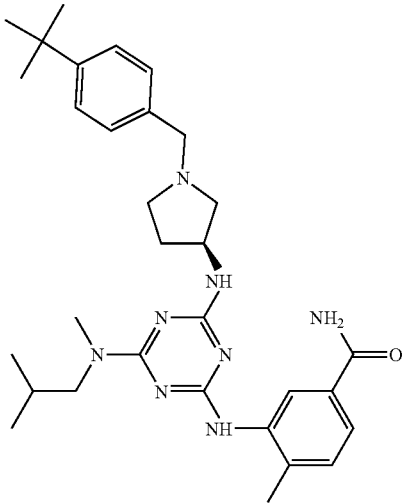 |
| 147 | 503.655 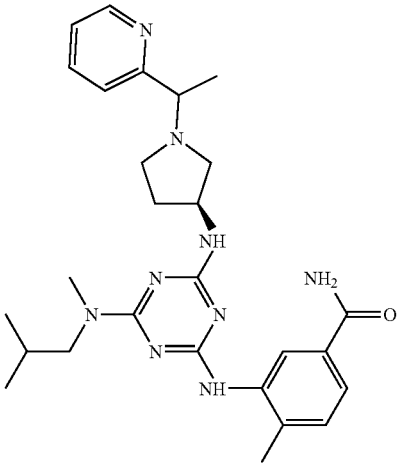 |
| 148 | 503.655 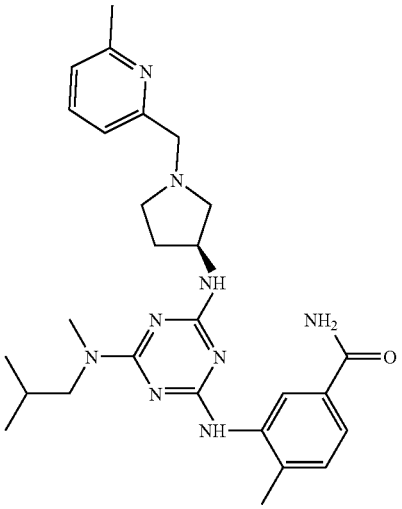 |

TABLE 1-continued
| # | MW |
|---|---|
| 149 | 503.655 |
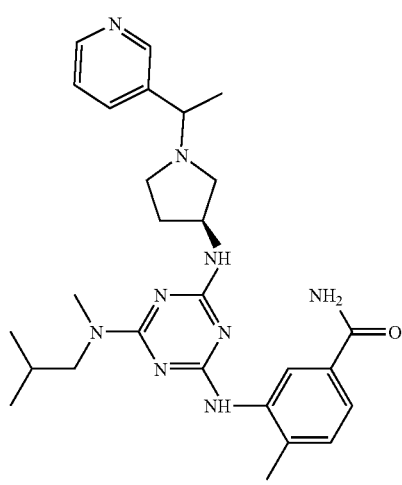
| 150 | 412.542 |
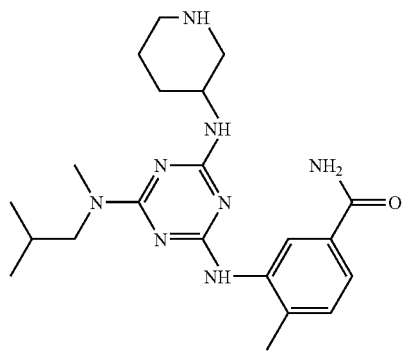
| 151 | 530.721 |
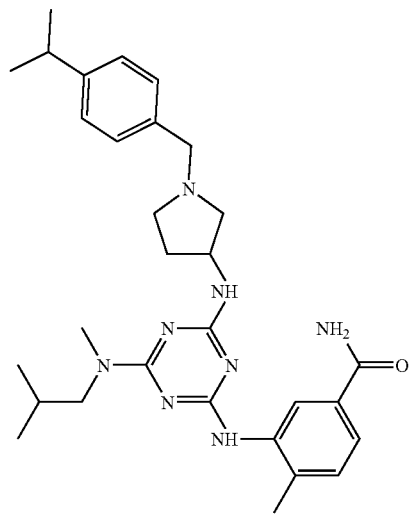

| # | MW |
|---|---|
| 152 | 518.666 |
| 153 | 504.639 |
| 154 | 504.639 |

TABLE 1-continued
| # | MW | |
|---|---|---|
| 155 | 523.085 | 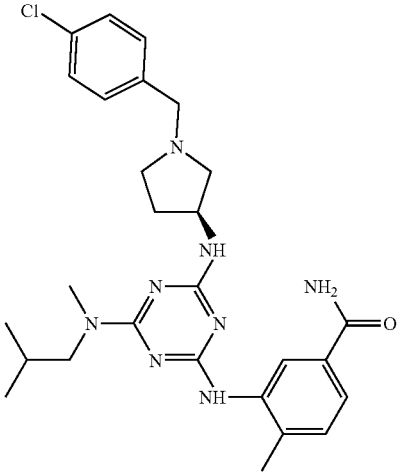 |
| 156 | 556.637 | 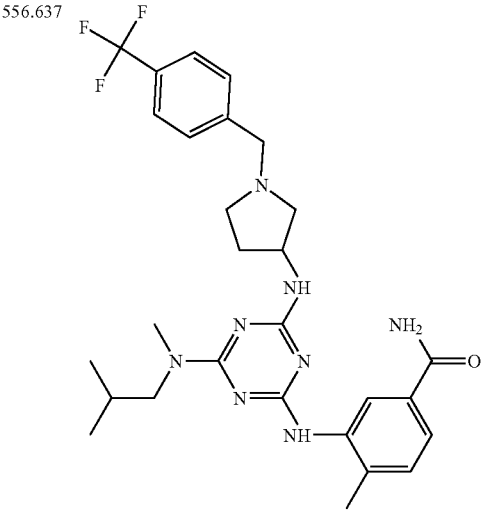 |
| 157 | 503.655 | 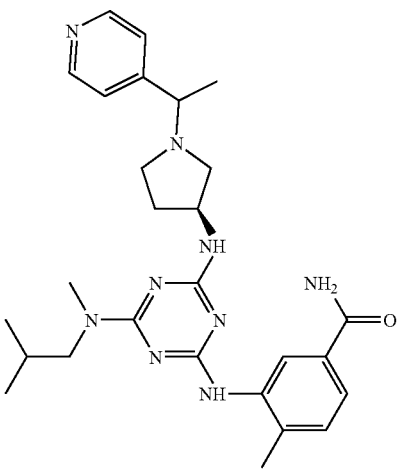 |

TABLE 1-continued
| # | MW | |
|---|---|---|
| 158 | 470.622 | 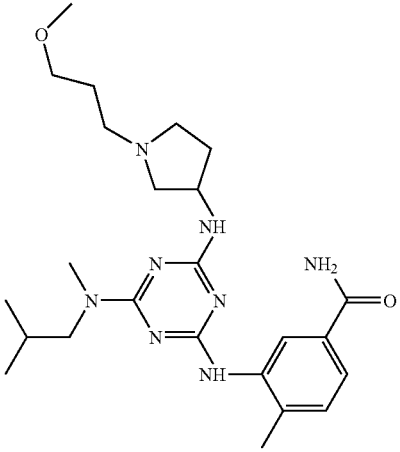 |
| 159 | 482.677 | 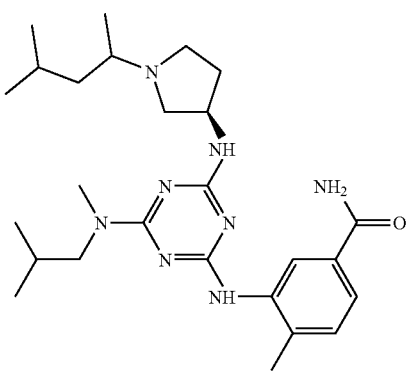 |
| 160 | 480.661 | 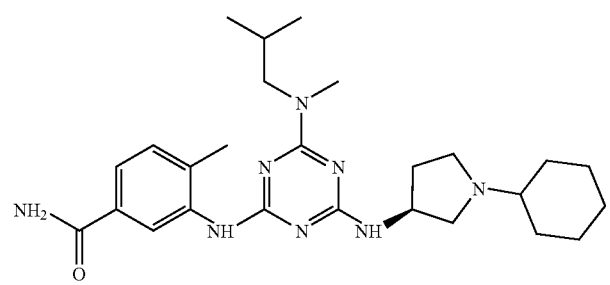 |
| 161 | 412.542 | 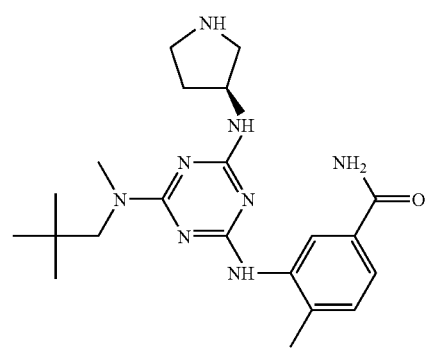 |

TABLE 1-continued
| # | MW | |
|---|---|---|
| 162 | 426.569 | 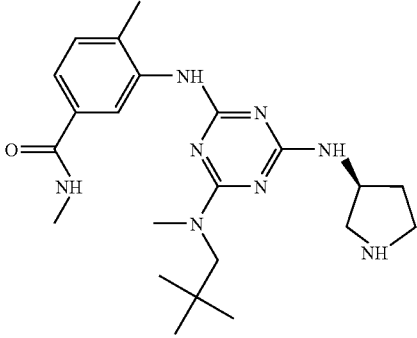 |
| 163 | 454.623 | 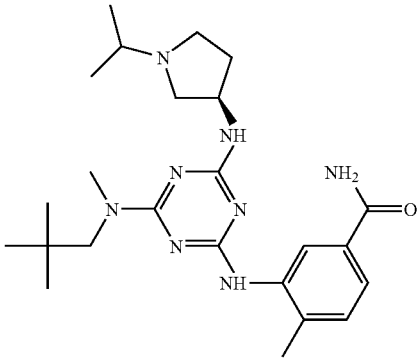 |
| 164 | 494.688 | 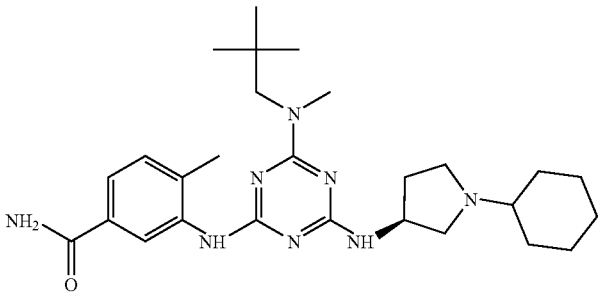 |
| 165 | 496.704 | 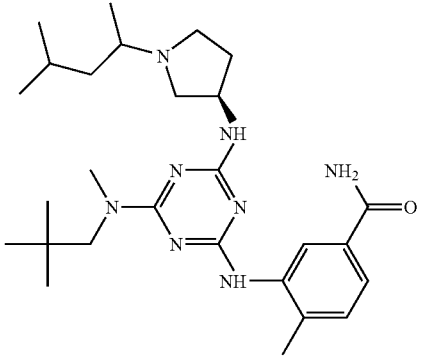 |

TABLE 1-continued
| # | MW |
|---|---|
| 166 | 504.639 |
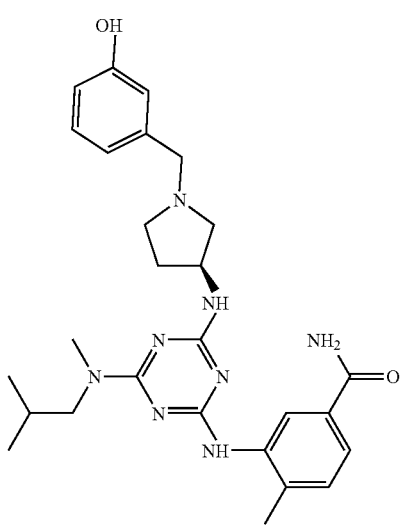
| 167 | 504.639 |
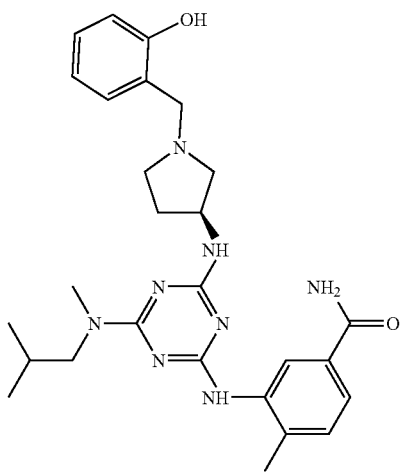
| 168 | 411.554 |
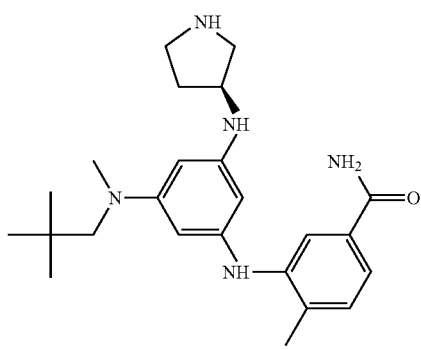

TABLE 1-continued
| # | MW |
|---|---|
| 169 | 396.499 |
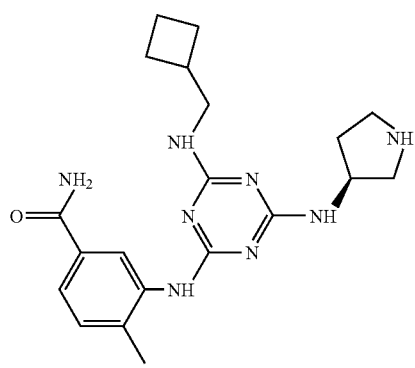
| 170 | 502.667 |
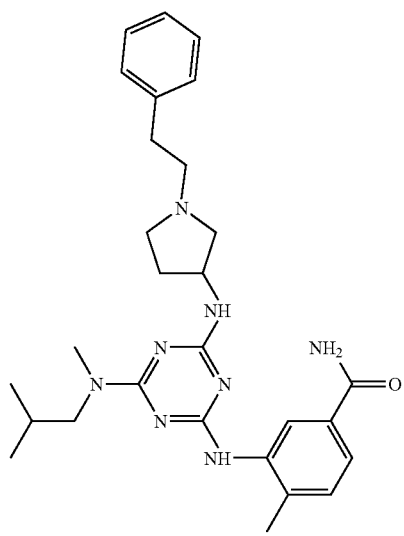
| 171 | 440.596 |
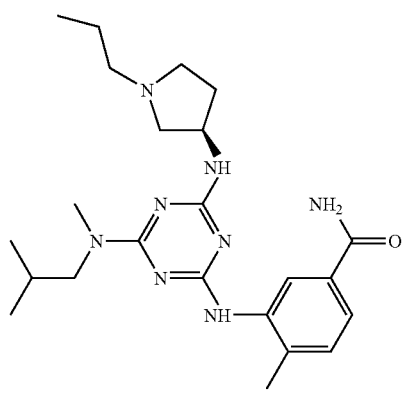

TABLE 1-continued

| # | MW |
|---|---|
| 172 | 454.623 |
| 173 | 470.622 |
| 174 | 468.65 |
| 175 | 490.656 |

TABLE 1-continued
| # | MW | |
|---|---|---|
| 176 | 518.666 | 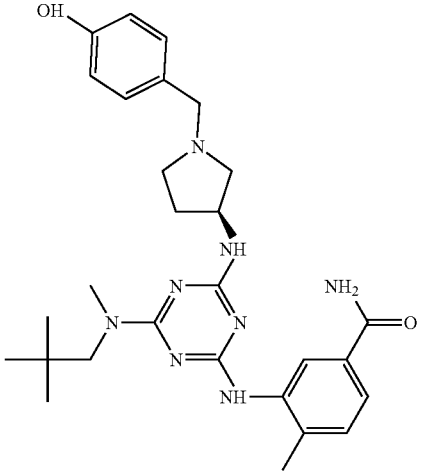 |
| 177 | 452.607 | 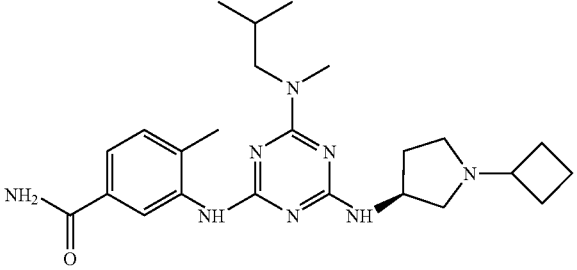 |
| 178 | 466.634 | 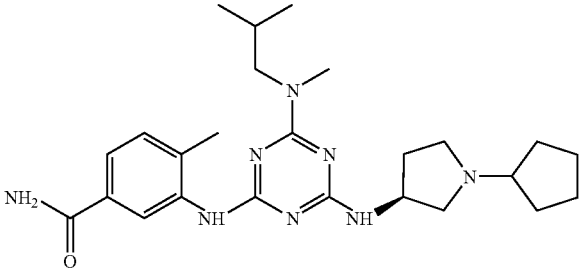 |
| 179 | 484.649 | 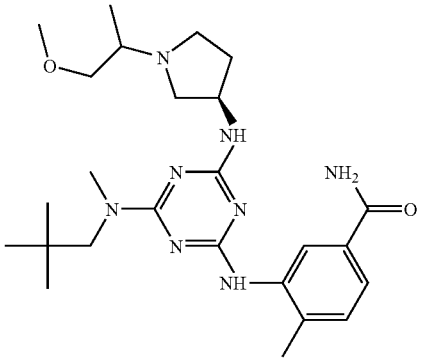 |

TABLE 1-continued
| # | MW | |
|---|---|---|
| 180 | 426.569 | 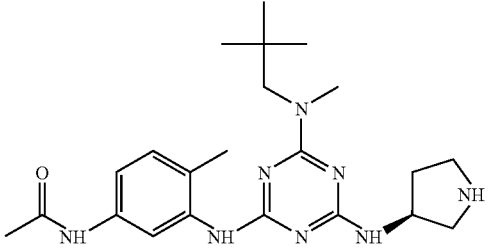 |
| 181 | 440.596 | 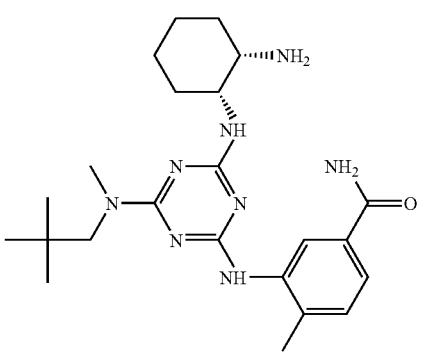 |
| 182 | 410.526 | 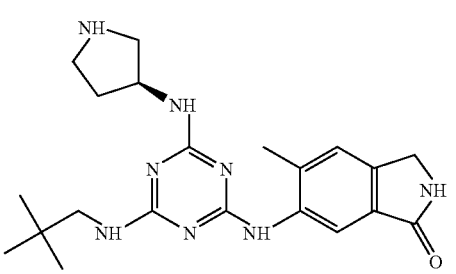 |
| 183 | 424.553 | 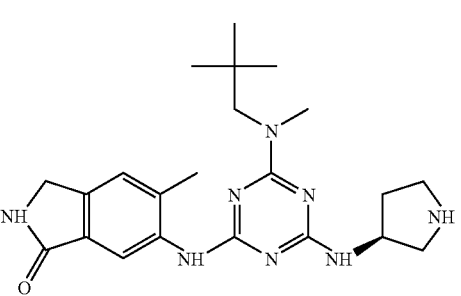 |
| 184 | 410.526 | 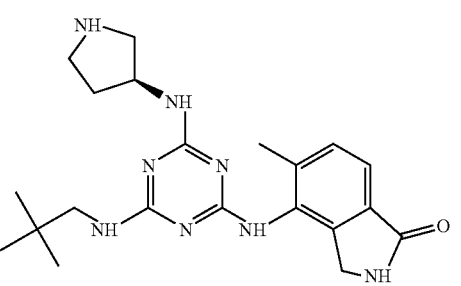 |

TABLE 1-continued

| # | MW | Structure |
|---|---|---|
| 185 | 424.553 | |
| 186 | 412.542 | |
| 187 | 466.634 | |
| 188 | 480.661 | |
| 189 | 470.622 | |

TABLE 1-continued
| # | MW |
|---|---|
| 190 | 454.623 |
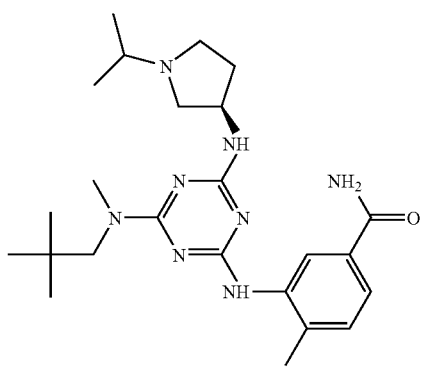
| 191 | 482.677 |
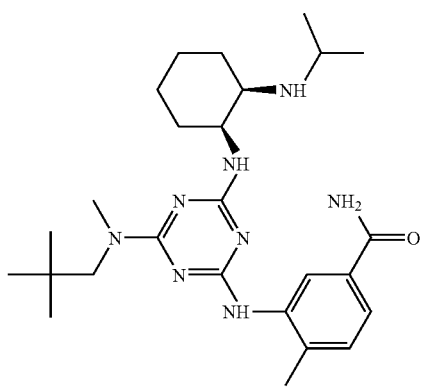
| 192 | 482.677 |
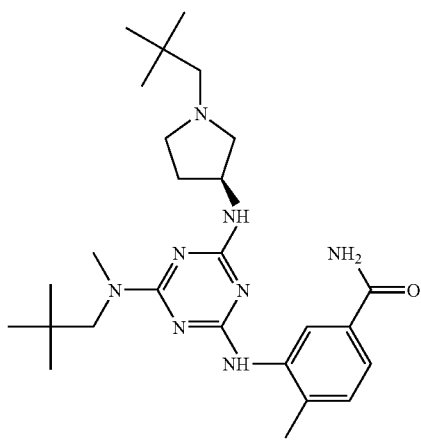

TABLE 1-continued
| # | MW | |
|---|---|---|
| 193 | 454.623 | 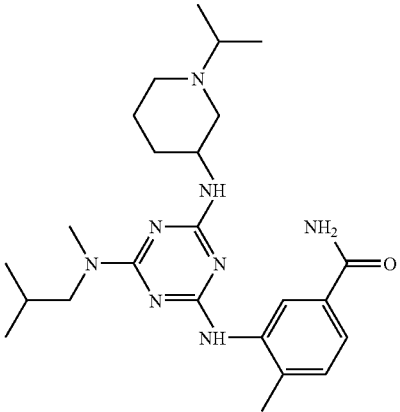 |
| 194 | 482.677 | 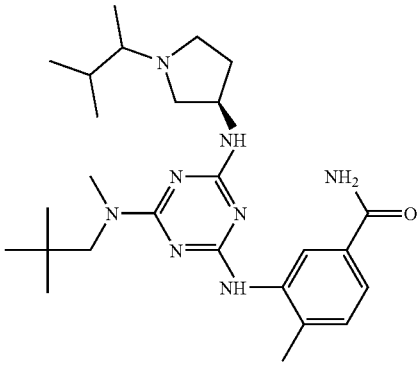 |
| 195 | 428.497 | 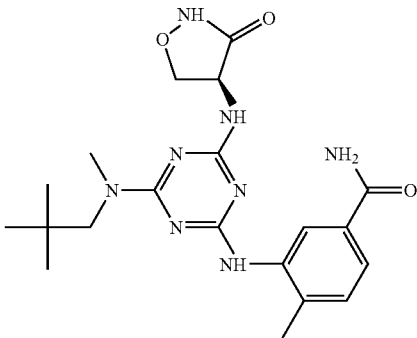 |
| 196 | 468.65 | 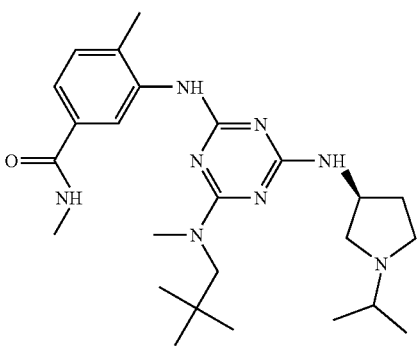 |

TABLE 1-continued
| # | MW | |
|---|---|---|
| 197 | 484.649 | 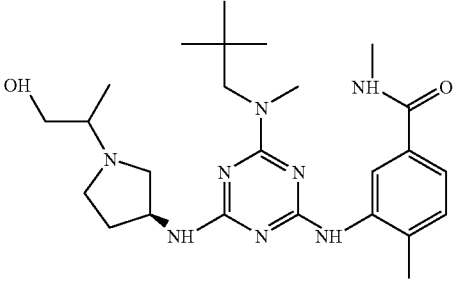 |
| 198 | 440.596 | 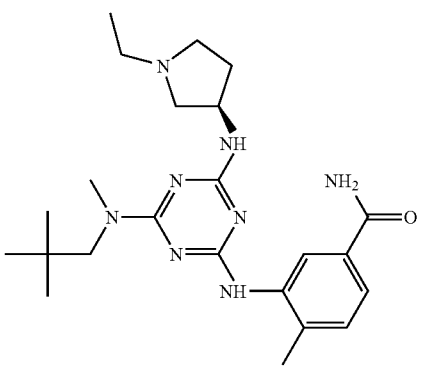 |
| 199 | 452.485 | 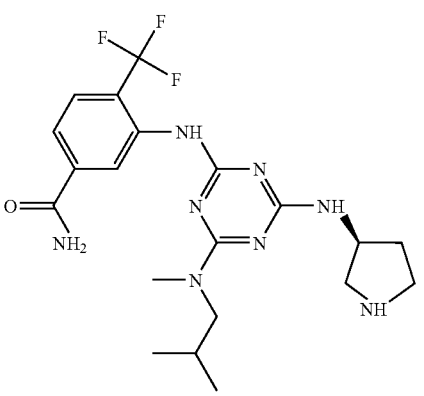 |
| 200 | 480.539 | 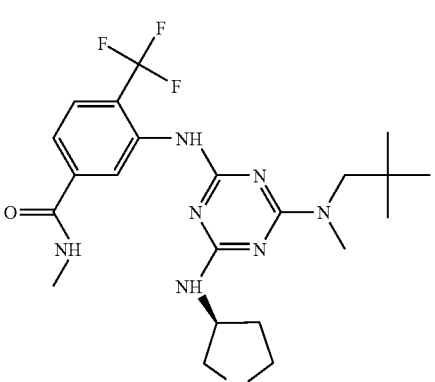 |

TABLE 1-continued
| # | MW | |
|---|---|---|
| 201 | 454.623 | 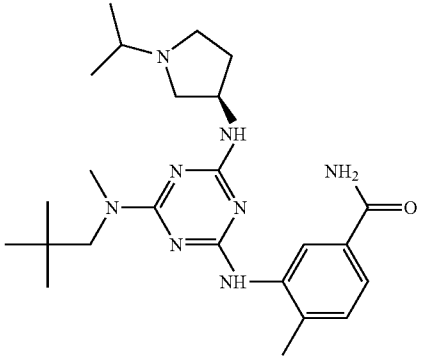 |
| 202 | 440.596 | 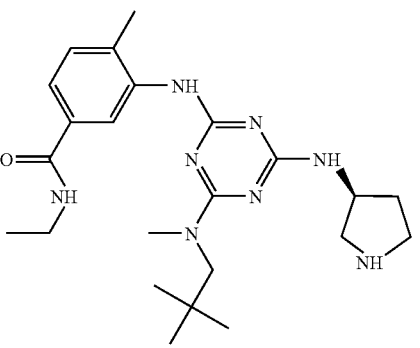 |
| 203 | 426.569 | 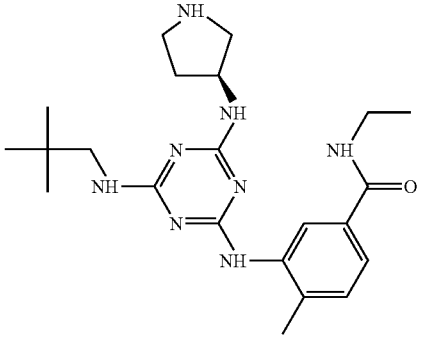 |
| 204 | 468.65 | 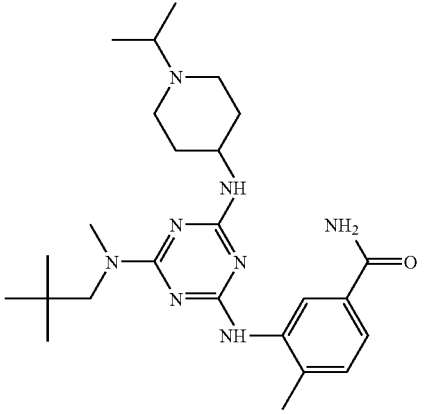 |

TABLE 1-continued

| # | MW | |
|---|---|---|
| 205 | 412.542 | |
| 206 | 383.5 | |
| 207 | 397.527 | |
| 208 | 423.908 | |

TABLE 1-continued

| # | MW |
|---|---|
| 209 | 426.569 |
| 210 | 426.569 |
| 211 | 426.569 |
| 212 | 488.64 |

TABLE 1-continued

| # | MW |
|---|---|
| 213 | 476.604 |
| 214 | 503.655 |
| 215 | 426.569 |
| 216 | 502.667 |

TABLE 1-continued
| # | MW | |
|---|---|---|
| 217 | 456.595 | 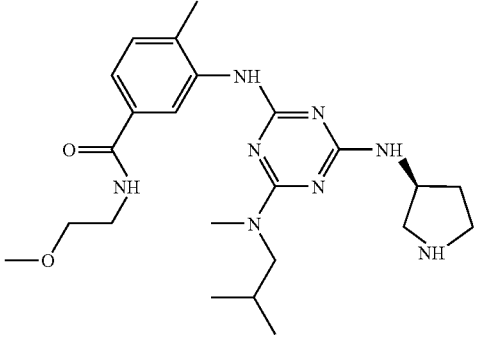 |
| 218 | 470.622 | 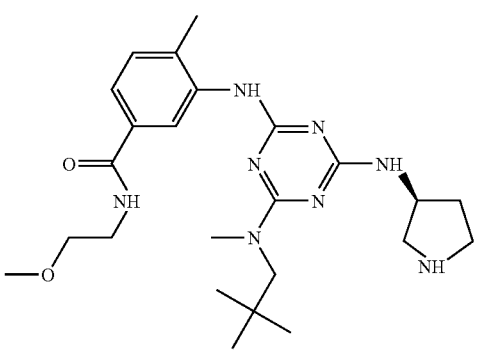 |
| 219 | 440.596 | 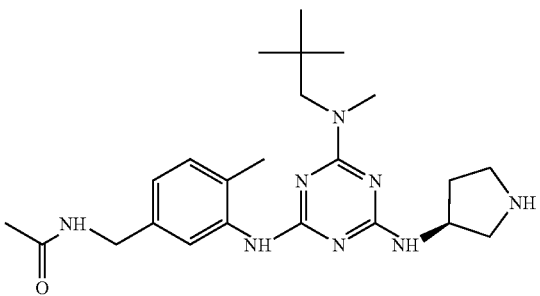 |
| 210 | 502.667 | 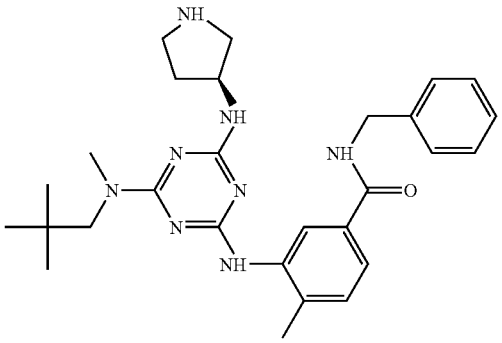 |

TABLE 1-continued
| # | MW | |
|---|---|---|
| 221 | 516.694 | 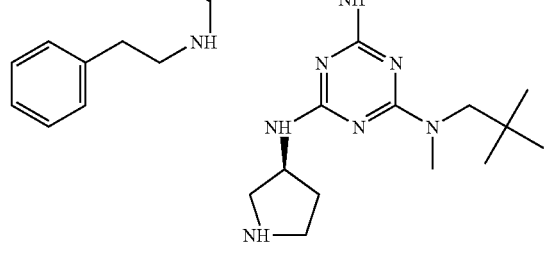 |
| 222 | 427.553 | 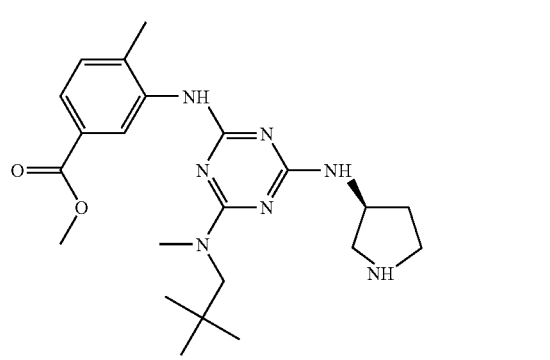 |
| 223 | 531.709 | 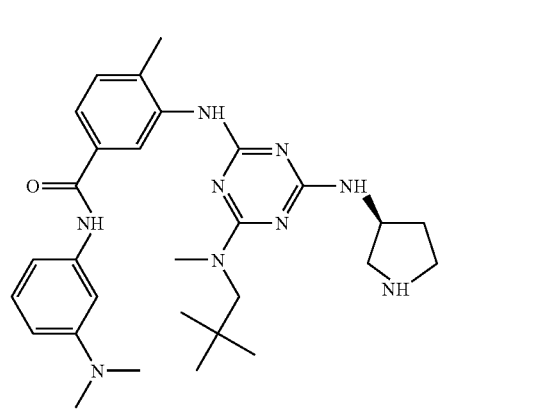 |
| 224 | 517.682 | 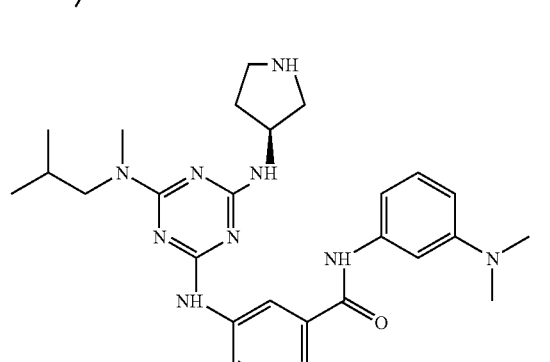 |

TABLE 1-continued
| # | MW | |
|---|---|---|
| 225 | 502.667 | 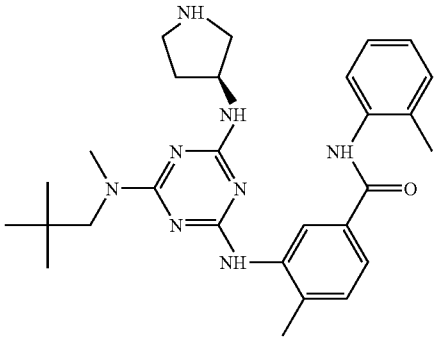 |
| 226 | 502.667 | 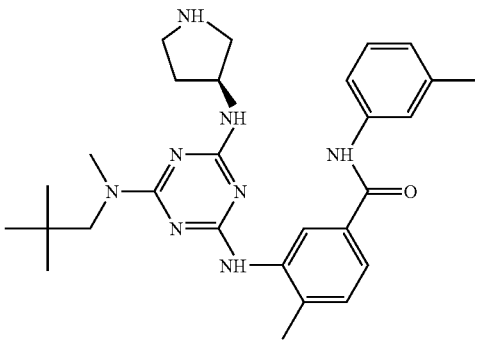 |
| 227 | 440.596 | 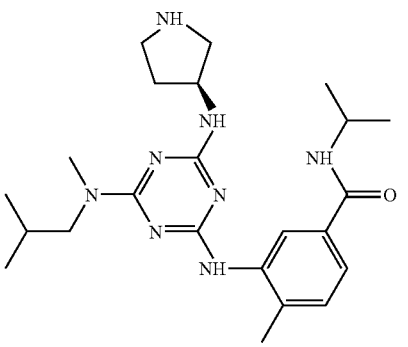 |
| 228 | 454.623 | 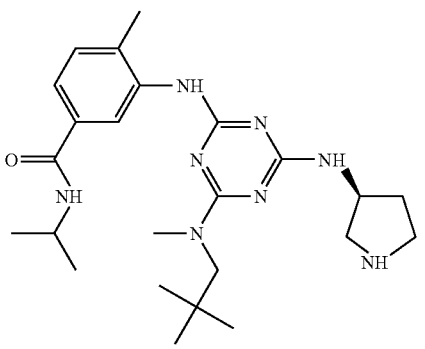 |

TABLE 1-continued

| # | MW |
|---|---|
| 229 | 426.569 |
| 230 | 426.569 |
| 231 | 468.65 |
| 232 | 475.601 |

TABLE 1-continued
| # | MW | |
|---|---|---|
| 233 | 489.628 | 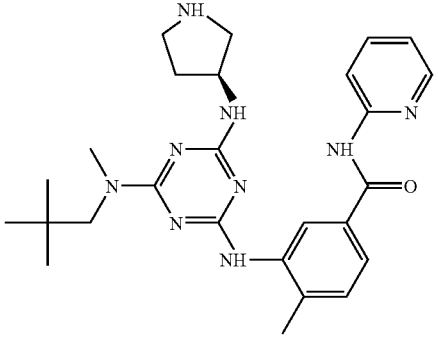 |
| 234 | 508.593 | 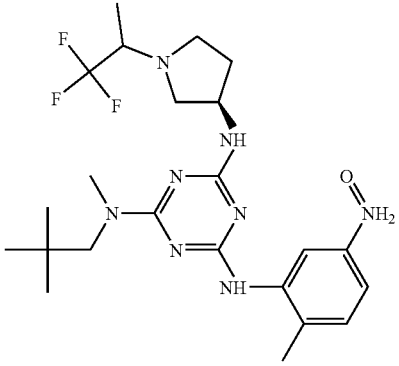 |
| 235 | 401.537 | 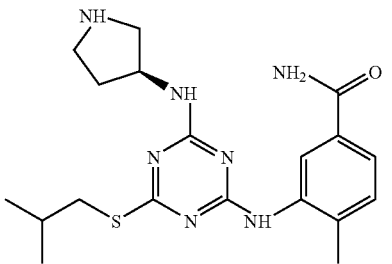 |
| 236 | 415.564 | 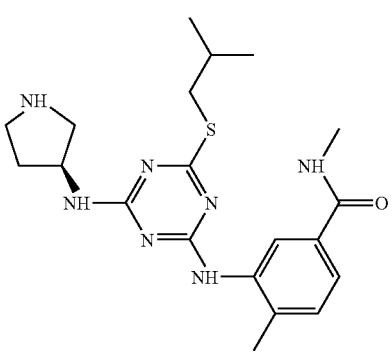 |

TABLE 1-continued

| # | MW |
|---|---|
| 237 | 454.623 |
| 238 | 480.661 |
| 239 | 468.65 |
| 240 | 494.688 |

TABLE 1-continued
| # | MW | |
|---|------|---|
| 241 | 488.64 | 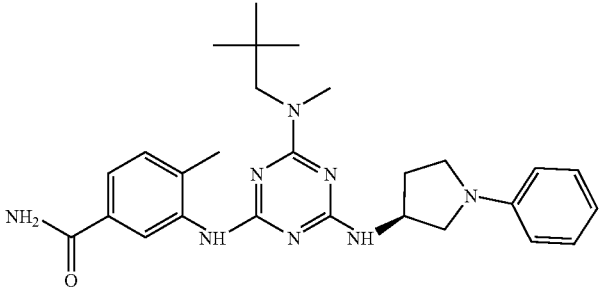 |
| 242 | 438.58 | 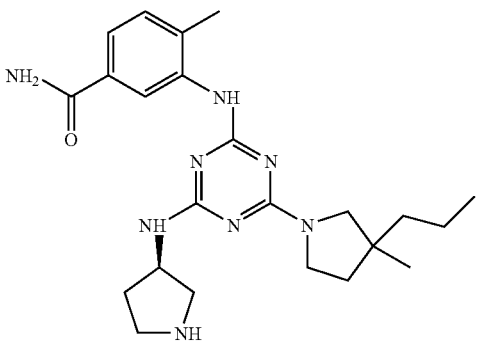 |
| 243 | 413.526 | 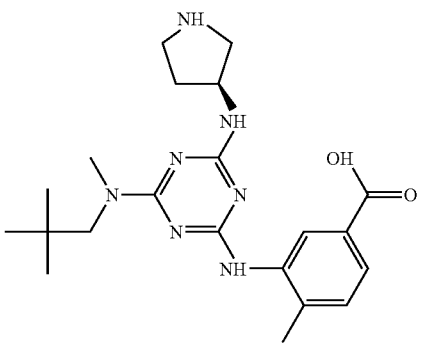 |
| 244 | 448.594 | 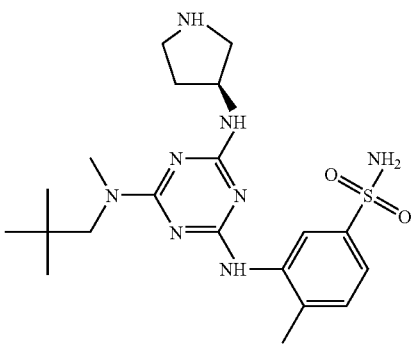 |

TABLE 1-continued

| # | MW |
|---|---|
| 245 | 412.542 |
| 246 | 413.526 |
| 247 | 482.677 |
| 248 | 424.553 |

TABLE 1-continued
| # | MW | |
|---|---|---|
| 249 | 424.553 | 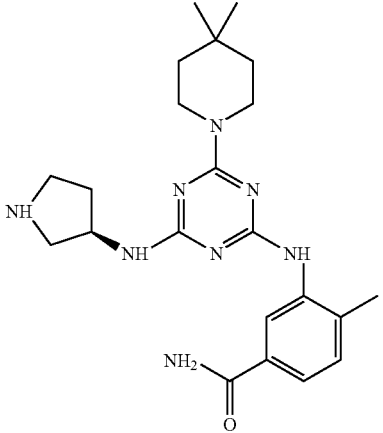 |
| 250 | 454.623 | 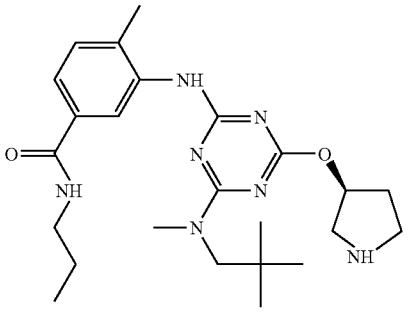 |
| 251 | 426.569 | 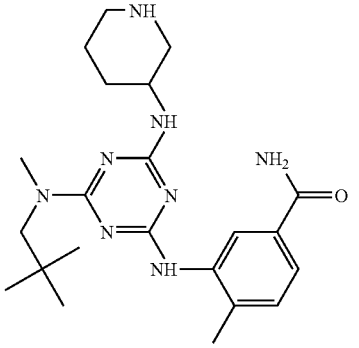 |
| 252 | 481.523 | 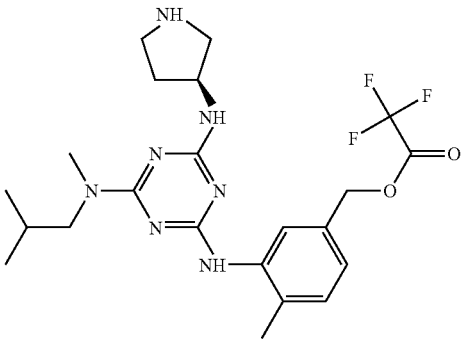 |

TABLE 1-continued
| # | MW | |
|---|---|---|
| 253 | 399.543 | 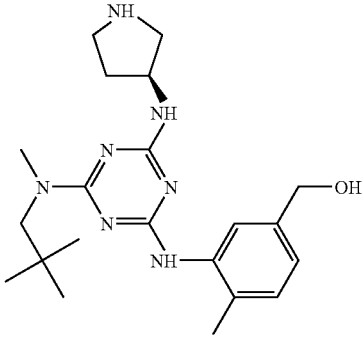 |
| 254 | 502.667 | 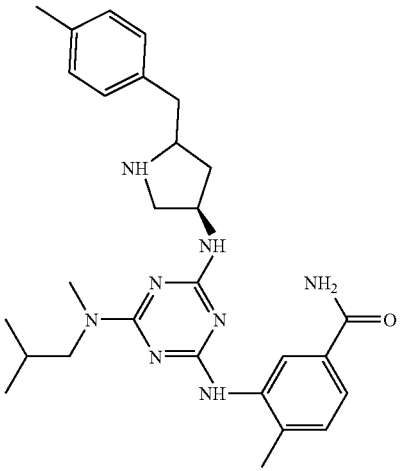 |
| 255 | 516.694 | 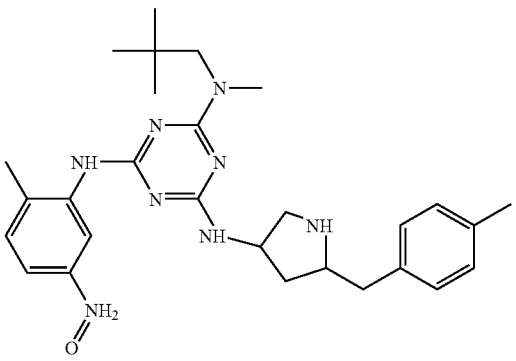 |
| 256 | 495.55 | 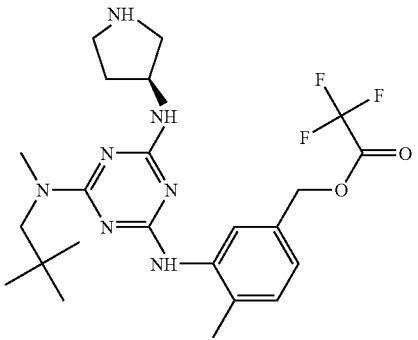 |

TABLE 1-continued

| # | MW |
|---|---|
| 257 | 456.595 |
| 258 | BLANK |
| 259 | 412.542 |
| 260 | 398.515 |
| 261 | 413.526 |

TABLE 1-continued
| # | MW | |
|---|---|---|
| 262 | 427.553 | 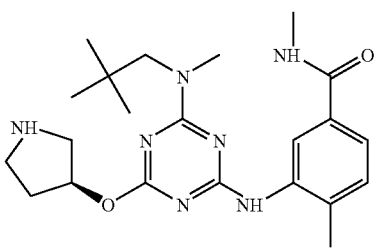 |
| 263 | 438.58 | 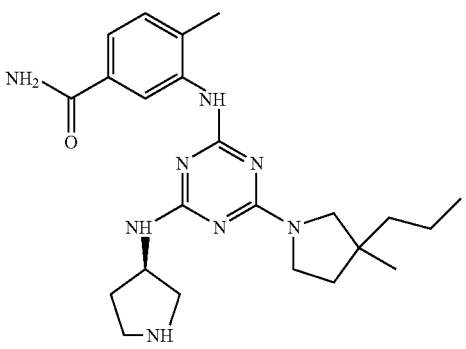 |
| 264 | 426.569 | 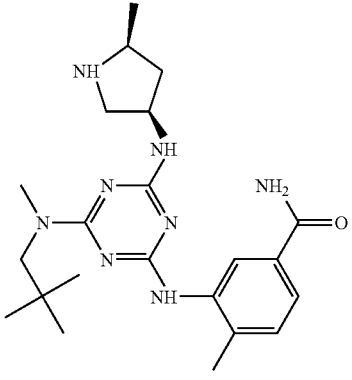 |
| 265 | 452.607 | 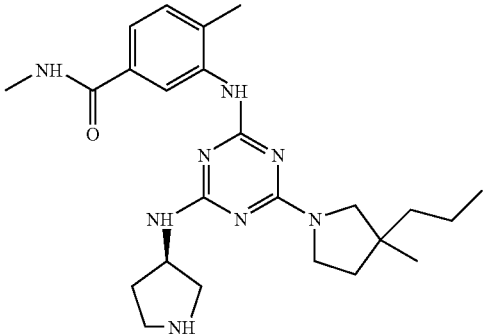 |

TABLE 1-continued
| # | MW | |
|---|---|---|
| 266 | 397.527 | 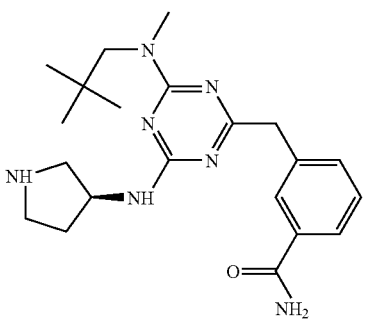 |
| 267 | 480.539 | 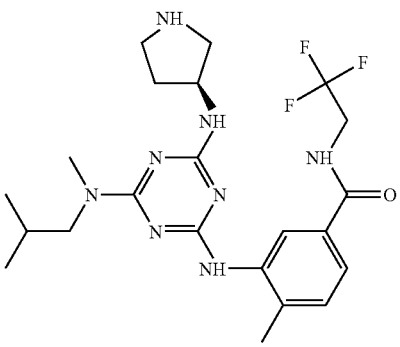 |
| 268 | 494.566 | 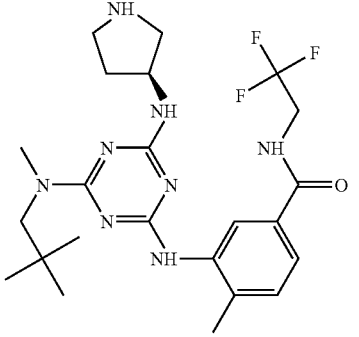 |
| 269 | 398.559 | 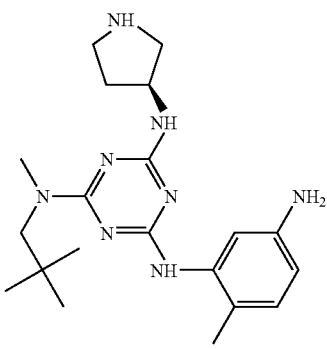 |

TABLE 1-continued

| # | MW | Structure |
|---|---|---|
| 270 | 442.568 | |
| 271 | 440.64 | |
| 272 | 440.64 | |
| 273 | 562.763 | |
| 274 | 426.569 | |

TABLE 1-continued
| # | MW | |
|---|---|---|
| 275 | 440.596 | 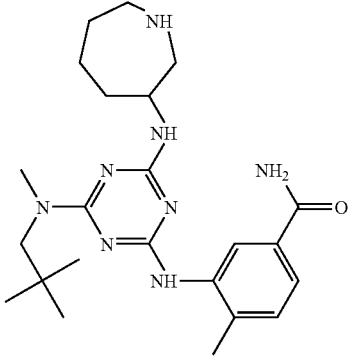 |
| 276 | 452.485 | 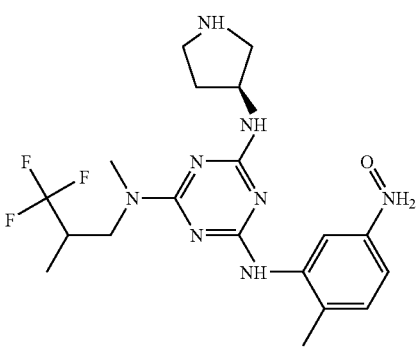 |
| 277 | 460.586 | 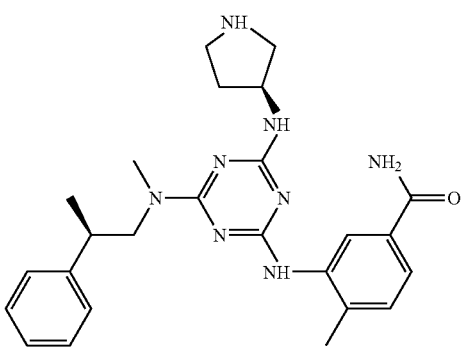 |
| 278 | 460.586 | 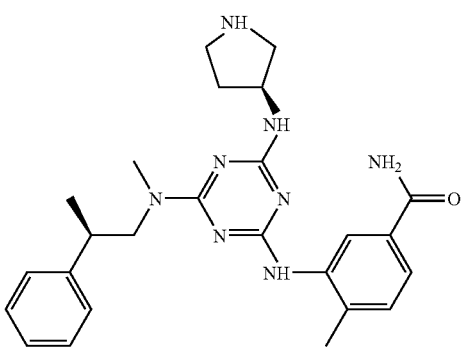 |

TABLE 1-continued

| # | MW |
|---|---|
| 279 | 557.53 |
| 280 | 454.623 |
| 281 | 438.58 |
| 282 | 440.596 |

TABLE 1-continued
| # | MW |
|---|---|
| 283 | 440.596 |
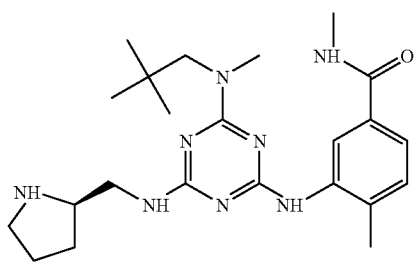
| 284 | 454.623 |
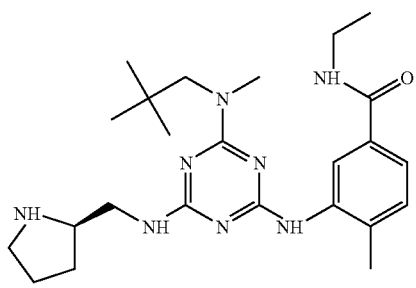
| 285 | 438.58 |
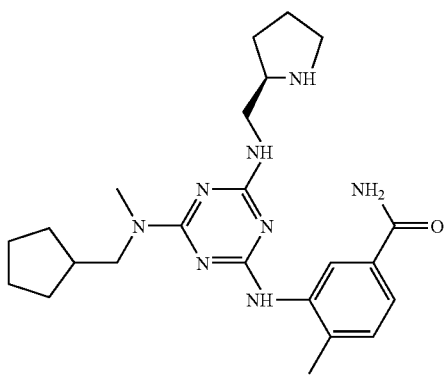
| 286 | 452.607 |
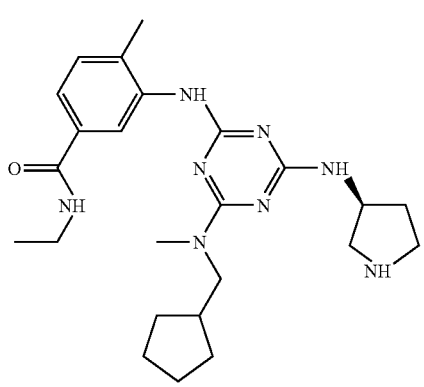

TABLE 1-continued
| # | MW | |
|---|---|---|
| 287 | 492.672 | 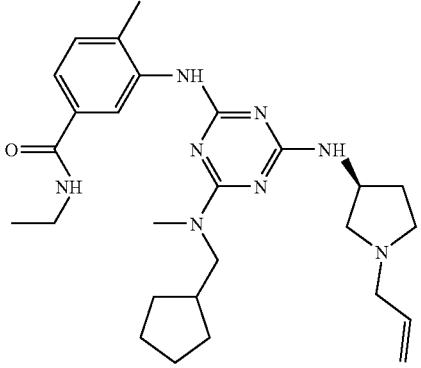 |
| 288 | 506.699 | 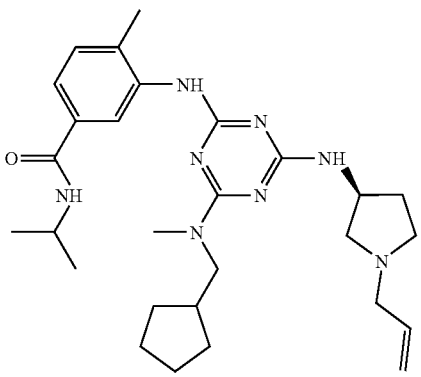 |
| 289 | 426.569 | 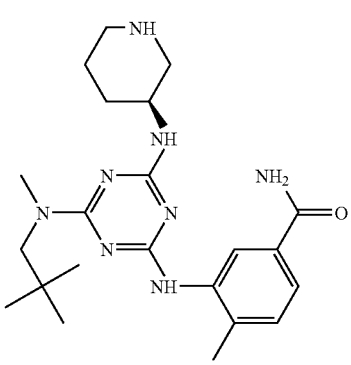 |
| 290 | 454.623 | 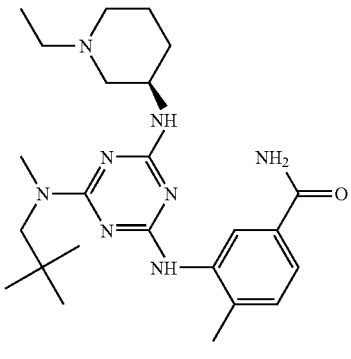 |

TABLE 1-continued
| # | MW | |
|---|---|---|
| 291 | 527.677 | 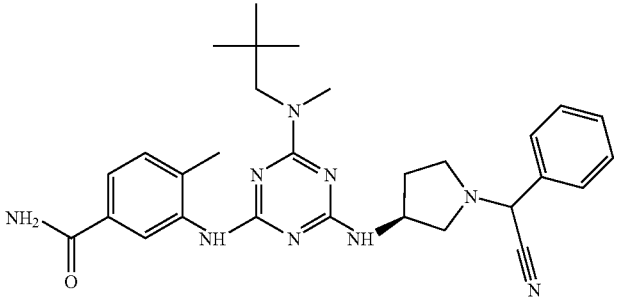 |
| 292 | 456.595 | 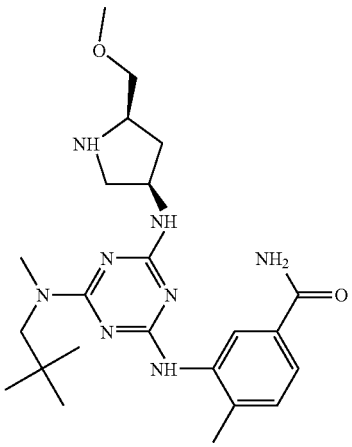 |
| 293 | 482.511 | 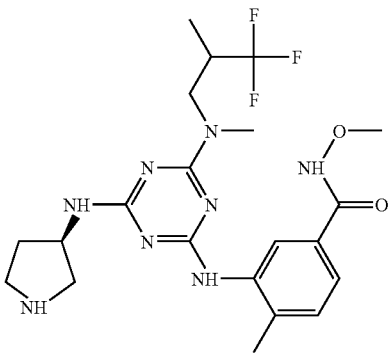 |
| 294 | 513.65 | 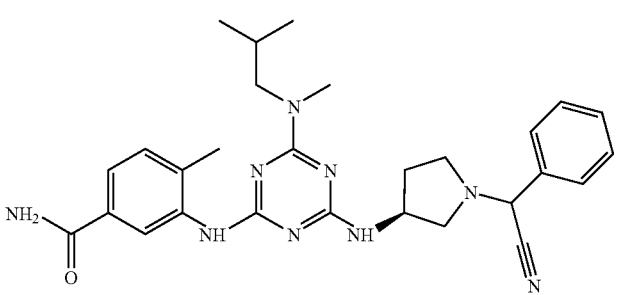 |

TABLE 1-continued
| # | MW | |
|---|---|---|
| 295 | 442.568 | 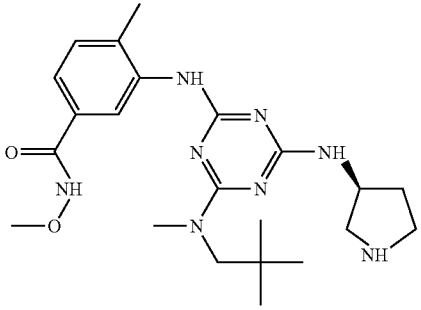 |
| 296 | 428.541 | 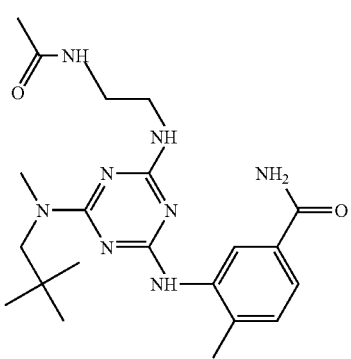 |
| 297 | 472.562 | 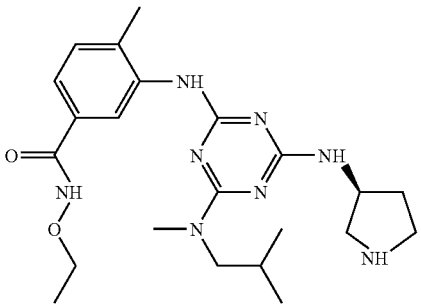 |
| 298 | 496.538 | 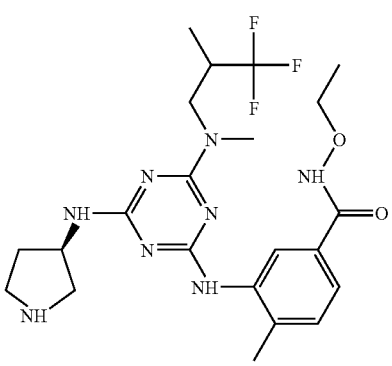 |

TABLE 1-continued
| # | MW |
|---|----|
| 299 | 456.595 |
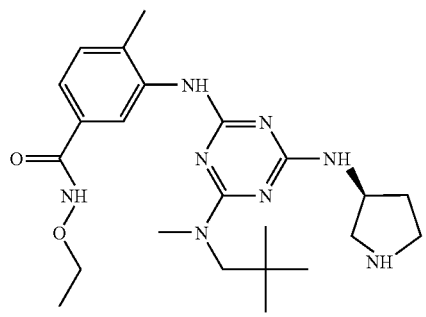
| 300 | 465.606 |
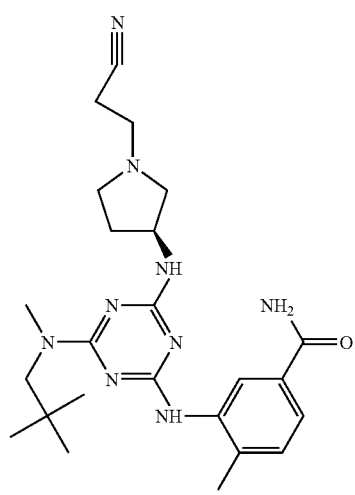
| 301 | 451.579 |
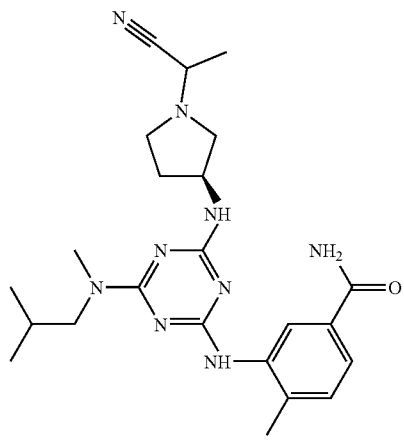

TABLE 1-continued
| # | MW | |
|---|---|---|
| 302 | 426.569 | 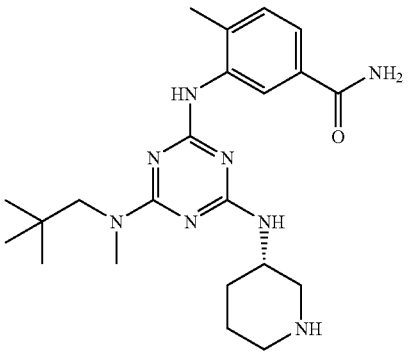 |
| 303 | 426.569 | 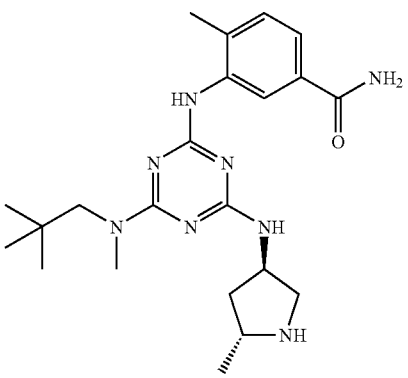 |
| 304 | 454.623 | 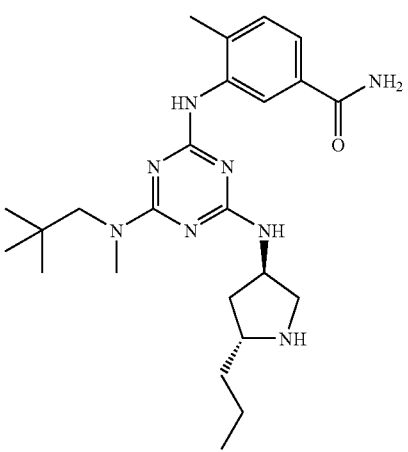 |
| 305 | 458.567 | 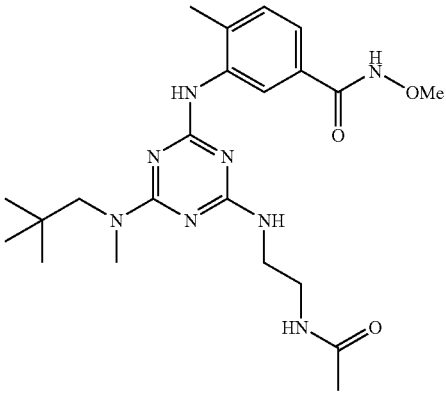 |

TABLE 1-continued
| # | MW |
|---|---|
| 306 | 464.574 |
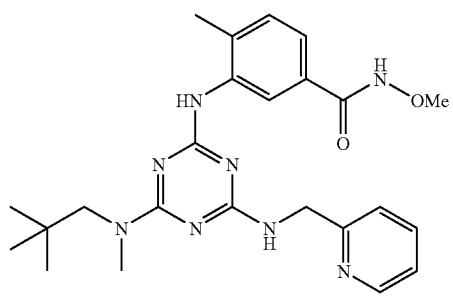
| | |
|---|---|
| 307 | 470.578 |
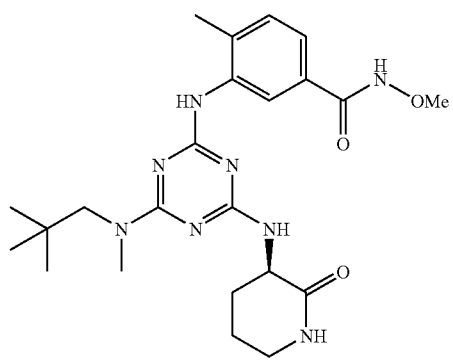
| | |
|---|---|
| 308 | 550.668 |
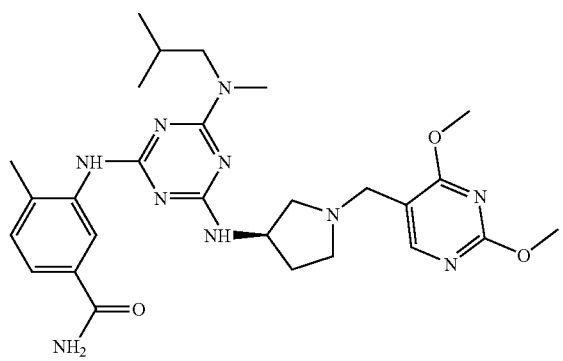
| | |
|---|---|
| 309 | 442.568 |
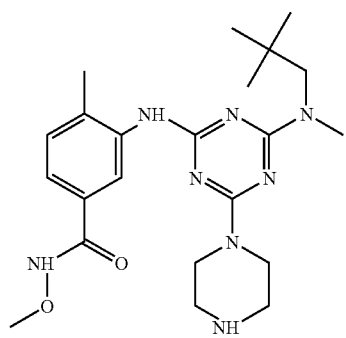

TABLE 1-continued
| # | MW | |
|---|---|---|
| 310 | 442.568 | 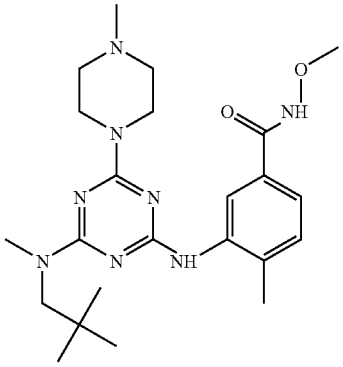 |
| 311 | 456.595 | 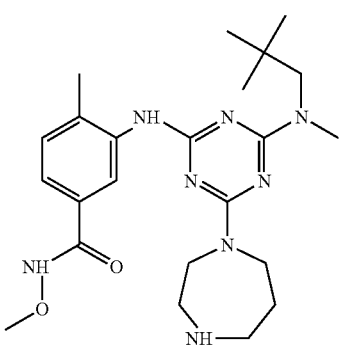 |
| 312 | 470.622 | 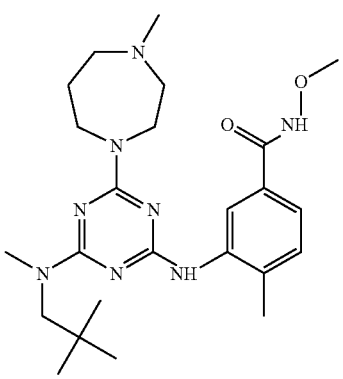 |
| 313 | 506.63 | 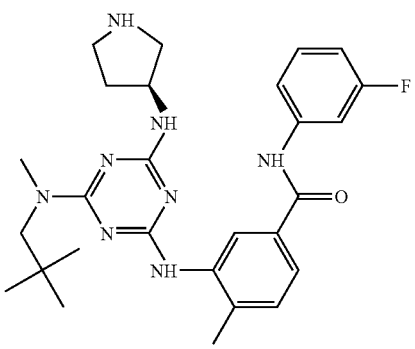 |

TABLE 1-continued
| # | MW | |
|---|---|---|
| 314 | 506.63 | 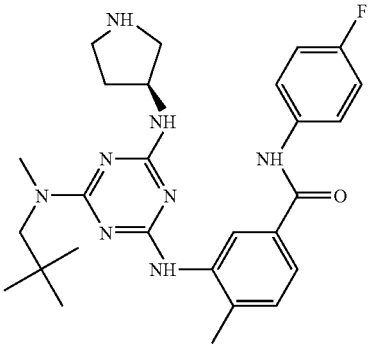 |
| 315 | 492.628 | 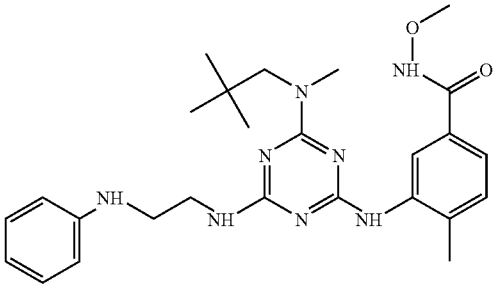 |
| 316 | 442.568 | 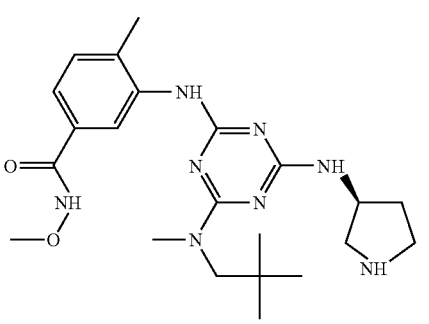 |
| 317 | 484.649 | 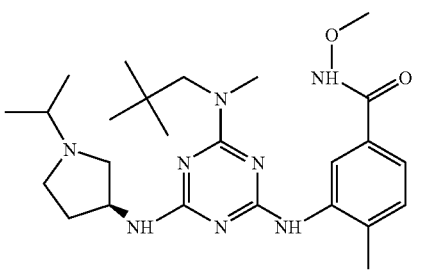 |
| 318 | 437.552 | 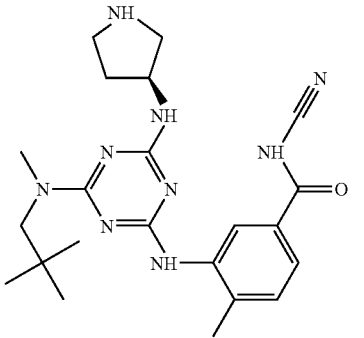 |

TABLE 1-continued
| # | MW | |
|---|---|---|
| 319 | 428.541 | 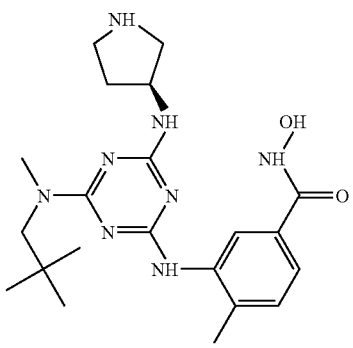 |
| 320 | 518.666 | 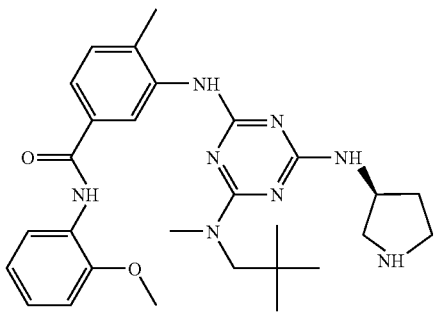 |
| 321 | 518.666 | 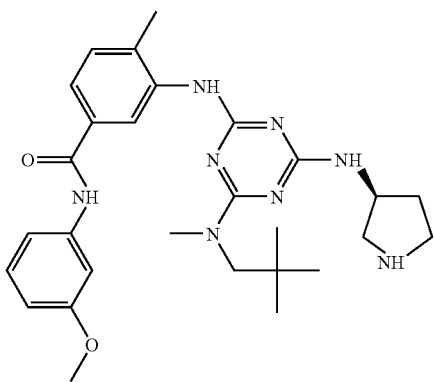 |
| 322 | 518.666 | 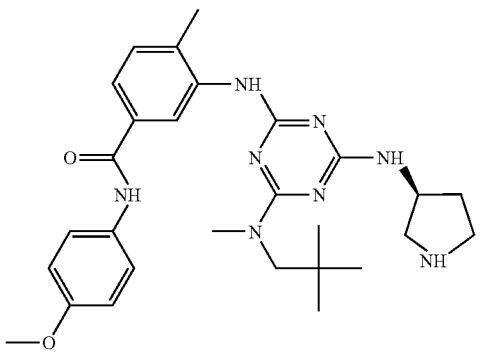 |

TABLE 1-continued
| # | MW |
|---|---|
| 323 | 463.586 |
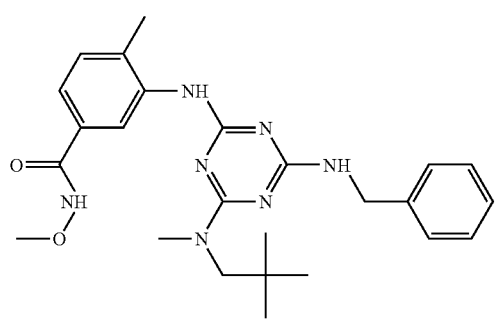
| 324 | 532.476 |
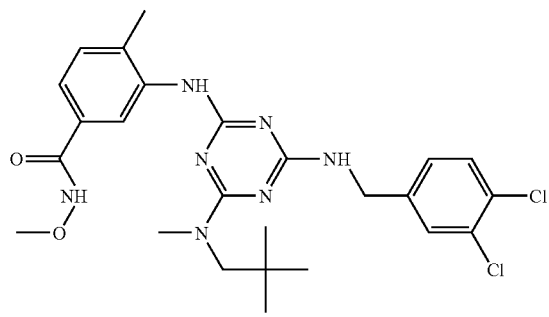
| 325 | 527.674 |
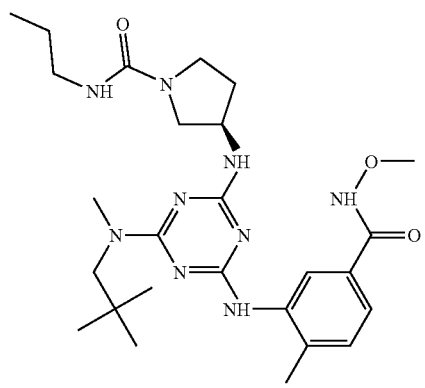
| 326 | 481.576 |
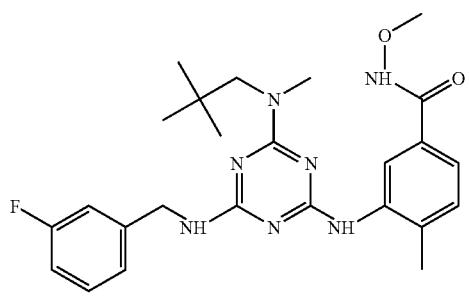

TABLE 1-continued

| # | MW |
|---|---|
| 327 | 478.601 |
| 328 | 456.551 |
| 329 | 478.601 |
| 330 | 500.648 |
| 331 | 484.649 |

TABLE 1-continued
| # | MW | |
|---|---|---|
| 332 | 481.605 | 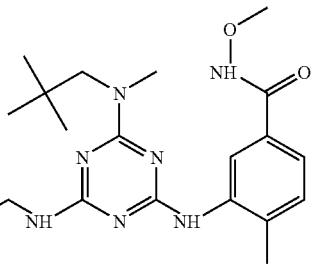 |
| 333 | 456.595 | 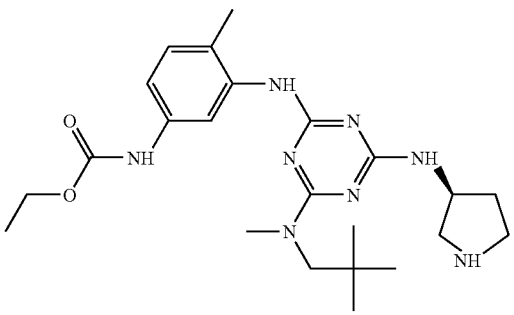 |
| 334 | 456.551 | 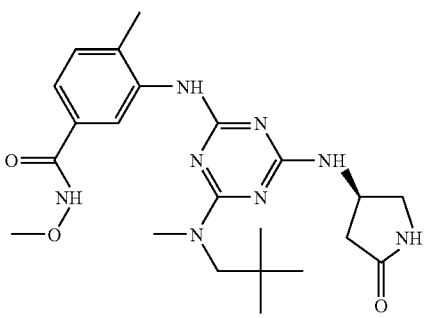 |
| 335 | 392.891 | 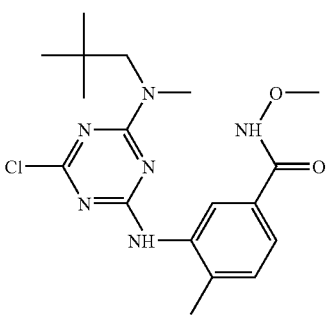 |
| 336 | 387.488 | 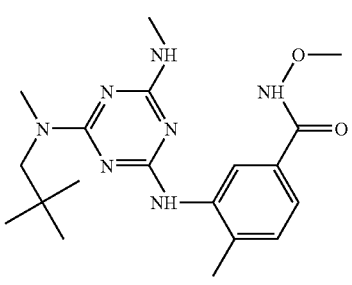 |

TABLE 1-continued

| # | MW | |
|---|---|---|
| 337 | 458.611 | |
| 338 | 456.595 | |
| 339 | 470.622 | |
| 340 | 470.622 | |
| 341 | 486.621 | |

TABLE 1-continued

| # | MW |
|---|---|
| 342 | 373.461 |
| 343 | 401.515 |
| 344 | 527.674 |
| 345 | 441.58 |

TABLE 1-continued
| # | MW | |
|---|---|---|
| 346 | 429.569 | 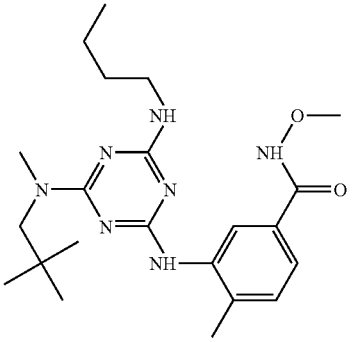 |
| 347 | 442.568 | 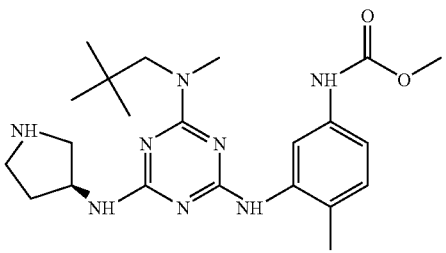 |
| 348 | 424.509 | 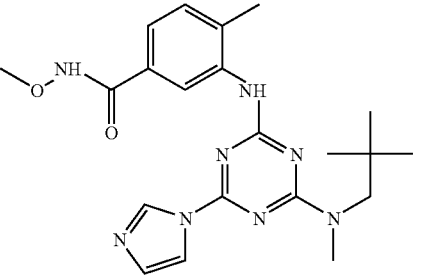 |
| 349 | 456.595 | 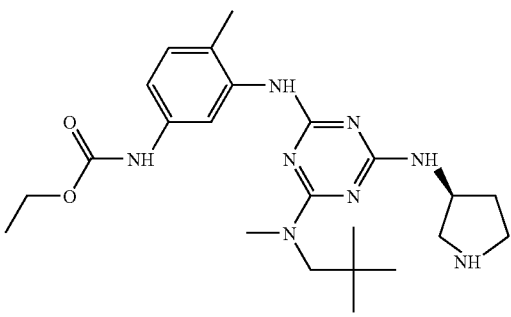 |
| 350 | 469.634 | 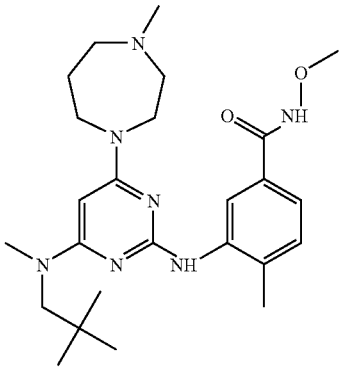 |

TABLE 1-continued
| # | MW | |
|---|---|---|
| 351 | 375.448 | 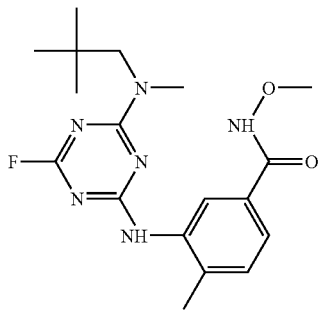 |
| 352 | 375.448 | 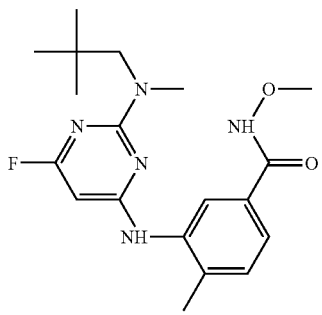 |
| 353 | 441.58 | 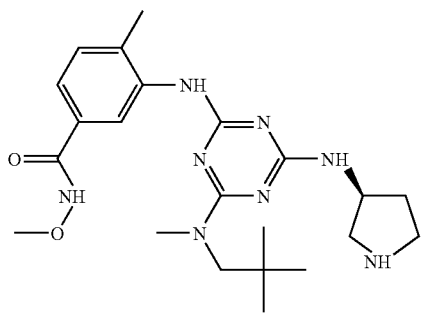 |
| 354 | 467.578 | 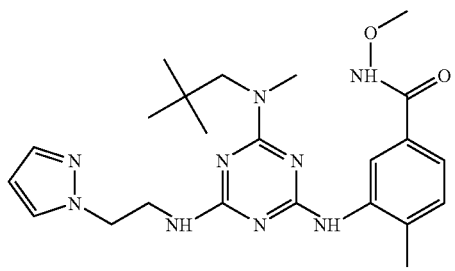 |
| 355 | 484.649 | 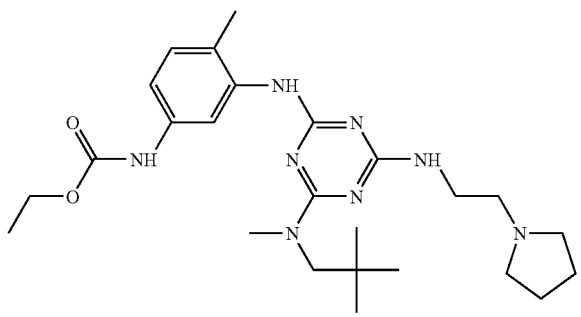 |

TABLE 1-continued
| # | MW | |
|---|---|---|
| 356 | 401.515 | 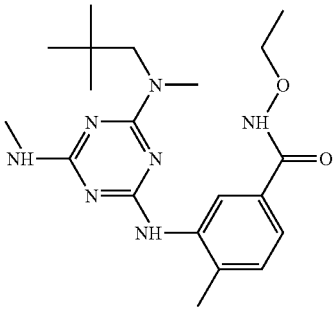 |
| 357 | 484.649 | 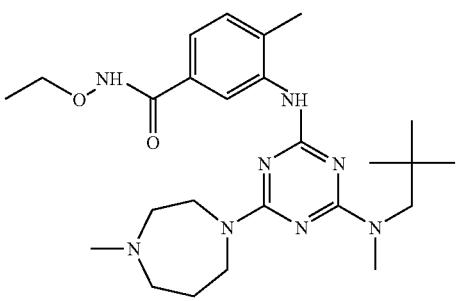 |
| 358 | 387.488 | 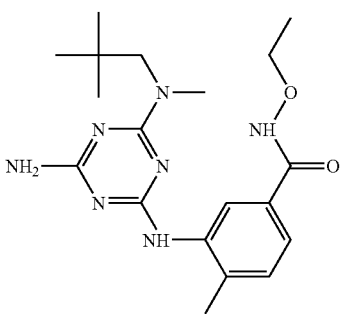 |
| 359 | 400.527 | 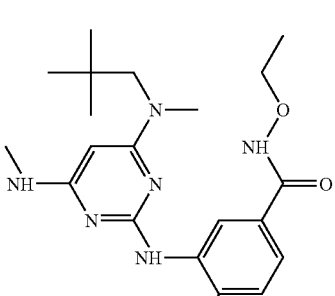 |
| 360 | 483.661 | 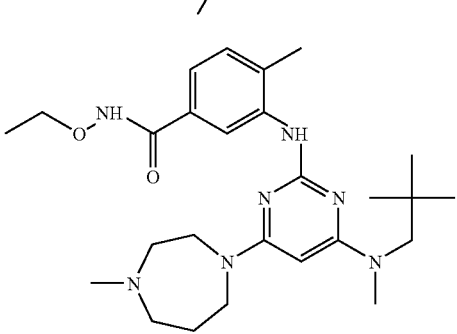 |

TABLE 1-continued

| # | MW |
|---|---|
| 361 | 470.622 |
| 362 | 483.661 |
| 363 | 483.661 |
| 400 | 463.62 |

TABLE 1-continued
| # | MW | |
|---|---|---|
| 401 | 435.57 | 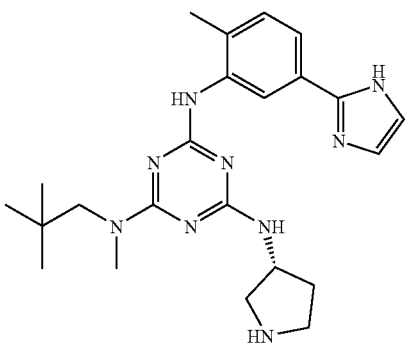 |
| 402 | 480.61 | 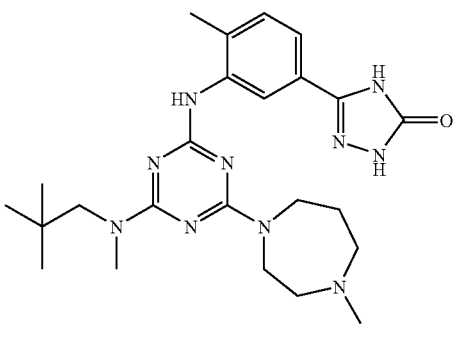 |
| 403 | 466.58 | 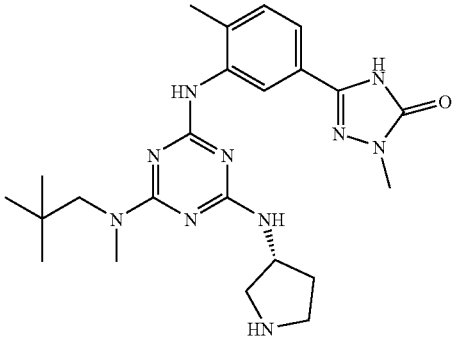 |
| 404 | 494.64 | 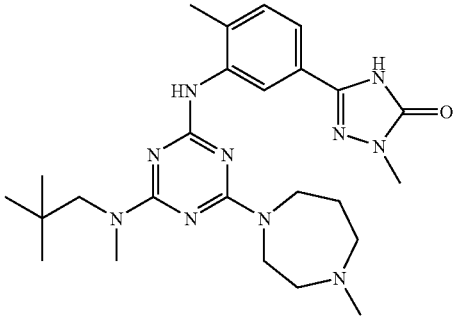 |

TABLE 1-continued

| # | MW |
|---|---|
| 405 | 452.56 |
| 406 | 437.54 |
| 407 | 450.58 |
| 408 | 436.56 |

TABLE 1-continued
| # | MW | |
|---|---|---|
| 409 | 485.63 | 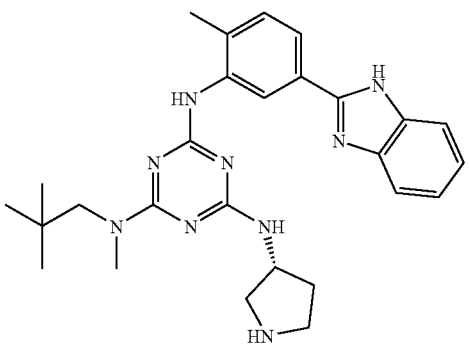 |
| 410 | 505.63 | 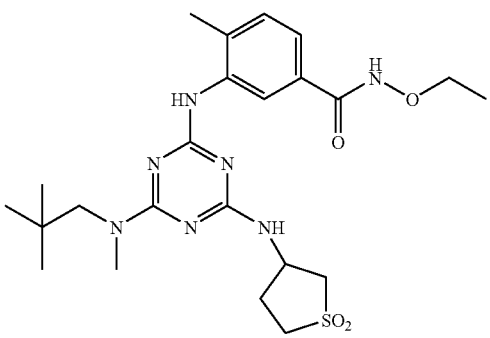 |
| 411 | 470.57 | 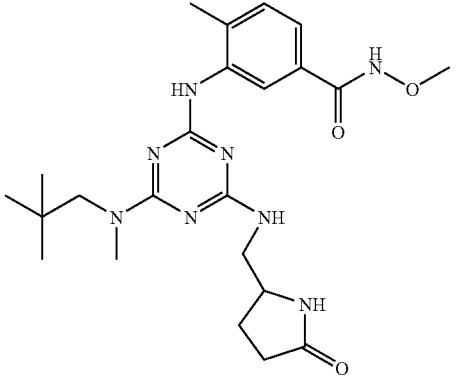 |
| 412 | 491.61 | 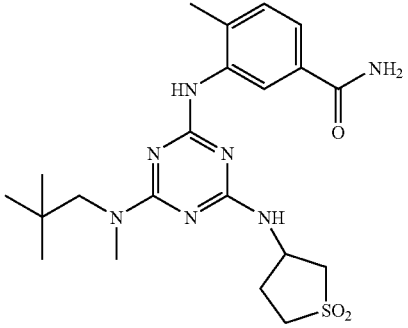 |

TABLE 1-continued

| # | MW |
|---|---|
| 413 | 440.59 |

TABLE 2

| # | R[20] | R[21] | Compound | HPLC Ret. Time(min) | Mass Spec MH[+](m/z) |
|---|---|---|---|---|---|
| 364 | CH₃ | (pyridin-2-ylmethyl)amino | O | 2.89 | 466 |
| 365 | H | 4-methyl-1,4-diazepan-1-yl | P | 3.01 | 458 |
| 366 | H | (pyridin-2-ylmethyl)amino | Q | 2.86 | 452 |
| 367 | OCH₃ | 4-methyl-1,4-diazepan-1-yl | R | 2.99 | 488 |
| 368 | OCH₃ | (pyridin-2-ylmethyl)amino | S | 2.87 | 482 |

TABLE 2-continued (Structure: 4-methyl-3-[[4-(neopentyl(methyl)amino)-6-R21-1,3,5-triazin-2-yl]thio]-N-R20-benzamide)

| # | R²⁰ | R²¹ | Compound | HPLC Ret. Time(min) | Mass Spec MH⁺(m/z) |
|---|---|---|---|---|---|
| 369 | OCH₃ | (3-pyrrolidinylamino) | T | 2.80 | 460 |
| 370 | CH₃ | (3-pyrrolidinylamino) | U | 2.80 | 444 |
| 371 | H | (3-pyrrolidinylamino) | V | 2.70 | 430 |

TABLE 3

(Structure: 4-fluoro-3-[[4-(neopentyl(methyl)amino)-6-R23-1,3,5-triazin-2-yl]thio]-N-R22-benzamide)

| # | R²² | R²³ | Compound | HPLC Ret. Time(min) | Mass Spec MH⁺(m/z) |
|---|---|---|---|---|---|
| 372 | H | (4-methyl-1,4-diazepan-1-yl) | C₁ | 2.27 | 445 |
| 373 | OCH₃ | (4-methyl-1,4-diazepan-1-yl) | D₁ | 2.5 | 475 |
| 374 | H | (3-pyrrolidinylamino) | E₁ | 1.99 | 417 |

TABLE 3-continued

[Structure: 4-fluoro-3-(triazinylthio)benzamide with R22 on amide N, R23 on triazine, and neopentyl(methyl)amino group]

| # | R²² | R²³ | Compound | HPLC Ret. Time(min) | Mass Spec MH⁺(m/z) |
|---|---|---|---|---|---|
| 375 | OCH₃ | ⟨NH-pyrrolidin-3-yl (NH)⟩ | F₁ | 2.1 | 447 |

TABLE 4

[Structure: 4-methyl-3-(triazinyloxy)benzamide with R24 on amide N, R25 on triazine, and neopentyl(methyl)amino group]

| # | R²⁴ | R²⁵ | Compound | HPLC Ret. Time(min) | Mass Spec MH⁺(m/z) |
|---|---|---|---|---|---|
| 376 | CH₃ | 4-methyl-1,4-diazepan-1-yl | K₁ | 2.71 | 456 |
| 377 | OCH₃ | 4-methyl-1,4-diazepan-1-yl | L₁ | 2.68 | 472 |
| 378 | H | NH-CH₂-(pyridin-2-yl) | M₁ | 2.57 | 436 |
| 379 | CH₃ | NH-CH₂-(pyridin-2-yl) | N₁ | 2.63 | 450 |

TABLE 4-continued

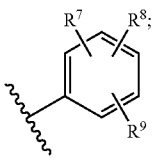

| # | R²⁴ | R²⁵ | Compound | HPLC Ret. Time(min) | Mass Spec MH⁺(m/z) |
|---|-----|-----|----------|---------------------|---------------------|
| 380 | OCH₃ | 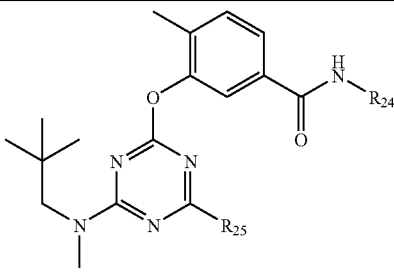 | O₁ | 2.61 | 466 |
| 381 | H | 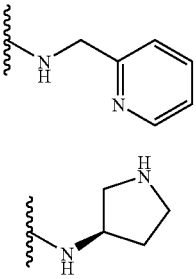 | P₁ | 2.51 | 414 |
| 382 | CH₃ | 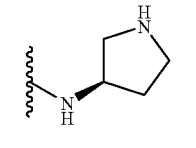 | Q₁ | 2.59 | 428 |
| 383 | OCH₃ | 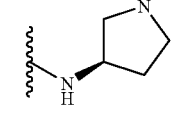 | R₁ | 2.57 | 444 |

What is claimed is:

1. A compound of Formula I, and an enantiomer, diastereomer, tautomer or pharmaceutically acceptable salt thereof

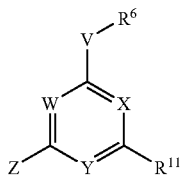

I wherein:
V is —CHR⁵— or —NR⁵;
two of W, X, and Y are each —N═ and the other is —CH═;
Z is —N(R¹)(R²), —S-aryl or S-substituted aryl;
—N(R¹)(R²) taken together may form a heterocyclyl or substituted heterocyclyl or R¹ and R² are selected as
  is alkyl, substituted alkyl, aryl, substituted aryl, cycloalkyl, substituted cycloalkyl, heterocyclyl or substituted heterocyclyl;

R⁵ is hydrogen;
R⁶ is

R⁷ is hydrogen, alkyl, substituted alkyl, alkoxy or halogen;
R⁸ is hydrogen;
R⁹ is —C(O)R¹⁰, heterocyclyl or substituted heterocyclyl;
R¹⁰ is alkyl, substituted alkyl, cycloalkyl, substituted cycloalkyl, aryl, substituted aryl, heterocyclyl, substituted heterocyclyl or —N(R³¹)(R³²);
R³¹ is hydrogen, alkyl or substituted alkyl;
R³² is hydrogen, alkyl, substituted alkyl, alkoxy, aryl, substituted aryl, cycloalkyl, substituted cycloalkyl, heterocyclyl or substituted heterocyclyl;
R¹¹ is —N(R¹²)(R¹³);
R¹² is hydrogen, alkyl or substituted alkyl;
R¹³ is —(CH₂)ₘR¹⁴; or
—N(R¹²)(R¹³) taken together form a heterocyclyl or substituted heterocyclyl;

m is 0, 1, 2 or 3;
$R^{14}$ is hydrogen, alkyl, substituted alkyl, —C(O)N($R^{31}$)($R^{32}$), —N($R^{33}$)C(O)$R^{34}$, aryl, substituted aryl, cycloalkyl, substituted cycloalkyl, heterocyclyl, substituted heterocyclyl or

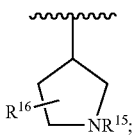

$R^{15}$ is hydrogen, alkyl or substituted alkyl;
$R^{16}$ is hydrogen or alkyl;
$R^{33}$ is hydrogen, alkyl or substituted alkyl; and
$R^{34}$ is alkyl, substituted alkyl, aryl or substituted aryl.

2. A compound of claim 1 wherein:
V is —NH—;
Z is —N($R^1$)($R^2$), —S-aryl, or S-substituted aryl;
$R^1$ is hydrogen or alkyl of 1 to 4 carbons;
$R^2$ is alkyl or substituted alkyl wherein alkyl is of 1 to 8 carbons;
$R^7$ is hydrogen, alkyl, of 1 to 4 carbons, alkoxy of 1 to 4 carbons, or halogen;
$R^8$ is hydrogen;
$R^9$ is —C(O)$R^{10}$, heterocyclyl or substituted heterocyclyl;
$R^{10}$ is —$NH_2$, —NH-alkyl, —NH-alkoxy, —NH-phenyl, or —NH—$CH_2$-phenyl wherein alkyl and alkoxy are of 1 to 6 carbons;
$R^{11}$ is —N($R^{12}$)($R^{13}$) wherein N($R^{12}$)($R^{13}$) taken together form a monocyclic heterocyclyl or substituted heterocyclyl of 5 to 7 atoms containing 1, 2, or 3 additional nitrogen atoms or wherein
$R^{12}$ is hydrogen;
$R^{13}$ is alkyl of 1 to 4 carbons or

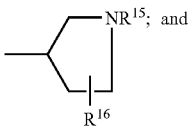

$R^{15}$ and $R^{16}$ are independently selected from hydrogen and methyl.

3. A compound of claim 2 wherein
V is —NH—;
$R^1$ is hydrogen or methyl;
$R^2$ is alkyl of 1 to 8 carbons;
$R^7$ is hydrogen, methyl, methoxy, Cl, Br, or F;
$R^8$ is hydrogen;
$R^9$ is —C(O)$R^{10}$, heterocyclyl or substituted heterocyclyl;
$R^{10}$ is —$NH_2$, —NH-alkyl, —NH-alkoxy, —NH-phenyl, or —NH—$CH_2$-phenyl wherein alkyl and alkoxy are of 1 to 6 carbons;
$R^{11}$ is —N($R^{12}$)($R^{13}$) wherein N($R^{12}$)($R^{13}$) taken together form a monocyclic heterocyclyl or substituted heterocyclyl of 5 to 7 atoms containing 1, 2, or 3 additional nitrogen atoms.

4. A compound of claim 3 wherein:
$R^{10}$ is —$NH_2$, —NH—$CH_3$, —NH—$C_2H_5$, —NH—$OCH_3$, or —NH—$OC_2H_5$.

5. A compound of claim 2 wherein:
V is —NH—;
$R^1$ is hydrogen or methyl;
$R^2$ is alkyl of 1 to 8 carbons;
$R^7$ is hydrogen, methyl, methoxy, Cl, Br, or F;
$R^8$ is hydrogen;
$R^9$ is —C(O)$R^{10}$, heterocyclyl or substituted heterocyclyl;
$R^{10}$ is —$NH_2$, —NH-alkyl, —NH-alkoxy, —NH-phenyl, or —NH—$CH_2$-phenyl wherein alkyl and alkoxy are of 1 to 6 carbons;

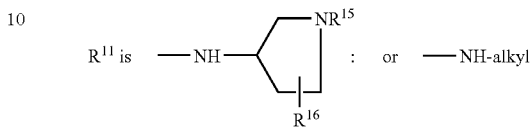

wherein alkyl is of 1 to 4 carbons; and
$R^{15}$ and $R^{16}$ are independently selected from hydrogen and methyl.

6. A compound of claim 5 wherein:
$R^{10}$ is —$NH_2$, —NH—$CH_3$, —NH—$C_2H_5$, —NH—$OCH_3$, or —NH—$OC_2H_5$.

7. A compound of claim 3 wherein:

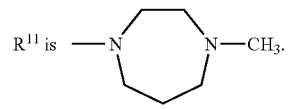

8. A pharmaceutical composition comprising a compound or a salt thereof according to claim 1 as an active ingredient, and a pharmaceutically acceptable carrier.

9. A pharmaceutical composition according to claim 8, further comprising one or more additional active ingredients.

10. A pharmaceutical composition according to claim 9, wherein said additional active ingredient is an anti-inflammatory compound or an immunosuppressive agent.

11. A pharmaceutical composition according to claim 10, wherein said additional active ingredient is chosen from a steroid and an NSAID.

12. A method of treating rheumatoid arthritis, comprising administering to a mammal in need of such treatment a pharmaceutical composition according to claim 8 in an effective amount of 0.1 to 100 mg/kg per day.

13. The method according to claim 12 wherein said composition according to claim 8 is administered with one or more additional anti-inflammatory or immunosuppressive agents as a single dose form or as separate dosage forms.

14. The compound of claim 1 wherein:
V is —NH—;
$R^1$ is hydrogen or methyl;
$R^2$ is an alkyl of 1 to 8 carbons;

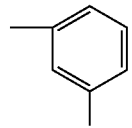

$R^{11}$ is —N($R^{12}$)($R^{13}$) wherein N($R^{12}$)($R^{13}$) taken together form a monocyclic heterocyclyl or substituted heterocyclyl of 5 to 7 atoms containing 1, 2 or 3 additional nitrogen atoms, is —NH-alkyl wherein the alkyl contains 1 to 4 carbons, or is

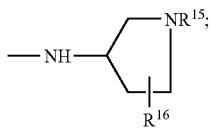

and $R^{15}$ and $R^{16}$ are independently hydrogen or methyl.

15. The compound of claim 1 wherein:

V is —NH—;

$R^1$ is hydrogen or methyl;

$R^2$ is an alkyl of 1 to 8 carbons;

$R^6$ is 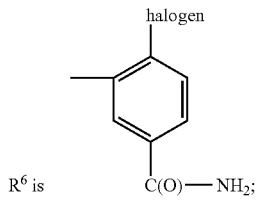

$R^{11}$ is —N($R^{12}$)($R^{13}$) wherein N($R^{12}$)($R^{13}$) taken together form a monocyclic heterocyclyl or substituted heterocyclyl of 5 to 7 atoms containing 1, 2 or 3 additional nitrogen atoms, is —NH-alkyl wherein the alkyl contains 1 to 4 carbons, or is

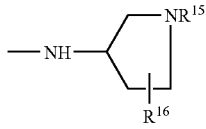

and $R^{15}$ and $R^{16}$ are independently hydrogen or methyl.

16. The compound of claim 1 wherein:

V is —NH—;

$R^1$ is hydrogen or methyl;

$R^2$ is alkyl of 1 to 8 carbons;

$R^6$ is 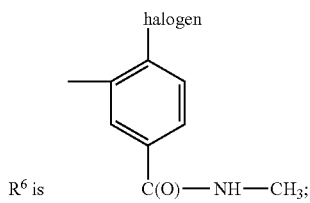

$R^{11}$ is —N($R^{12}$)($R^{13}$) wherein N($R^{12}$)($R^{13}$) taken together form a monocyclic heterocyclyl or substituted heterocyclyl of 5 to 7 atoms containing 1, 2 or 3 additional nitrogen atoms, is —NH-alkyl wherein the alkyl contains 1 to 4 carbons, or is

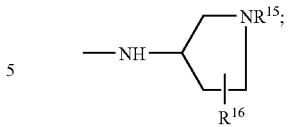

and $R^{15}$ and $R^{16}$ are independently hydrogen or methyl.

17. The compound of claim 1 wherein:

V is —NH—;

$R^1$ is hydrogen or methyl;

$R^2$ is alkyl of 1 to 8 carbons;

$R^6$ is 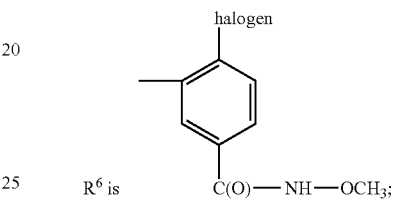

$R^{11}$ is —N($R^{12}$)($R^{13}$) wherein N($R^{12}$)($R^{13}$) taken together form a monocyclic heterocyclyl or substituted heterocyclyl of 5 to 7 atoms containing 1, 2 or 3 additional nitrogen atoms, is —NH-alkyl wherein the alkyl contains 1 to 4 carbons, or is

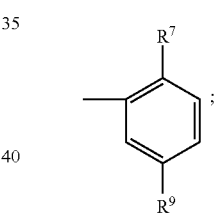

and $R^{15}$ and $R^{16}$ are independently hydrogen or methyl.

18. The compound of claim 1 wherein:

V is —NH—;

$R^1$ is hydrogen or methyl;

$R^2$ is alkyl of 1 to 8 carbons;

$R^6$ is 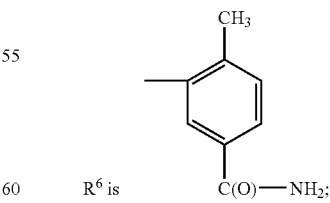

$R^{11}$ is —N($R^{12}$)($R^{13}$) wherein N($R^{12}$)($R^{13}$) taken together form a monocyclic heterocyclyl or substituted heterocyclyl of 5 to 7 atoms containing 1, 2 or 3 additional nitrogen atoms, is —NH-alkyl wherein the alkyl contains 1 to 4 carbons, or is

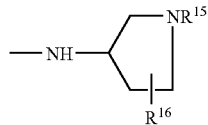

and $R^{15}$ and $R^{16}$ are independently hydrogen or methyl.

19. The compound of claim 1 wherein;

V is —NH—;

$R^1$ is hydrogen or methyl;

$R^2$ is alkyl of 1 to 8 carbons;

$R^6$ is 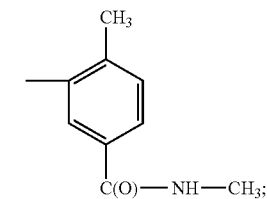

$R^{11}$ is —N($R^{12}$)($R^{13}$) wherein N($R^{12}$)($R^{13}$) taken together form a monocyclic heterocyclyl or substituted heterocyclyl of 5 to 7 atoms containing 1, 2 or 3 additional nitrogen atoms, is —NH-alkyl wherein the alkyl contains 1 to 4 carbons, or is

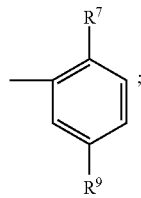

and $R^{15}$ and $R^{16}$ are independently hydrogen or methyl.

20. The compound of claim 1 wherein:

V is —NH—;

$R^1$ is hydrogen or methyl;

$R^2$ is alkyl of 1 to 8 carbons;

$R^6$ is 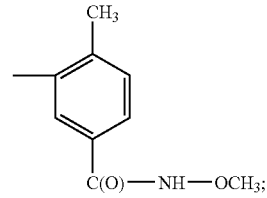

$R^{11}$ is —N($R^{12}$)($R^{13}$) wherein N($R^{12}$)($R^{13}$) taken together form a monocyclic heterocyclyl or substituted heterocyclyl of 5 to 7 atoms containing 1, 2 or 3 additional nitrogen atoms, is —NH-alkyl wherein the alkyl contains 1 to 4 carbons, or is

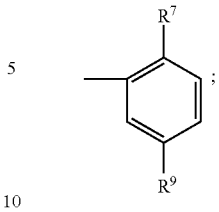

and $R^{15}$ and $R^{16}$ are independently hydrogen or methyl.

21. The compound of claim 1 wherein:

V is —NH—;

$R^1$ is hydrogen or methyl;

$R^2$ is alkyl of 1 to 8 carbons;

$R^6$ is 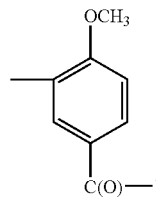

$R^{11}$ is —N($R^{12}$)($R^{13}$) wherein N($R^{12}$)($R^{13}$) taken together form a monocyclic heterocyclyl or substituted heterocyclyl of 5 to 7 atoms containing 1, 2 or 3 additional nitrogen atoms, is —NH-alkyl wherein the alkyl contains 1 to 4 carbons, or is

and $R^{15}$ and $R^{16}$ are independently hydrogen or methyl.

22. The compound of claim 1 wherein:

V is —NH—;

$R^1$ is hydrogen or methyl;

$R^2$ is alkyl of 1 to 8 carbons;

$R^6$ is 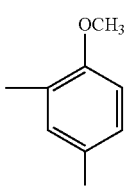

$R^{11}$ is —$N(R^{12})(R^{13})$ wherein $N(R^{12})(R^{13})$ taken together form a monocyclic heterocyclyl or substituted heterocyclyl of 5 to 7 atoms containing 1, 2 or 3 additional nitrogen atoms, is —NH-alkyl wherein the alkyl contains 1 to 4 carbons, or is

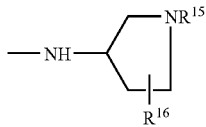

and $R^{15}$ and $R^{16}$ are independently hydrogen or methyl.

23. The compound of claim 1 wherein:

V is —NH—;

$R^1$ is hydrogen or methyl;

$R^2$ is alkyl of 1 to 8 carbons;

$R^6$ is 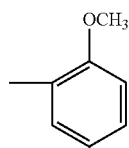

$R^{11}$ is —$N(R^{12})(R^{13})$ wherein $N(R^{12})(R^{13})$ taken together form a monocyclic heteroocyclyl or substituted heterocyclyl of 5 to 7 atoms containing 1, 2 or 3 additional nitrogen atoms, is —NH-alkyl wherein the alkyl contains 1 to 4 carbons, or is

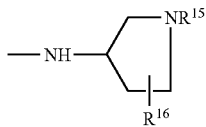

and $R^{15}$ and $R^{16}$ are independently hydrogen or methyl.

24. The compound of claim 1 wherein:

V is —NH—;

Z is-$N(R^1)(R^2)$;

$R^1$ is hydrogen or methyl;

$R^2$ is alkyl of 1 to 8 carbons;

$R^6$ is

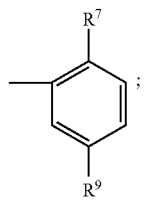

$R^7$ is hydrogen, methyl, methoxy, halogen or cyano;

$R^9$ is chosen from unsubstituted or substituted triazole, oxadiazole, imidazole, thiazole or benzimidazole;

$R^{11}$ is —$N(R^{12})(R^{13})$ wherein $N(R^{12})(R^{13})$ taken together form a monocyclic heterocyclyl or substituted heterocyclyl of 5 to 7 atoms containing 1, 2 or 3 additional nitrogen atoms, is —NH-alkyl wherein the alkyl contains 1 to 4 carbons, or is

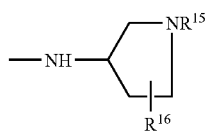

and $R^{15}$ and $R^{16}$ are independently hydrogen or methyl.

25. A compound of claim 24 wherein:

$R^9$ is substituted or unsubstituted 1,2,4-triazole.

26. A compound of claim 24 wherein:

$R^9$ is substituted or unsubstituted 1,2,4-triazole connected via a C3 or C5 position.

27. A compound of claim 24 wherein:

$R^9$ is substituted or unsubstituted 1,2,4-triazole connected via an N4, N1 or N2 position.

28. A compound of claim 24 wherein:

$R^9$ is substituted or unsubstituted thiazole connected via a C2 position.

29. A compound of claim 24 wherein:

$R^9$ is substituted or unsubstituted thiazole connected via a C4 position.

30. A compound of claim 24 wherein:

$R^9$ is substituted or unsubstituted thiazole connected via a C5 position.

31. A compound of claim 24 wherein:

$R^9$ is substituted or unsubstituted 1,3,4-oxdiazole connected via a 2 or 5 position.

32. A compound of claim 24 wherein:

$R^9$ is substituted or unsubstituted imidazole connected via a C2, C4, C5, N1 or N3 position.

* * * * *

UNITED STATES PATENT AND TRADEMARK OFFICE
CERTIFICATE OF CORRECTION

PATENT NO. : 7,479,495 B2  Page 1 of 2
APPLICATION NO. : 11/143430
DATED : January 20, 2009
INVENTOR(S) : Kevin Joseph Moriarty et al.

It is certified that error appears in the above-identified patent and that said Letters Patent is hereby corrected as shown below:

In the Claims:

Claim 5:

Column 288, line 12, change ":" to -- ; --.

Claim 17:

Column 290, lines 36 to 42, change

"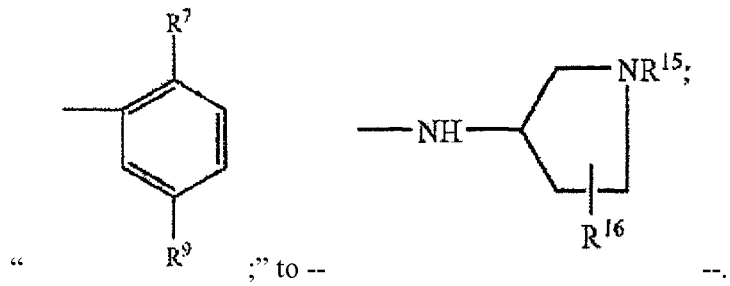 ;" to -- --.

Claim 19:

Column 291, line 12, change ";" to -- : --.

Signed and Sealed this
Twenty-second Day of March, 2011

David J. Kappos
*Director of the United States Patent and Trademark Office*

CERTIFICATE OF CORRECTION (continued)
U.S. Pat. No. 7,479,495 B2

In the Claims:

Claim 19 (continued):

Column 291, lines 35 to 42, change

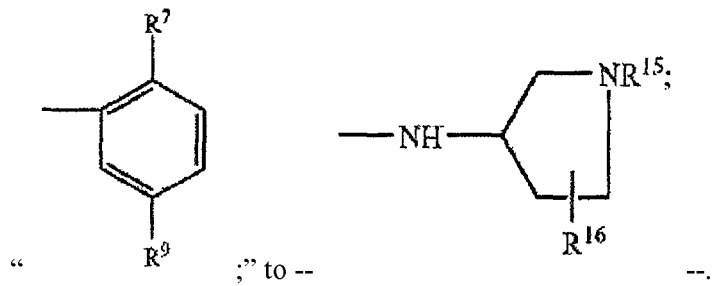

" ;" to -- --.

Claim 20:

Column 292, lines 1 to 9, change

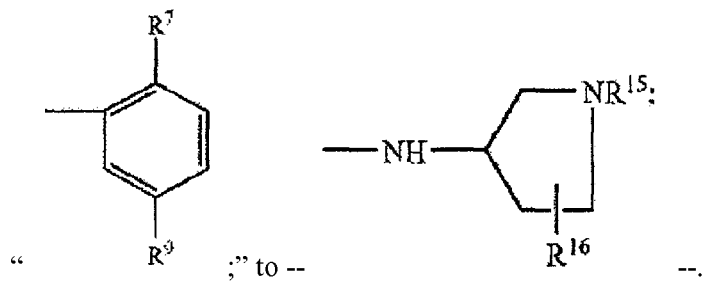

" ;" to -- --.